US009557336B2

(12) United States Patent
Fasan et al.

(10) Patent No.: US 9,557,336 B2
(45) Date of Patent: Jan. 31, 2017

(54) METHODS AND COMPOSITIONS FOR SITE-SPECIFIC LABELING OF PEPTIDES AND PROTEINS

(71) Applicant: University of Rochester, Rochester, NY (US)

(72) Inventors: Rudi Fasan, Rochester, NY (US); John R. Frost, Niagara Falls, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 14/426,599

(22) PCT Filed: Sep. 5, 2013

(86) PCT No.: PCT/US2013/058322
§ 371 (c)(1),
(2) Date: Mar. 6, 2015

(87) PCT Pub. No.: WO2014/039715
PCT Pub. Date: Mar. 13, 2014

(65) Prior Publication Data
US 2015/0241440 A1 Aug. 27, 2015

Related U.S. Application Data

(60) Provisional application No. 61/698,045, filed on Sep. 7, 2012.

(51) Int. Cl.
*C40B 40/10* (2006.01)
*C12P 21/04* (2006.01)
*A61K 47/48* (2006.01)
*C08G 63/48* (2006.01)
*C08G 63/91* (2006.01)
*C08L 89/00* (2006.01)
*A61K 38/00* (2006.01)
*C07K 5/00* (2006.01)
*C07K 7/00* (2006.01)
*C07K 16/00* (2006.01)
*C07K 17/00* (2006.01)
*C07D 235/02* (2006.01)
*C07D 311/02* (2006.01)
*G01N 33/58* (2006.01)
*G01N 33/68* (2006.01)
*C07D 495/04* (2006.01)
*C09B 57/02* (2006.01)
*C12N 9/42* (2006.01)
*A61K 49/00* (2006.01)

(52) U.S. Cl.
CPC ....... *G01N 33/582* (2013.01); *A61K 47/48338* (2013.01); *A61K 49/0039* (2013.01); *A61K 49/0054* (2013.01); *C07D 495/04* (2013.01); *C09B 57/02* (2013.01); *C12N 9/2442* (2013.01); *G01N 33/6803* (2013.01); *C07K 2319/20* (2013.01); *C07K 2319/21* (2013.01); *C07K 2319/50* (2013.01); *C07K 2319/60* (2013.01); *C07K 2319/92* (2013.01)

(58) Field of Classification Search
CPC ..... G01N 33/582; C09B 57/02; C07D 495/04; C12N 9/2442; C07K 2319/92; C07K 2319/60
See application file for complete search history.

(56) References Cited

U.S. PATENT DOCUMENTS

| 6,388,127 | B1 | 5/2002 | Quallich et al. |
| 7,449,558 | B2 | 11/2008 | Yao et al. |
| 7,622,552 | B2 | 11/2009 | Cotton |
| 8,242,058 | B2 | 8/2012 | Raines et al. |
| 2006/0134691 | A1 | 6/2006 | Auer et al. |

FOREIGN PATENT DOCUMENTS

| WO | WO 2012100176 A2 * | 7/2012 | ............. C07K 1/026 |
| WO | WO-2012100176 A2 | 7/2012 | |

OTHER PUBLICATIONS

CAS RN 112682-76-5. Published Feb. 7, 1988.*
Satyanarayana et al. "Diverse organo-peptide macrocycles via a fast and catalyst-free oxime/intein-mediated dual ligation" Chem. Commun. 48:1461-1463. Published Sep. 7, 2011.*
Schimelpfenig C "Synthesis of 2-Anilinoethanethiol by Hydride Reduction" J. Org. Chem. 27:3323-3324. Published 1962.*
CAS RN 102495-17-0. Published May 31, 1986.*
CAS RN 1260379-40-5. Published Jan. 25, 2011.*
CAS RN 1062574-92-8. Published Oct. 17, 2008.*
Lee et al. "Solid-State Thermocromism and Phase Transitions of Charge Transfer 1,3-Diamino-4,6-dinitrobenzene Dyes" J. Phys. Chem. A 115:10087-10096. Published Jul. 26, 2011.*
CAS RN 5891-08-7. Published Nov. 16, 1984.*
Korean Intellectual Property Office, International Search Report and Written Opinion of the International Searching Authority for PCT/US2013/058322 mailed Dec. 16, 2013 (12 pages).
Volkmann, Gerrit et al., "Protein C-Terminal Labeling and Biotinylation Using Synthetic Peptide and Split-Intein," Dec. 2009 Plos one, vol. 4, No. 12 (13 pages).

(Continued)

Primary Examiner — James H Alstrum Acevedo
Assistant Examiner — Zachary J Miknis
(74) Attorney, Agent, or Firm — Harris Beach PLLC

(57) ABSTRACT

Methods and compositions are provided for covalently linking a chemical species to a recombinant or synthetic polypeptide. The methods involve the reaction of a thioester-comprising polypeptide with a reagent comprising a reactive amino-thiol group connected to the chemical species which is to be covalently linked to the polypeptide, via a linker. Such chemical species can be a functional group, a label or tag molecule, a biological molecule, a ligand, or a solid support. Efficient and catalyst-free methods for C-terminal protein labeling are also provided. The methods expand current capabilities in the area of protein functionalization, providing useful and complementary tools for the isolation, detection, characterization, and analysis of proteins in a variety of in vitro and in vivo applications.

15 Claims, 18 Drawing Sheets

(56) References Cited

OTHER PUBLICATIONS

Figure 1:
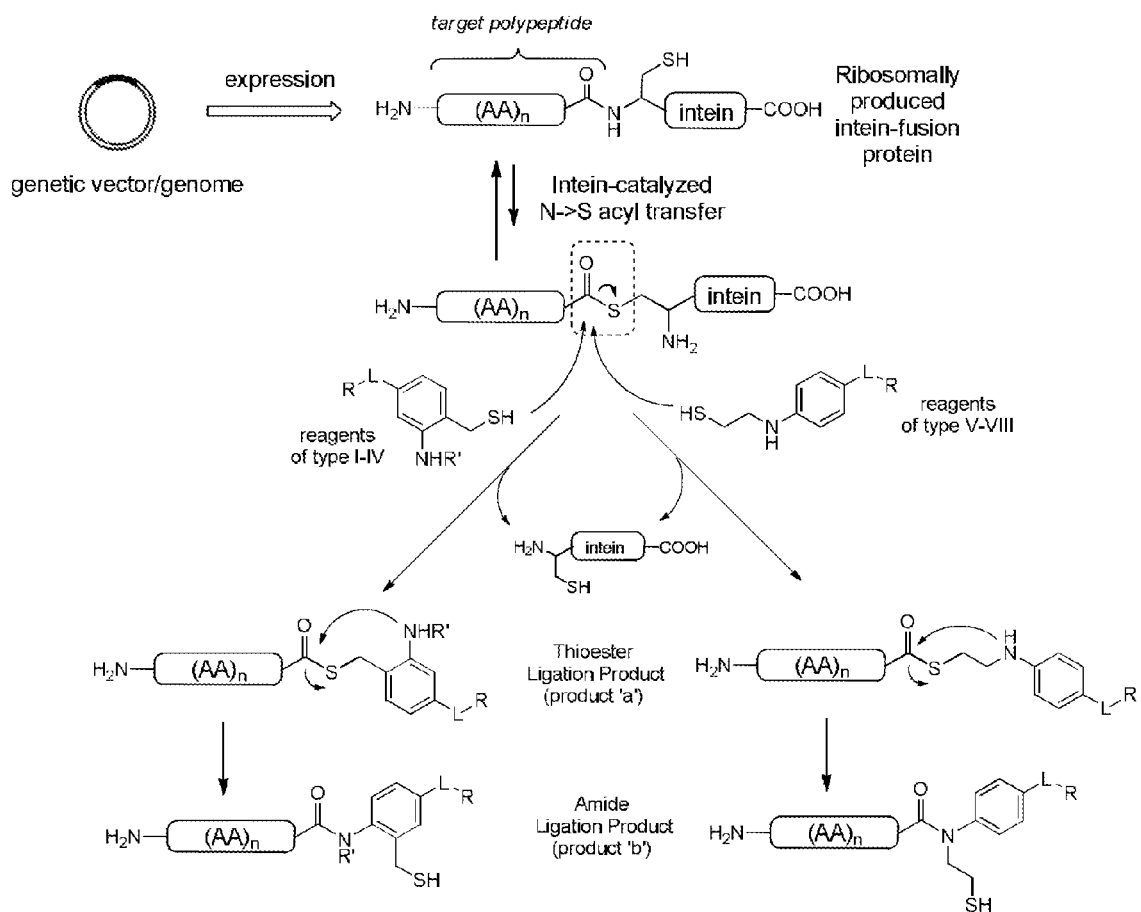

Hahn, Michael E. et al., "Manipulating proteins with chemistry: a cross-section of chemical biology," Jan. 2005, Trends in Biochemical Sciences, vol. 30, No. 1, pp. 26-34.
European Patent Office—Extended European Search Report for EP Application No. 13834888.3 dated Mar. 10, 2016 (10 pgs).
Kuznetsova, E.A. et al., "Synthesis of 2-mercaptobenzthiazole derivatives. VI. Reactions of Dihydrothiazolo- and Dihydrothiazino [2, 3-b] Benzothiazolium Salts with some Nucleophilic Reagents," 1967 Chemistry of Heterocyclic Compounds, vol. 3, No. 5 (pp. 659-661).
Chan, Edward Y. et al., "Benzothiazepinones, Related Compounds, and the Smiles Rearrangement," 1979 Phosphorus and Sulfur, vol. 7 (pp. 41-45).
Tolbert, Thomas J. et al., "Intein—Mediated Synthesis of Proteins Containing Carbohydrates and Other Molecular Probes," 2000 J. Am. Chem. Soc., vol. 122, No. 23 (pp. 5421-5428).

\* cited by examiner

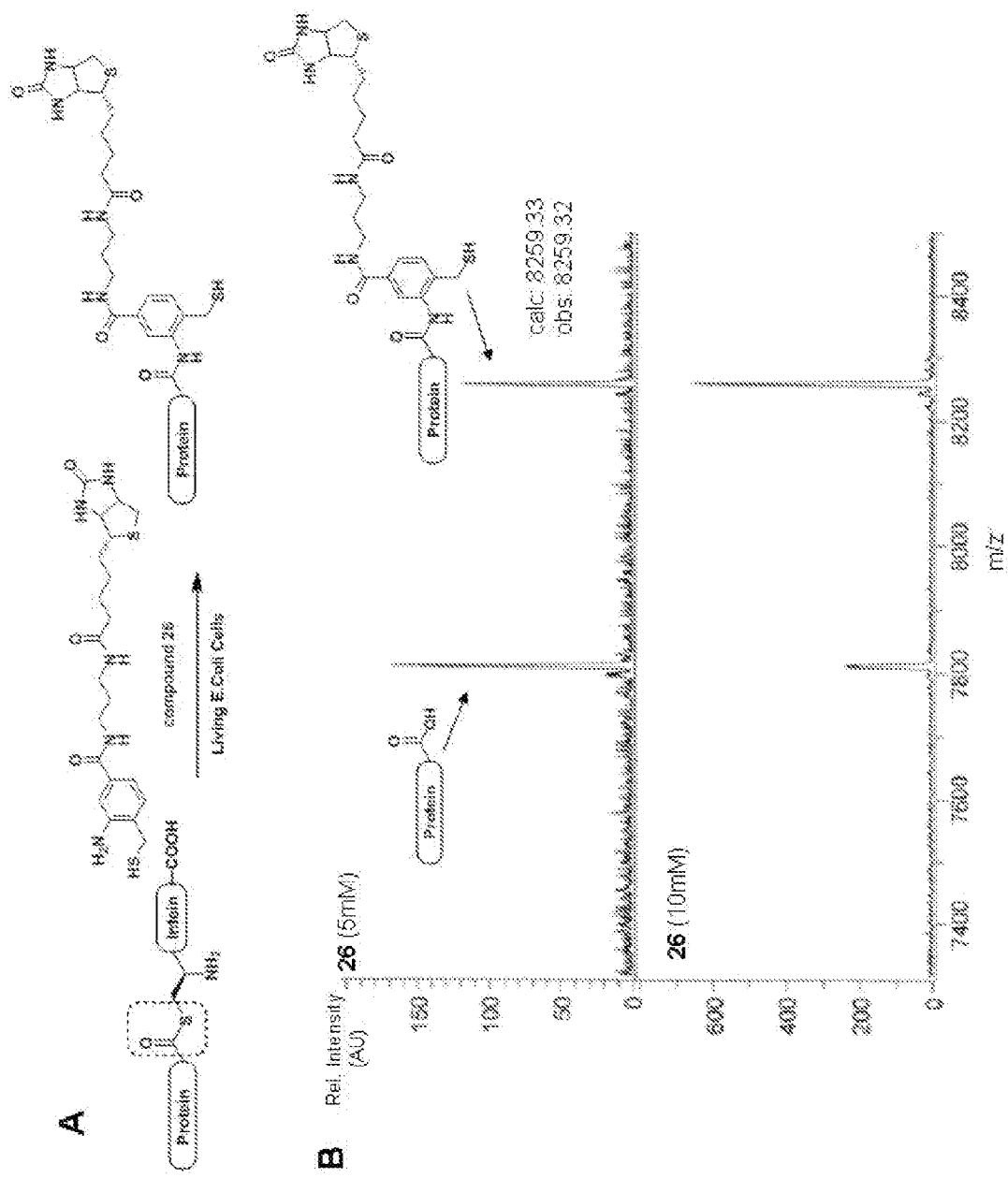
Figure 15A-B

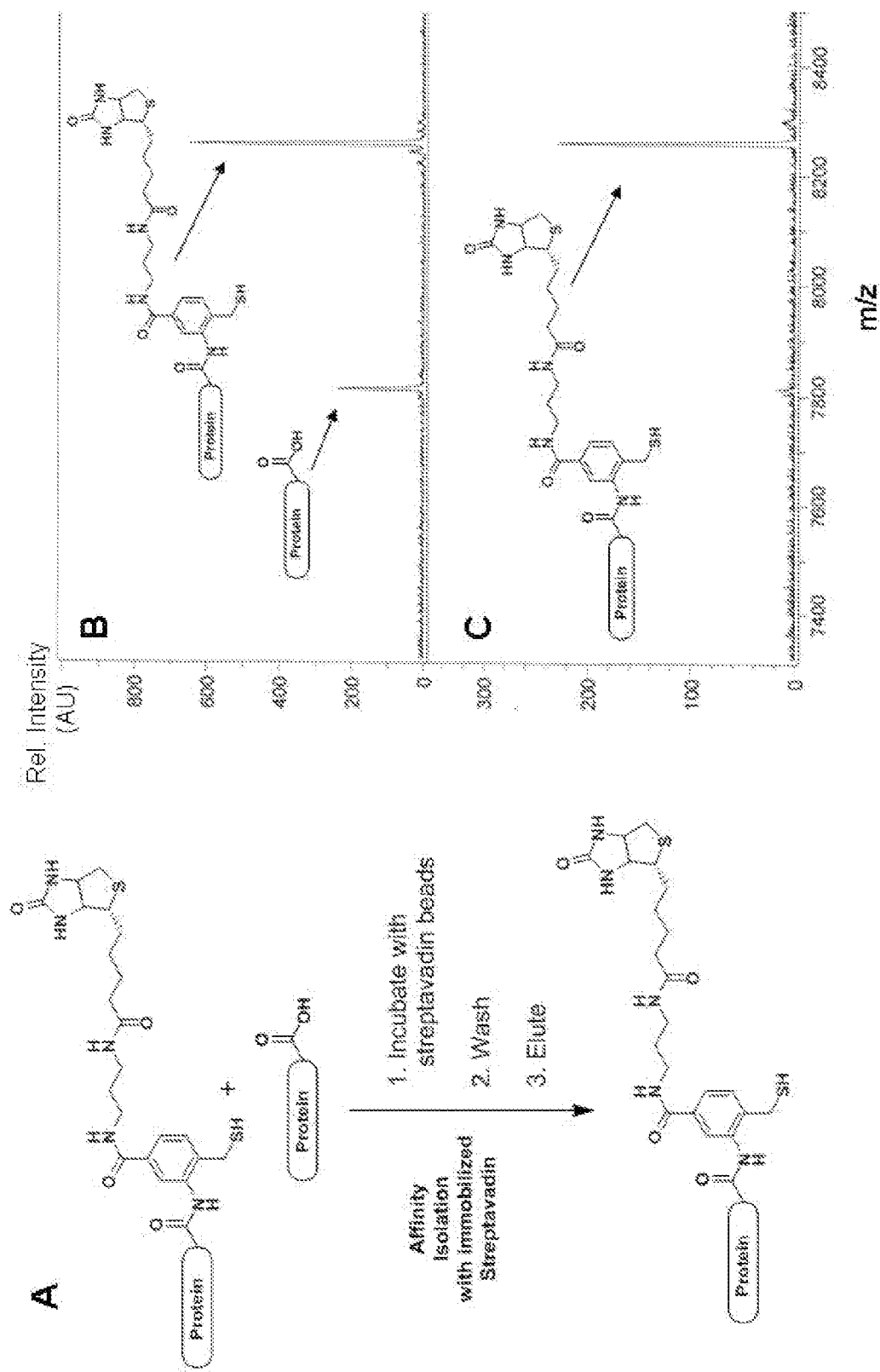
Figure 16A-C

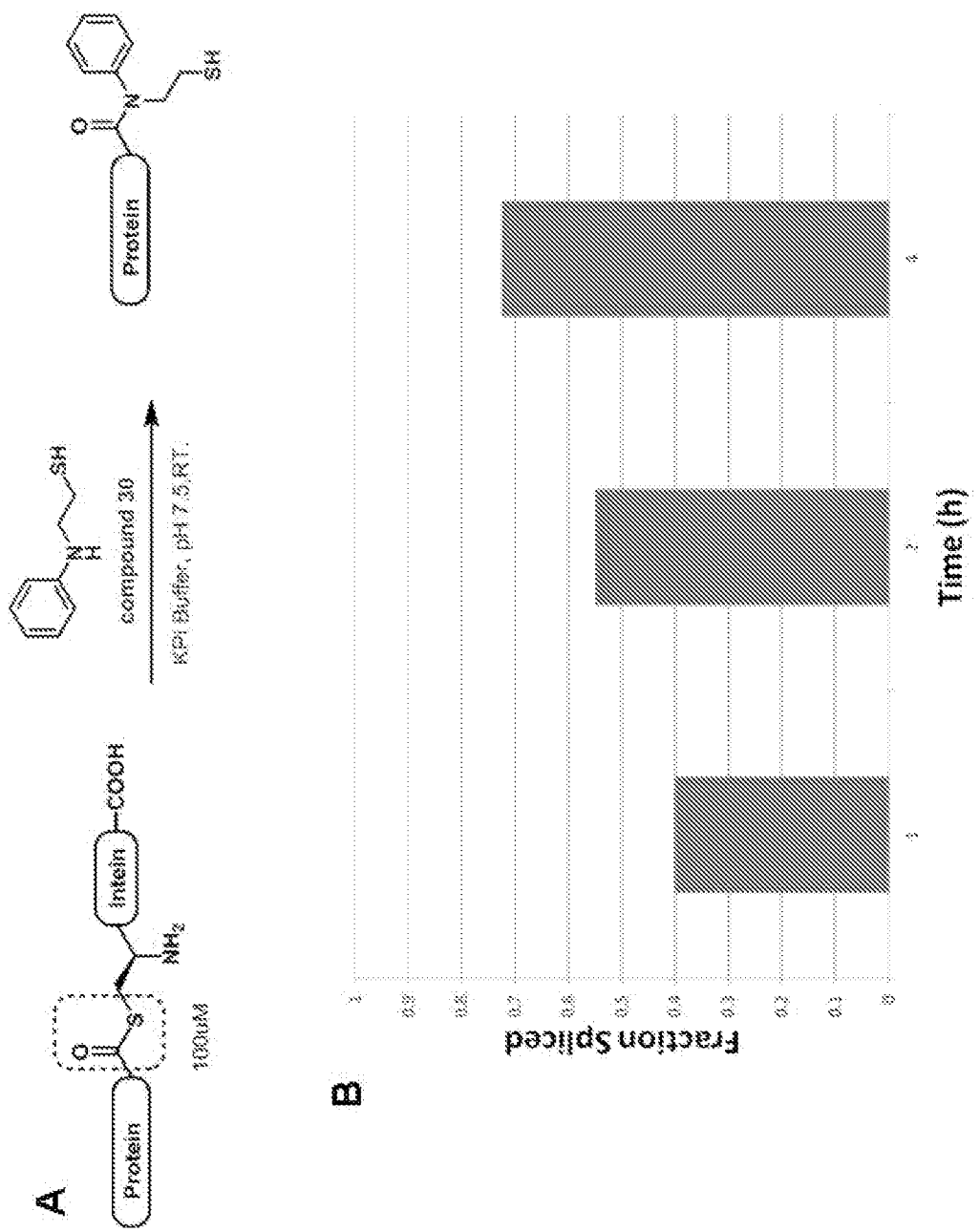
Figure 17A-B

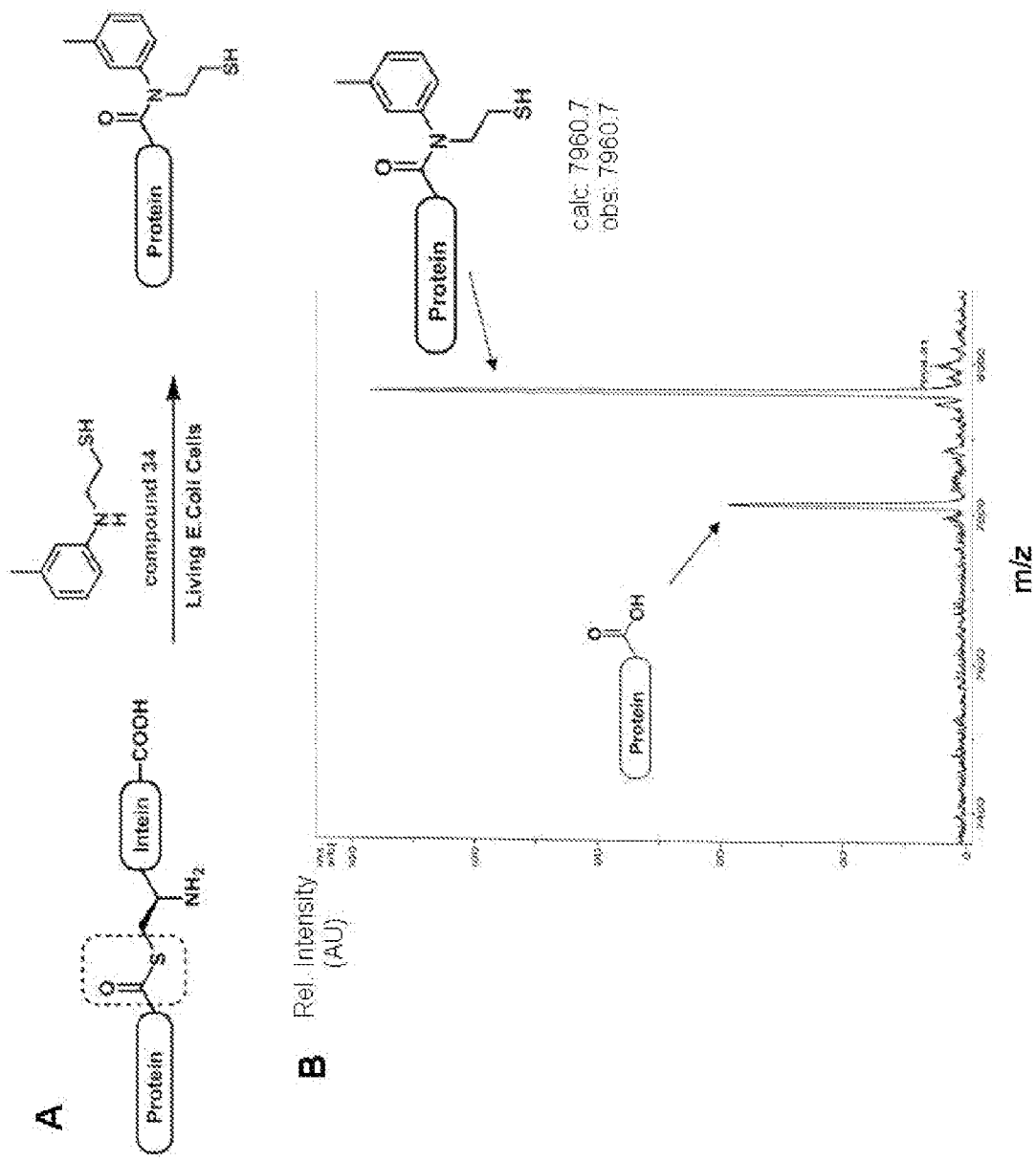
Figure 18A-B ns of Peptides
METHODS AND COMPOSITIONS FOR SITE-SPECIFIC LABELING OF PEPTIDES AND PROTEINS

CROSS-REFERENCE TO RELATED APPLICATIONS

This application is a national stage application under 35 U.S.C. §371 of PCT Application No. PCT/US2013/058322, filed Sep. 5, 2013, which claims priority to and the benefit of U.S. provisional patent application Ser. No. 61/698,045 entitled "Methods and Reagents for Site-Specific Labeling of Peptides and Proteins," filed Sep. 7, 2012, which is incorporated herein by reference in its entirety.

STATEMENT REGARDING FEDERALLY SPONSORED RESEARCH OR DEVELOPMENT

This invention was made with government support under grant no. CHE-1112342 awarded by the National Science Foundation. The government has certain rights in the this invention.

1. TECHNICAL FIELD

The present invention relates to methods and compositions for covalently linking a chemical species to a recombinant or synthetic polypeptide.

2. BACKGROUND OF THE INVENTION

Chemical methods for site-specific functionalization of proteins and peptides are useful in a variety of research and biomedical applications. For example, the site-specific attachment of a chromophore such as a fluorescent dye to a target protein can be useful to enable detection of such protein in a complex mixture or to track expression and localization of the target protein within a cell or living organism. On the other hand, site-specific functionalization of a protein with an affinity tag can be used to facilitate protein isolation, purification, and characterization. Site-specific functionalization can also be useful in the preparation of protein microarrays, which in turn can be useful for screening protein-ligand, protein-protein, antigen-antibody interactions. As another example, methods to chemically link a protein such as a therapeutic protein to a polymer (e.g., polyethylene glycol), a small-molecule drug, a cell receptor ligand, or another protein or peptide can be valuable to enhance and modulate the pharmacological, pharmacokinetic, or tissue-targeting properties of the therapeutic protein.

Several methods for the functionalization of peptides and proteins are known in the art (see, e.g., Hermanson 1996; Jing and Cornish 2011; Crivat and Taraska 2012). Conventional strategies have taken advantage of nucleophilic side-chain functionalities in certain amino acids (e.g., thiol group in cysteine, amino group in lysine) to couple a chemical species to the polypeptide via an electrophilic reagent (Hermanson 1996). An inherent limitation of these approaches is than more than one such amino acid can be present in the target polypeptide, preventing accurate control on the site-selectivity of the reaction. Furthermore, using these strategies, selective labeling of an individual protein in complex biological mixtures (e.g., cell lysate or within a cell) is not possible owing to the occurrence of numerous other proteins having similar reactive functionalities.

More recent approaches for protein labeling have involved the genetic fusion of a protein to a protein tag such as a fluorescent protein (e.g., green fluorescent protein and variants thereof) or an enzyme, which can be covalently modified via an irreversible inhibitor to indirectly link a certain chemical species (e.g., fluorophore or affinity label) to the protein of interest (Jing and Cornish 2011; Crivat and Taraska 2012). Examples of the latter include the so-called SNAP tag (Keppler, Gendreizig et al. 2003), HaloTag (Los, Encell et al. 2008), and the TMP-tag (Calloway, Choob et al. 2007). A common drawback of these approaches is however that permanent fusion of the target protein to a non-native protein tag may affect the biological function, dynamics, conformational properties, and/or cellular localization of the protein of interest.

Other approaches in the area of protein labeling have involved the use of short (e.g., 6-20 amino acid-long) peptide sequences which are genetically fused to the protein of interest and serve as recognition sites for enzyme-catalyzed posttranslational modifications. By action of these enzymes or engineered variants thereof and utilizing modified co-substrates, fluorophores or other small molecule labels have been attached to these peptide sequences, and thus, to the target protein. Examples of these strategies include the use of biotin ligase BirA (Chen, Howarth et al. 2005), sortase (Popp, Antos et al. 2007), lipoic acid ligase (Cohen, Zou et al. 2012), and phosphopantetheine transferase (PPTase) (Yin, Liu et al. 2004). Also in this case, however, the target protein must be permanently fused to a non-native peptide sequence, which can alter the properties of the former. In addition, the addition (or co-expression) of an auxiliary processing enzyme is required for both in vitro and in vivo applications.

In general, 'traceless' methods for protein labeling that involve no modifications or extensions of the primary sequence of the target protein are highly desirable in order to minimize the risks of altering its structure/function/cellular localization. In particular, the ability to site-specifically attach new chemical entities to the carboxy-terminus of a protein or enzyme is most valuable as the C-terminus is often solvent-exposed and typically not directly involved in binding or catalysis. Thus, efficient methods for C-terminal functionalization of a protein can be of great value toward protein labeling or immobilization under non-disruptive conditions.

Recently developed technologies have made possible the generation of recombinant proteins comprising a thioester group at their C-terminal end. The C-terminal thioester group provides a unique reactive chemical functionality within the protein which can be exploited for site-specific labeling of a target protein. Recombinant C-terminal thioester proteins can be generated by exploiting the mechanism of inteins, which are naturally occurring proteins capable of excising themselves from the internal region of a precursor polypeptide via a posttranslational process known as protein splicing (Paulus 2000). The first step in protein splicing involves an intein-catalyzed N→S (or N→O) acyl transfer in which the polypeptide chain flanking the intein N-terminus (N-extein) is transferred to the side-chain thiol or hydroxy group of a conserved cysteine, serine, or threonine residue at the N-terminus of the intein. Further intramolecular rearrangements follow that ultimately lead to the excision of the intein from the precursor polypeptide and the ligation of N-extein unit to the C-extein unit (=polypeptide chain flanking the intein C-terminus) via a peptide bond. By genetically fusing a protein of interest to the N-terminus of engineered intein variants which are unable to undergo C-terminal splicing (e.g., via mutation of the conserved asparagine residue at the intein C-terminus or removal of the C-extein unit), it is possible to promote only the first step of protein splicing, thereby producing a recombinant protein with a reactive C-terminal thioester linkage. The sequencing and characterization of several naturally occurring intein-comprising proteins show that inteins share a similar mechanism as well as a number of conserved primary sequence regions called 'intein motifs', whereas generally there are no specific sequence requirements for the N- and C-extein units. To date, more than 500 experimentally validated and putative intein sequences have been identified.

The ability to generate recombinant C-terminal thioester proteins via the genetic fusion of a protein to the N-terminus of a natural intein, or engineered (or synthetic or artificial) variant thereof, provides the opportunity to link a chemical entity to the protein C-terminus via nucleophilic substitution at the thioester group. A known methodology in this area involves the reaction between a recombinant C-terminal thioester protein with another polypeptide (i.e., a recombinant or synthetic peptideprotein) comprising an N-terminal cysteine. This procedure, also known as Expressed Protein Ligation (Muir, Sondhi et al. 1998), involves an intermolecular transthioesterification reaction followed by an intramolecular S→N acyl shift to give a native peptide bond between the two polypeptide chains. Similarly, cysteine-comprising reagents have been used for labeling/immobilization of recombinant C-terminal thioester proteins (Chattopadhaya, Abu Bakar et al. 2009). Alternatively, and also in the context of protein labeling/immobilization applications, recombinant C-terminal thioester proteins have been functionalized at the C-terminus via the use of hydrazine-, hydrazide-, or oxyamine-comprising chemical reagents, in which the hydrazine, hydrazide, or oxyamine group acts as the nucleophile to promote the C-terminal ligation of the protein of interest to a given chemical species (e.g., a fluorescent dye) (Cotton, U.S. Pat. No. 7,622,552; Raines et al. U.S. Pat. Appl. 20080020942).

Unfortunately, all the aforementioned methods for protein C-terminal labeling are characterized by slow reaction kinetics resulting in low labeling efficiencies, in particular at short reaction times. In addition, high concentrations of reagents (either the target C-terminal thioester protein, or the labeling reagent, or both) are typically required to achieve satisfactory yields of the desired protein functionalized product. Furthermore, thiol catalysts such as, for example, thiophenol, mercaptoethanol, or MESNA, are typically necessary to expedite and/or increase the yields of these protein functionalization procedures. As a result of these drawbacks, the utility of these methods for protein C-terminal labeling/immobilization remains limited. For example, these reactions conditions can be hardly attained at the intracellular level, severely limiting the scope of these methods in the context of in vivo protein labeling applications. Furthermore, fast protein labeling procedures are required to enable the detection and isolation of transient or short-lived protein species in the context of proteomic or cell biology studies. Finally, the limited stability of certain proteins may not be compatible with the need for high reagent or catalyst concentrations associated to these methods.

Citation or identification of any reference in Section 2, or in any other section of this application, shall not be considered an admission that such reference is available as prior art to the present invention.

3. SUMMARY OF THE INVENTION

Methods, kits and compositions are provided for covalently linking a chemical species to a recombinant or synthetic polypeptide. The methods involve the reaction of a thioester-comprising polypeptide with a reagent comprising a reactive amino-thiol group connected to the chemical species which is to be covalently linked to the polypeptide, via a linker. Such chemical species may be a functional group, a label or tag molecule, a biological molecule, a ligand, or a solid support.

Efficient and catalyst-free methods for C-terminal protein labeling are also provided. These methods expand current capabilities in the area of protein functionalization, providing useful and complementary tools for the isolation, detection, characterization, and analysis of proteins in a variety of in vitro and in vivo applications.

A method is provided for forming a covalent linkage between a polypeptide and a chemical species, the method comprising the steps of:

a. providing a polypeptide, wherein the polypeptide comprises a thioester group and/or wherein the polypeptide is C-terminally fused to an intein;

b. providing a chemical reagent of formula (I), (II), (III), (IV), (V), (VI), (VII) or (VIII):

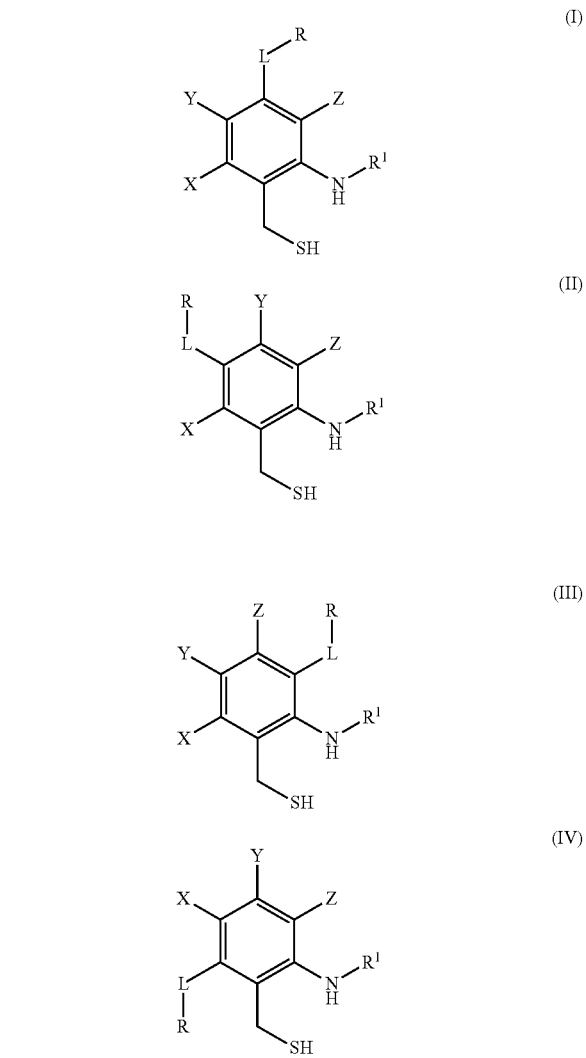

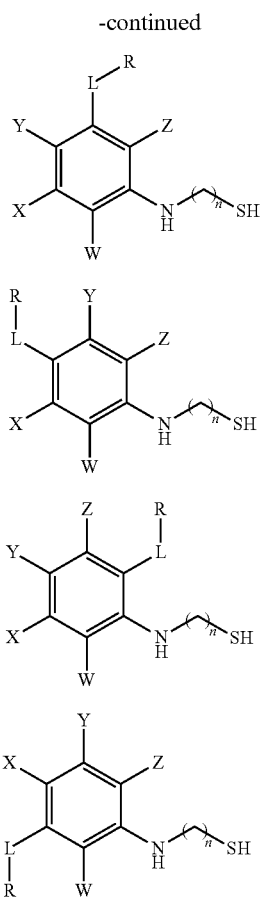

or a salt of the chemical reagent, wherein:

i. R is a chemical species to be covalently linked to the polypeptide, ii. $R_1$ is hydrogen, a substituted or non-substituted aliphatic group, or a substituted or non-substituted aryl group, iii. X, Y, W, and Z are hydrogen and/or non-hydrogen substituents selected from the group consisting of alkyl, heteroatom-comprising alkyl, alkenyl, heteroatom-comprising alkenyl, alkynyl, heteroatom-comprising alkynyl, aryl, heteroatom-comprising aryl, alkoxy, heteroatom-comprising alkoxy, aryloxy, heteroatom-comprising aryloxy, halo, —OH, —OR', —SR, —COOH, —COOR', —CONR'$_2$, —NR'$_2$, —NO$_2$, —SO$_3$R', —SO$_2$NR$_2$', —C≡N, —O—C≡N, —P(O)$_k$R' where k is 2 or 3, and —S—C≡N, wherein each R' is independently H, alkyl, or substituted alkyl, iv. n is 2 or 3; and v. L is a linker or a linker group selected from the group consisting of a single bond, $C_1$-$C_{24}$ alkyl, $C_1$-$C_{24}$ substituted alkyl, $C_1$-$C_{24}$ substituted heteroatom-comprising alkyl, $C_1$-$C_{24}$ substituted heteroatom-comprising alkyl, $C_2$-$C_{24}$ alkenyl, $C_2$-$C_{24}$ substituted alkenyl, $C_2$-$C_{24}$ substituted heteroatom-comprising alkenyl, $C_2$-$C_{24}$ substituted heteroatom-comprising alkenyl, $C_2$-$C_{24}$ alkynyl, $C_2$-$C_{24}$ substituted alkynyl, $C_2$-$C_{24}$ substituted heteroatom-comprising alkynyl, $C_2$-$C_{24}$ substituted heteroatom-comprising alkynyl, $C_5$-$C_{24}$ aryl, $C_5$-$C_{24}$ substituted aryl, $C_5$-$C_{24}$ substituted heteroatom-comprising aryl, $C_5$-$C_{24}$ substituted heteroatom-comprising aryl, $C_1$-$C_{24}$ alkoxy, $C_5$-$C_{24}$ aryloxy, —O—, —S—, —NR'—, —C(O)—, —C(S)—, —C(O)NR'—, —C(S)NR'—, —N(R')C(O)—, —S(O)$_k$— where k is 1, 2, or 3, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')— group, where each R' is independently an H, an aliphatic, a substituted aliphatic, an aryl, or a substituted aryl group; and c. allowing the polypeptide to react with the chemical reagent so that a covalent linkage between the reagent and the polypeptide is formed.

In one embodiment of the method, R is a functional group, a label molecule, a tag molecule, an affinity label molecule, a photoaffinity label, a dye, a chromophore, a fluorescent molecule, a phosphorescent molecule, a chemiluminescent molecule, an energy transfer agent, a photocrosslinker molecule, a redox-active molecule, an isotopic label molecule, a spin label molecule, a metal chelator, a metal-comprising moiety, a heavy atom-comprising-moiety, a radioactive moiety, a contrast agent molecule, a MRI contrast agent, an isotopically labeled molecule, a PET agent, a photocaged moiety, a photoisomerizable moiety, a chemically cleavable group, a photocleavable group, an electron dense group, a magnetic group, an amino acid, a polypeptide, an antibody or antibody fragment, a carbohydrate, a monosaccharide, a polysaccharide, a nucleotide, a nucleoside, a DNA, a RNA, a siRNA, a polynucleotide, an antisense polynucleotide, a peptide nucleic acid (PNA), a fatty acid, a lipid, a cofactor, biotin, a biotin analogue, a biomaterial, a polymer, a water-soluble polymer, a polyethylene glycol derivative, a water-soluble dendrimer, a cyclodextrin, a small molecule, a protein-, nucleic acid-, or receptor-binding molecule, a biologically active molecule, a drug or drug candidate, a cytotoxic molecule, a solid support, a surface, a resin, a nanoparticle, or a quantum dot, or any combination thereof.

In another embodiment of the method,

R is a bioorthogonal functional group selected from the group consisting of —NR'NR'$_2$, —C(O)NR'NR'$_2$, —ONH$_2$, —N$_3$, —C≡CR', —CR'═CR'$_2$, —PR'$_2$, 2-cyanobenzothiazole, tetrazole, tetrazine, aziridine, dihydroazirine, and norbornadiene groups, and each R' is independently an H, an aliphatic, a substituted aliphatic, an aryl, or a substituted aryl group.

In another embodiment of the method, R is a fluorescent molecule selected from the group consisting of a coumarin derivative, a naphthalene derivative, a pyrene derivative, a fluorescein derivative, a rhodamine derivative, a naphthoxanthene derivative, a phenanthridine derivative, a boron difluoride dipyrromethene (BODIPY) derivative, a cyanine derivatives, a phthalocyanine derivative, and an oxazine derivative.

In another embodiment of the method, R is biotin, a biotin analogue, or a perfluorinated alkyl chain $CF_3$—$(CF_2)_m$— where m=3-15.

In another embodiment of the method, R is a poly (ethyleneglycol) molecule.

In another embodiment of the method, R is a resin or a nanoparticle

In another embodiment of the method, R is a functionalized surface.

In another embodiment of the method, the surface is a microarray.

In another embodiment of the method, the intein is a naturally occurring intein, an engineered variant of a naturally occurring intein, a fusion of the N-terminal and C-terminal fragments of a naturally occurring split intein, or a fusion of the N-terminal and C-terminal fragments of an artificial split intein.

In another embodiment of the method, the intein is a polypeptide of SEQ ID NO:1-76, or an engineered (or synthetic) variant thereof.

In another embodiment of the method:
the C-terminal terminal asparagine, aspartic acid, or glutamine residue in the intein is mutated to an amino acid other than asparagine, aspartic acid, or glutamine, or
the N-terminal serine is mutated to a cysteine residue and the C-terminal asparagine, aspartic acid, or glutamine residue in the intein is mutated to an amino acid other than asparagine, aspartic acid, or glutamine.

In another embodiment of the method, the intein is C-terminally fused to a polypeptide affinity tag selected from the group consisting of polyhistidine tag, Avi-Tag, FLAG tag, Strep-tag II, c-myc tag, S-Tag, calmodulin-binding peptide, streptavidin-binding peptide, chitin-binding domain, glutathione S-transferase, and maltose-binding protein. These tags and their sequences are well known in the art.

In another embodiment of the method, the polypeptide C-terminally fused to the intein comprises one or a plurality of the features selected from the group consisting of: the residue at position 1 prior to the intein (hereinafter "intein-1" or "I-1") being F, Y, A, T, W, N, R or Q; the residue at position 2 prior to the intein (hereinafter "intein-2" or "I-2") being G, P, or S; and the residue at position 3 prior to the intein (hereinafter "intein-3" or "I-3") being G or S.

In another embodiment of the method, the intein-fused polypeptide is inside a cell or associated with the exterior surface of a cell membrane. The polypeptide can be inside the cell, e.g., in the cytoplasm or in another intracellular compartment such as the nucleus, or on the surface of the cell, e.g. associated with the cell membrane on its interior or exterior surface.

In another embodiment of the method, the cell is a prokaryotic or eukaryotic cell.

In another embodiment of the method, the prokaryotic cell is *E. coli*.

In another embodiment of the method, the eukaryotic cell is a yeast cell, an insect cell, a worm cell, a fish cell or a mammalian cell.

In another embodiment of the method, $R_1$, X, Y, and Z are hydrogen atoms,
L is selected from the group consisting of —C(O)NR'—, —C(O)NR'CH$_2$C(O)—, —C(O)NR'(CH$_2$)n-, and —C(O)NR'(CH$_2$—CH$_2$—O)n-,
R' is a hydrogen, alkyl or aryl group, and
n is an integer number from 1 to 15.

In another embodiment of the method, R is selected from the group consisting of biotin, a biotin analogue, and a coumarin derivative.

In another embodiment of the method, the reagent is:
a. a compound of formula (I), wherein:
$R_1$, X, Y, and Z are hydrogen atoms,
R is —ONH$_2$ or —N$_3$, and
L is a single bond;
b. a compound of formula (I), wherein:
$R_1$, X, Y, and Z are hydrogen atoms,
R is —ONH$_2$, and
L is a linker or linker group of formula

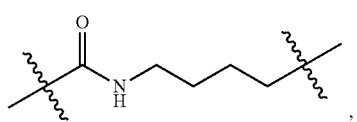
(IX)

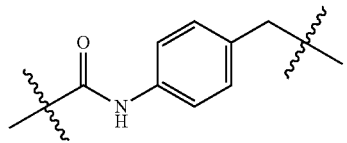
(X)

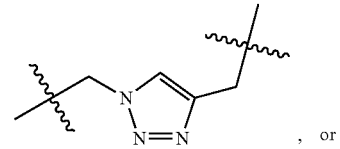
(XI)

, or

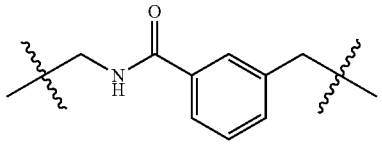
(XII)

;

c. a compound of formula (I), wherein:
$R_1$, X, Y, and Z are hydrogen atoms,
R is 7-amino-4-(trifluoromethyl)-2H-chromen-2-one, and
L is —C(O)NHCH$_2$C(O)—; or
d. a compound of formula (I), wherein:
$R_1$, X, Y, and Z are hydrogen atoms,
R is biotin, and
L is —C(O)NH(CH$_2$)$_3$NH—

A kit is provided for forming a covalent linkage between a polypeptide and a chemical species, the kit comprising:
a. at least one chemical reagent of formula (I), (II), (III), (IV), (V), (VI), (VII), or (VIII), or a salt of the reagent; and
b. one or a plurality of containers, wherein at least one container comprises a pre-selected or desired amount of at least one of the chemical reagents of formula (I), (II), (III), (IV), (V), (VI), (VII), or (VIII), or a salt of the reagent, wherein:
i. R is the chemical species which is to be covalently linked to the polypeptide,
ii. $R_1$ is hydrogen, a substituted or non-substituted aliphatic group, or a substituted or non-substituted aryl group,
iii. X, Y, W, and Z are hydrogen and/or non-hydrogen substituents selected from the group consisting of alkyl, heteroatom-comprising alkyl, alkenyl, heteroatom-comprising alkenyl, alkynyl, heteroatom-comprising alkynyl, aryl, heteroatom-comprising aryl, alkoxy, heteroatom-comprising alkoxy, aryloxy, heteroatom-comprising aryloxy, halo, —OH, —OR', —SR', —COOH, —COOR', —CONR'$_2$, —NR'$_2$, —NO$_2$, —SO$_3$R', —SO$_2$NR$_2$', —C≡N, —O—C≡N, —P(O)$_k$R' where k is 2 or 3, and —S—C≡N, wherein each R' is independently an H, an aliphatic, a substituted aliphatic, an aryl, or a substituted aryl group,
iv. n is 2 or 3, and
v. L is a linker or a linker group selected from the group consisting of a single bond, $C_1$-$C_{24}$ alkyl, $C_1$-$C_{24}$ substituted alkyl, $C_1$-$C_{24}$ substituted heteroatom-comprising alkyl, $C_1$-$C_{24}$ substituted heteroatom-comprising alkyl, $C_2$-$C_{24}$ alkenyl, $C_2$-$C_{24}$ substituted alkenyl, $C_2$-$C_{24}$ substituted heteroatom-comprising alkenyl, $C_2$-$C_{24}$ substituted heteroatom-comprising alkenyl, $C_2$-$C_{24}$ alkynyl, $C_2$-$C_{24}$ substituted alkynyl, $C_2$-$C_{24}$ substituted heteroatom-comprising alkynyl, $C_2$-$C_{24}$ substituted heteroatom-comprising alkynyl, $C_5$-$C_{24}$ aryl, $C_5$-$C_{24}$ substituted aryl, $C_5$-$C_{24}$ substituted heteroatom-comprising aryl, $C_5$-$C_{24}$ substituted heteroatom-comprising aryl, $C_1$-$C_{24}$ alkoxy, $C_5$-$C_{24}$ aryloxy, —O—, —S—, —NR'—, —C(O)—, —C(S)—, —C(O)NR'—, —C(S)NR'—, —N(R')C(O)—, —S(O)$_k$— where k is 1, 2, or 3, —S(O)$_k$N(R')—, —N(R')C(O)N(R')—, —N(R')C(S)N(R')—, —N(R')S(O)$_k$N(R')—, —N(R')—N=, —C(R)=N—, —C(R')=N—N(R')—, —C(R')=N—N=, —C(R')$_2$—N=N—, and —C(R')$_2$—N(R')—N(R')—, wherein each R' is independently an H, an aliphatic, a substituted aliphatic, an aryl, or a substituted aryl group.

In one embodiment of the kit, R is a functional group, a label molecule, a tag molecule, an affinity label molecule, a photoaffinity label, a dye, a chromophore, a fluorescent molecule, a phosphorescent molecule, a chemiluminescent molecule, an energy transfer agent, a photocrosslinker molecule, a redox-active molecule, an isotopic label molecule, a spin label molecule, a metal chelator, a metal-comprising moiety, a heavy atom-comprising-moiety, a radioactive moiety, a contrast agent molecule, a MRI contrast agent, an isotopically labeled molecule, a PET agent, a photocaged moiety, a photoisomerizable moiety, a chemically cleavable group, a photocleavable group, an electron dense group, a magnetic group, an amino acid, a polypeptide, an antibody or antibody fragment, a carbohydrate, a monosaccharide, a polysaccharide, a nucleotide, a nucleoside, a DNA, a RNA, a siRNA, a polynucleotide, an antisense polynucleotide, a peptide nucleic acid (PNA), a fatty acid, a lipid, a cofactor, biotin, a biotin analogue, a biomaterial, a polymer, a water-soluble polymer, a polyethylene glycol derivative, a water-soluble dendrimer, a cyclodextrin, a small molecule, a protein-, nucleic acid-, or receptor-binding molecule, a biologically active molecule, a drug or drug candidate, a cytotoxic molecule, a solid support, a surface, a resin, a nanoparticle, or a quantum dot, or any combination thereof.

In another embodiment of the kit, R is a bioorthogonal functional group selected from the group consisting of —NR'NR'$_2$, —C(O)NR'NR'$_2$, —ONH$_2$, —N$_3$, —C≡CR', —CR'=CR'$_2$, —PR'$_2$, 2-cyanobenzothiazole, tetrazole, tetrazine, aziridine, dihydroazirine, norbornadiene groups, wherein each R' is independently H, aliphatic, substituted aliphatic, aryl, or substituted aryl group.

In another embodiment of the kit, R is a fluorescent molecule selected from the group consisting of a coumarin derivative, a naphthalene derivative, a pyrene derivative, a fluorescein derivative, a rhodamine derivative, a naphthoxanthene derivative, a phenanthridine derivative, a boron difluoride dipyrromethene (BODIPY) derivative, a cyanine derivatives, a phthalocyanine derivative, and a oxazine derivative.

In another embodiment of the kit, R is biotin, a biotin analogue, or a perfluorinated alkyl chain CF$_3$—(CF$_2$)$_m$— where m=3-15

In another embodiment of the kit, the at least one reagent comprises at least one compound selected from the group consisting of:

a. a compound of formula (I), wherein:
R$_1$, X, Y, and Z are hydrogen atoms,
R is —ONH$_2$ or —N$_3$, and
L is a single bond:

b. a compound of formula (I), wherein:
R$_1$, X, Y, and Z are hydrogen atoms,
R is —ONH$_2$, and
L is a linker or linker group of formula (IX)

(X)

(XI)

, or (XII)

;

c. a compound of formula (I), wherein:
R$_1$, X, Y, and Z are hydrogen atoms,
R is 7-amino-4-(trifluoromethyl)-2H-chromen-2-one, and
L is —C(O)NHCH$_2$C(O)—; or d. a compound of formula (I), wherein:
R$_1$, X, Y, and Z are hydrogen atoms,
R is biotin, and
L is —C(O)NH(CH$_2$)$_3$NH—.

In another embodiment of the kit, the kit further comprises a functionalized solid support with which the functional group R reacts. Functionalized solid supports and surfaces with which functional groups R can react are well known in the art.

A kit is also provided for immobilizing a polypeptide to a surface, the kit comprising:

a. a chemical reagent of formula (Ib), (IIb), (Mb), (IVb), (Vb), (VIb), (VIIb), or (VIIIb):

(Ib)

(IIb)

-continued

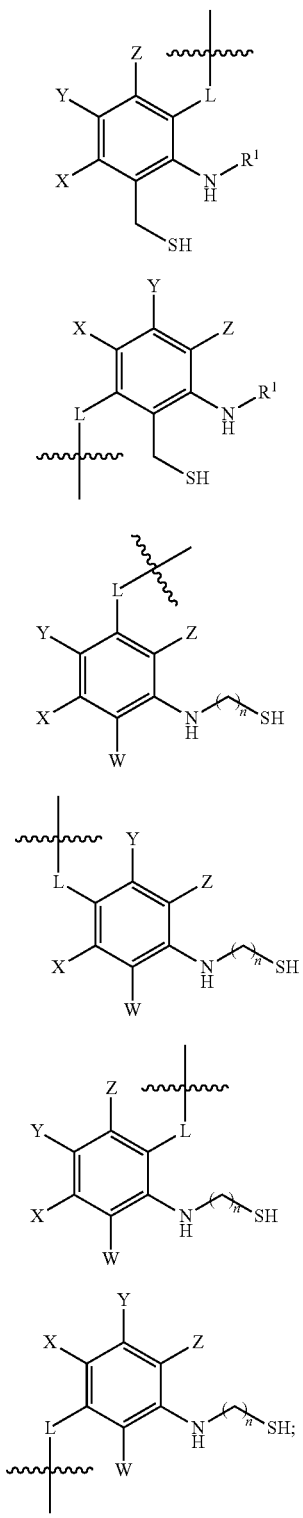

and
b. one or a plurality of containers, wherein at least one container comprises a surface to which a chemical reagent of formula (Ib), (IIb), (Mb), (IVb), (Vb), (VIb), (VIIb), or (VIIIb) is covalently bound, and wherein:
i. $R_1$ is hydrogen, a substituted or non-substituted aliphatic group, or a substituted or non-substituted aryl group, ii. X, Y, W, and Z are hydrogen or non-hydrogen substituents selected from the group consisting of alkyl, heteroatom-comprising alkyl, alkenyl, heteroatom-comprising alkenyl, alkynyl, heteroatom-comprising alkynyl, aryl, heteroatom-comprising aryl, alkoxy, heteroatom-comprising alkoxy, aryloxy, heteroatom-comprising aryloxy, halo, —OH, —OR', —SR, —COOH, —COOR', —CONR'$_2$, —NR'$_2$, —NO$_2$, —SO$_3$R', —SO$_2$NR$_2$', —C≡N, —O—C≡N, —P(O)$_k$R' where k is 2 or 3, and —S—C≡N, and wherein each R' is independently an H, an aliphatic, a substituted aliphatic, an aryl, or a substituted aryl group, iii. n is 2 or 3, and iv. L is a linker or a linker group selected from the group consisting of a single bond, $C_1$-$C_{24}$ alkyl, $C_1$-$C_{24}$ substituted alkyl, $C_1$-$C_{24}$ substituted heteroatom-comprising alkyl, $C_1$-$C_{24}$ substituted heteroatom-comprising alkyl, $C_2$-$C_{24}$ alkenyl, $C_2$-$C_{24}$ substituted alkenyl, $C_2$-$C_{24}$ substituted heteroatom-comprising alkenyl, $C_2$-$C_{24}$ substituted heteroatom-comprising alkenyl, $C_2$-$C_{24}$ alkynyl, $C_2$-$C_{24}$ substituted alkynyl, $C_2$-$C_{24}$ substituted heteroatom-comprising alkynyl, $C_2$-$C_{24}$ substituted heteroatom-comprising alkynyl, $C_5$-$C_{24}$ aryl, $C_5$-$C_{24}$ substituted aryl, $C_5$-$C_{24}$ substituted heteroatom-comprising aryl, $C_5$-$C_{24}$ substituted heteroatom-comprising aryl, $C_1$-$C_{24}$ alkoxy, $C_5$-$C_{24}$ aryloxy, —O—, —S—, —NR'—, —C(O)—, —C(S)—, —C(O)NR'—, —C(S)NR'—, —N(R')C(O)—, —S(O)$_k$— where k is 1, 2, or 3, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, wherein each R' is independently an H, an aliphatic, a substituted aliphatic, an aryl, or a substituted aryl group.

In one embodiment of the kit, the surface is a solid support.

In another embodiment of the kit, the solid support is a resin, a nanoparticle, or the surface of a microarray.

A compound (also referred to herein as a "reagent", a "chemical reagent" or a "composition") is provided having the formula (I), (II), (III), (IV), (V), (VI), (VII) or (VIII):

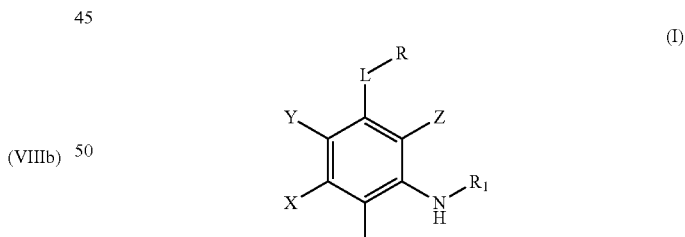

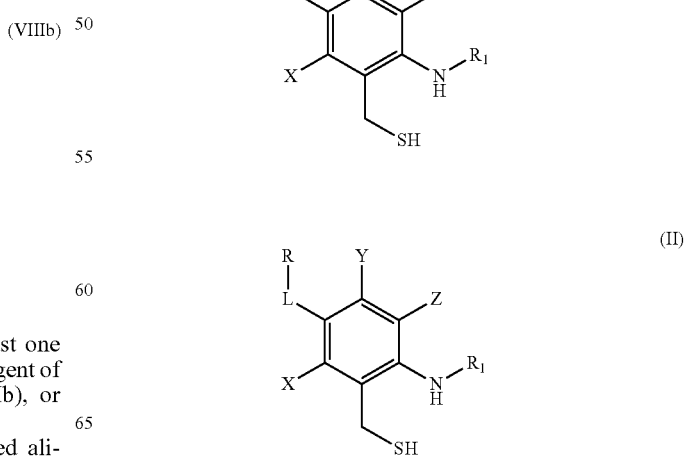

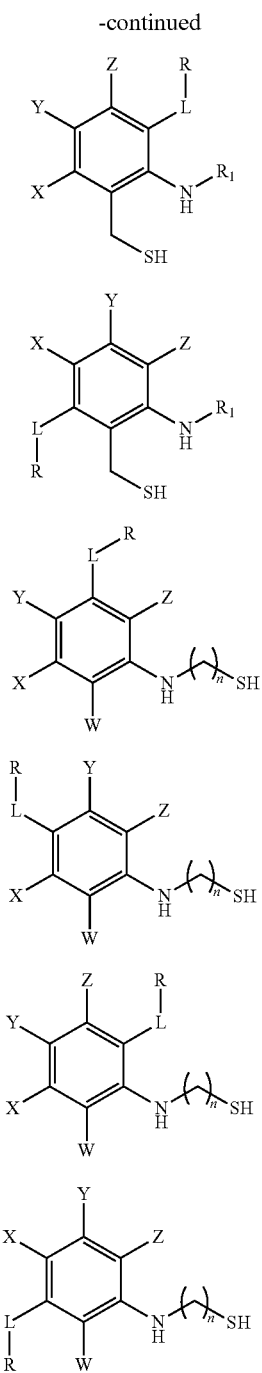

or a salt thereof, wherein:

i. R is a functional group, a label molecule, a tag molecule, an affinity label molecule, a photoaffinity label, a dye, a chromophore, a fluorescent molecule, a phosphorescent molecule, a chemiluminescent molecule, an energy transfer agent, a photocrosslinker molecule, a redox-active molecule, an isotopic label molecule, a spin label molecule, a metal chelator, a metal-comprising moiety, a heavy atom-comprising-moiety, a radioactive moiety, a contrast agent molecule, a MRI contrast agent, an isotopically labeled molecule, a PET agent, a photocaged moiety, a photoisomerizable moiety, a chemically cleavable group, a photocleavable group, an electron dense group, a magnetic group, an amino acid, a polypeptide, an antibody or antibody fragment, a carbohydrate, a monosaccharide, a polysaccharide, a nucleotide, a nucleoside, a DNA, a RNA, a siRNA, a polynucleotide, an antisense polynucleotide, a peptide nucleic acid (PNA), a fatty acid, a lipid, a cofactor, biotin, a biotin analogue, a biomaterial, a polymer, a water-soluble polymer, a polyethylene glycol derivative, a water-soluble dendrimer, a cyclodextrin, a small molecule, a protein-, nucleic acid-, or receptor-binding molecule, a biologically active molecule, a drug or drug candidate, a cytotoxic molecule, a solid support, a surface, a resin, a nanoparticle, a quantum dot, or any combination thereof, ii. $R_1$ is hydrogen, a substituted or non-substituted aliphatic group, or a substituted or non-substituted aryl group, iii. X, Y, W, and Z are hydrogen and/or non-hydrogen substituents selected from the group consisting of alkyl, heteroatom-comprising alkyl, alkenyl, heteroatom-comprising alkenyl, alkynyl, heteroatom-comprising alkynyl, aryl, heteroatom-comprising aryl, alkoxy, heteroatom-comprising alkoxy, aryloxy, heteroatom-comprising aryloxy, halo, —OH, —OR', —SR', —COOH, —COOR', —CONR'$_2$, —NR'$_2$, —NO$_2$, —SO$_3$R', —SO$_2$NR$_2$', —C≡N, —O—C≡N, —P(O)$_k$R' where k is 2 or 3, and —S—C≡N, wherein each R' is independently H, alkyl, or substituted alkyl, iv. n is 2 or 3; and v. L is a linker or a linker group selected from the group consisting of a single bond, $C_1$-$C_{24}$ alkyl, $C_1$-$C_{24}$ substituted alkyl, $C_1$-$C_{24}$ substituted heteroatom-comprising alkyl, $C_1$-$C_{24}$ substituted heteroatom-comprising alkyl, $C_2$-$C_{24}$ alkenyl, $C_2$-$C_{24}$ substituted alkenyl, $C_2$-$C_{24}$ substituted heteroatom-comprising alkenyl, $C_2$-$C_{24}$ substituted heteroatom-comprising alkenyl, $C_2$-$C_{24}$ alkynyl, $C_2$-$C_{24}$ substituted alkynyl, $C_2$-$C_{24}$ substituted heteroatom-comprising alkynyl, $C_2$-$C_{24}$ substituted heteroatom-comprising alkynyl, $C_5$-$C_{24}$ aryl, $C_5$-$C_{24}$ substituted aryl, $C_5$-$C_{24}$ substituted heteroatom-comprising aryl, $C_5$-$C_{24}$ substituted heteroatom-comprising aryl, $C_1$-$C_{24}$ alkoxy, $C_5$-$C_{24}$ aryloxy, —O—, —S—, —NR'—, —C(O)—, —C(S)—, —C(O)NR'—, —C(S)NR'—, —N(R') C(O)—, —S(O)$_k$— where k is 1, 2, or 3, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')— group, where each R' is independently an H, an aliphatic, a substituted aliphatic, an aryl, or a substituted aryl group.

In one embodiment of the compound, R is a bioorthogonal functional group selected from the group consisting of NR'NR'$_2$, —C(O)NR'NR'$_2$, —ONH$_2$, —N$_3$, —C≡CR', —CR'═CR'$_2$, —PR'$_2$, 2-cyanobenzothiazole, tetrazole, tetrazine, aziridine, dihydroazirine, and norbornadiene groups, and each R' is independently an H, an aliphatic, a substituted aliphatic, an aryl, or a substituted aryl group.

In another embodiment of the compound, R is a fluorescent molecule selected from the group consisting of a coumarin derivative, a naphthalene derivative, a pyrene derivative, a fluorescein derivative, a rhodamine derivative, a naphthoxanthene derivative, a phenanthridine derivative, a boron difluoride dipyrromethene (BODIPY) derivative, a cyanine derivatives, a phthalocyanine derivative, and an oxazine derivative.

In another embodiment of the compound, R is biotin, a biotin analogue, or a perfluorinated alkyl chain $CF_3$—$CF_2)_m$— where m=3-15.

In another embodiment of the compound, R is a poly (ethyleneglycol) molecule.

In another embodiment of the compound, R is a resin or a nanoparticle.

In another embodiment of the compound, R is a functionalized surface.

In another embodiment of the compound, $R_1$, X, Y, and Z are hydrogen atoms,

L is selected from the group consisting of —C(O)NR'—, —C(O)NR'CH$_2$C(O)—, —C(O)NR'(CH$_2$)n-, and —C(O)NR'(CH$_2$—CH$_2$—O)n-, R' is a hydrogen, alkyl or aryl group, and n is an integer number from 1 to 15.

In another embodiment of the compound, R is selected from the group consisting of biotin, a biotin analogue, and a coumarin derivative.

In another embodiment of the compound, the compound has formula (I), wherein:

a. $R_1$, X, Y, and Z are hydrogen atoms,
R is —ONH$_2$ or —N$_3$, and
L is a single bond;

b. $R_1$, X, Y, and Z are hydrogen atoms,
R is —ONH$_2$, and
L is a linker or linker group of formula

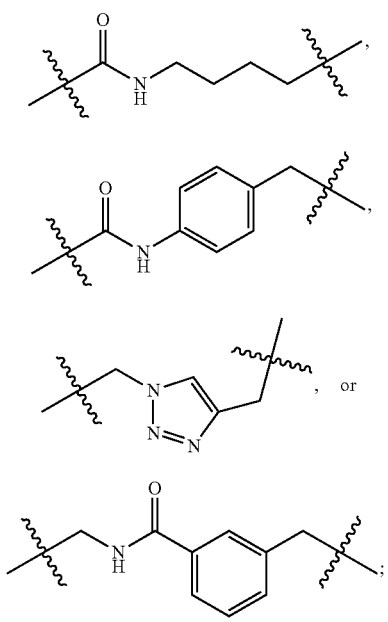

c. $R_1$, X, Y, and Z are hydrogen atoms,
R is 7-amino-4-(trifluoromethyl)-2H-chromen-2-one, and
L is —C(O)NHCH$_2$C(O)—; or d. $R_1$, X, Y, and Z are hydrogen atoms,
R is biotin, and
L is —C(O)NH(CH$_2$)$_3$NH—.

Methods for synthesizing the foregoing compounds are also provided.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1. Schematic representation of one embodiment of the invention illustrating the application of the methods described herein for C-terminal functionalization of an intein-fused target polypeptide via reagents of type (I)-(IV) or reagents of type (V)-(VIII).

Figure 2:
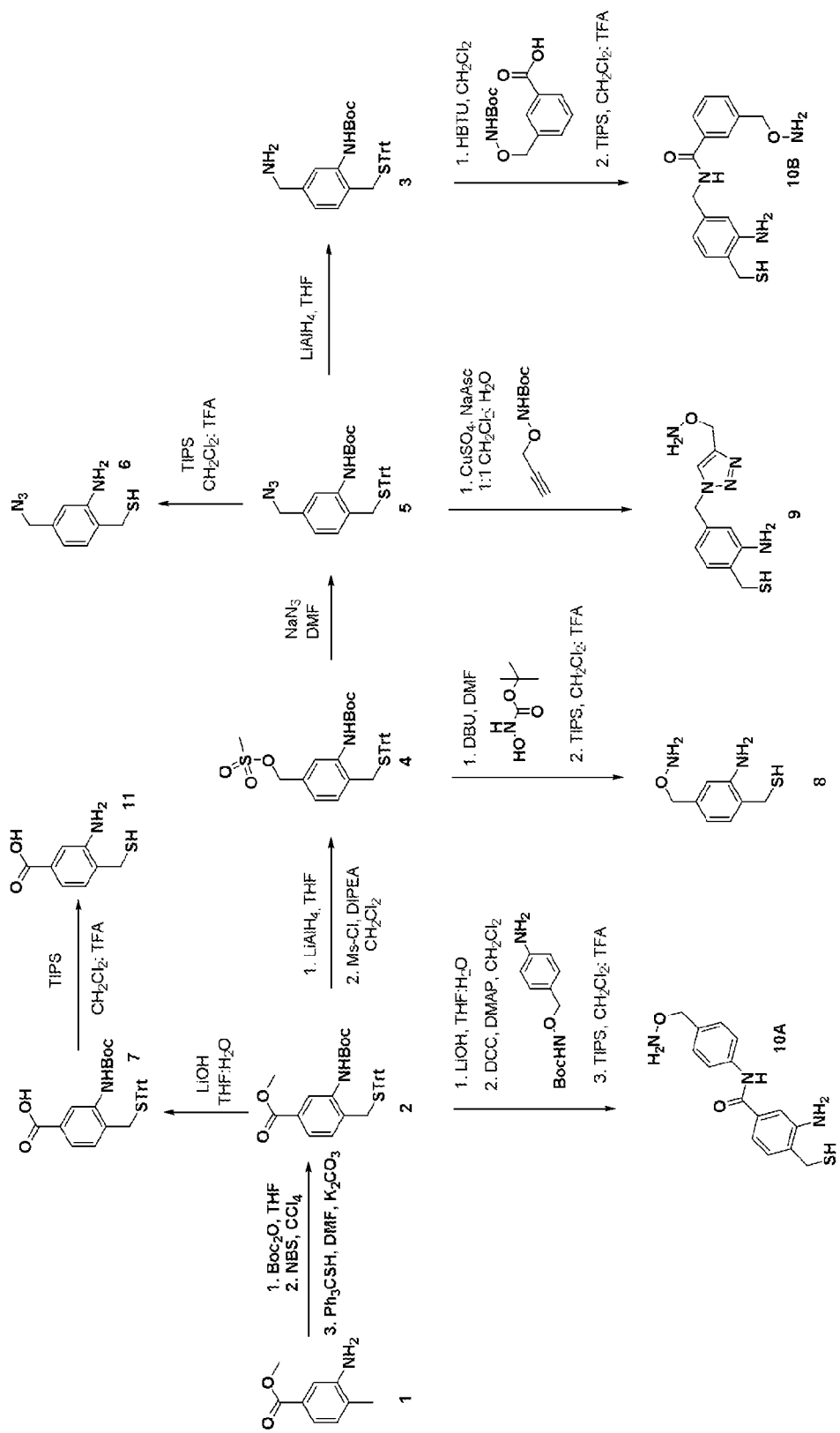

FIG. 2. Synthetic route for the preparation of various reagents of general formula (I) comprising either a bioorthogonal oxyamino functional group (compounds 8, 9, 10A, 10B), a bioorthogonal azide functional group (compound 6) or a carboxylic acid group (compound 11) as the R group.

Figure 3:
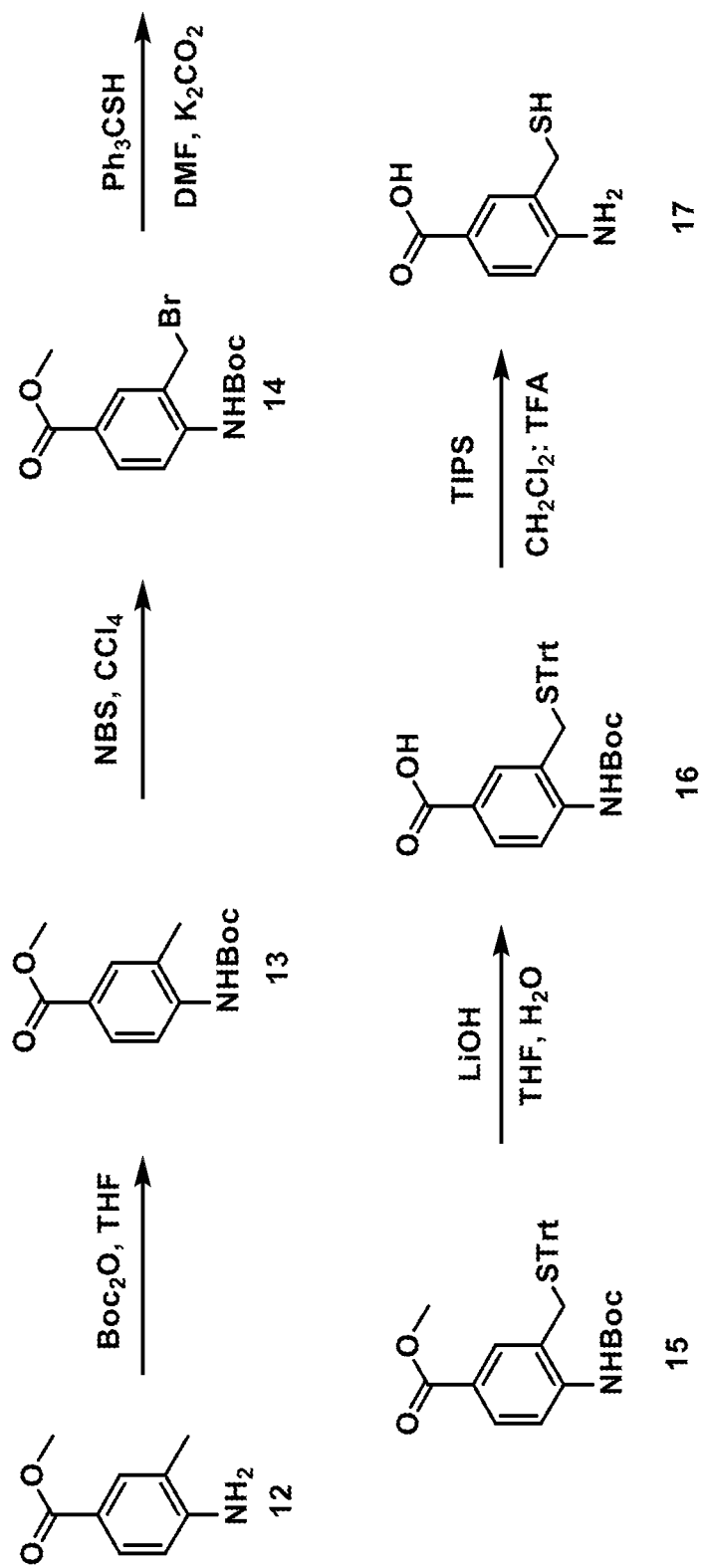

FIG. 3. Synthetic route for the preparation a reagent of general formula (II) comprising a carboxylic acid group as the R group.

Figure 4:
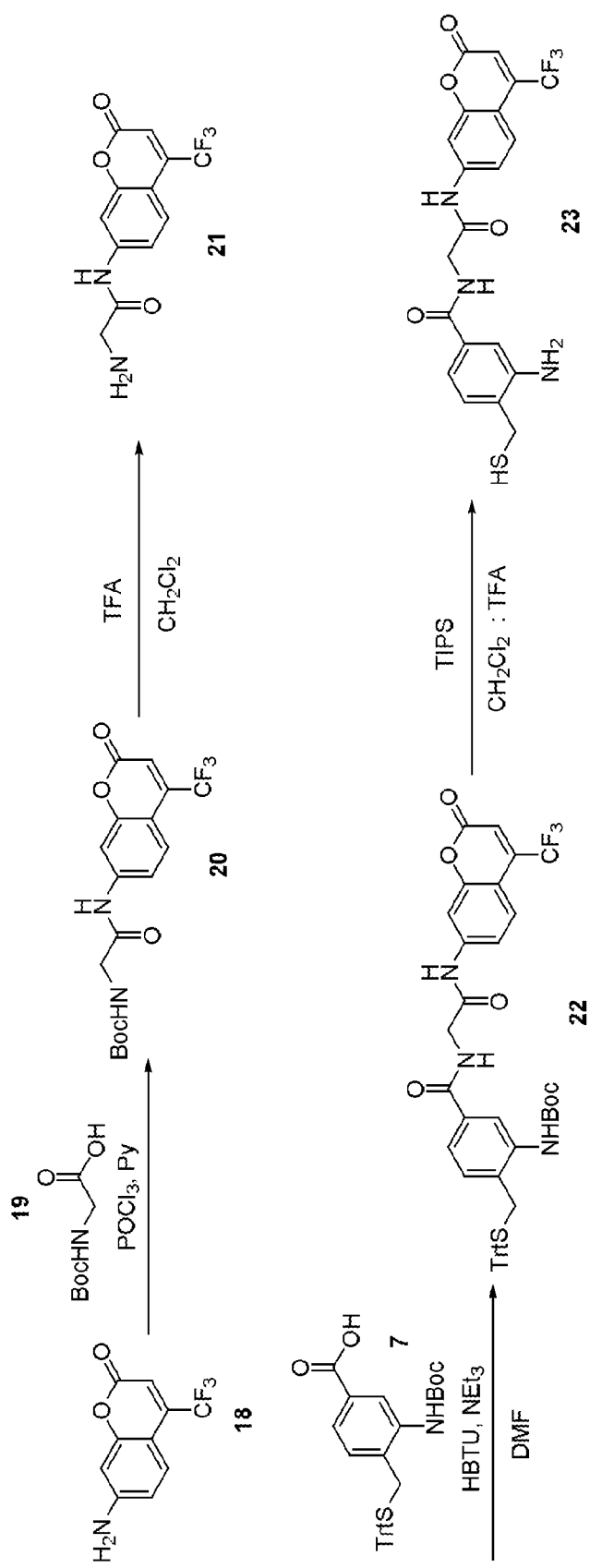

FIG. 4. Synthetic route for the preparation a reagent of general formula (I) comprising a coumarin-based fluorescent probe molecule as the R group.

Figure 5:
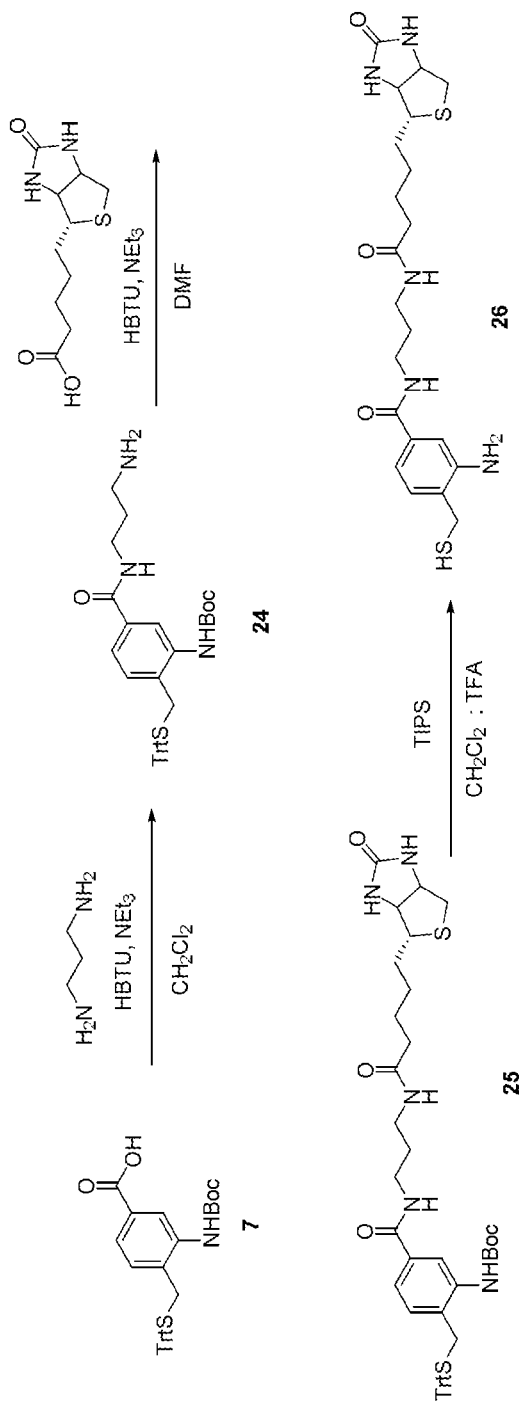

FIG. 5. Synthetic route for the preparation a reagent of general formula (I) comprising a biotin-based affinity tag molecule as the R group.

Figure 6:
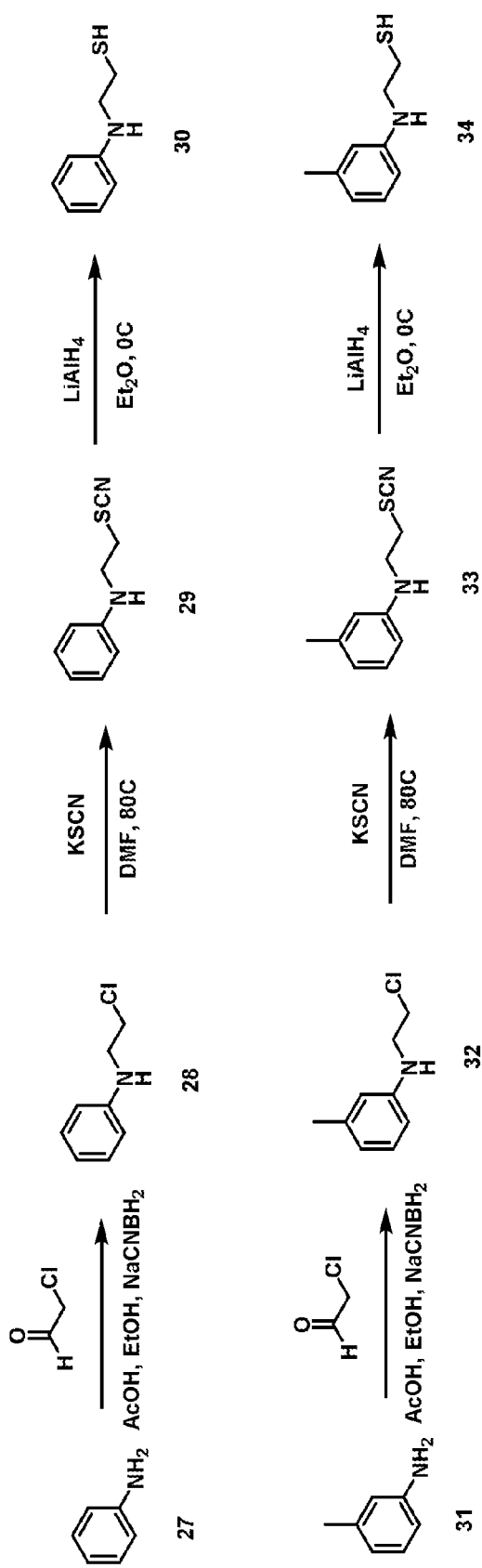

FIG. 6. Synthetic route for the preparation reagents of general formula (V).

Figure 7:
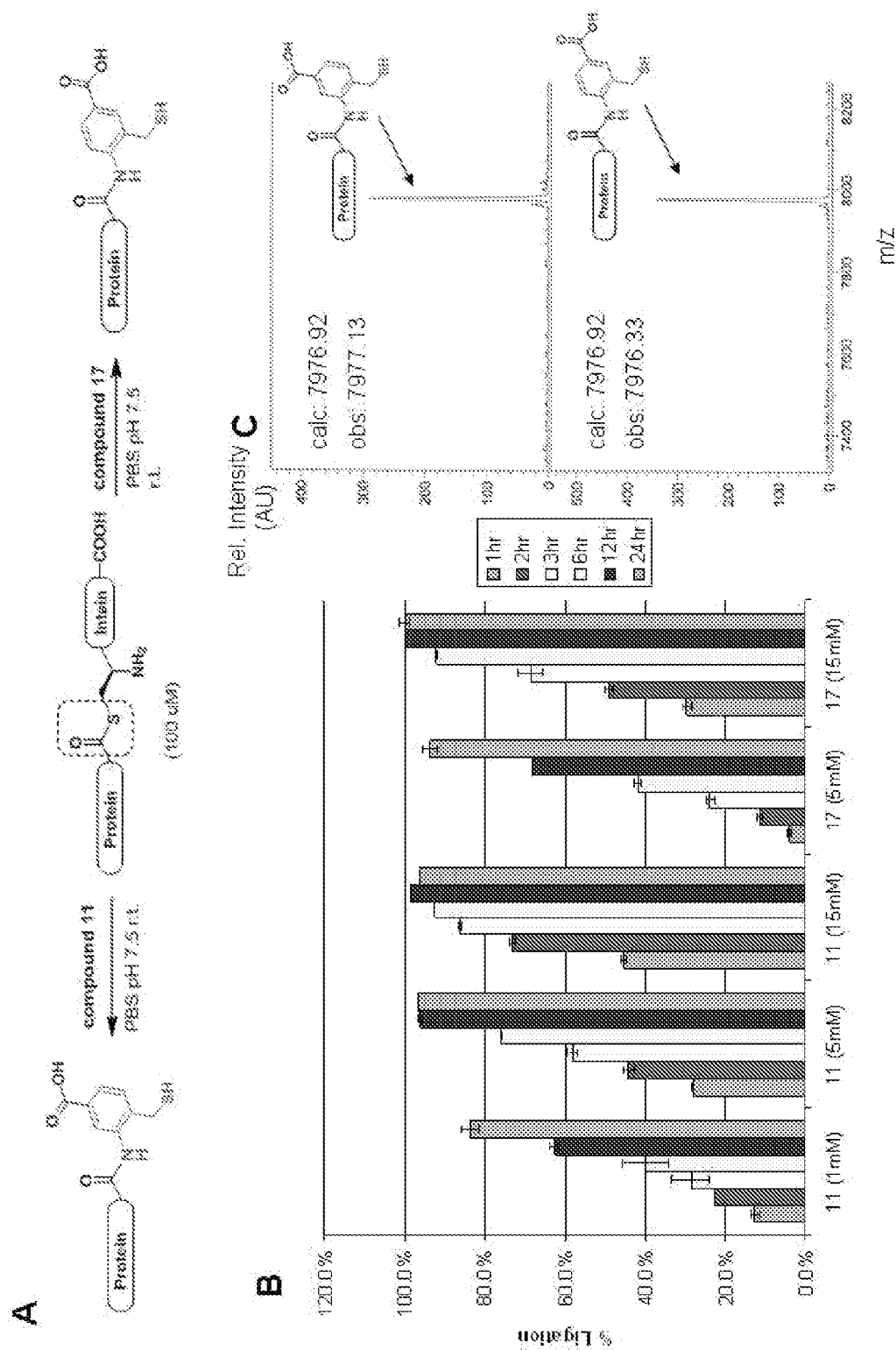

FIG. 7A-C. Functionalization of the target intein-fusion protein CBD-3 with 1-amino-2-(mercaptomethyl)-aryl-based reagents 11 and 17. A) General scheme of the protein labeling reactions. B) Percentage of protein labeling at different time points in the presence of different concentrations of reagents 11 and 17 as measured by SDS-PAGE; C) MALDI-TOF MS spectra of the labeled protein products.

Figure 8:
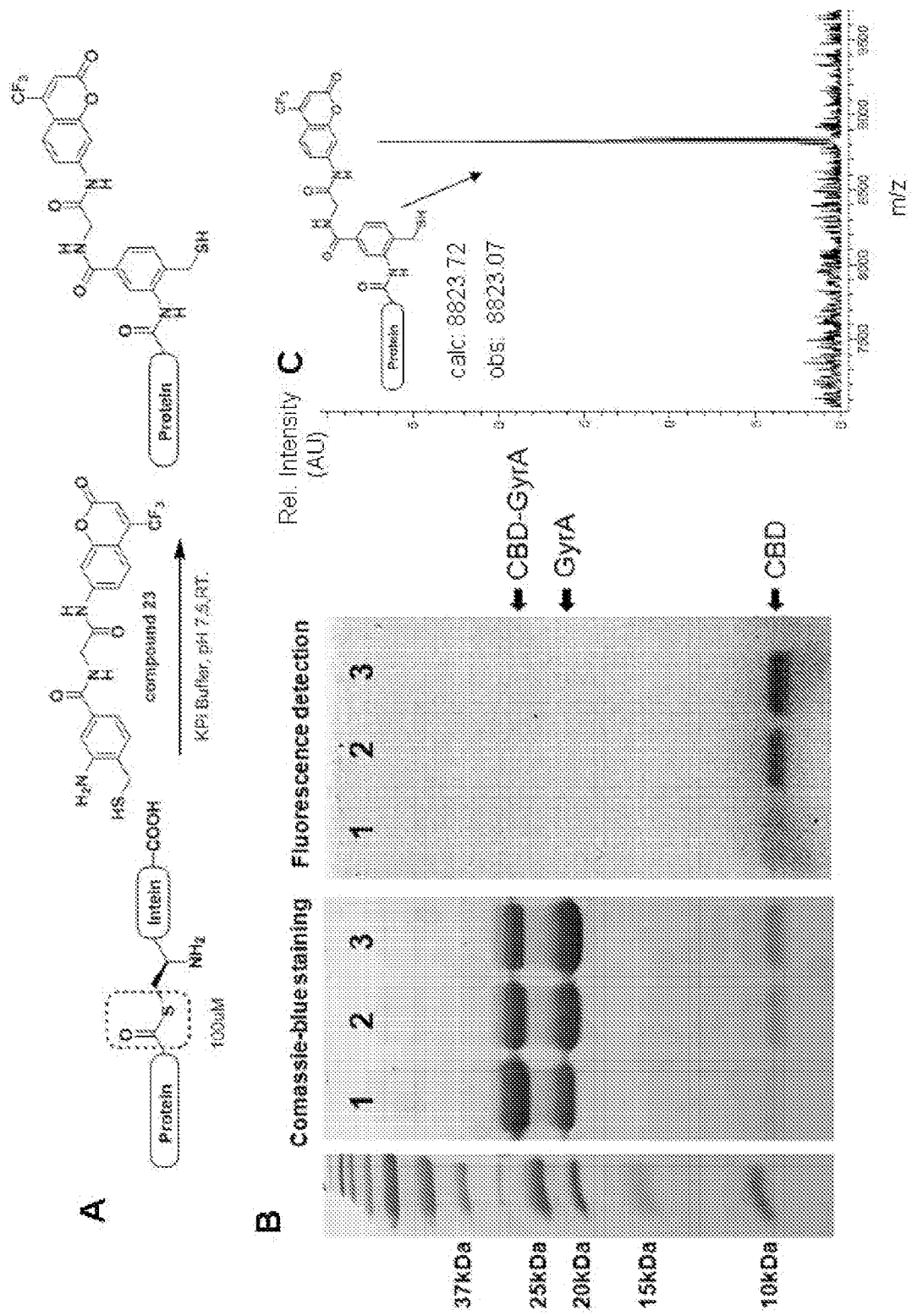

FIG. 8A-C. Fluorescent labeling of the target intein-fusion protein CBD-2 with coumarin-comprising reagent 23. A) General scheme of the protein labeling reaction. B) SDS-PAGE gel analysis of the reaction between CBD-2 and 23 after 1 hour (lane 1), 5 hours (lane 2), and 12 hours (lane 3). A protein MW marker is included. Left panel: Comassie-blue stained gel. Right panel: fluorescence visualization of the gel upon excitation with 365-nm light. C) MALDI-TOF MS spectra of the desired fluorescently labeled protein products.

Figure 9:
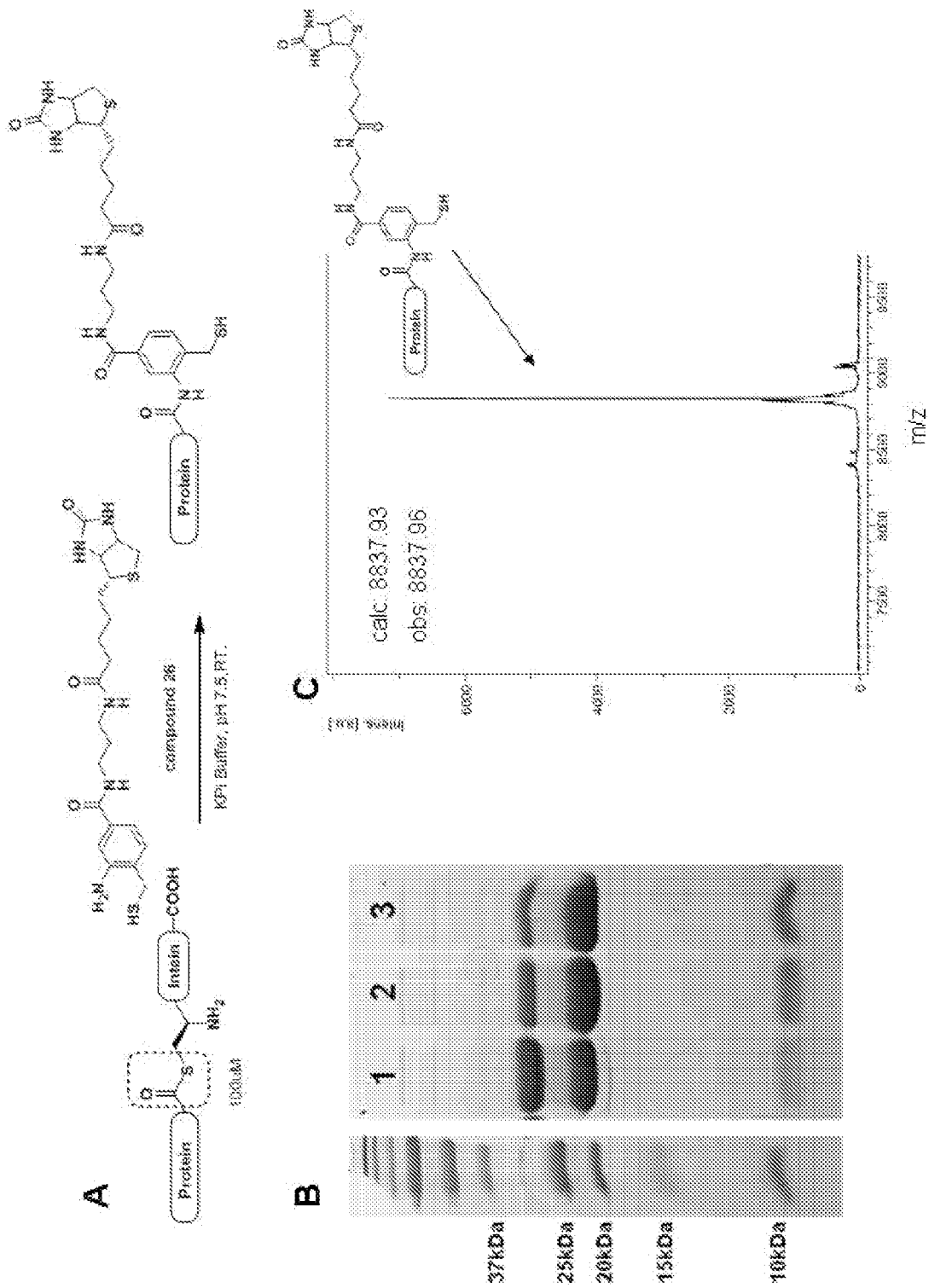

FIG. 9A-C. Biotinylation of the target intein-fusion protein CBD-2 with biotin-comprising reagent 26. A) General scheme of the protein labeling reaction. B) SDS-PAGE gel analysis of the reaction between CBD-2 and 26 after 1 hour (lane 1), 5 hours (lane 2), and 12 hours (lane 3). C) MALDI-TOF MS spectrum of the desired biotinylated protein product.

Figure 10:
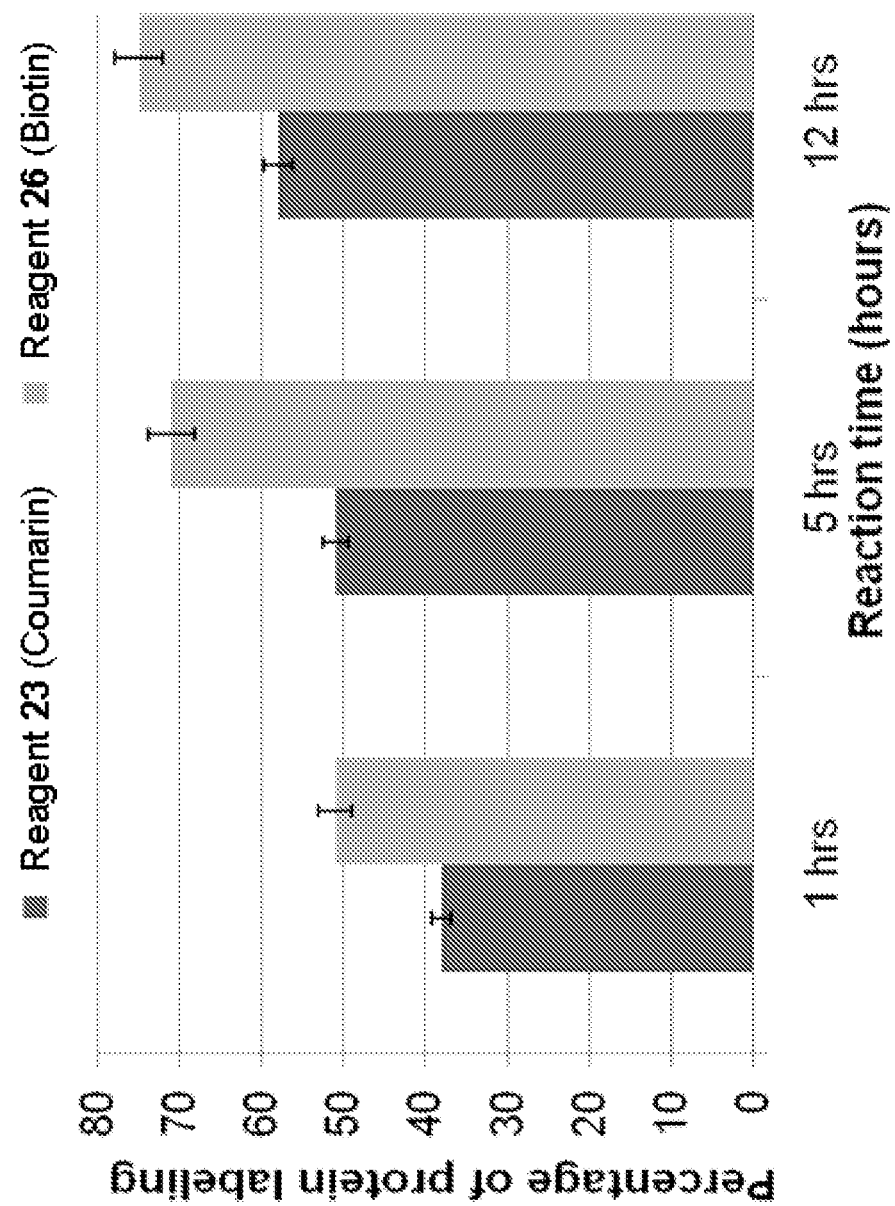

FIG. 10. Percentage of protein labeling at different time points for the reaction between protein CBD-2 and reagents 23 and 26 as determined by SDS-PAGE gel densitometry.

Figure 11:
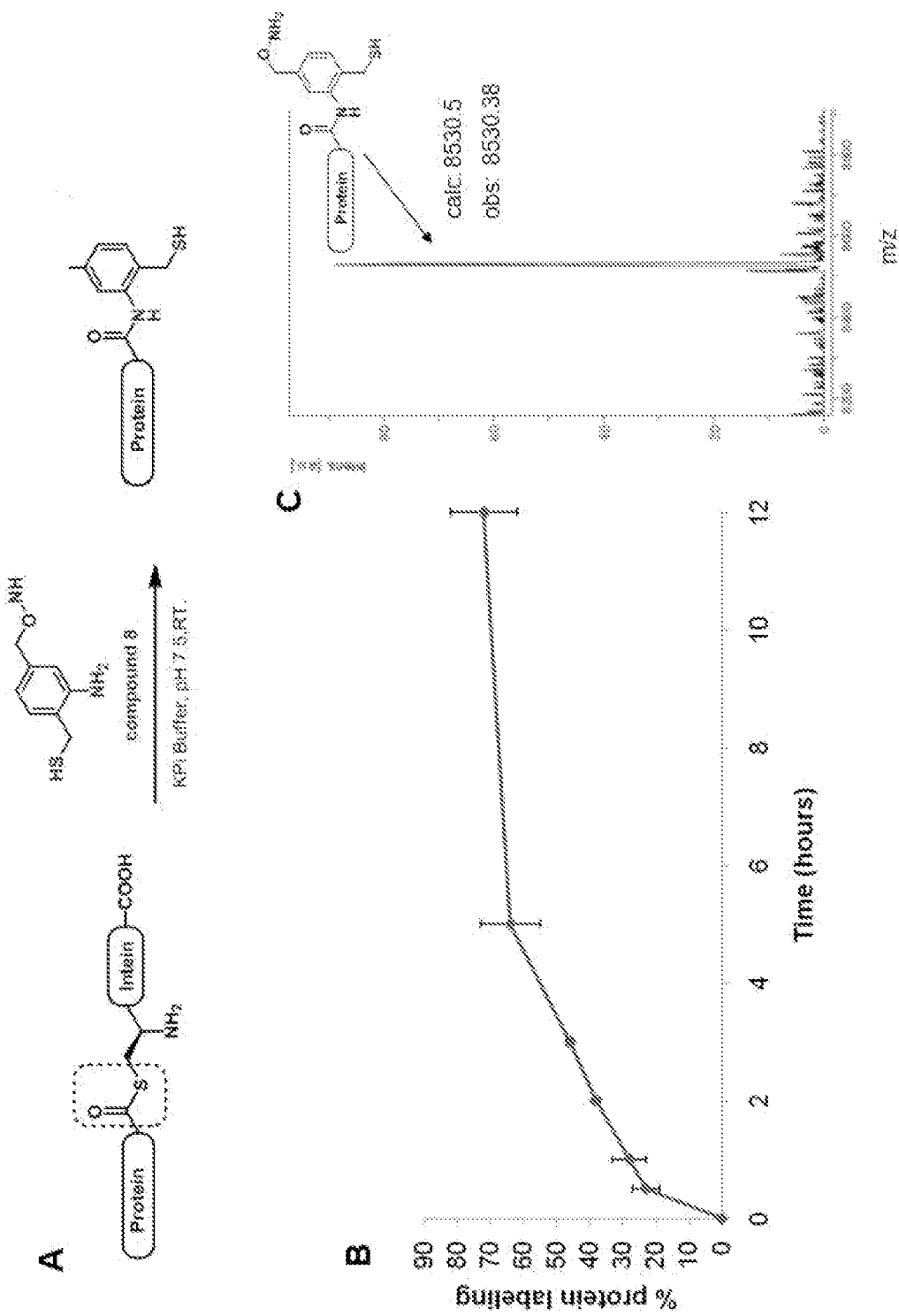

FIG. 11A-C. Functionalization of target protein CBD-1 with oxyamino-comprising reagent 8. A) General scheme of the protein labeling reaction. B) Percentage of protein labeling over time as determined by SDS-PAGE gel densitometry. C) MALDI-TOF MS spectrum of the desired CBD-8 product.

Figure 12:
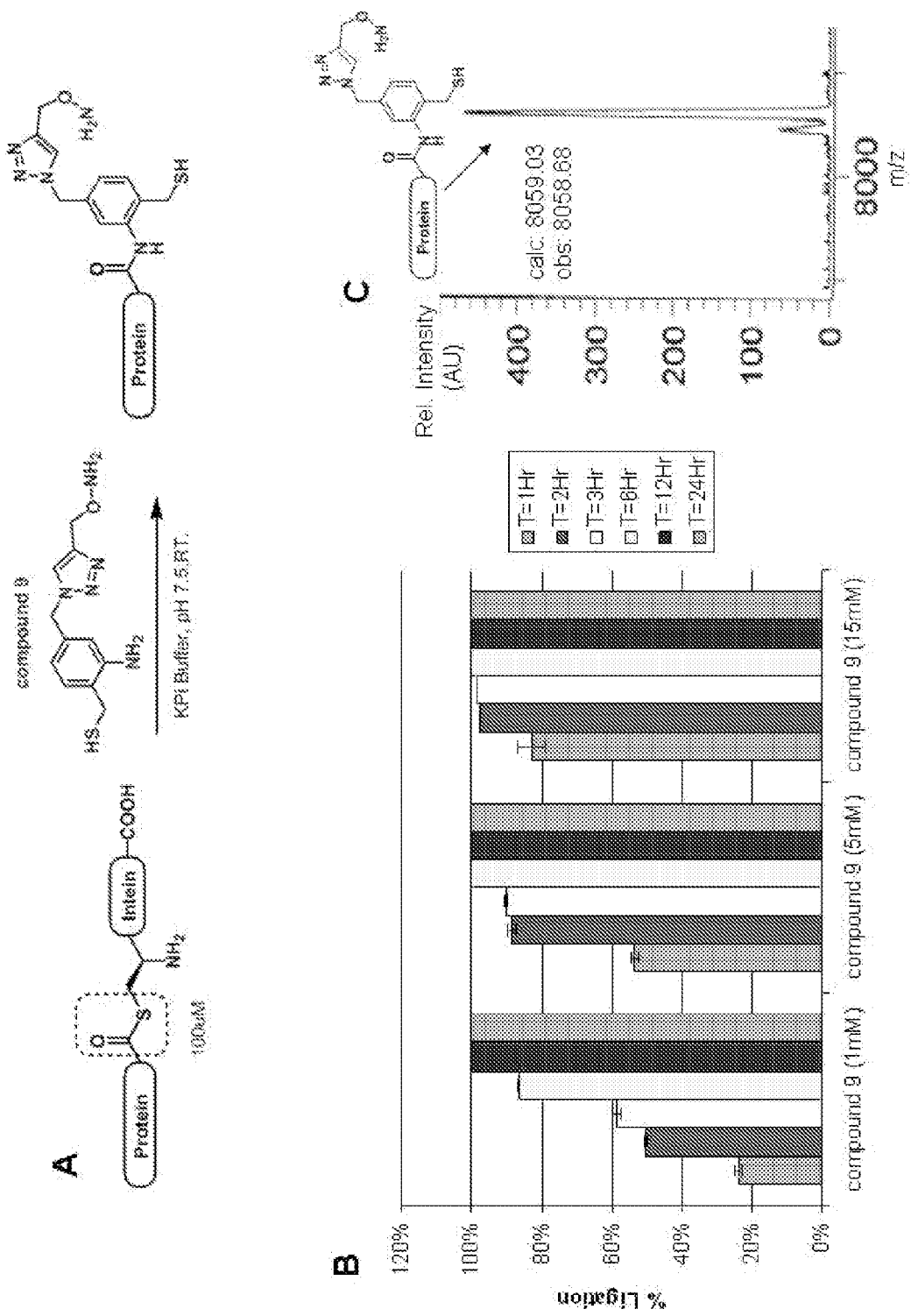

FIG. 12A-C. Functionalization of target protein CBD-3 with oxyamino-comprising reagent 9. A) General scheme of the protein labeling reaction. B) Percentage of protein labeling at the 1-, 2-, 3-, 6-, 12-, and 24-hour time point in the presence of different concentration of 9 as determined by SDS-PAGE gel densitometry. C) MALDI-TOF MS spectrum of the reaction mixture, indicating the clean formation of the oxyamine-functionalized protein product, CBD-9.

Figure 13:
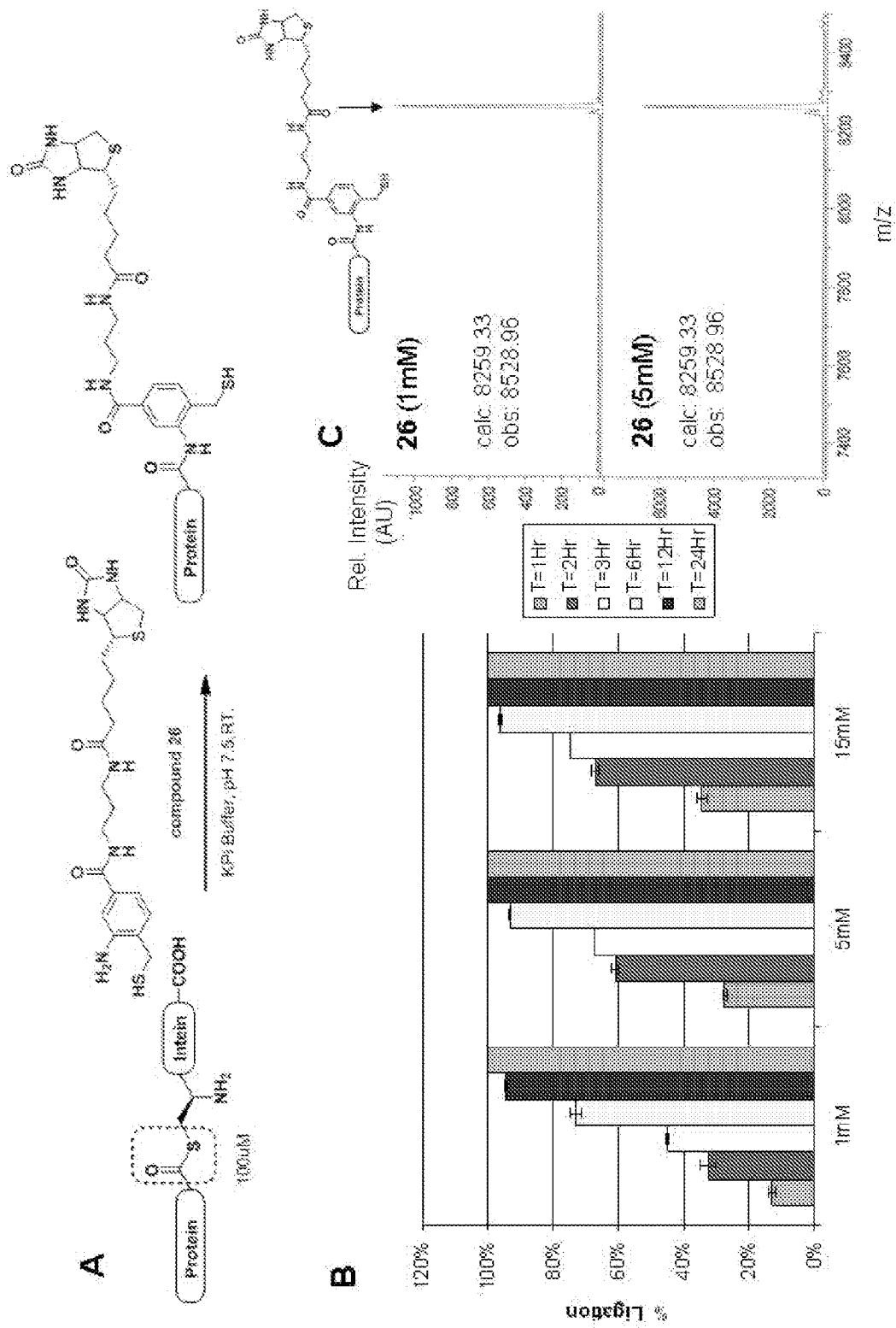

FIG. 13A-C. Protein biotinylation with biotin-comprising reagent 26. A) General scheme of the protein labeling reaction. B) Percentage of protein labeling at the 1-, 2-, 3-, 6-, 12-, and 24-hour time point in the presence of different concentration of 26 as determined by SDS-PAGE gel densitometry. C) MALDI-TOF MS spectrum of the reaction mixture, indicating the clean formation of the desired biotinylated protein product, CBD-26.

Figure 14:
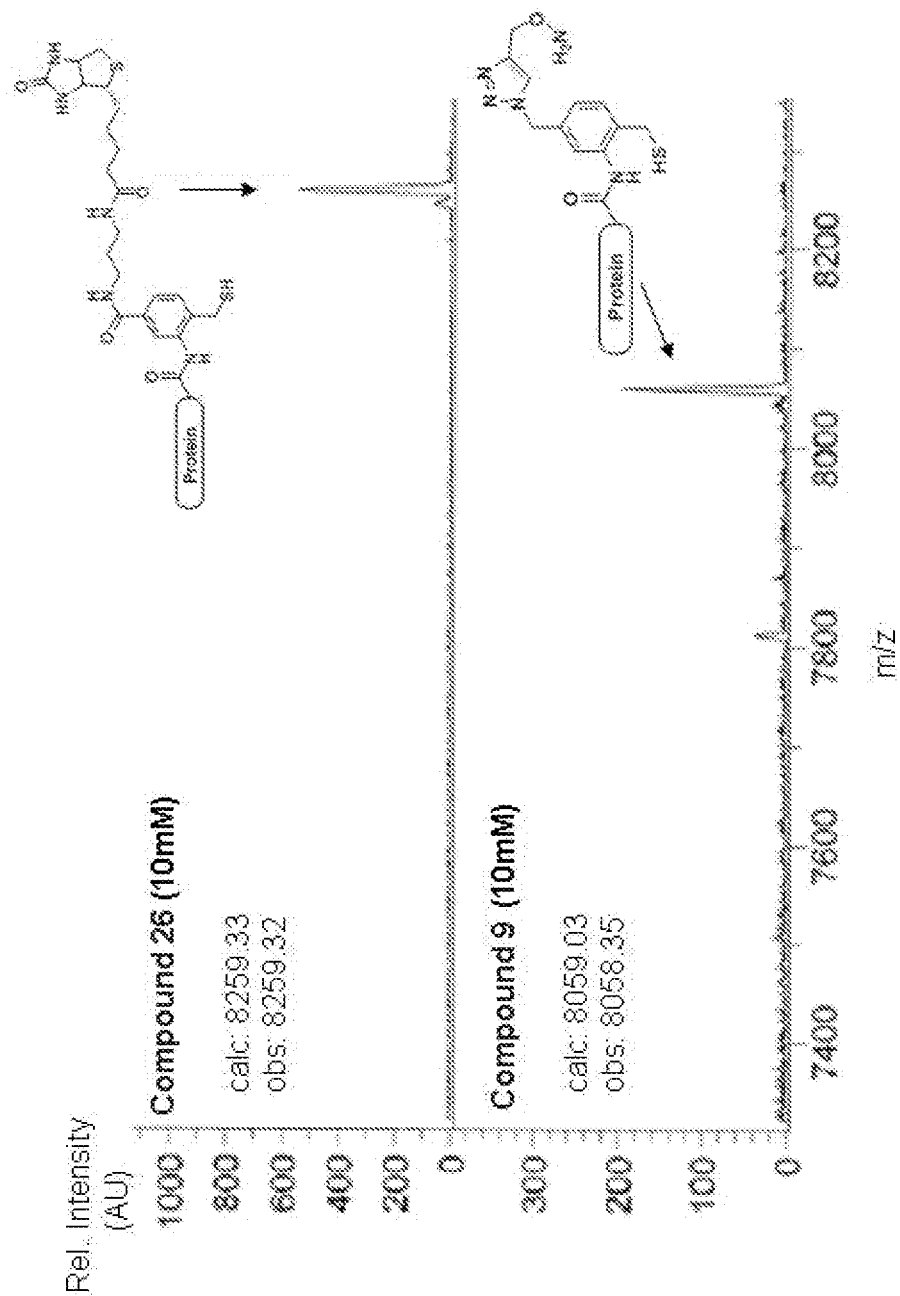

FIG. 14. Protein labeling in cell lysate with reagents 26 and 9. MALDI-TOF MS spectra of cell lysates of CBD-3-expressing *E. coli* cells after incubation with reagent 26 or reagent 9 at 10 mM for 4 hours. The peaks corresponding to the desired functionalized protein products, CDB-26 and CBD-9, respectively, are indicated.

FIG. 15A-B. Protein labeling in living *E. coli* cells. A) General scheme of the protein labeling reaction. Briefly, *E. coli* cells expressing CBD-3 were incubated with compound 26, washed and then lysed. B) MALDI-TOF MS spectra of the cell lysates after the labeling procedure (at 5 and 10 mM reagent concentration), indicating the formation of the desired biotinylated protein product, CBD-26. The minor product (CBD-COOH) resulting from spontaneous hydrolysis of the intein-fusion protein is also indicated.

FIG. 16A-C. Affinity purification of in vivo biotinylated protein. A) Schematic representation of the affinity purification procedure for isolating the in vivo biotinylated protein CBD-26 with streptavidin-coated beads. B-C) MALDI-TOF spectra of the *E. coli* cell lysate after in vivo labeling of CBD-3 with compound 26 prior to (B) and after (C) the biotin-capturing procedure.

FIG. 17A-B. In vitro protein labeling with reagent N-(2-mercaptoethyl)-amino-aryl-based reagent. A) General scheme of the protein labeling reaction. B) Percentage of protein labeling at different time points for the reaction between CBD-2 and reagent 30 as determined by SDS-PAGE gel densitometry.

FIG. 18A-B. In vivo protein labeling with reagent N-(2-mercaptoethyl)-amino-aryl-based reagent. A) General scheme of the protein labeling reaction. Briefly, *E. coli* cells expressing CBD-3 were incubated with compound 34, then washed, and lysed. B) MALDI-TOF MS spectra of the cell lysates after the labeling procedure (34 at 10 mM), indicating the formation of the functionalized protein product, CBD-34. The minor product (CBD-COOH) resulting from spontaneous hydrolysis of the intein-fusion protein is also indicated.

5. DETAILED DESCRIPTION OF THE INVENTION

Methods, kits and compositions are provided for covalently linking a chemical species to a recombinant or synthetic polypeptide. The methods involve the reaction of a thioester-comprising polypeptide with a reagent comprising a reactive amino-thiol group connected to the chemical species which is to be covalently linked to the polypeptide, via a linker. Such chemical species may be, for example, a functional group, a label or tag molecule, a biological molecule, a ligand, or a solid support.

Efficient and catalyst-free methods for C-terminal protein labeling are also provided. These methods expand current capabilities in the area of protein functionalization, providing useful and complementary tools for the isolation, detection, characterization, and analysis of proteins in a variety of in vitro and in vivo applications.

For clarity of disclosure, and not by way of limitation, the detailed description of the invention is divided into the subsections set forth below.

5.1. Methods

Methods, kits and compositions (also referred to herein as "reagents") for site-selective functionalization of proteins and peptides are provided. The site-selective functionalization methods provided herein overcome a number of problems associated with previous methods for site-selective functionalization of proteins and peptides and, generally, involve the reaction between a protein or peptide comprising a permanent or transiently formed thioester group at its C-terminus with a chemical reagent comprising a reactive amino-thiol group.

The methods and reagents provided herein can be applied to covalently link a polypeptide (i.e., a protein or a peptide) to another chemical entity, which may be a functional group, a label or tag molecule (e.g., a fluorescent dye, an affinity tag, or a isotopically labeled molecule), a biological molecule (e.g., a peptide, a protein, a carbohydrate, a nucleoside or nucleotide, or a lipid), a small molecule (e.g., a protein-, nucleic acid-, or receptor-binding ligand, a drug or drug candidate), or a solid support (e.g., a solid surface or a resin bead). The functionalization procedure can be carried out under mild reaction conditions, that is, in aqueous buffer, at pH ranging from 6.0 to 9.0, and at temperatures ranging from 4 to 40 degrees ° C. The possibility to perform this procedure under mild conditions minimizes the risks of denaturation or degradation of the target protein or peptide which is to be functionalized. The functionalization can be carried out in vitro, that is in a cell-free environment, or in vivo, that is with the target protein or peptide residing inside a cell or being covalently or non-covalently attached to the surface of a cell.

Accordingly, a method is provided for linking a chemical entity or species to the C-terminus of a target polypeptide, the method comprising the steps of:

a) providing a polypeptide comprising a permanent or transiently formed thioester group at its C-terminus;

b) providing a chemical species of general formula I, II, III, or IV:

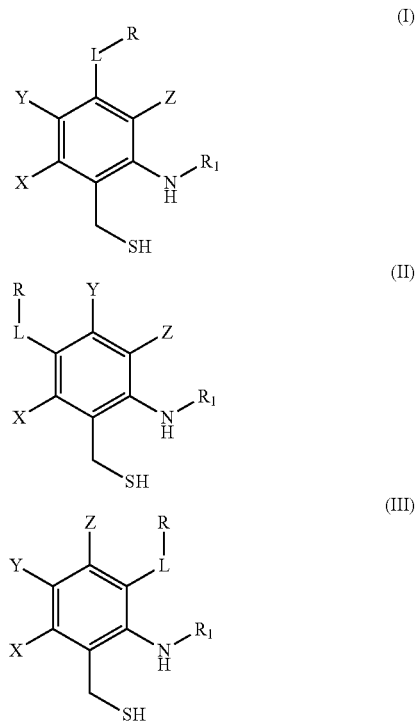

-continued

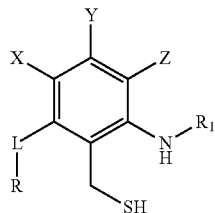
(IV)

or salts thereof wherein:

R is the chemical entity or species which is to be covalently linked to the target polypeptide;

$R_1$ is hydrogen, aliphatic, substituted aliphatic, aryl or substituted aryl group;

X, Y, and Z is hydrogen or a non-hydrogen substituent;

L is a linker group; and c) allowing the polypeptide to react with the chemical species of general formula I, II, III, or IV so that a covalent linkage between the reagent and the polypeptide is formed by virtue of a nucleophilic substitution reaction at the level of the thioester group.

In a specific embodiment, the method comprises the steps of:

a. providing a polypeptide, wherein the polypeptide comprises a thioester group and/or wherein the polypeptide is C-terminally fused to an intein;

b. providing a chemical reagent of formula (I), (II), (III), (IV), (V), (VI), (VII) or (VIII):

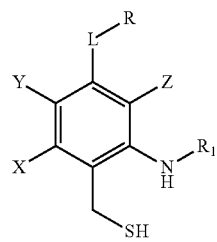
(I)

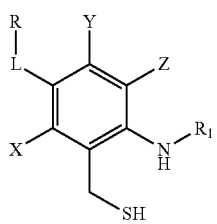
(II)

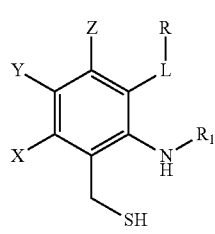
(III)

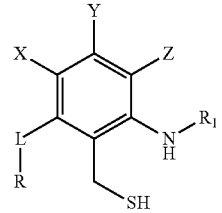
(IV)

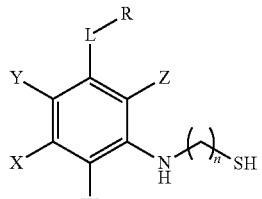
(V)

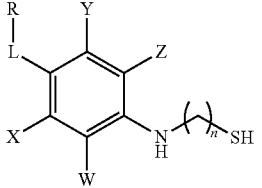
(VI)

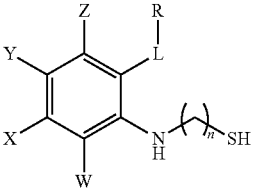
(VII)

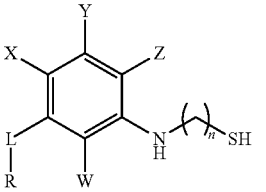
(VIII)

or a salt of the chemical reagent, wherein:

i. R is a chemical species to be covalently linked to the polypeptide, ii. $R_1$ is hydrogen, a substituted or non-substituted aliphatic group, or a substituted or non-substituted aryl group, iii. X, Y, W, and Z are hydrogen and/or non-hydrogen substituents selected from the group consisting of alkyl, heteroatom-comprising alkyl, alkenyl, heteroatom-comprising alkenyl, alkynyl, heteroatom-comprising alkynyl, aryl, heteroatom-comprising aryl, alkoxy, heteroatom-comprising alkoxy, aryloxy, heteroatom-comprising aryloxy, halo, —OH, —OR', —SR, —COOH, —COOR', —CONR'$_2$, —NR'$_2$, —NO$_2$, —SO$_3$R', —SO$_2$NR$_2$', C≡N, —O—C≡N, —P(O)$_k$R' where k is 2 or 3, and —S—C≡N, wherein each R' is independently H, alkyl, or substituted alkyl, iv. n is 2 or 3; and v. L is a linker or a linker group selected from the group consisting of a single bond, $C_1$-$C_{24}$ alkyl, $C_1$-$C_{24}$ substituted alkyl, $C_1$-$C_{24}$ substituted heteroatom-comprising, $C_1$-$C_{24}$ substituted heteroatom-comprising alkyl, $C_2$-$C_{24}$ alkenyl, $C_2$-$C_{24}$ substituted alkenyl, $C_2$-$C_{24}$ substituted heteroatom-comprising alkenyl, $C_2$-$C_{24}$ substituted heteroatom-comprising alkenyl, $C_2$-$C_{24}$ alkynyl, $C_2$-$C_{24}$ substituted alkynyl, $C_2$-$C_{24}$ substituted heteroatom-comprising alkynyl, $C_2$-$C_{24}$ substituted heteroatom-comprising alkynyl, $C_5$-$C_{24}$ aryl, $C_5$-$C_{24}$ substituted aryl, $C_5$-$C_{24}$ substituted heteroatom-comprising aryl, $C_5$-$C_{24}$ substituted heteroatom-comprising aryl, $C_1$-$C_{24}$ alkoxy, $C_5$-$C_{24}$ aryloxy, —O—, —S—, —NR'—, —C(O)—, —C(S)—, —C(O)NR'—, —C(S)NR'—, —N(R')C(O)—, —S(O)$_k$— where k is 1, 2, or 3, —S(O)$_k$N(R')—, —N(R')C(O)N(R')—, —N(R')C(S)N(R')—, —N(R')S(O)$_k$N(R')—, —N(R)—N=, —C(R')=N—, —C(R')=N—N(R')—, —C(R')=N—N=, —C(R')$_2$—N=N, and —C(R')$_2$—N(R')—N(R')— group, where each R' is independently an H, an aliphatic, a substituted aliphatic, an aryl, or a substituted aryl group; and c. allowing the polypeptide to react with the chemical reagent so that a covalent linkage between the reagent and the polypeptide is formed.

In one embodiment of the method, R is a functional group, a label molecule, a tag molecule, an affinity label molecule, a photoaffinity label, a dye, a chromophore, a fluorescent molecule, a phosphorescent molecule, a chemiluminescent molecule, an energy transfer agent, a photocrosslinker molecule, a redox-active molecule, an isotopic label molecule, a spin label molecule, a metal chelator, a metal-comprising moiety, a heavy atom-comprising-moiety, a radioactive moiety, a contrast agent molecule, a MRI contrast agent, an isotopically labeled molecule, a PET agent, a photocaged moiety, a photoisomerizable moiety, a chemically cleavable group, a photocleavable group, an electron dense group, a magnetic group, an amino acid, a polypeptide, an antibody or antibody fragment, a carbohydrate, a monosaccharide, a polysaccharide, a nucleotide, a nucleoside, a DNA, a RNA, a siRNA, a polynucleotide, an antisense polynucleotide, a peptide nucleic acid (PNA), a fatty acid, a lipid, a cofactor, biotin, a biotin analogue, a biomaterial, a polymer, a water-soluble polymer, a polyethylene glycol derivative, a water-soluble dendrimer, a cyclodextrin, a small molecule, a protein-, nucleic acid-, or receptor-binding molecule, a biologically active molecule, a drug or drug candidate, a cytotoxic molecule, a solid support, a surface, a resin, a nanoparticle, or a quantum dot, or any combination thereof.

In another embodiment of the method, R is a bioorthogonal functional group selected from the group consisting of —NR'NR'$_2$, —C(O)NR'NR'$_2$, —ONH$_2$, —N$_3$, —C≡CR', —CR'=CR'$_2$, —PR', 2-cyanobenzothiazole, tetrazole, tetrazine, aziridine, dihydroazirine, and norbornadiene groups, and each R' is independently an H, an aliphatic, a substituted aliphatic, an aryl, or a substituted aryl group.

In another embodiment of the method, R is a fluorescent molecule selected from the group consisting of a coumarin derivative, a naphthalene derivative, a pyrene derivative, a fluorescein derivative, a rhodamine derivative, a naphthoxanthene derivative, a phenanthridine derivative, a boron difluoride dipyrromethene (BODIPY) derivative, a cyanine derivatives, a phthalocyanine derivative, and an oxazine derivative.

In another embodiment of the method, R is biotin, a biotin analogue, or a perfluorinated alkyl chain $CF_3$—$(CF_2)_m$— where m=3-15.

In another embodiment of the method, R is a poly(ethyleneglycol) molecule.

In another embodiment of the method, R is a resin or a nanoparticle

In another embodiment of the method, R is a functionalized surface.

In another embodiment of the method, the surface is a microarray.

In another embodiment of the method, the intein is a naturally occurring intein, an engineered variant of a naturally occurring intein, a fusion of the N-terminal and C-terminal fragments of a naturally occurring split intein, or a fusion of the N-terminal and C-terminal fragments of an artificial split intein.

In another embodiment of the method, the intein is a polypeptide of SEQ ID NO:1-76, or an engineered (or synthetic) variant thereof.

In another embodiment of the method:

the C-terminal terminal asparagine, aspartic acid, or glutamine residue in the intein is mutated to an amino acid other than asparagine, aspartic acid, or glutamine, or the N-terminal serine is mutated to a cysteine residue and the C-terminal asparagine, aspartic acid, or glutamine residue in the intein is mutated to an amino acid other than asparagine, aspartic acid, or glutamine.

In another embodiment of the method, the intein is C-terminally fused to a polypeptide affinity tag selected from the group consisting of polyhistidine tag, Avi-Tag, FLAG tag, Strep-tag II, c-myc tag, S-Tag, calmodulin-binding peptide, streptavidin-binding peptide, chitin-binding domain, glutathione S-transferase, and maltose-binding protein. These tags and their sequences are well known in the art.

In another embodiment of the method, the polypeptide C-terminally fused to the intein comprises one or a plurality of the features selected from the group consisting of: the residue at position 1 prior to the intein (hereinafter "intein-1" or "I-1") being F, Y, A, T, W, N, R or Q; the residue at position 2 prior to the intein (hereinafter "intein-2" or "I-2") being G, P, or S; and the residue at position 3 prior to the intein (hereinafter "intein-3" or "I-3") being G or S.

In another embodiment of the method, the intein-fused polypeptide is inside a cell or associated with the exterior surface of a cell membrane. The polypeptide can be inside the cell, e.g., in the cytoplasm or in another intracellular compartment such as the nucleus, or on the surface of the cell, e.g. associated with the cell membrane on its interior or exterior surface.

In another embodiment of the method, the cell is a prokaryotic or eukaryotic cell.

In another embodiment of the method, the prokaryotic cell is E. coli.

In another embodiment of the method, the eukaryotic cell is a yeast cell, an insect cell, a worm cell, a fish cell or a mammalian cell.

In another embodiment of the method, $R_1$, X, Y, and Z are hydrogen atoms,

L is selected from the group consisting of —C(O)NR'—, —C(O)NR'CH$_2$C(O)—, —C(O)NR'(CH$_2$)n-, and —C(O)NR'(CH$_2$CH$_2$—O)n-, R' is a hydrogen, alkyl or aryl group, and n is an integer number from 1 to 15.

In another embodiment of the method, R is selected from the group consisting of biotin, a biotin analogue, and a coumarin derivative.

In another embodiment of the method, the reagent is:

a. a compound of formula (I), wherein:

$R_1$, X, Y, and Z are hydrogen atoms,

R is —ONH$_2$ or —N$_3$, and

L is a single bond;

b. a compound of formula (I), wherein:

$R_1$, X, Y, and Z are hydrogen atoms,

R is ONH$_2$, and

L is a linker or linker group of formula

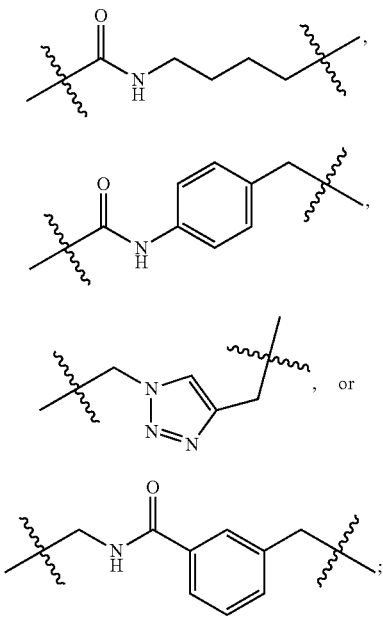

c. a compound of formula (I), wherein:

R₁, X, Y, and Z are hydrogen atoms,

R is 7-amino-4-(trifluoromethyl)-2H-chromen-2-one, and

L is —C(O)NHCH₂C(O)—; or d. a compound of formula (I), wherein:

R₁, X, Y, and Z are hydrogen atoms,

R is biotin, and

L is —C(O)NH(CH₂)₃NH—.

A method is also provided for linking a chemical entity or species to the C-terminus of a target polypeptide, the method comprising the steps of:

a) providing a polypeptide comprising a permanent or transiently formed thioester group at its C-terminus;

b) providing a chemical species of general formula V, VI, VII, or VIII:

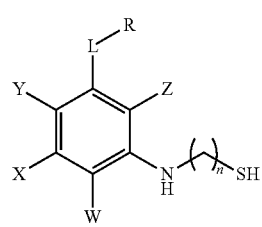

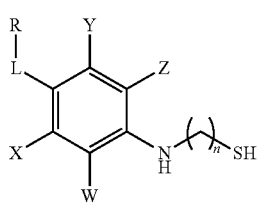

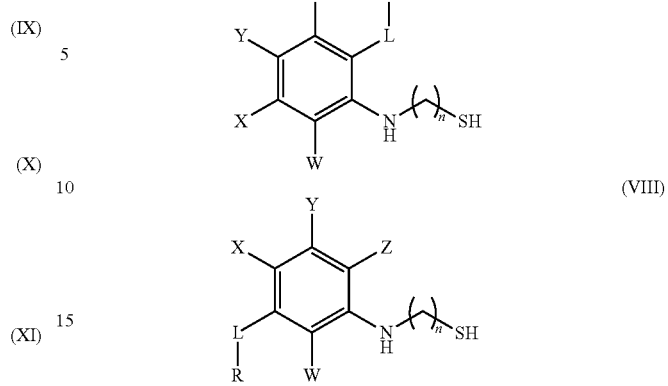

or salts thereof wherein:

R is the chemical entity or species which is to be covalently linked to the target polypeptide;

n is 2 or 3;

X, Y, W, and Z is hydrogen or a non-hydrogen substituent;

L is a linker group; and c) allowing the polypeptide to react with the chemical species of general formula V, VI, VII, or VIII so that a covalent linkage between the reagent and the polypeptide is formed by virtue of a nucleophilic substitution reaction at the level of the thioester group.

The reactivity of the reagents of formula (I) through (VIII) toward functionalization of a thioester-comprising polypeptide is conferred by the amino-thiol moiety comprised in these compounds (i.e., the 1-amino-2-(mercaptomethyl)-aryl moiety in compounds (I)-(IV) and the N-(2-mercaptoethyl)-amino-aryl moiety in compounds (V)-(VIII)) as discovered by the inventors. These amino-thiol moieties are able to efficiently promote a nucleophilic substitution at the C-terminal thioester group, thereby forming a covalent linkage between the target polypeptide and the reagent, and thus the between target polypeptide and the chemical entity or species comprised in the reagent.

As described in FIG. 1, this reaction typically involves a thioesterification reaction by action of the thiol group in the reagents (I)-(VIII) to generate a stable thioester product (product 'a' in FIG. 1). This reaction product can then undergo an intramolecular S→N acyl transfer reaction to give a stable amide linkage between the reagent of formula (I)-(VIII) and the polypeptide which is to be functionalized (product 'b' in FIG. 1). For the purpose of protein/peptide functionalization, both the thioester product (product 'a') and the amide product (product 'b') are useful, albeit the latter is expected to generally exhibit greater stability against hydrolysis and thus, depending on the specific application of the methods provided herein, may be in some cases preferred.

The R₁ group in the reagents of formula (I), (II), (III), and (IV) can be hydrogen, an aliphatic, a substituted aliphatic, an aryl, or a substituted aryl group. The nature of the R₁ group can affect the rate of the intramolecular S→N acyl transfer process after the transthioesterification reaction, that is the conversion of product 'a' into product 'b' in FIG. 1. In general, when the R₁ group is small (e.g., hydrogen atom, methyl or ethyl group) the formation of product 'b' is favored, whereas when the R₁ group is large (e.g., phenyl or benzyl group) the formation of product 'a' is favored. The choice of the R₁ group is thus made according to the specific applications of the methods provided herein and the preferred product (either product 'a' or product 'b') in each case. Preferably, the $R_1$ group is selected from the group consisting of hydrogen, methyl, ethyl, and propyl group. Most preferably, the $R_1$ group is hydrogen.

L is a linker or a linker group that provides a spacer function between the R group and the thioester-reactive amino-thiol moiety in reagents (I) through (VIII). In one embodiment, L is a linker or a linker group selected from the group consisting of aliphatic, substituted aliphatic, aryl, substituted aryl, heteroatom-comprising aliphatic, substituted heteroatom-comprising aliphatic, heteroatom-comprising aryl, substituted heteroatom-comprising aryl, alkoxy, aryloxy groups. In particular, Y is a linker group selected from the group consisting of $C_1$-$C_{24}$ alkyl, $C_1$-$C_{24}$ substituted alkyl, $C_1$-$C_{24}$ substituted heteroatom-comprising alkyl, $C_1$-$C_{24}$ substituted heteroatom-comprising alkyl, $C_2$-$C_{24}$ alkenyl, $C_2$-$C_{24}$ substituted alkenyl, $C_2$-$C_{24}$ substituted heteroatom-comprising alkenyl, $C_2$-$C_{24}$ substituted heteroatom-comprising alkenyl, $C_2$-$C_{24}$ alkynyl, $C_2$-$C_{24}$ substituted alkynyl, $C_2$-$C_{24}$ substituted heteroatom-comprising alkynyl, $C_2$-$C_{24}$ substituted heteroatom-comprising alkynyl, $C_5$-$C_{24}$ aryl, $C_5$-$C_{24}$ substituted aryl, $C_5$-$C_{24}$ substituted heteroatom-comprising aryl, $C_5$-$C_{24}$ substituted heteroatom-comprising aryl, $C_1$-$C_{24}$ alkoxy, $C_5$-$C_{24}$ aryloxy, —O—, —S—, —NR'—, —C(O)—, —C(S)—, —C(O)NR'—, —C(S)NR'—, —N(R')C(O)—, —S(O)$_k$— where k is 1, 2, or 3, —S(O)$_k$N(R')—, —N(R')C(O)N(R')—, —N(R')C(S)N(R')—, —N(R')S(O)$_k$N(R')—, —N(R')—N=, —C(R)=N—, —C(R')=N—N(R')—, —C(R')=N—N=, —C(R')$_2$—N=N, and —C(R')$_2$—N(R')—N(R')— group, where each R' is independently an H, an aliphatic, a substituted aliphatic, an aryl, or a substituted aryl group.

In some embodiments, L is an amino acid such as, for example, the α-amino acid glycine. In other embodiments, L is a polymer such as poly(ethyleneglycol). In still other embodiments, L is a polyether of formula —(CH$_2$—CH$_2$—O)$_n$—, where n in an integer number between 1 and 15.

The X, Y, W, and Z groups in the compounds of formula (I) through (VIII) can be hydrogen atoms or non-hydrogen substituents selected from the group consisting of alkyl, heteroatom-comprising alkyl, alkenyl, heteroatom-comprising alkenyl, alkynyl, heteroatom-comprising alkynyl, aryl, heteroatom-comprising aryl, alkoxy, heteroatom-comprising alkoxy, aryloxy, heteroatom-comprising aryloxy, halo, hydroxyl (—OH), ether (—OR'), thioether (—SR), carboxy (—COOH), ester (—COOR'), amide (—CONR'$_2$), amino (—NR'$_2$), nitro (—NO$_2$), sulfo (—SO$_2$—OH), sulfono (—SO$_2$—OR'), sufonamide (—SO$_2$NR'$_2$), cyano (—C≡N), cyanato (—O—C≡N), thiocyanato (—S—C≡N), phosphono (—P(O)(—OR')$_2$), phosphate (—O—P(O)(—OR')$_2$) group, where each R' is independently an H, an aliphatic, a substituted aliphatic, an aryl, or a substituted aryl group. In addition, any of the non-hydrogen substituent X, Y, W, and Z can be connected to one or more of the substituents to form a ring structure. For example, the substituent in X in compound of formula (III) can be connected to either Y or Z or both to form a ring structure. Non-limiting examples of ring structures include, for example, furan, thiophene, pyrrole, pyrroline, pyrrolidine, dioxolane, oxazole, thiazole, imidazole, imidazoline, imidazolidine, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, trithiane, indolizine, indole, isoindole, indoline, benzofuran, benzothiophene, indazole, benzimidazole, benzthiazole, purine, quinolizine, quinoline, isoquinoline, cinnoline, phthalazine, quinazoline, quinoxaline, naphthyridine, pteridine, quinuclidine, carbazole, acridine, phenazine, phenthiazine, phenoxazine, phenyl, indene, naphthalene, azulene, fluorene, anthracene, and phenanthracene groups.

The use of non-hydrogen substituents as X, Y, W, or Z group can be useful to modulate the physico-chemical properties of the reagents (I)-(VIII), such as, for example, their water-solubility or cell permeability. At the same time, the replacement of these groups with sterically bulky substituents can affect the reactivity of the reagents toward functionalization of the target thioester-comprising polypeptide, in particular when the substituent is most proximal (i.e., in ortho position) to the thiol-comprising substituent (i.e., the methanethiol group in compounds (I)-(IV); the aminoalkylthiol group in compounds (V)-(VIII)). Accordingly, it is generally preferable that either none, one, or at most two groups among the X, Y, W, or Z groups are non-hydrogen substituents. In particular, it is generally preferred that the position in ortho to the thiol-comprising substituent is occupied by a hydrogen atom (e.g., X=H in compounds of general formula (I), (II), and (III)).

With respect to the linker or linker group L comprised in the reagents of general formula (I) through (VIII), the L group is chosen so that, preferably, none of the substituents or functional groups comprised within this group can react with a thiol or amino group, or any of the functional groups comprised in the R group. Similarly, when any of the X, Y, W, or Z groups is a non-hydrogen substituent, the X, Y, W, or Z groups are chosen so that, preferably, none of these groups or functional groups comprised within these groups can react with a thiol or amino group, or any of the functional groups comprised in the R group. Those of ordinary skill in the art can select suitable linkers or linker groups L that meet these requirements based on general knowledge in the art. Accordingly, the L, X, Y, W, and Z group preferably do not comprise thiol groups, selenol groups, thioester groups, aldehyde or ketone groups, α,β-unsaturated acid, α,β-unsaturated amide, or α,β-unsaturated ester groups, α-halo-acid, α-halo-amide, or α-halo-ester groups, unless these groups are protected with suitable protecting groups which make them unreactive under the conditions applied in the methods provided herein. A large amount of information is known in the art concerning the use of protecting groups and one of ordinary skills in the art will be capable of selecting appropriate protecting groups for a given application.

The R group can be any chemical entity or species that is to be covalently linked to the target thioester-comprising polypeptide. Accordingly, in one embodiment, the R group is a selected from the group consisting of a functional group, a label molecule, a tag molecule, an affinity label molecule, a photoaffinity label, a dye, a chromophore, a fluorescent molecule, a phosphorescent molecule, a chemiluminescent molecule, an energy transfer agent, a photocrosslinker molecule, a redox-active molecule, an isotopic label molecule, a spin label molecule, a metal chelator, a metal-comprising moiety, a heavy atom-comprising-moiety, a radioactive moiety, a contrast agent molecule, a MRI contrast agent, an isotopically labeled molecule, a PET agent, a photocaged moiety, a photoisomerizable moiety, a chemically cleavable group, a photocleavable group, an electron dense group, a magnetic group, an amino acid, a polypeptide, an antibody or antibody fragment, a carbohydrate, a monosaccharide, a polysaccharide, a nucleotide, a nucleoside, a DNA, a RNA, a siRNA, a polynucleotide, an antisense polynucleotide, a peptide nucleic acid (PNA), a fatty acid, a lipid, a cofactor, biotin, a biotin analogue, a biomaterial, a polymer, a water-soluble polymer, a polyethylene glycol derivative, a water-soluble dendrimer, a cyclodextrin, a small molecule a protein-, nucleic acid-, or receptor-binding ligand, a drug or drug candidate), or a solid support (e.g., a solid surface or a resin bead).

In some embodiments, the R group in reagents (I) through (VIII) is a functional group. In some specific embodiments, the R group is a bioorthogonal functional group. Several bioorthogonal functional groups are known in the art and these include, but are not limited to, hydrazino (—NHNH$_2$), hydrazido (—C(O)NHNH$_2$), oxyamino (—ONH$_2$), azido (—N$_3$), alkynyl (—C≡CR'), alkenyl (—CR'=CR'$_2$), phosphine (—PR'$_2$), 2-cyanobenzothiazole, tetrazole, tetrazine, aziridine, dihydroazirine, norbornadiene, boronaryl (Ar—B(—OH)$_2$), bromoaryl (Ar—Br), iodoaryl (Ar—I) groups, where R' is a hydrogen, alkyl or aryl group and Ar is an aryl group. In specific embodiments, the R group is a hydrazino (—NR'NR'$_2$), hydrazido (—C(O)NR'NR'$_2$), oxyamino group (—ONH$_2$), azido (—N$_3$), alkynyl (—C≡CR'), alkenyl (—CR'=CR'$_2$), phosphine (—PR'$_2$), 2-cyanobenzothiazole, tetrazole, tetrazine, aziridine, dihydroazirine, norbornadiene groups, where each R' is independently H, aliphatic, substituted aliphatic, aryl, or substituted aryl group.

When R is a bioorthogonal functional group, such functional group can be used to further couple the functionalized polypeptide to another chemical entity according to methods known in the art. For example, an alkynyl group (—C≡CR') and azido (—N$_3$) group can be engaged in a bioorthogonal bond-forming reaction (i.e., Huisgen 1,3-dipolar cycloaddition) via the addition of Cu(I) as catalyst or using a strained alkyne (e.g., cyclooctyne). A bioorthogonal Staudinger ligation can be carried out between a phosphine (—PR'$_2$) and an azido group. A tetrazole and an alkenyl group (—CR'=CR'$_2$) can be engaged in a bioorthogonal bond-forming reaction ('photoclick' cycloaddition) upon irradiation with 290-350 nm light.

In some embodiments, the R group in reagents (I) through (VIII) is a fluorescent molecule. In some specific embodiments, the R group is a fluorescent molecule selected from the group consisting of a coumarin derivative (e.g., Alexa™ dyes), a naphthalene derivative, a pyrene derivative, a fluorescein derivative, a rhodamine derivative, a naphthoxanthene derivative, a phenanthridine derivative, a boron difluoride dipyrromethene (BODIPY) derivative, a cyanine derivatives (e.g., CyDyes), a phthalocyanine derivative, and a oxazine derivative (e.g., resorufin).

In some embodiments, the R group in reagents (I) through (VIII) is an affinity label molecule. In some specific embodiments, the R group is biotin or a biotin analogue.

In some embodiments, the R group in reagents (I) through (VIII) is a polymer. In some specific embodiments, the R group is selected from the group consisting of a functionalized or non-functionalized linear poly(ethyleneglycol) molecule, and a functionalized or non-functionalized branched poly(ethyleneglycol) molecule. In some embodiments, the R group is a polyether of formula —(CH$_2$—CH$_2$—O)$_n$—, where n in an integer number between 10 and 1000.

In some embodiments, the R group in reagents (I) through (VIII) is a water-soluble polymer. Such water-soluble polymers include, but are not limited to, polyethylene glycol, polyethylene glycol propionaldehyde, mono C$_1$-C$_{10}$ alkoxy or aryloxy derivatives thereof monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxideethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, serum albumin, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof.

In other embodiments, the R group in reagents (I) through (VIII) is a solid support. Accordingly, the methods provided herein can be applied to immobilize a target polypeptide onto a solid support. Because the functionalization procedure occurs site-specifically at the C-terminus of the target polypeptide, the orientation of the target polypeptide immobilized onto the solid support can be predicted and controlled. Such control of the orientation of the polypeptide attachment to the solid support can be useful, for example, in the evaluation of the biophysical properties of the polypeptide (e.g., via surface plasmon resonance, enzyme-linked immunoassay, and the like), for the construction of protein (micro)arrays, for the preparation of affinity chromatographic media, and related applications.

Examples of solid supports well known in the art that can be used include, but are not limited to, solid and semisolid matrixes, such as aerogels and hydrogels, resins, beads, biochips (including thin film coated biochips), microfluidic chip, a silicon chip, multi-well plates (also referred to as microtitre plates or microplates), membranes, cells, conducting and nonconducting metals, glass (including microscope slides) and magnetic supports. Other non-limiting examples of solid supports used in the methods and compositions described herein include silica gels, polymeric membranes, particles, derivatized plastic films, derivatized glass, derivatized silica, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like. In certain embodiments, the supports used in the methods and compositions described herein are supports used for surface analysis such as surface acoustic wave devices or devices utilizing evanescent wave analysis, such as surface plasmon resonance analysis. Other supports used in the methods and compositions described herein include, but are not limited to, resins used in peptide synthesis such as, by way of example only, polystyrene, PAM-resin, POLY-HIPE™ resin, polyamide resin, polystyrene resin grafted with poly(ethylene glycol), polydimethyl-acrylamide resin and PEGA beads. The solid support can be, but is not limited to, in the form of a sheet, a multi-well plate, a bead or microbead, a slide, a microarray tray, and a test tube. Other suitable shapes and configurations for the solid support will also be recognized by the skilled artisan.

In certain embodiment, the surfaces of the solid supports can have reactive functional groups, which can be used to covalently or non-covalently link a reagent of formula (I) through (VIII) to the solid support. Such functional groups can include, but are not limited to, hydroxyl, carboxyl, halogen, nitro, cyano, amido, urea, carbonate, carbamate, isocyanate, sulfone, sulfonate, sulfonamide and sulfoxide groups. In other embodiments, the surfaces of the solid supports are covalently or non-covalently coated to streptavidin or avidin. In this case, reagents (I) through (VIII) comprising a biotin or biotin analogue within the R group can be linked to the solid support via a tight biotin-(strept) avidin non-covalent interaction.

In specific embodiments, the target polypeptide comprises one or more thioester groups. In preferred embodiments, the target polypeptide comprises a single thioester group. In most preferred embodiments, the target polypeptide comprises a single, C-terminal thioester group.

The thioester-comprising polypeptide may be synthetically or recombinantly produced. Several methods are known in the art to produce synthetic thioester-comprising polypeptides. For example, synthetic thioester-comprising peptides may be produced via solid-phase peptide synthesis (SPPS) using BOC chemistry and suitable resins for generating a C-terminal thioester upon cleavage of the polypeptide chain from the resin (Hojo et al., Bull. Chem. Soc. Jpn. 1993, 66, 2700-06). Alternatively, safety-catch linker resins can be used in combination with Fmoc-based SPPS to generate synthetic thioester-comprising peptides (Shin, Winans et al. 1999).

In preferred embodiments, the target polypeptide is a recombinant polypeptide. In most preferred embodiments, the target polypeptide which is to be functionalized is genetically fused to the N-terminus of an intein so that a thioester group is transiently formed at the junction between the target polypeptide and the intein via intein-catalyzed N,S acyl transfer as described above.

Accordingly, a method is also provided for linking a chemical entity or species to a recombinant polypeptide, the method comprising the steps:
  d) providing a precursor polypeptide, the precursor polypeptide comprising the target polypeptide fused to the N-terminus of an intein;
  e) providing a chemical reagent of general formula (I), (II), (III), (IV), (V), (VI), (VII), or (VIII) as described above;
  f) allowing the precursor polypeptide to react with the chemical reagent so that a covalent linkage between the chemical reagent and the target polypeptide is formed with concomitant release of the intein.

In certain embodiments of the method, the intein to be fused to the C-terminus of the target polypeptide can be a naturally occurring intein, an engineered variant of a naturally occurring intein, a fusion of the N-terminal and C-terminal fragments of a naturally occurring split intein and a fusion of the N-terminal and C-terminal fragments of an artificial split intein.

Nucleotide sequences encoding for intein domains that can be used for preparing the biosynthetic precursors and self-processing biosynthetic precursors within the invention can be derived from naturally occurring inteins and engineered variants thereof. A rather comprehensive list of such inteins is provided by the Intein Registry (http:www.neb.comnebinteins.html). Inteins that can be used can include, but are not limited to, any of the naturally occurring inteins from organisms belonging to the Eucarya, Eubacteria, and Archea. Among these, inteins of the GyrA group (e.g., Mxe GyrA, Mfl GyrA, Mgo GyrA, Mkas GyrA, Mle-TN GyrA, Mma GyrA), DnaB group (e.g., Ssp DnaB, Mtu-CDC1551 DnaB, Mtu-H37Rv DnaB, Rma DnaB), RecA group (e.g., Mtu-H37Rv RecA, Mtu-So93 RecA), RIR1 group (e.g., Mth RIR1, Chy RIR1, Pfu RIR1-2, Ter RIR1-2, Pab RIR1-3), and Vma group (e.g., Sce Vma, Ctr Vma) are preferred and intein Mxe GyrA (SEQ ID NO:1) and the engineered 'mini Ssp DnaB ('eDnaB', SEQ ID NO:2) are particularly preferred.

In particular, natural inteins whose self-splicing mechanism has been confirmed experimentally can be used within the invention. These include, but are not limited to, Mxe GyrA (SEQ ID NO:1), Ssp eDnaB (SEQ ID NO:2), Hsp-NRC1 CDC21 (SEQ ID NO:3), Ceu ClpP (SEQ ID NO:4), Tag Pol-1 (SEQ ID NO:5), Tfu Pol-1 (SEQ ID NO:6), Tko Pol-1 (SEQ ID NO:7), Psp-GBD Pol (SEQ ID NO:8), Tag Pol-2 (SEQ ID NO:9), Thy Pol-1 (SEQ ID NO:10), Tko Pol-2 (SEQ ID NO:11), Tli Pol-1 (SEQ ID NO:12), Tma Pol (SEQ ID NO:13), Tsp-GE8 Pol-1 (SEQ ID NO:14), Tthi Pol (SEQ ID NO:15), Tag Pol-3 (SEQ ID NO:16), Tfu Pol-2 (SEQ ID NO:17), Thy Pol-2 (SEQ ID NO:18), Tli Pol-2 (SEQ ID NO:19), Tsp-GE8 Pol-2 (SEQ ID NO:20), Pab Pol-II (SEQ ID NO:21), Mtu-CDC1551 DnaB (SEQ ID NO:22), Mtu-H37Rv DnaB (SEQ ID NO:23), Rma DnaB (SEQ ID NO:24), Ter DnaE-1 (SEQ ID NO:25), Ssp GyrB (SEQ ID NO:26), Mfl GyrA (SEQ ID NO:27), Mgo GyrA (SEQ ID NO:28), Mkas GyrA (SEQ ID NO:29), Mle-TN GyrA (SEQ ID NO:30), Mma GyrA (SEQ ID NO:31), Ssp DnaX (SEQ ID NO:32), Pab Lon (SEQ ID NO:33), Mja PEP (SEQ ID NO:34), Afu-FRR0163 PRP8 (SEQ ID NO:35), Ani-FGSCA4 PRP8 (SEQ ID NO:36), Cne-A PRP8 (SEQ ID NO:37), Hca PRP8 (SEQ ID NO:38), Pch PRP8 (SEQ ID NO:39), Pex PRP8 (SEQ ID NO:40), Pvu PRP8 (SEQ ID NO:41), Mtu-H37Rv RecA (SEQ ID NO:42), Mtu-So93 RecA (SEQ ID NO:43), Mfl RecA (SEQ ID NO:44), Mle-TN RecA (SEQ ID NO:45), Nsp-PCC7120 RIR1 (SEQ ID NO:76), Ter RIR1-1 (SEQ ID NO:46), Pab RIR1-1 (SEQ ID NO:47), Pfu RIR1-1 (SEQ ID NO:48), Chy RIR1 (SEQ ID NO:49), Mth RIR1 (SEQ ID NO:50), Pab RIR1-3 (SEQ ID NO:51), Pfu RIR1-2 (SEQ ID NO:52), Ter RIR1-2 (SEQ ID NO:53), Ter RIR1-4 (SEQ ID NO:54), CIV RIR1 (SEQ ID NO:55), Ctr VMA (SEQ ID NO:56), Sce VMA (SEQ ID NO:57), Tac-ATCC25905 VMA (SEQ ID NO:58), Ssp DnaB (SEQ ID NO:59).

Putative ('theoretical') inteins can also be used within the invention, provided they are able to catalyze the required N,S acyl transfer reaction. This property can be established experimentally based on the ability of intein-fused polypeptides to splice in the presence of thiophenol or other thiols. These putative inteins include, but are not limited to, Gth DnaB (GenBank accession number 078411), Ppu DnaB (GenBank accession number P51333), Mfl RecA (GenBank accession number not given), Mle DnaB (GenBank accession number CAA17948.1), Mja KIbA (GenBank accession number Q58191), Pfu KIbA (PF_949263 in UMBI), Pfu IF2 (PF_1088001 in UMBI), Pho Lon (GenBank accession number Baa29538.1), Mja r-Gyr (GenBank accession number G64488), Pho RFC (GenBank accession number F71231), Pab RFC-2 (GenBank accession number C75198), Mja RtcB (GenBank accession number Q58095), Pho VMA (NT01PH1971 in Tigr), AP-APSE1 dpol (AAF03988.1 in NCBI), Bde-JEL197 RPB2 (ABC17934 in NCBI), CbP-C-St RNR (BAE47774 in NCBI), CCy Hyp1-Csp-1 (EAZ88681.1 in NCBI), CCy Hyp1-Csp-2 (ACB52109.1 in NCBI), Cne-AD PRP8 (AAX39419 in NCBI), Cth-ATCC27405 TerA (ACG65137.1 in NCBI), Ctr ThrRS (CZ284364 in NCBI), Dhan GLT1 (AAW82371.1 in NCBI), Dra Snf2 (7471820 in NCBI), Hwa MCM-3 (YP_003131067 in NCBI), Hwa PolB-1 (CAJ51833 in NCBI), Mca MupF (NP_852755 in NCBI0, Mja Klba (Q58191 in NCBI), Mja PEP (ZP_00175589 in NCBI), Mja RFC-1 (YP_659332 in NCBI), Mja RFC-3 (ABR56888.1 in NCBI), Mja RNR-1 (ACI21751.1 in NCBI), Mja RNR-2 (H64403 in NCBI), Mja rPol A" (CAJ53490 in NCBI), Mja UDP GD (ZP_01799256.1 in NCBI), MP-Be gp51 (AAR89772 in NCBI), Mtu SufB (NP_855148.1 in NCBI), Npu GyrB (ZP_01622715.1 in NCBI), Pfu RIR1-2 (ABM31270 in NCBI), Pho CDC21-2 (YP_137231 in NCBI), Pho CDC21-2 (CAJ53749.1 in NCBI), Pho LHR (ZP_06213967.1 in NCBI), Pho Pol-II (YP_001403293.1 in NCBI), Pho RadA (YP_288864 in NCBI), PI-PKoI (YP_003246437.1 in NCBI), Pko Pol-1 (ZP_06214852.1 in NCBI), Psy Fha (AAY90835 in NCBI), ShP-Sfv-5 Primase (ABY49883.1 in NCBI), Ssp DnaX (ZP_03271562.1 in NCBI), Ter DnaE-1 (YP_002730690.1 in NCBI), Ter DnaE-2 (YP_002616796 in NCBI), Ter RIR1-4 (ZP_03765843.1 in NCBI), and Tth-HB8-2 DnaE (TIGR contig:4743).

In other variations, intein sequences that can be used within the invention can be derived by fusing together the N-fragment and C-fragment of a naturally occurring split intein. Split inteins include, but are not limited to, Ssp DnaE (SEQ ID NO:60-SEQ ID NO:61), Neq Pol (SEQ ID NO:62-SEQ ID NO:63), Asp DnaE (SEQ ID NO:64-SEQ ID NO:65), Npu-PCC73102 DnaE (SEQ ID NO:66-SEQ ID NO:67), Nsp-PCC7120 DnaE (SEQ ID NO:68-SEQ ID NO:69), Oh DnaE (SEQ ID NO:70-SEQ ID NO:71), Ssp-PCC7002 DnaE (SEQ ID NO:72-SEQ ID NO:73), Tvu DnaE (SEQ ID NO:74-SEQ ID NO:75).

In preferred embodiments, the intein fused to the C-terminus of the target polypeptide is an engineered variant of a natural intein, which has been modified so that the ability of the intein to undergo C-terminal splicing is minimized or prevented. According to strategies well known in the art, this can be achieved, for example, by using an intein comprising no C-extein unit, or by removing the C-terminal amino acid in the intein (most typically, an asparagine or histidine residue), or by mutating the latter to an unreactive amino acid residue (e.g., via substitution to an alanine or glycine). Examples of the latter approach are provided in Section 6, Examples, below.

In the precursor polypeptide, the nature of the amino acids residues preceding the intein can affect the extent of premature hydrolysis during protein expression as well as the efficiency by which the reagents of formula (I) through (VIII) undergo ligation to the C-terminus of the target polypeptide. In particular, the inventors found that the last three C-terminal amino acid residues preceding the intein in the precursor polypeptide can affect the ligation efficiency, whereas the last residue preceding the intein can also affect the extent of premature hydrolysis of the precursor polypeptide during protein expression. These amino acid residues are here referred to as "I-1", "I-2", and "I-3" to indicate, respectively, the last, penultimate and antepenultimate amino acid residue of the target polypeptide prior to the intein protein in the primary sequence of the precursor polypeptide. For example, it was found that when the intein is Mxe GyrA intein (SEQ ID NO:1), most efficient functionalization of the target polypeptide was achieved with the I-1 amino acid residue being F, Y, A, T, W, N, R or Q, the I-2 amino acid residue being G, P, or S, and the I-3 amino acid residue being G or S. It is expected that different structure-reactivity trends may be observed in the case of other inteins. In these case, studies such as those described in (Frost, Vitali et al. 2013) can be carried out to identify optimal C-terminal amino acid residues for maximizing the efficiency of ligation of reagents (I)-(VIII) to a target polypeptide.

Accordingly, in specific embodiments, the precursor polypeptide consists of Mxe GyrA intein (SEQ ID NO:1), or an engineered variant thereof, fused to the C-terminus of a target polypeptide comprising one or more of the features selected from: I-1 is F, Y, A, T, W, N, R or Q; 1-2 is G, P, or S; 1-3 is G or S.

In some embodiments, a genetically encoded affinity tag is fused to the C-terminus of the intein. In this way, the precursor target polypeptide-intein fusion protein can be readily isolated after recombinant expression using affinity chromatography. This procedure can also facilitate the isolation of the desired functionalized polypeptide product via, for example, first immobilizing the polypeptide-intein fusion protein onto a solid support (e.g., affinity resin bead), and then contacting the immobilized protein to the reagents of formula (I) through (VIII) so that, upon functionalization, the functionalized polypeptide is released in the solution and the intein remains bound to the solid support.

In some embodiments, an affinity tag is linked to the N-terminus of the target polypeptide. In this way, the target thioester-comprising polypeptide or the precursor target polypeptide-intein fusion protein can be readily purified using affinity chromatography. This procedure can also facilitate the isolation of the functionalized target polypeptide via, for example, immobilizing the precursor polypeptide-intein fusion protein onto a solid support (e.g., affinity resin bead), and contacting the immobilized protein to the reagents of formula I-IV, so that, upon functionalization, the intein is released in the solution and the functionalized polypeptide remains bound to the solid support. After washing of the solid support, the functionalized polypeptide can then be recovered by competitive elution or by changing the buffer composition (e.g., changing pH).

Several affinity tags are known in the art, which can be used for the specific applications described above. Examples of these affinity tags include, but are not limited to, a polyhistidine tag (e.g., HHHHHH) (SEQ ID NO:77), an Avi-Tag (SGLNDIFEAQKIEWHELEL) (SEQ ID NO:78), a FLAG tag (DYKDDDDK) (SEQ ID NO:79), a Strep-tag II (WSHPQFEK) (SEQ ID NO:80), a c-myc tag (EQKLISEEDL) (SEQ ID NO:81), a S-Tag (KETAAAKFERQHMDS) (SEQ ID NO:82), a calmodulin-binding peptide (KRRWKKNFIAVSAANRFKKI-SSSGAL) (SEQ ID NO:83), a streptavidin-binding peptide (MDEKTTGWRG-GHVVEGLAGELEQLRARL-EHHPQGQREP) (SEQ ID NO:84), a chitin-binding domain (CBD), a glutathione S-transferase (GST), and a maltose-binding protein (MBP).

In addition to direct fusion of the target polypeptide to the N-terminus of an intein as described above, a target thioester-comprising polypeptide may be produced in certain embodiments by reacting a precursor polypeptide (i.e., an intein-fused target polypeptide) with a thiol, such as, for example, thiophenol, benzyl mercaptan, sodium 2-mercaptoethane sulfonate (MESNA), beta-mercaptethanol, dithiothreitol (DTT), and the like. This reaction results in the formation of a C-terminal thioester polypeptide (with concomitant release of the intein) which can be then functionalized at the C-terminus according to the methods as described above.

In another embodiment, a recombinant intein-fused target polypeptide can be produced by introducing a polynucleotide encoding for the polypeptide construct into an expression vector, introducing the resulting vectors into an expression host, and inducing the expression of the encoded polypeptide. Numerous methods for making nucleic acids encoding peptides of a known or random sequence are known to a person skilled in the art. For example, polynucleotides having a predetermined sequence can be prepared chemically by solid phase synthesis using commercially available equipments and reagents. Polynucleotides can then be amplified using a polymerase chain reaction, digested via endonucleases, and ligated together according to standard molecular biology protocols known in the art (e.g., Sambrook et al. *Molecular Cloning: A Laboratory Manual* (Third Edition), Cold Spring Harbor Press, 2001). Suitable vectors for protein expression include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell, and, if replication is desired, which is replicable and viable in the relevant host can be used. A large number of expression vectors and expression hosts are known in the art, and many of these are commercially available. Expression hosts that may be used for the preparation of the precursor polypeptide within the invention include any system that supports the transcription, translation, and/or replication of a nucleic acid. These systems include prokaryotes such as bacteria (e.g., *Escherichia coli*) and eukaryotes such as yeast, insect, and mammalian cells. These systems also include lysates of prokaryotic cells (e.g., bacterial cells) and lysates of eukaryotic cells (e.g., yeast, insect, or mammalian cells). These systems also include in vitro transcriptiontranslation systems, many of which are commercially available. The choice of the expression vector and host system depends on the type of application intended for the methods provided herein and a person skilled in the art will be able to select a suitable expression host based on known features and application of the different expression hosts.

As demonstrated herein, the functionalization methods provided herein can be used for the site-specific functionalization of a target polypeptide in vitro, in a complex biologically-derived medium (e.g., cell lysate), or in the context of a cell (e.g., in a cell (for example, in the cytoplasm or another cellular compartment) or on a cell (for example, associated with the exterior surface of a cell membrane)).

In the context of a cell, a thioester-comprising polypeptide can be generated by recombinantly expressing the target polypeptide as fused to the N-terminus of a natural intein, or engineered variant thereof, so that a thioester group is transiently formed at the junction between the polypeptide and the intein by intein-catalyzed N,S acyl transfer as described above. The resulting precursor polypeptide can be soluble (i.e., not membrane-bound), covalently bound to a membrane of the cell, or non-covalently associated to a membrane of the cell.

Accordingly, in some embodiments, the precursor polypeptide that is to be targeted for functionalization using the methods provided herein is in a cell. In this case, the functionalization procedure involves (i) exposing the cell to one of the reagents of formula (I), (II), (III), (IV), (V), (VI), (VII), or (VIII), and (ii) allowing the precursor polypeptide to react with the chemical reagent so that a covalent linkage between the chemical reagent and the target polypeptide is formed with concomitant release of the intein. Virtually any cells, prokaryotic or eukaryotic, which can be transformed with heterologous DNA or RNA to direct the expression of a precursor polypeptide consisting of a target polypeptide C-terminally fused to an intein, and which can be grown in culture, may be used within the scope of the invention. Accordingly, in one embodiment, the cell is a bacterial cell, while in another it is a eukaryotic cell. Examples of bacterial cells include but are not limited to *Escherichia coli*. Examples of eukaryotic cell include but are not limited to a mammalian cell, a Zebrafish cell, a *Xenopus* cell, a *C. elegans* cell, a yeast cell (e.g., *Saccharomyces cerevisiae*), an insect cell (e.g., *Drosophila* cell), a plant cell, and the like.

In other embodiments, derivatives of the reagents (I), (II), (III), (IV), (V), (VI), (VII), and (VIII) such as salts, esters, N-protected, S-protected derivatives are provided. Such derivatives can be routinely produced by one of ordinary skill in the art.

5.2. Kits

The invention also provides kits for carrying out the methods provided herein for functionalization of peptides and/or proteins, for ligation of peptides or proteins to various chemical species and/or for immobilization of functionalized peptides or proteins onto one or more surfaces. Such kits may comprise a carrier, such as a box, carton, tube or the like, adapted to receive one or more containers, such as vials, tubes, ampules, bottles and the like. Containers of the kit comprise selected amounts of one or more compounds, reagents, or buffers or solvents useful in carrying out a method provided herein.

In specific embodiments, a kit comprises one or more reagents of chemical formula (I) through (VIII). In more specific embodiments, a kit can comprise one or more reagents of chemical formula (I) through (VIII), in which the R group is selected from the group consisting of a functional group, a label molecule, a tag molecule, an affinity label molecule, a photoaffinity label, a dye, a chromophore, a fluorescent molecule, a phosphorescent molecule, a chemiluminescent molecule, an energy transfer agent, a photocrosslinker molecule, a redox-active molecule, an isotopic label molecule, a spin label molecule, a metal chelator, a metal-comprising moiety, a heavy atom-comprising-moiety, a radioactive moiety, a contrast agent molecule, a MRI contrast agent, an isotopically labeled molecule, a PET agent, a photocaged moiety, a photoisomerizable moiety, a chemically cleavable group, a photocleavable group, an electron dense group, a magnetic group, an amino acid, a polypeptide, an antibody or antibody fragment, a carbohydrate, a monosaccharide, a polysaccharide, a nucleotide, a nucleoside, a DNA, a RNA, a siRNA, a polynucleotide, an antisense polynucleotide, a peptide nucleic acid (PNA), a fatty acid, a lipid, a cofactor, biotin, a biotin analogue, a biomaterial, a polymer, a water-soluble polymer, a polyethylene glycol derivative, a water-soluble dendrimer, a cyclodextrin, a small molecule, a protein-, nucleic acid-, or receptor-binding molecule, a biologically active molecule, a drug or drug candidate, a cytotoxic molecule, a solid support, a surface, a resin, a nanoparticle, a quantum dot, and any combination thereof.

Kits may further comprise one or more additional components necessary for carrying out one or more particular applications of the methods and reagents of the present invention. For example, the kit may comprise one or more chemical species which are to be ligated to a peptide or protein employing the methods and/or reagents provided herein. In a specific example, the kit can provide one or more reagents of formula (I) through (VIII), in which the R group comprises one or more bioorthogonal functional groups selected from the group consisting of hydrazino (—NHNH$_2$), hydrazido (—C(O)NHNH$_2$), oxyamino (—ONH$_2$), azido (—N$_3$), alkynyl (—C≡CR'), alkenyl (—CR'=CR'$_2$), phosphine (—PR$_2$), 2-cyanobenzothiazole, tetrazole, tetrazine, aziridine, dihydroazirine, and norbornadiene group. The kit can comprise a chemical species or a functionalized solid support which can be reacted with the bioorthogonal group in order to attach the target polypeptide to the chemical species or solid support. In another specific example, the kit can provide one or more reagents of formula (I) through (VIII), in which the R group comprises a fluorescent molecule selected from the group consisting of a coumarin derivative (e.g., Alexa™ dyes), a naphthalene derivative, a pyrene derivative, a fluorescein derivative, a rhodamine derivative, a naphthoxanthene derivative, a phenanthridine derivative, a boron difluoride dipyrromethene (BODIPY) derivative, a cyanine derivatives (e.g., CyDyes), a phthalocyanine derivative, and a oxazine derivative (e.g., resorufin). In another specific example, the kit can provide one or more reagents of formula (I) through (VIII), in which the R group comprises a biotin or biotin analogue.

In general, kits may also comprise one or more buffers, reaction containers or tools for carrying out the functionalization of the target polypeptide(s), means for purification of the functionalized polypeptide(s), control samples, one or more sets of instructions, and the like.

In another specific embodiment, the invention provides a kit which comprises reagents, buffers and one or more other components for forming a thioester-comprising polypeptide by intein-mediated splicing. Such kits can also comprise, in certain embodiments, a surface upon which the protein thioester is formed for subsequent reaction with a reagent provided herein. Such kits can further comprise one or more reagents provided herein, one or more buffers for carrying out a method provided herein, one or more surfaces for immobilization of the functionalized polypeptide(s), one or more chemical species for attachment to the functionalized polypeptide(s), one or more means for assaying the functionalized polypeptide(s) and instructions for carrying out one or more of the methods provided herein.

In a specific embodiment, a kit is provided for forming a covalent linkage between a polypeptide and a chemical species, the kit comprising:
   a. at least one chemical reagent of formula (I), (II), (III), (IV), (V), (VI), (VII), or (VIII), or a salt of the reagent; and
   b. one or a plurality of containers, wherein at least one container comprises a pre-selected or desired amount of at least one of the chemical reagents of formula (I), (II), (III), (IV), (V), (VI), (VII), or (VIII), or a salt of the reagent, wherein:
      i. R is the chemical species which is to be covalently linked to the polypeptide,
      ii. $R_1$ is hydrogen, a substituted or non-substituted aliphatic group, or a substituted or non-substituted aryl group,
      iii. X, Y, W, and Z are hydrogen and/or non-hydrogen substituents selected from the group consisting of alkyl, heteroatom-comprising alkyl, alkenyl, heteroatom-comprising alkenyl, alkynyl, heteroatom-comprising alkynyl, aryl, heteroatom-comprising aryl, alkoxy, heteroatom-comprising alkoxy, aryloxy, heteroatom-comprising aryloxy, halo, —OH, —OR', —SR', —COOH, —COOR', —CONR'$_2$, —NR'$_2$, —NO$_2$, —SO$_3$R', —SO$_2$NR$_2$', —C≡N, —O—C≡N, —P(O)$_k$R' where k is 2 or 3, and —S—C≡N, wherein each R' is independently an H, an aliphatic, a substituted aliphatic, an aryl, or a substituted aryl group,
      iv. n is 2 or 3, and
      v. L is a linker or a linker group selected from the group consisting of a single bond, $C_1$-$C_{24}$ alkyl, $C_1$-$C_{24}$ substituted alkyl, $C_1$-$C_{24}$ substituted heteroatom-comprising alkyl, $C_1$-$C_{24}$ substituted heteroatom-comprising alkyl, $C_2$-$C_{24}$ alkenyl, $C_2$-$C_{24}$ substituted alkenyl, $C_2$-$C_{24}$ substituted heteroatom-comprising alkenyl, $C_2$-$C_{24}$ substituted heteroatom-comprising alkenyl, $C_2$-$C_{24}$ alkynyl, $C_2$-$C_{24}$ substituted alkynyl, $C_2$-$C_{24}$ substituted heteroatom-comprising alkynyl, $C_2$-$C_{24}$ substituted heteroatom-comprising alkynyl, $C_5$-$C_{24}$ aryl, $C_5$-$C_{24}$ substituted aryl, $C_5$-$C_{24}$ substituted heteroatom-comprising aryl, $C_5$-$C_{24}$ substituted heteroatom-comprising aryl, $C_1$-$C_{24}$ alkoxy, $C_5$-$C_{24}$ aryloxy, —O—, —S—, —NR'—, —C(O)—, —C(S)—, —C(O)NR'—, —C(S)NR'—, —N(R')C(O)—, —S(O)$_k$— where k is 1, 2, or 3, —S(O)$_k$N(R')—, —N(R')C(O)N(R')—, —N(R')C(S)N(R')—, —N(R')S(O)$_k$N(R')—, —N(R')—N=, —C(R)=N—, —C(R')=N—N(R')—, —C(R')=N—N=, —C(R')$_2$—N=N—, and —C(R')$_2$—N(R')—N(R)—, wherein each R' is independently an H, an aliphatic, a substituted aliphatic, an aryl, or a substituted aryl group.

In another embodiment of the kit, R is a functional group, a label molecule, a tag molecule, an affinity label molecule, a photoaffinity label, a dye, a chromophore, a fluorescent molecule, a phosphorescent molecule, a chemiluminescent molecule, an energy transfer agent, a photocrosslinker molecule, a redox-active molecule, an isotopic label molecule, a spin label molecule, a metal chelator, a metal-comprising moiety, a heavy atom-comprising-moiety, a radioactive moiety, a contrast agent molecule, a MRI contrast agent, an isotopically labeled molecule, a PET agent, a photocaged moiety, a photoisomerizable moiety, a chemically cleavable group, a photocleavable group, an electron dense group, a magnetic group, an amino acid, a polypeptide, an antibody or antibody fragment, a carbohydrate, a monosaccharide, a polysaccharide, a nucleotide, a nucleoside, a DNA, a RNA, a siRNA, a polynucleotide, an antisense polynucleotide, a peptide nucleic acid (PNA), a fatty acid, a lipid, a cofactor, biotin, a biotin analogue, a biomaterial, a polymer, a water-soluble polymer, a polyethylene glycol derivative, a water-soluble dendrimer, a cyclodextrin, a small molecule, a protein-, nucleic acid-, or receptor-binding molecule, a biologically active molecule, a drug or drug candidate, a cytotoxic molecule, a solid support, a surface, a resin, a nanoparticle, or a quantum dot, or any combination thereof.

In another embodiment of the kit, R is a bioorthogonal functional group selected from the group consisting of —NR'NR'$_2$, —C(O)NR'NR'$_2$, —ONH$_2$, —N$_3$, —C≡CR', —CR'=CR'$_2$, —PR'$_2$, 2-cyanobenzothiazole, tetrazole, tetrazine, aziridine, dihydroazirine, norbornadiene groups, wherein each R' is independently H, aliphatic, substituted aliphatic, aryl, or substituted aryl group.

In another embodiment of the kit, R is a fluorescent molecule selected from the group consisting of a coumarin derivative, a naphthalene derivative, a pyrene derivative, a fluorescein derivative, a rhodamine derivative, a naphthoxanthene derivative, a phenanthridine derivative, a boron difluoride dipyrromethene (BODIPY) derivative, a cyanine derivatives, a phthalocyanine derivative, and a oxazine derivative.

In another embodiment of the kit, R is biotin, a biotin analogue, or a perfluorinated alkyl chain $CF_3$—$(CF_2)_m$— where m=3-15

In another embodiment of the kit, the at least one reagent comprises at least one compound selected from the group consisting of:
   a. a compound of formula (I), wherein:
      $R_1$, X, Y, and Z are hydrogen atoms,
      R is —ONH$_2$ or N$_3$, and L is a single bond:
b. a compound of formula (I), wherein:
R₁, X, Y, and Z are hydrogen atoms,
R is —ONH₂, and
L is a linker or linker group of formula

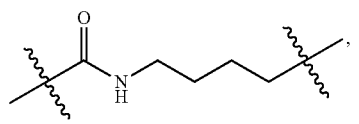 (IX)

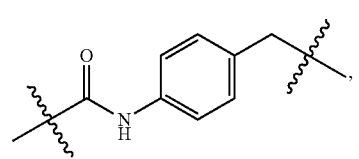 (X)

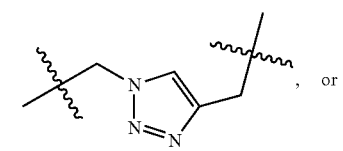 (XI), or

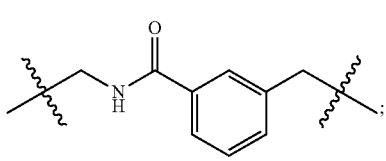 (XII);

c. a compound of formula (I), wherein:
R₁, X, Y, and Z are hydrogen atoms,
R is 7-amino-4-(trifluoromethyl)-2H-chromen-2-one, and
L is —C(O)NHCH₂C(O)—; or
d. a compound of formula (I), wherein:
R₁, X, Y, and Z are hydrogen atoms,
R is biotin, and
L is —C(O)NH(CH₂)₃NH—.

In another embodiment of the kit, the kit further comprises a functionalized solid support with which the functional group R reacts. Functionalized solid supports and surfaces with which functional groups R can react are well known in the art.

In another specific embodiment, a kit is provided for immobilizing a polypeptide to a surface, the kit comprising:
a. a chemical reagent of formula (Ib), (IIb), (Mb), (IVb), (Vb), (VIb), (VIIb), or (VIM):

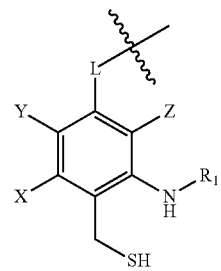 (Ib)

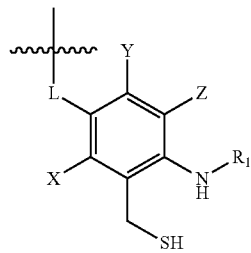 (IIb)

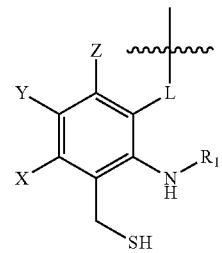 (IIIb)

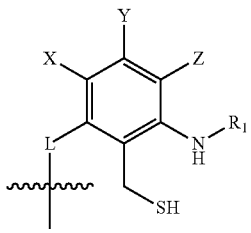 (IVb)

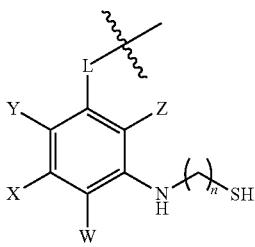 (Vb)

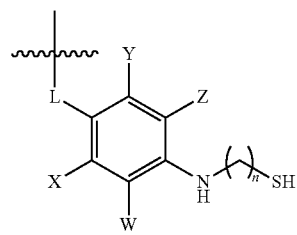 (VIb)

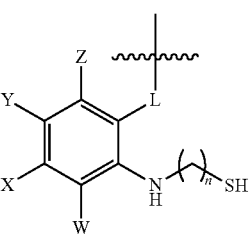 (VIIb)

-continued

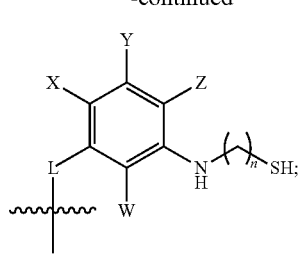
(VIIIb)

and
b. one or a plurality of containers, wherein at least one container comprises a surface to which a chemical reagent of formula (Ib), (IIb), (Mb), (IVb), (Vb), (VIb), (VIIb), or (VIIIb) is covalently bound, and wherein:
  v. $R_1$ is hydrogen, a substituted or non-substituted aliphatic group, or a substituted or non-substituted aryl group,
  vi. X, Y, W, and Z are hydrogen or non-hydrogen substituents selected from the group consisting of alkyl, heteroatom-comprising alkyl, alkenyl, heteroatom-comprising alkenyl, alkynyl, heteroatom-comprising alkynyl, aryl, heteroatom-comprising aryl, alkoxy, heteroatom-comprising alkoxy, aryloxy, heteroatom-comprising aryloxy, halo, —OH, —OR', —SR, —COOH, —COOR', —CONR'$_2$, —NR'$_2$, —NO$_2$, —SO$_3$R', —SO$_2$NR$_2$', —C≡N, —O—C≡N, —P(O)$_k$R' where k is 2 or 3, and —S—C≡N, and wherein each R' is independently an H, an aliphatic, a substituted aliphatic, an aryl, or a substituted aryl group,
  vii. n is 2 or 3, and
  viii. L is a linker or a linker group selected from the group consisting of a single bond, $C_1$-$C_{24}$ alkyl, $C_1$-$C_{24}$ substituted alkyl, $C_1$-$C_{24}$ substituted heteroatom-comprising alkyl, $C_1$-$C_{24}$ substituted heteroatom-comprising alkyl, $C_2$-$C_{24}$ alkenyl, $C_2$-$C_{24}$ substituted alkenyl, $C_2$-$C_{24}$ substituted heteroatom-comprising alkenyl, $C_2$-$C_{24}$ substituted heteroatom-comprising alkenyl, $C_2$-$C_{24}$ alkynyl, $C_2$-$C_{24}$ substituted alkynyl, $C_2$-$C_{24}$ substituted heteroatom-comprising alkynyl, $C_2$-$C_{24}$ substituted heteroatom-comprising alkynyl, $C_5$-$C_{24}$ aryl, $C_5$-$C_{24}$ substituted aryl, $C_5$-$C_{24}$ substituted heteroatom-comprising aryl, $C_5$-$C_{24}$ substituted heteroatom-comprising aryl, $C_1$-$C_{24}$ alkoxy, $C_5$-$C_{24}$ aryloxy, —O—, —S—, —NR'—, —C(O)—, —C(S)—, —C(O)NR'—, —C(S)NR'—, —N(R')C(O)—, —S(O)$_k$— where k is 1, 2, or 3, —S(O)$_k$N(R')—, —N(R')C(O)N(R')—, —N(R')C(S)N(R')—, —N(R')S(O)$_k$N(R')—, —N(R')—N—, —C(R)═N—, —C(R')═N—N(R')—, —C(R')═N—N═, —C(R')$_2$—N═N—, and —C(R')$_2$—N(R')—N(R')—, wherein each R' is independently an H, an aliphatic, a substituted aliphatic, an aryl, or a substituted aryl group.

In one embodiment of the kit, the surface is a solid support.

In another embodiment of the kit, the solid support is a resin, a nanoparticle, or the surface of a microarray.

5.3. Compounds and Compositions

Compounds and compositions are also provided. These compounds and compositions can be used as reagents (also referred to herein as "chemical reagents") according to the methods provided herein.

Examples 1-4 set forth methods that can be used to synthesize the compounds and compositions.

A compound (also referred to herein as a "reagent", a "chemical reagent" or a "composition") is provided having the formula (I), (II), (III), (IV), (V), (VI), (VII) or (VIII):

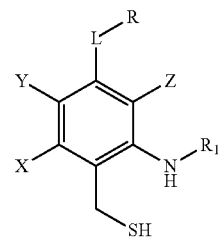
(I)

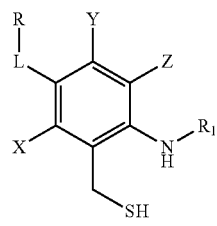
(II)

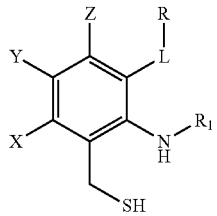
(III)

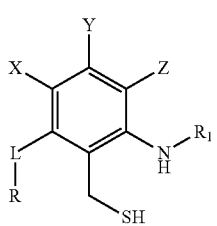
(IV)

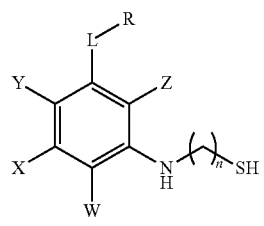
(V)

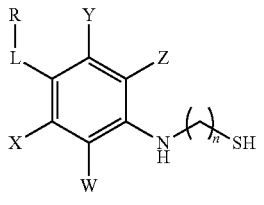
(VI)

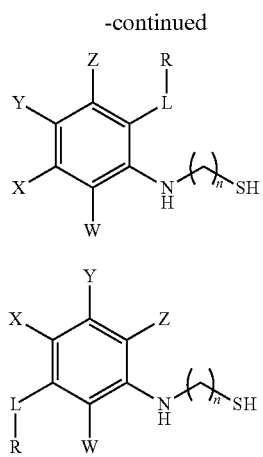

or a salt thereof, wherein:
i. R is a functional group, a label molecule, a tag molecule, an affinity label molecule, a photoaffinity label, a dye, a chromophore, a fluorescent molecule, a phosphorescent molecule, a chemiluminescent molecule, an energy transfer agent, a photocrosslinker molecule, a redox-active molecule, an isotopic label molecule, a spin label molecule, a metal chelator, a metal-comprising moiety, a heavy atom-comprising-moiety, a radioactive moiety, a contrast agent molecule, a MRI contrast agent, an isotopically labeled molecule, a PET agent, a photocaged moiety, a photoisomerizable moiety, a chemically cleavable group, a photocleavable group, an electron dense group, a magnetic group, an amino acid, a polypeptide, an antibody or antibody fragment, a carbohydrate, a monosaccharide, a polysaccharide, a nucleotide, a nucleoside, a DNA, a RNA, a siRNA, a polynucleotide, an antisense polynucleotide, a peptide nucleic acid (PNA), a fatty acid, a lipid, a cofactor, biotin, a biotin analogue, a biomaterial, a polymer, a water-soluble polymer, a polyethylene glycol derivative, a water-soluble dendrimer, a cyclodextrin, a small molecule, a protein-, nucleic acid-, or receptor-binding molecule, a biologically active molecule, a drug or drug candidate, a cytotoxic molecule, a solid support, a surface, a resin, a nanoparticle, a quantum dot, or any combination thereof,
ii. $R_1$ is hydrogen, a substituted or non-substituted aliphatic group, or a substituted or non-substituted aryl group,
iii. X, Y, W, and Z are hydrogen and/or non-hydrogen substituents selected from the group consisting of alkyl, heteroatom-comprising alkyl, alkenyl, heteroatom-comprising alkenyl, alkynyl, heteroatom-comprising alkynyl, aryl, heteroatom-comprising aryl, alkoxy, heteroatom-comprising alkoxy, aryloxy, heteroatom-comprising aryloxy, halo, —OH, —OR', —SR', —COOH, —COOR', —CONR'$_2$, —NR'$_2$, —NO$_2$, —SO$_3$R', —SO$_2$NR$_2$', —Cl\1, C≡N, —P(O)$_k$R' where k is 2 or 3, and —S—C≡N, wherein each R' is independently H, alkyl, or substituted alkyl,
iv. n is 2 or 3; and
v. L is a linker or a linker group selected from the group consisting of a single bond, $C_1$-$C_{24}$ alkyl, $C_1$-$C_{24}$ substituted alkyl, $C_1$-$C_{24}$ substituted heteroatom-comprising alkyl, $C_1$-$C_{24}$ substituted heteroatom-comprising alkyl, $C_2$-$C_{24}$ alkenyl, $C_2$-$C_{24}$ substituted alkenyl, $C_2$-$C_{24}$ substituted heteroatom-comprising alkenyl, $C_2$-$C_{24}$ substituted heteroatom-comprising alkenyl, $C_2$-$C_{24}$ alkynyl, $C_2$-$C_{24}$ substituted alkynyl, $C_2$-$C_{24}$ substituted heteroatom-comprising alkynyl, $C_2$-$C_{24}$ substituted heteroatom-comprising alkynyl, $C_5$-$C_{24}$ aryl, $C_5$-$C_{24}$ substituted aryl, $C_5$-$C_{24}$ substituted heteroatom-comprising aryl, $C_5$-$C_{24}$ substituted heteroatom-comprising aryl, $C_1$-$C_{24}$ alkoxy, $C_5$-$C_{24}$ aryloxy, —O—, —S—, —NR'—, —C(O)—, —C(S)—, —C(O)NR'—, —C(S)NR'—, —N(R') C(O)—, —S(O)$_k$— where k is 1, 2, or 3, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')— group, where each R' is independently an H, an aliphatic, a substituted aliphatic, an aryl, or a substituted aryl group.

In one embodiment of the compound, R is a bioorthogonal functional group selected from the group consisting of NR'NR'$_2$, —C(O)NR'NR'$_2$, —ONH$_2$, —N$_3$, —C≡CR', —CR'=CR'$_2$, —PR'$_2$, 2-cyanobenzothiazole, tetrazole, tetrazine, aziridine, dihydroazirine, and norbornadiene groups, and each R' is independently an H, an aliphatic, a substituted aliphatic, an aryl, or a substituted aryl group.

In another embodiment of the compound, R is a fluorescent molecule selected from the group consisting of a coumarin derivative, a naphthalene derivative, a pyrene derivative, a fluorescein derivative, a rhodamine derivative, a naphthoxanthene derivative, a phenanthridine derivative, a boron difluoride dipyrromethene (BODIPY) derivative, a cyanine derivatives, a phthalocyanine derivative, and an oxazine derivative.

In another embodiment of the compound, R is biotin, a biotin analogue, or a perfluorinated alkyl chain $CF_3$—$(CF_2)_m$— where m=3-15.

In another embodiment of the compound, R is a poly (ethyleneglycol) molecule.

In another embodiment of the compound, R is a resin or a nanoparticle.

In another embodiment of the compound, R is a functionalized surface.

In another embodiment of the compound, $R_1$, X, Y, and Z are hydrogen atoms,

L is selected from the group consisting of —C(O)NR'—, —C(O)NR'CH$_2$C(O)—, —C(O)NR'(CH$_2$)n-, and —C(O)NR'(CH$_2$—CH$_2$—O)n-, R' is a hydrogen, alkyl or aryl group, and n is an integer number from 1 to 15.

In another embodiment of the compound, R is selected from the group consisting of biotin, a biotin analogue, and a coumarin derivative.

In another embodiment of the compound, the compound has formula (I), wherein:
a. $R_1$, X, Y, and Z are hydrogen atoms,
R is —ONH$_2$ or —N$_3$, and
L is a single bond;
b. $R_1$, X, Y, and Z are hydrogen atoms,
R is —ONH$_2$, and
L is a linker or linker group of formula

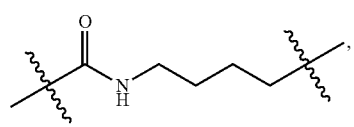

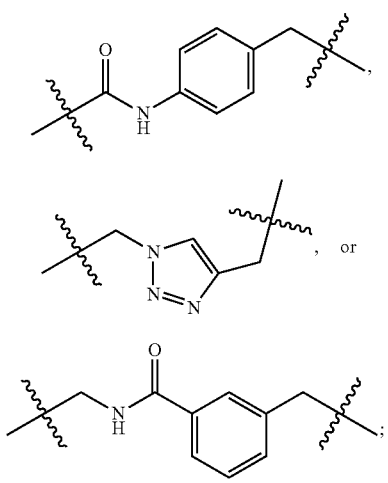

c. $R_1$, X, Y, and Z are hydrogen atoms,
R is 7-amino-4-(trifluoromethyl)-2H-chromen-2-one, and
L is —C(O)NHCH$_2$C(O)—; or
d. $R_1$, X, Y, and Z are hydrogen atoms,
R is biotin, and
L is —C(O)NH(CH$_2$)$_3$NH—.

The compositions and reagents encompassed by the invention may comprise one or more chiral centers. Accordingly, the compounds are intended to include racemic mixtures, diastereomers, enantiomers, and mixture enriched in one or more stereoisomer. When a group of substituents is disclosed herein, all the individual members of that group and all subgroups, including any isomers, enantiomers, and diastereomers are intended to be included in the disclosure. Additionally, all isotopic forms of the compounds provided herein are intended to be included in the disclosure. For example, it is understood that any one or more hydrogens in a molecule disclosed herein can be replaced with deuterium or tritium.

A skilled artisan will appreciate that starting materials, biological materials, reagents, synthetic methods, purification methods, analytical methods, assay methods, and biological methods other than those specifically exemplified can be employed in the practice of the invention. All art-known functional equivalents of any such materials and methods are intended to be included in the invention.

Unless otherwise indicated, the disclosure is not limited to specific molecular structures, substituents, synthetic methods, reaction conditions, or the like, as such may vary. It is to be understood that the embodiments are not limited to particular compositions or biological systems, which can, of course, vary.

5.4. Uses for the Methods, Kits and Compositions

Efficient methods for C-terminal functionalization of a protein can be used for protein labeling or immobilization under non-disruptive conditions.

The methods provided herein for protein C-terminal labeling and/or immobilization are characterized by faster reaction kinetics than current methods known in the art, and have high labeling efficiencies, in particular at short reaction times. According to the methods provided herein, much lower concentrations of reagents (either the target C-terminal thioester protein, or the labeling reagent, or both) are needed to achieve satisfactory yields of the desired protein-functionalized product. Furthermore, thiol catalysts such as, for example, thiophenol, mercaptoethanol, or MESNA, are not required to expedite and/or increase the yields of the protein-functionalization methods provided herein. The methods provided herein can be these used at the intracellular level for in vivo protein labeling applications. Furthermore, the rapid protein labeling methods provided herein enable the detection and isolation of transient or short-lived protein species in the context of proteomic or cell biology studies. Finally, certain proteins with limited stability, which may not be compatible with the need for high reagent or catalyst concentrations associated with other methods known in the art, can be functionalized and/or immobilized using the methods provided herein.

5.5. Terms and Expressions

The terms and expressions that are employed herein are used as terms of description and not of limitation, and there is no intention that in the use of such terms and expressions of excluding any equivalents of the features shown and described and portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to those skilled in the art, and that such modifications and variations are considered to be within the scope of the invention as defined by the appended claims.

Unless otherwise stated herein, all technical and scientific terms used herein have the same meaning as commonly understood by one of ordinary skill in the art to which the disclosure pertains.

The term "functional group" as used herein refers to a contiguous group of atoms that, together, may undergo a chemical reaction under certain reaction conditions. Examples of functional groups are, among many others, —OH, —NH$_2$, —SH, —(C═O)—, —N$_3$, —C≡CH.

The term "aliphatic" is used in the conventional sense to refer to an open-chain or cyclic, linear or branched, saturated or unsaturated hydrocarbon group, including but not limited to alkyl group, alkenyl group and alkynyl groups. The term "heteroatom-comprising aliphatic" as used herein refer to an aliphatic moiety where at least one carbon atom is replaced with a non-carbon atom, e.g., oxygen, nitrogen, sulphur, selenium, phosphorus, or silicon, and typically oxygen, nitrogen, or sulphur.

The terms "alkyl" and "alkyl group" as used herein refer to a linear, branched, or cyclic saturated hydrocarbon typically comprising 1 to 24 carbon atoms, preferably 1 to 12 carbon atoms, such as methyl, ethyl, n-propyl, isopropyl, n-butyl, isobutyl, t-butyl, octyl, decyl and the like. The term "heteroatom-comprising alkyl" as used herein refers to an alkyl moiety where at least one carbon atom is replaced with a heteroatom, e.g., oxygen, nitrogen, sulphur, phosphorus, or silicon, and typically oxygen, nitrogen, or sulphur.

The terms "alkenyl" and "alkenyl group" as used herein refer to a linear, branched, or cyclic hydrocarbon group of 2 to 24 carbon atoms, preferably of 2 to 12 carbon atoms, comprising at least one double bond, such as ethenyl, n-propenyl, isopropenyl, n-butenyl, isobutenyl, octenyl, decenyl, and the like. The term "heteroatom-comprising alkenyl" as used herein refer to an alkenyl moiety where at least one carbon atom is replaced with a heteroatom.

The terms "alkynyl" and "alkynyl group" as used herein refer to a linear, branched, or cyclic hydrocarbon group of 2 to 24 carbon atoms, preferably of 2 to 12 carbon atoms, comprising at least one triple bond, such as ethynyl, n-propynyl, and the like. The term "heteroatom-comprising alkynyl" as used herein refer to an alkynyl moiety where at least one carbon atom is replaced with a heteroatom.

The terms "aryl" and "aryl group" as used herein refer to an aromatic substituent comprising a single aromatic or multiple aromatic rings that are fused together, directly linked, or indirectly linked (such as linked through a methylene or an ethylene moiety). Preferred aryl groups comprise 5 to 24 carbon atoms, and particularly preferred aryl groups comprise 5 to 14 carbon atoms. The term "heteroatom-comprising aryl" as used herein refer to an aryl moiety where at least one carbon atom is replaced with a heteroatom.

The terms "alkoxy" and "alkoxy group" as used herein refer to an aliphatic group or a heteroatom-comprising aliphatic group bound through a single, terminal ether linkage. Preferred aryl alkoxy groups comprise 1 to 24 carbon atoms, and particularly preferred alkoxy groups comprise 1 to 14 carbon atoms. The terms "aryloxy" and "aryloxy group" as used herein refer to an aryl group or a heteroatom-comprising aryl group bound through a single, terminal ether linkage. Preferred aryloxy groups comprise 5 to 24 carbon atoms, and particularly preferred aryloxy groups comprise 5 to 14 carbon atoms.

The terms "halo" and "halogen" are used in the conventional sense to refer to a fluoro, chloro, bromo or iodo substituent. By "substituted" it is intended that in the alkyl, alkenyl, alkynyl, aryl, or other moiety, at least one hydrogen atom is replaced with one or more "substituents".

The term "substituents" refers to a contiguous group of atoms. Examples of "substituents" include, but are not limited to: alkoxy, aryloxy, alkyl, heteroatom-comprising alkyl, alkenyl, heteroatom-comprising alkenyl, alkynyl, heteroatom-comprising alkynyl, aryl, heteroatom-comprising aryl, alkoxy, heteroatom-comprising alkoxy, aryloxy, heteroatom-comprising aryloxy, halo, hydroxyl (—OH), sulfhydryl (—SH), substituted sulfhydryl, carbonyl (—CO—), thiocarbonyl, (—CS—), carboxy (—COOH), amino (—NH$_2$), substituted amino, nitro (—NO$_2$), nitroso (—NO), sulfo (—SO$_2$—OH), cyano (—C≡N), cyanato (—O—C≡N), thiocyanato (—S—C≡N), formyl (—CO—H), thioformyl (—CS—H), phosphono (—P(O)OH$_2$), substituted phosphono, and phospho (—PO$_2$).

The term "contact" as used herein with reference to interactions of chemical units indicates that the chemical units are at a distance that allows short range non-covalent interactions (such as Van der Waals forces, hydrogen bonding, hydrophobic interactions, electrostatic interactions, dipole-dipole interactions) to dominate the interaction of the chemical units. For example, when a protein is 'contacted' with a chemical species, the protein is allowed to interact with the chemical species so that a reaction between the protein and the chemical species can occur.

The term "bioorthogonal" as used herein with reference to a reaction, reagent, or functional group, indicates that such reaction, reagent, or functional group does not exhibit significant or detectable reactivity towards biological molecules such as those present in a bacterial, yeast or mammalian cell. The biological molecules can be, e.g., proteins, nucleic acids, fatty acids, or cellular metabolites.

In general, the term "mutant" or "variant" as used herein with reference to a molecule such as polynucleotide or polypeptide, indicates that such molecule has been mutated from the molecule as it exists in nature. In particular, the term "mutate" and "mutation" as used herein indicates any modification of a nucleic acid and/or polypeptide that results in an altered nucleic acid or polypeptide. Mutations include any process or mechanism resulting in a mutant protein, enzyme, polynucleotide, or gene. A mutation can occur in a polynucleotide or gene sequence, by point mutations, deletions, or insertions of single or multiple nucleotide residues. A mutation in a polynucleotide includes mutations arising within a protein-encoding region of a gene as well as mutations in regions outside of a protein-encoding sequence, such as, but not limited to, regulatory or promoter sequences. A mutation in a coding polynucleotide such as a gene can be "silent", i.e., not reflected in an amino acid alteration upon expression, leading to a "sequence-conservative" variant of the gene. A mutation in a polypeptide includes but is not limited to mutation in the polypeptide sequence and mutation resulting in a modified amino acid. Non-limiting examples of a modified amino acid include a glycosylated amino acid, a sulfated amino acid, a prenylated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like.

The term "engineer" refers to any manipulation of a molecule that result in a detectable change in the molecule, wherein the manipulation includes but is not limited to inserting a polynucleotide and/or polypeptide heterologous to the cell and mutating a polynucleotide and/or polypeptide native to the cell.

The term "nucleic acid molecule" as used herein refers to deoxyribonucleotides, deoxyribonucleosides, ribonucleosides or ribonucleotides and polymers thereof in either single- or double-stranded form. By way of example only, such nucleic acids and nucleic acid polymers include, but are not limited to, analogues of natural nucleotides that have similar properties as a reference nucleic acid and oligonucleotide analogues including, but are not limited to, PNA (peptidonucleic acid), analogues of DNA used in antisense technology (phosphorothioates, phosphoroamidates, and the like).

The terms "polypeptide," "peptide" and "protein" as used herein refer to any chain of two or more amino acids bonded in sequence, regardless of length or post-translational modification. That is, a description directed to a polypeptide applies equally to a description of a peptide and a description of a protein, and vice versa Amino acid residues include residues resulting from natural and unnatural amino acids. The terms "polypeptide," "peptide" and "protein" apply to naturally-occurring amino acid polymers as well as to amino acid polymers in which one or more amino acid residues is an unnatural amino acid. Additionally, such "polypeptides," "peptides" and "proteins" include amino acid chains of any length, including full length proteins, wherein the amino acid residues are linked by covalent peptide bonds or other linkages. The terms "target polypeptide", "thioester-comprising polypeptide", or "target thioester-comprising polypeptide" as used herein refer to a polypeptide that is to be targeted for functionalization according to the protein functionalization methods provided herein. The target polypeptide can be a polypeptide produced synthetically or recombinantly or via a combination of synthetic and recombinant methods.

The term "precursor polypeptide" or "intein-fused target polypeptide" as used herein refers to a polypeptide construct in which the target polypeptide is C-terminally fused to an intein protein or an engineered variant thereof. According to their common use in the art, the term "peptide" refers to any polypeptide consisting of 2 and up to 40-50 amino acid residues, whereas the term "protein" refers to any polypeptide consisting of more than 50 amino acid residues. These definitions are however not intended to be limiting.

The term "intein" and "intein domain" as used herein refers to a naturally occurring or artificially constructed polypeptide sequence embedded within a precursor protein that can catalyze a splicing reaction during post-translational processing of the protein. The NEB Intein Registry (http://www.neb.comnebinteins.html) provides a list of known inteins. The term "split intein" as used herein refers to an intein that has two or more separate components not fused to one another.

The term "splicing" as used herein refers to the process involving the cleavage of the main backbone of an intein-comprising polypeptide by virtue of a reaction or process catalyzed by an intein or portions of an intein. "N-terminal splicing" refers to the cleavage of a polypeptide chain fused to the N-terminus of an intein, such reaction typically involving the scission of the thioester (or ester) bond formed via intein-catalyzed N→S (or N→O acyl) transfer, by action of a nucleophilic functional group or a chemical species comprising a nucleophilic functional group. "C-terminal splicing" refers to the cleavage of a polypeptide chain fused to the C-terminus of an intein. "Self-splicing" as used herein refers to the process involving the cleavage of an intein from a polypeptide, within which the intein is embedded.

The term "ligation" as used herein refers to a process or reaction that lead to formation of a bond connecting two molecules. The term 'intein-mediated ligation' as used herein refers to a chemical bond-forming reaction that involves a nucleophilic substitution at a thioester or ester linkage formed via intein-catalyzed N→S or N→O acyl transfer, by action of a nucleophilic functional group or a chemical species comprising a nucleophilic functional group.

The terms "vector" and "vector construct" as used herein refer to a vehicle by which a DNA or RNA sequence (e.g., a foreign gene) can be introduced into a host cell, so as to transform the host and promote expression (e.g., transcription and translation) of the introduced sequence. A common type of vector is a "plasmid", which generally is a self-contained molecule of double-stranded DNA that can be readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. The terms "express" and "expression" refer to allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

The term "fused" as used herein means being connected through one or more covalent bonds. The term "bound" as used herein means being connected through non-covalent interactions. Examples of non-covalent interactions are van der Waals, hydrogen bond, electrostatic, and hydrophobic interactions. Thus, a "polypeptide tethered to a solid support" refers to a polypeptide that is connected to a solid support (e.g., surface, resin bead) either via non-covalent interactions or through covalent bonds.

The terms "label molecule" or "tag molecule" as used herein refer to a molecule that allows detection of or monitoring of the structural changes in another molecule covalently bound to it (e.g., a target polypeptide) by physical detection methods. Examples of physical detection methods include, but are not limited to, mass spectrometry, UV absorbance, fluorescence, luminescence, circular dichroism, nuclear magnetic resonance, and the like. The terms "affinity label molecule" or "affinity tag" as used herein refer to a molecule that allows for the isolation of another molecule covalently bound to it (e.g., a target polypeptide) by physical methods. Examples of physical methods include, but are not limited to, affinity chromatography, reverse-phase chromatography, ion-exchange chromatography, gel-permeation chromatography, and related techniques. The term "photoaffinity label," as used herein, refers to a label molecule with a functional group, which, upon exposure to light, forms a linkage with a molecule for which the label molecule has an affinity. By way of example only, such a linkage may be covalent or non-covalent.

The term "dye," as used herein, refers to a soluble, coloring substance that comprises a chromophore. The term "chromophore," as used herein, refers to a molecule that absorbs light of visible wavelengths, UV wavelengths or IR wavelengths. The term "fluorescent molecule" as used herein refers to a molecule which upon excitation emits photons and is thereby fluorescent. The term "chemiluminescent molecule" as used herein refers to a molecule that emits light as a result of a chemical reaction without the addition of heat. By way of example only, luminol (5-amino-2,3-dihydro-1,4-phthalazinedione) reacts with oxidants like hydrogen peroxide ($H_2O_2$) in the presence of a base and a metal catalyst to produce an excited state product (3-aminophthalate, 3-APA) subsequently resulting in the release of detectable light. The term "energy transfer agent," as used herein, refers to a molecule that can either donate or accept energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The term "photocrosslinker," as used herein, refers to a compound comprising two or more functional groups which, upon exposure to light, are reactive and form a covalent or non-covalent linkage with two or more monomeric or polymeric molecules.

The term "redox-active agent," as used herein, refers to a molecule that oxidizes or reduces another molecule, whereby the redox active agent becomes reduced or oxidized. Examples of redox active agent include, but are not limited to, ferrocene, quinones, $Ru^{2+/3+}$ complexes, $Co^{2+/3+}$ complexes, and $Os^{2+/3+}$ complexes.

The term "spin label," as used herein, refers to molecules that comprise an atom or a group of atoms exhibiting an unpaired electron spin (i.e., a stable paramagnetic group) that can be detected by electron spin resonance spectroscopy and can be attached to another molecule. Such spin-label molecules include, but are not limited to, nitryl radicals and nitroxides, and may be single spin-labels or double spin-labels.

The term "heavy atom," as used herein, refers to an atom that is usually heavier than carbon. Such ions or atoms include, but are not limited to, silicon, tungsten, gold, lead, and uranium.

The term "radioactive moiety," as used herein, refers to a group whose nuclei spontaneously release nuclear radiation, such as alpha, or beta particles, or gamma radiation.

The term "contrast agent" as used herein refer to a molecule that can be visualized, typically in the context of a biological tissue or organism, by means of physical detection methods. The term "MRI contrast agent" as used herein refer to a molecule that can be visualized, typically in biological tissue or organism, by means of magnetic resonance imaging (MRI). An example of an MRI contrast agents are gadolinium-based complexes and the like. The term "PET agent" as used herein refer to a molecule that can be visualized, typically in biological tissue or organism, by means of positron emission tomography (PET).

The term "photocaged moiety," as used herein, refers to a group that, upon illumination at certain wavelengths, covalently or non-covalently binds ions or other molecules. The term "photoisomerizable moiety," as used herein, refers to a group wherein upon illumination with light changes from one isomeric form to another.

The term "chemically cleavable group" as used herein refers to a functional group that breaks or cleaves upon exposure to acid, base, oxidizing agents, reducing agents, chemical inititiators, or radical initiators. The term "photocleavable group" as used herein refers to a functional group that breaks or cleaves upon exposure to light.

The term "electron dense group," as used herein, refers to a group that scatters electrons when irradiated with an electron beam. Such groups include, but are not limited to, ammonium molybdate, bismuth subnitrate cadmium iodide, carbohydrazide, ferric chloride hexahydrate, hexamethylene tetramine, and potassium ferricyanide.

The term "antibody fragment" as used herein refers to any form of an antibody other than the full-length form. Antibody fragments include but are not limited to Fv, Fc, Fab, and (Fab')2, single chain Fv (scFv), diabodies, combinations of CDRs, heavy chains, or light chains, bispecific antibodies, and the like.

The term "biotin analogue," or also referred to as "biotin mimic," as used herein, is any molecule, other than biotin, that binds with high affinity to avidin and/or streptavidin.

The term "isotopically labeled molecule" as used herein refers to a molecule that contains an enriched amount of a specific isotope of (a) certain atom(s) within the molecule as compared to the normal isotopic distribution. Example of "isotopically labeled molecules" include, but are not limited to, molecules comprising enriched amounts of $^2H$, $^3H$, $^{13}C$, $^{14}N$, $^{18}F$, and the like.

The term "polymer," as used herein, refers to a molecule composed of repeated subunits. Such molecules include, but are not limited to, proteins, polypeptides, peptides, polynucleotides, polysaccharides, polyalkylene glycols, polyethylene, and polystyrene. As used herein, the term "water soluble polymer" refers to any polymer that is soluble in aqueous solvents. Such water soluble polymers include, but are not limited to, polyethylene glycol, polyethylene glycol propionaldehyde, mono $C_1$-$C_{10}$ alkoxy or aryloxy derivatives thereof monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, serum albumin, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. By way of example only, coupling of such water soluble polymers to the target polypeptide according to the methods provided herein, result in changes including, but not limited to, increased water solubility, increased or modulated serum half-life, increased or modulated therapeutic half-life relative to the unmodified form, increased bioavailability, modulated biological activity, extended circulation time, modulated immunogenicity, modulated physical association characteristics including, but not limited to, aggregation and multimer formation, altered receptor binding, altered binding to one or more binding partners, and altered receptor dimerization or multimerization.

The term "biologically active molecule" as used herein refers to any molecule that can affect any physical or biochemical properties of a biological system, pathway, molecule, or interaction relating to an organism, including but not limited to, viruses, bacteria, bacteriophage, transposon, prion, insects, fungi, plants, animals, and humans. Examples of biologically active molecules include, but are not limited to, peptides, proteins, DNA, RNA, small-molecule drugs, polysaccharides, carbohydrates, lipids, radionuclides, toxins, cells, viruses, liposomes, microparticles and micelles.

The term "drug" as used herein refers to any substance used in the prevention, diagnosis, alleviation, treatment, or cure of a disease or condition.

The term "cytotoxic" as used herein, refers to a compound that harms cells.

The term "solid support" is used in the commonly accepted meaning to indicate any solid inorganic or organic, polymeric or non-polymeric material onto which a given molecule can be covalently or non-covalently bound so that the molecule is immobilized onto the solid support. Non-limiting examples of "solid supports" include, but are not limited to, solid and semisolid matrixes, such as aerogels and hydrogels, resins, beads, biochips (including thin film coated biochips), microfluidic chip, a silicon chip, multi-well plates (also referred to as microtitre plates or microplates), membranes, cells, conducting and nonconducting metals, glass (including microscope slides) and magnetic supports. Other non-limiting examples of "solid supports" used in the methods and compositions described herein include silica gels, polymeric membranes, particles, derivatized plastic films, derivatized glass, controlled pore glass, derivatized silica, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like. The configuration of the solid support can be in the form of beads, spheres, particles, gel, a membrane, or a surface. In certain embodiments, the solid supports used in the methods and compositions described herein are solid supports used for surface analysis such as surface acoustic wave devices or devices utilizing evanescent wave analysis, such as surface plasmon resonance analysis.

The term "resin" as used herein refers to high molecular weight, insoluble polymer beads. By way of example only, such beads may be used as supports for solid phase peptide synthesis, or sites for attachment of molecules prior to purification.

The term "nanoparticle" as used herein refers to a particle that has a particle size between about 500 nm (i.e., 500 nm±10%) to about 1 nm (i.e., 1 nm±10%).

The term "about" as used herein to modify a number, quantity, amount or numerical measurement, refers to a variation in that number, quantity, amount or numerical measurement from ±0% to ±10%.

The following examples are offered by way of illustration and not by way of limitation.

6. EXAMPLES

Example 1

Synthesis of 1-amino-2-(mercaptomethyl)-aryl compounds

This example demonstrates the synthesis of a protected amino-thiol-aryl precursor for the generation of 1-amino-2-(mercaptomethyl)-aryl reagents for protein/peptide functionalization using the methods provided herein. In particular, this example illustrates how a N- and S-protected, carboxylic group-functionalized 1-amino-2-(mercaptomethyl)-aryl moiety can be prepared, which can be used as synthetic intermediate for the preparation of reagents of general formula (I) as further described in Examples 6 and 7. Additionally, this protected intermediate can converted to 3-amino-4-(mercaptomethyl)benzoic acid, which can be used directly for protein functionalization as described in Example 10.

As described in the scheme of FIG. 2, the target compound 3-amino-4-(mercaptomethyl)benzoic acid (11) was prepared starting from methyl 3-amino-4-methylbenzoate 1 in five steps. Boc protection of the amino group in 1, followed by benzylic bromination, followed by substitution of the benzyl bromide with triphenylmethylmercaptan yielded the N-Boc,S-trityl protected intermediate 2. Hydrolysis of the methyl ester group in 2 under basic conditions then yielded the corresponding N-Boc,S-trityl protected benzoic acid derivative which contains a convenient carboxy group functionality that can be used for coupling various chemical entities (fluorescent dyes, affinity tags, etc.) to the 1-amino-2-(mercaptomethyl)-aryl moiety as described in Examples 6 and 7. This intermediate 7 was de-protected under acidic conditions to yield the carboxylic acid functionalized reagent 11, which can be used directly for protein functionalization.

Experimental Details for Example 1

Methyl 3-amino-4-methylbenzoate 1 (9.7 g, 58.7 mmol) and di-tert-butyl dicarbonate (17 mL, 74 mmol, 1.2 eq) were dissolved in 200 mL dry THF. The reaction mixture was heated to reflux for 72 h. Solvent was removed by rotovap to afford a pink-white solid. The crude material was suspended in 30 mL ice-cold hexanes and filtered to afford methyl 3-((tert-butoxycarbonyl)amino)-4-methylbenzoate as a white solid, (99% yield). $^1$H NMR (500 MHz, CDCl$_3$) δ=8.45 (s, 1H), 7.69 (d, J=7.9 Hz, 1H), 7.21 (d, J=7.9 Hz, 1H), 6.29 (s, 1H), 3.90 (s, 3H), 2.30 (s, 3H), 1.55 ppm (d, J=11.2 Hz, 9H). $^{13}$C NMR (126 MHz, CDCl$_3$) δ=166.97, 152.81, 136.43, 132.60, 130.37, 128.96, 124.90, 121.83, 80.84, 52.04, 28.31, 17.99 ppm. This material (6.63 g, 25 mmol) was dilute in 100 mL carbon tetrachloride and the flask was heated to 70° C. to aid solubility. N-Bromosuccinamide (4.89 g, 27.5 mmol, 1.1 eq) was added. The reaction vessel was equipped with a reflux condenser and irradiated with UV light for 3 hours. The reaction was cooled to room temperature then filtered. The filtrate was dilute in 100 mL DCM, washed with Saturated K$_2$CO$_3$ (aq), Brine, then dried over anhydrous MgSO$_4$. Volatiles were removed to afford methyl 4-(bromomethyl)-3-((tert butoxycarbonyl)amino) benzoate 6.7 g (78%) as a orange-white solid. $^1$H NMR (500 MHz, CDCl$_3$) δ=8.47 (s, 1H), 7.73 (dd, J=8.0, 1.7 Hz, 1H), 7.36 (d, J=8.0 Hz, 1H), 6.75 (s, 1H), 4.50 (s, 2H), 3.91 (s, 3H), 1.55 ppm (s, 9H). $^{13}$C NMR (126 MHz, CDCl$_3$) δ=28.2, 29.9, 52.3, 81.3, 123.8, 125.1, 130.0, 131.5, 131.7, 136.9, 152.6, 166.2 ppm. Methyl 4-(bromomethyl)-3-((tert-butoxycarbonyl)amino)benzoate (6.7 g, 19.59 mmol), Triphenyl-methyl mecaptan (6.49 g, 23.5 mmol, 1.2 eq) and Potassium Carbonate (3.25 g, 23.5 mmol, 1.2 eq) were dissolved in 100 mL dry DMF. The reaction stirred under argon at room temperature for 15 hours, concentrated to 10 mL under reduced pressure, then resuspended in DCM. The solution was washed once with ice-cold H$_2$O, once with Saturated NaHCO$_3$, and finally once with brine. The organic layer was dried over anhydrous MgSO$_4$, filtered, and volatiles were removed to afford a golden-yellow solid methyl 3-((tert-butoxycarbonyl)amino)-4-((tritylthio)methyl)benzoate 2 (10.24 g, 97% crude yield). Material was carried forward without further purification. $^1$H NMR (500 MHz, CDCl$_3$) δ=8.41 (s, 1H), 7.65 (d, J=7.9 Hz, 1H), 7.48 (d, J=8.0 Hz, 5H), 7.34 (t, J=7.8 Hz, 6H), 7.25 (t, J=7.3 Hz, 5H), 7.18 (d, J=8.0 Hz, 1H), 6.72 (s, 1H), 3.88 (s, 3H), 3.21 (s, 2H), 1.56 ppm (d, J=2.5 Hz, 9H). $^{13}$C NMR (126 MHz, CDCl$_3$) δ=166.69, 152.84, 144.09, 136.93, 130.75, 129.34, 128.23, 126.98, 124.89, 123.09, 80.77, 67.42, 52.14, 34.08, 28.38 ppm.

Methyl 3-((tert-butoxycarbonyl)amino)-4-((tritylthio) methyl)benzoate 2 (1.6 g, 2.96 mmol) was dissolved in 37 mL THF. 1.0 M Lithium Hydroxide (aq) (7.54 mL) was added and the reaction mixture stirred under argon at ambient temperature for 48 hours. Following completion, volatiles were removed under reduced pressure and the resulting material was dissolved in ethyl acetate and washed once with 0.25M HCl (aq) and once with brine. The organic layer was dried over anhydrous MgSO$_4$ filtered and concentrated in vacuuo to yield carboxylic acid AMA derivative 7 as an off-white solid (1.6 g, quant. yield). $^1$HNMR (400 MHz, D4-MeOH) δ 7.99 (s, 1H), 7.67 (dd, J=7.97, 1.62 Hz, 1H), 7.43 (q, J=3.13 Hz, 6H), 7.31 (t, J=7.46 Hz, 6H), 7.23 (t, J=7.31 Hz, 3H), 7.09 (d, J=8.07 Hz, 2H), 3.33 (s, 2H), 1.49 ppm (s, 9H).

3-((tert-butoxycarbonyl)amino)-4-((tritylthio)methyl) benzoic acid 7 (175.6 mg, 0.334 mmol) was dissolved in 2 mL anhydrous dichloromethane under argon. Triisopropylsilane (135 uL, 0.668 mmol) was added and the solution was cooled to 0° C. Trifluoroacetic acid (1 mL) was added and the reaction mixture was stirred for 20 minutes before being warmed to room temperature and stirred for another 20 minutes. Volatiles were removed under reduced pressure and the resulting solid was suspended in cold hexanes and filtered. The resulting white solid was collected as trifluoroaceticacetate salt of 3-amino-4-(mercaptomethyl)benzoic acid 11 (Quantitative yield) LCMS [M+H]$^+$ for disulfide C$_{16}$H$_{16}$N$_2$O$_4$S$_2$ calculated 365.43 found 365.68.

Example 2

Synthesis of additional 1-amino-2-(mercaptomethyl)-aryl Compounds

This example demonstrates the synthesis of compounds of general formula (II) which can be used for the purpose of protein/peptide functionalization using the methods provided herein. As described by the scheme in FIG. 3, the desired reagent 3-(mercaptomethyl)-4-amino-benzoic acid (17) from prepared starting from methyl 4-amino-3-methylbenzoate 12 in five steps. Introduction of a tertiary butyl carbamate protecting group to the aryl amino group followed by benzylic bromination and introduction of a thiol functionality through substitution of the benzylic position using the reagent triphenylmethylmercaptan yielded a N-Boc, S-trityl protected intermediate 15. Hydrolysis of the methyl ester to the free carboxylic acid using aqueous lithium hydroxide could provide a convenient chemical handle, which can be used for coupling various chemical entities (fluorescent dyes, affinity tags, etc.) to the aminothiol moiety. The carboxylic acid intermediate 16 was deprotected using trifluoroacetic acid in the presence of triisopropylsilane to yield reagent 17 which was used directly in protein ligation studies in Example 10. It is understood that other regioisomers of the reagents of formula (I) and (II) such as reagents of general formula (III) and (IV), can be prepared in a similar manner.

Experimental Details for Example 2

Methyl 4-amino-3-methylbenzoate 12 (1.0 g, 6.06 mmol) and Di-tert-butyl dicarbonate (1.59 g, 7.27 mmol, 1.2 eq) were dissolved in 20 mL dry THF. The reaction mixture was heated to reflux for 96 hours. Solvent was removed by rotovap to afford a pink-white solid. The crude material was suspended in 30 mL ice-cold hexanes and filtered to afford methyl 4-((tert-butoxycarbonyl)amino)-3-methylbenzoate 13 as a white solid, (1.57 g, 98% yield). This material (1.57 g, 5.93 mmol) was dilute in 20 mL carbon tetrachloride and the flask was heated to 70° C. to aid solubility. N-Bromosuccinamide (1.16 g, 6.53 mmol, 1.1 eq) was added. The reaction vessel was equipped with a reflux condenser and irradiated with UV light for 3 hours. The reaction was cooled to room temperature then filtered. The filtrate was dilute in 100 mL DCM, washed with Saturated $K_2CO_3$ (aq), Brine, then dried over anhydrous $MgSO_4$. Volatiles were removed to afford methyl 3-(bromomethyl)-4-((tert butoxycarbonyl)amino)benzoate 14 (1.78 g, 87%) orange-white solid.

Methyl 3-(bromomethyl)-4-((tert-butoxycarbonyl)amino) benzoate 14 (1.78 g, 5.17 mmol), Triphenyl-methyl mecaptan (1.71 g, 6.2 mmol, 1.2 eq) and Potassium Carbonate (0.857 g, 6.20 mmol, 1.2 eq) were dissolved in 100 mL dry DMF. The reaction stirred under argon at room temperature for 15 hours, concentrated to 10 mL by rotovap, then resuspended in DCM. The solution was washed once with ice-cold $H_2O$, once with Saturated $NaHCO_3$, and finally once with brine. The organic layer was dried over anhydrous $MgSO_4$, filtered, and volatiles were removed to afford a golden-yellow solid methyl 4-((tert-butoxycarbonyl) amino)-3-((tritylthio)methyl)benzoate 15 (80% crude yield). Material was carried forward without further purification.

Methyl 4-((tert-butoxycarbonyl)amino)-3-((tritylthio) methyl)benzoate 15 (0.7 g, 1.29 mmol) was dissolved in 8 mL THF. 1.0 M lithium hydroxide (aq) (3.25 mL) was added and the reaction mixture stirred under argon at ambient temperature for 48 hours. Following completion, volatiles were removed under reduced pressure and the resulting material was dissolved in ethyl acetate and washed once with 0.25M HCl (aq) and once with brine. The organic layer was dried over anhydrous $MgSO_4$ filtered and concentrated in vacuuo to yield carboxylic acid AMA derivative 16 as an off-white solid (0.678 g, quant. yield).

4-((tert-butoxycarbonyl)amino)-3-((tritylthio)methyl) benzoic acid 16 (0.678 g, 1.29 mmol) was dissolved in 6 mL anhydrous dichloromethane under argon. Triisopropylsilane (808 uL, 4 mmol) was added and the solution was cooled to 0° C. 3 mL Trifluoroacetic acid was added and the reaction mixture was stirred for 20 minutes before being warmed to room temperature and stirred for another 20 minutes. Volatiles were removed under reduced pressure and the resulting solid was suspended in cold hexanes and filtered. The resulting white solid was collected as trifluoroaceticacetate salt of 4-amino-3-(mercaptomethyl)benzoic acid 17 (quant. yield) LCMS $[M+H]^+$ for disulfide $C_{16}H_{16}N_2O_4S_2$ calculated 365.43 found 365.56.

Example 3

Synthesis of Oxyamine-Comprising Protein Labeling Reagents

This example demonstrates the synthesis of a protein labeling reagent of general formula (I) comprising a bioorthogonal oxyamine functional group ($-ONH_2$) as the R group. According to the methods described herein, this reagent can be used for linking a target polypeptide to a bioorthogonal oxyamino functionality, which can be used for further coupling a chemical species to the polypeptide via oxime ligation.

As described in the scheme in FIG. 2, methyl ester 2 was reduced to a benzylic alcohol using Lithium Aluminum Hydride. This benzylic alcohol was activated with methanesulfonyl chloride to prepare the mesylate derivative 4 which was then reacted with N-Boc-hydroxylamine to produce the protected intermediate. This compound was subsequently deprotected with trifluoroacetic acid in the presence of triisopropylsilane to yield the oxyamino-containing reagent 8.

Experimental Details for Example 3

2 (20.32 g, 48 mmol) was dissolved in 400 mL anhydrous THF then cooled to 0° C. 1M lithium aluminum hydride in THF solution (52.8 mL, 52.8 mmol, 1.1 eq) was slowly added. The reaction stirred under argon at 0° C. for 3 hours. The reaction was quenched by the slow addition of 3 mL cold $H_2O$ and 1 mL 4 N NaOH(aq) at 0° C. then stirred for 10 min at room temperature. The resulting mixture was concentrated under reduced pressure to 20 mL and taken up in a mixture of 300 mL EtOAc and 30 mL Saturated $NaHCO_3$, agitated to suspend insoluble solids then filtered through a Celite pad. The filtrate was washed once with Saturated $NaHCO_3$ then with brine. The organic layer was dried with anhydrous $MgSO_4$ and volatiles were removed to afford a yellow solid which was purified via flash column chromatography (silica gel, Hex: EtOAc) to afford a yellow oil (18 g, 95% yield). $^1H$ NMR (500 MHz, $CDCl_3$) δ 7.78 (s, 1H), 7.49 (d, J=7.3 Hz, 5H), 7.34 (t, J=7.7 Hz, 5H), 7.26 (t, J=3.0 Hz, 5H), 7.13 (d, J=7.8 Hz, 1H), 7.01 (d, J=7.8 Hz, 1H), 6.73 (s, 1H), 4.63 (s, 2H), 3.17 (s, 2H), 1.54 ppm (s, 9H). $^{13}C$ NMR (126 MHz, $CDCl_3$) δ 153.06, 144.28, 141.49, 136.85, 130.96, 129.35, 128.18, 126.88, 124.50, 122.23, 120.36, 80.49, 67.17, 65.09, 33.91, 28.41 ppm. This material (9.3 g, 18.19 mmol) was dissolved in 100 mL anhydrous DCM and the solution was cooled to 0° C. Methane Sulfonylchloride (1.8 mL, 23.66 mmol, 1.3 eq) and DIPEA (4.2 mL, 23.66 mmol, 1.3 eq) were added. The reaction stirred under argon at 0° C. for 2 hours. Following completion, the reaction mixture was dilute to 300 mL of DCM, washed twice with Saturated $NaHCO_3$, then once with brine. The organic layer was dried over magnesium sulfate and volatiles were removed to afford yellow solid 4 (9.42 g, 88% yield). The material was carried forward without further purification. $^1$H NMR (500 MHz, CDCl3) δ 7.88 (s, 1H), 7.49 (d, J=7.3 Hz, 5H), 7.34 (t, J=7.7 Hz, 5H), 7.26 (d, J=14.6 Hz, 5H), 7.16 (d, J=7.8 Hz, 1H), 7.04 (d, J=9.5 Hz, 1H), 6.75 (s, 1H), 5.18 (s, 2H), 3.17 (s, 2H), 2.90 (s, 3H), 1.54 ppm (s, 9H). $^{13}$C NMR (126 MHz, $CDCl_3$) δ 152.85, 144.14, 137.33, 133.72, 131.28, 129.32, 128.23, 126.97, 126.26, 123.83, 121.95, 80.79, 71.27, 67.32, 38.45, 33.92, 28.40 ppm.

4 (1.06 g, 1.8 mmol) was dissolved in 18 mL dry MeCN. The solution was cooled to 0° C. and tert-Butyl N-Hydroxycarbamate (0.32 g, 2.4 mmol, 1.3 eq) then 1,8-diazabicyclounedec-7-ene (DBU) (0.37 ml, 2.4 mmol, 1.3 eq) were slowly added. The reaction stirred at 0° C. for 1 hour and was then warmed to ambient temperature and stirred under argon overnight. Following completion volatiles were removed and the resulting crude mixture was dissolved in DCM, washed with saturated $K_2CO_3$ (aq) then with brine. The organic layer was dried over anhydrous $MgSO_4$ then concentrated afford a yellow oil. The crude material was purified via flash chromatography (silica gel, Hex:EtOAc) to afford a yellow oil (1.005 g, 89% yield). MS-ESI [M+Na]$^+$ calculated for $C_{37}H_{42}N_2O_5S$ calculated 649.79 found 649.33; $^1$HNMR (400 MHz, $CDCl_3$) δ 7.81 (s, 1H), 7.49 (d, J=7.6 Hz, 6H), 7.32 (q, J=7.6 Hz, 6H), 7.24 (t, J=7.2 Hz, 3H), 7.13 (d, J=7.6 Hz, 2H), 7.02 (dd, J=8 Hz, 1.6 Hz, 1H), 6.74 (s, 1H), 4.79 (s, 2H), 3.17 (s, 1H), 1.54 (s, 9H), 1.46 ppm (s, 4H); $^{13}$CNMR (126 MHz, $CDCl_3$) δ 156.58, 152.91, 144.23, 136.89, 136.29, 130.84, 129.33, 128.16, 126.86, 125.41, 124.17, 122.32, 81.61, 80.46, 77.9, 67.19, 33.95, 28.37, 27.56 ppm. The protected precursor (0.551 g, 0.88 mmol) was dissolved in 9 mL anhydrous DCM. The solution was cooled to 0° C. and triisopropylsilane (TIPS) (0.45 mL, 2.2 mmol) was added followed by the slow addition of 2 mL Trifluoroacetic acid (TFA). The reaction stirred under argon at 0° C. for 30 minutes, then warmed to ambient temperature and concentrated under reduced pressure to afford an off-white solid. This solid was washed with ice-cold hexanes to afford 8 as an off-white solid (0.366 g, quantitative yield). MS-ESI [M+H]$^+$ for disulfide $C_{16}H_{22}N_4O_2S_2$ calculated 367.51 found 367.53. $^1$H NMR (500 MHz, D4 MeOH) δ=7.06 (d, J=8 Hz, 1H), 6.76 (d, J=1.5 Hz, 1H), 6.65 (dd, J=8, 1.5 Hz, 1H), 4.56 (s, 2H), 3.69 (s, 2H), 1.38 ppm (s, 1H); $^{13}$C NMR (126 MHz, D4 MeOH) δ=146.52, 136.56, 130.43, 126.62, 118.90, 117.34, 78.92, 25.84 ppm.

Example 4

Synthesis of an Azide-Containing Protein Labeling Reagent

This example demonstrates the synthesis of a protein labeling reagent of general formula (I) comprising a bioorthogonal azide functional group (—$N_3$) as R group. According to the methods of the invention, this reagent can be used for linking a target polypeptide to a bioorthogonal azide functionality, which can be used for further coupling a chemical species to the polypeptide using methods know in the art (e.g. via Cu(I)-catalyzed azide/alkyne 1,3-dipolar cycloaddition)

As described in the scheme in FIG. 2, mesylate derivative 4 was reacted with sodium azide to produce the protected intermediate 5. This compound was subsequently deprotected with trifluoroacetic acid in the presence of triisopropylsilane to yield the azide-containing reagent 6.

Experimental Details for Example 4

Compound 4 (2.5 g, 4.24 mmol) and sodium azide (0.56 g, 8.6 mmol) were dissolved in anhydrous DMF (30 mL), and the mixture was stirred under argon at ambient temperature for 12 h. The reaction mixture was then dissolved in $CH_2Cl_2$ (150 mL) and washed with saturated $NaHCO_3$ (aq) and with brine. The organic layer was dried over anhydrous $MgSO_4$, filtered, and concentrated under reduced pressure to afford a yellow oil, which was purified on silica gel with hexanes/EtOAc (1:1) as eluent to afford 5 as a yellow oil (2.3 g, quant.). $^1$H NMR ($CDCl_3$, 400 MHz): δ=7.80 (s, 1H), 7.50 (t, J=4.38 Hz, 6H), 7.34 (t, J=7.64 Hz, 6H), 7.25 (t, J=7.28 Hz, 3H), 7.14 (d, J=7.80 Hz, 1H), 6.94 (dd, J=7.98, 1.70 Hz, 1H), 6.76 (s, 1H), 4.28 (s, 2H), 3.17 (s, 2H), 1.55 ppm (s, 9H); $^{13}$C NMR ($CDCl_3$, 126 MHz): δ=152.9, 144.2, 137.2, 135.8, 131.2, 129.3, 128.2, 126.9, 123.2, 121.3, 80.6, 67.2, 54.4, 33.9, 28.4 ppm; MS-ESI: calcd for $C_{32}H_{32}N_4O_2S$: 559.68 [M+Na]$^+$. found: 559.22.

Azide 5 (20 mg, 0.037 mmol) was dissolved in 2 mL anhydrous dichloromethane under Argon. Triisopropylsilane (23.6 uL, 0.117 mmol) was added and the solution was cooled to 0° C. 1 mL Trifluoroacetic acid was added and the reaction mixture was stirred for 20 minutes before being warmed to room temperature and stirred for another 20 minutes. Volatiles were removed under reduced pressure and the resulting solid was washed exhaustively with ice cold hexanes. The resulting yellow oil was collected as trifluoroaceticacetate salt of (2-amino-4-(azidomethyl)phenyl)methanethiol 6 (Quantitative yield) LCMS [M+H]$^+$ for disulfide $C_{16}H_{18}N_8S_2$ calculated 387.50 found 3387.57.

Example 5

Synthesis of Additional Oxyamine-Comprising Protein Labeling Reagents

This example further demonstrates the synthesis of protein labeling reagents of general formula (I) comprising a bioorthogonal oxyamine functional group (—$ONH_2$) as R group. According to the methods described herein, this reagent can be used for functionalizing a target polypeptide with a bioorthogonal oxyamino functionality, which can be used for further coupling a chemical species to the polypeptide via oxime ligation.

As described in the scheme in FIG. 2, azide derivative 5 was reacted with tert-butyl (prop-2-yn-1-yloxy)carbamate via copper catalyzed 1,3-dipolar cyclo-addition. This compound was subsequently deprotected with trifluoroacetic acid in the presence of triisopropylsilane to yield the oxyamino-containing reagent 9. Experimental details for the synthesis of oxyamine-comprising labeling reagents 10A and 10B (FIG. 2) can be found in (Frost, Vitali et al. 2013).

Experimental Details for Example 5

Propargyl bromide (80% by weight in toluene; 1.6 g, 13.44 mmol) was dissolved in dry MeCN (40 mL), and the mixture was cooled to 0° C. tert-Butyl-N-hydroxycarbamate (2.32 g, 17.47 mmol, 1.3 equiv) and DBU (2.61 mL, 17.47 mmol, 1.3 equiv) were added. The reaction mixture was stirred for 20 min at 0° C., then warmed to ambient temperature, and stirred for another 1 h. Volatiles were removed under reduced pressure, and the resulting yellow oil was suspended in $CH_2Cl_2$, washed twice with saturated $NaHCO_3$ (aq) and once with brine, then dried over anhydrous $MgSO_4$. Volatiles were removed under reduced pressure, and the resulting crude material was purified on silica gel (Hexanes/EtOAc 8:1>7:3) to give tert-butyl (prop-2-yn-1-yloxy)carbamate (1.5 g, 65% yield). $^1$H NMR ($CDCl_3$, 400 MHz): δ=7.39 (s, 1H), 4.48 (d, J=2 Hz, 2H), 2.5 (s, 1H), 1.49 ppm (s, 1H); $^{13}$C NMR ($CDCl_3$, 126 MHz): δ=156.5, 82.1, 78.3, 75.6, 63.7, 28.2 ppm.

Compounds 5 (0.1 g, 0.186 mmol) and tert-butyl (prop-2-yn-1-yloxy)carbamate (0.127 g, 0.745 mmol, 4 equiv) were dissolved in $THF/H_2O$ (1:1, 6 mL). $CuSO_4$ (0.045 g, 0.28 mmol, 1.5 equiv) and sodium ascorbate (0.147 g, 0.745 mmol, 4 equiv) were added, and the reaction mixture was stirred at room temperature for 30 min, then dissolved in $CH_2Cl_2$ and washed twice with concentrated ammonium hydroxide, once with saturated $NaHCO_3$ (aq), and once with brine, then dried over anhydrous $MgSO_4$. Volatiles were removed under reduced pressure, and the resulting material was purified on silica gel (hexanes/EtOAc 7:3) to yield a protected precursor (0.094 g, 72% yield). $^1$H NMR ($CDCl_3$, 400 MHz): δ=7.77 (br s, 1H), 7.54 (s, 1H), 7.47 (d, J=4 Hz, 6H), 7.38 (s, 1H), 7.33 (t, J=8 Hz, 6H), 7.26-7.23 (m, 3H), 7.11 (d, J=8 Hz, 1H), 6.68-6.83 (m, 1H), 6.76 (s, 1H), 5.47 (s, 2H), 4.96 (s, 2H), 3.15 (s, 2H), 1.53 (s, 9H), 1.45 ppm (s, 1H); MS-ESI: calculated for $C_{40}H_{45}N_5O_5S$: 730.87 $[M+Na]^+$. found: 730.26.

The protected precursor (0.094 g, 0.133 mmol) was deprotected with TFA in $CH_2Cl_2$, as described above for 6, to afford 9 (0.065 g, quant.). $^1$H NMR ($CD_3OD$, 500 MHz): δ=8.00 (s, 1H), 7.08 (d, J=8 Hz, 1H), 6.71 (d, J=1.5 Hz, 1H), 6.63 (dd, J=8, 1.5 Hz, 1H), 5.468 (s, 2H), 4.933 (s, 2H), 3.671 ppm (s, 2H); $^{13}$C NMR ($CD_3OD$, 126 MHz): δ=146.8, 143.4, 136.4, 131.0, 127.3, 126.0, 118.9, 116.8, 68.9, 54.9, 25.6 ppm; MS-ESI: calculated for disulfide $C_{22}H_{28}N_{10}O_2S_2$: 529.66 $[M+H]^+$. found: 529.18.

Example 6

Synthesis of Coumarin-Comprising Protein Labeling Reagent

This example demonstrates the synthesis of a protein labeling reagent of general formula (I) comprising a fluorescent dye as the R group. According to the methods described herein, this reagent can be used for labeling a target polypeptide with a fluorescent label molecule.

As described in the scheme of FIG. 4, 7-amino-4-(trifluoromethyl)Coumarin 18 was first coupled to N-Boc protected glycine 19. The glycine served as a linker unit and adds an additional amide bond to increase the solubility of the labeling reagent in aqueous buffer. The Boc group on the glycine was removed under acidic conditions to yield a primary amine (compound 21). This intermediate was then coupled to the carboxylic acid functionalized protected intermediate 7 (FIG. 2) to yield the protected intermediate 22. This compound was then deprotected under acidic conditions to yield the fluorescent labeling reagent 23.

Experimental Details for Example 6

7-amino-4-(trifuloromethyl)coumarin 18 (550 mg, 2.4 mmol) and N-Boc-glycine 19 (462.5 mg, 2.64 mmol) were dissolved in 9 mL dry pyridine and the solution was cooled to −15° C. Phosphoryl chloride (245 uL, 2.64 mmol) was slowly added drop wise and the solution was stirred at −15° C. for 1 hour. The reaction mixture was poured into water and extracted with EtOAc. The EtOAc layer was washed once with 10% aqueous citric acid, once with aqueous saturated sodium bicarbonate and once with brine. The organic layer was dried over anhydrous Magnesium Sulfate, filtered, filtered and concentrated under reduced pressure. The crude product was purified by flash column chromatography (silic gel, Hex: EtOAc) to yield 291 mg of desired product 20 (31%) MS (ESI) $[2M+Na]^+$ calculated: 795.72, observed: 796.25.

Product 20 (291 mg, 0.75 mmol) was dissolved in 4 mL anhydrous Dichloromethane and cooled to 0° C. Trifluoroacetic acid (2 mL) was slowly added to the reaction mixture and the solution was stirred at 0° C. for 30 minutes. The reaction mixture was warmed to room temperature and concentrated in vaccuo then re suspended in dichloromethane. The organic layer was washed once with saturated potassium carbonate then once with brine, dried over magnesium sulfate, filtered and concentrated in vaccuo to yield 21 (200 mg, 93%) This material was used without further purification.

Amine 21 (70.78 mg, 0.247 mmol) and the carboxylic acid 7 (100 mg, 0.19 mmol) were dissolved in 2 mL dry DMF. To that solution was added HBTU (108.08 mg, 0.285 mmol) then Triethylamine (39 uL, 0.285 mmol). The reaction mixture was stirred for 18 hr at room temperature then dissolved in Ethyl Acetate and washed once with saturated aqueous ammonium chloride, once with saturated aqueous Sodium Bicarbonate, and once with brine then dried over anhydrous magnesium sulfate, filtered, and concentrated in vaccuo. The crude material was chromatographed on silica gel (Hex:EtOAc) and the resulting material was loaded on a silica plug and eluted with a mixture of 70% dichloromethane, 24% chloroform, 5.4% methanol and 0.6% ammonium hydroxide. Volatiles were removed in vaccuo to yield protected Coumarin-containing reagent 22 (24 mg, 16%). MS (ESI) $[M+Na]^+$ calculated: 816.8, observed: 816.14

22 (24 mg, 0.03 mmol) was dissolved in 0.7 mL of anhydrous $CH_2Cl_2$ and the solution was cooled to 0° C. Triisopropylsilane (18.2 uL, 0.09 mmol) was added followed by the drop wise addition of 300 uL trifluoroacetic acid. The reaction mixture was stirred at 0° C. for 30 min then warmed to room temperature. Volatiles were removed under reduced pressure and the material was washed with ice cold hexanes to yield yellow solid 23 (quantitative yield). LCMS $[M+H]^+$ for disulfide $C_{40}H_{30}F_6N_6O_8S_2$ calculated 901.82 found 901.56.

Example 7

Synthesis of Biotin-Comprising Protein Labeling Reagent

This example demonstrates the synthesis of a protein labeling reagent of general formula (I) comprising a biotin affinity tag as the R group. According to the methods described herein, this reagent can be applied for labeling a target polypeptide with an affinity tag molecule to enable the isolation/immobilization of the polypeptide via affinity chromatography/capturing using, for example, streptavidin-functionalized solid supports.

As described in the scheme in FIG. 5, 1,3-diaminopropane was first coupled to the carboxylic acid functionalized intermediate 7 (FIG. 2) to add a liker to the latter.

Biotin was then coupled to the amine intermediate 24 to yield the protected product 25. This compound was then de-protected to yield the biotin-containing protein labeling reagent 26.

Experimental Details for Example 7

Carboxylic acid 7 (300 mg, 0.57 mmol) was dissolved in 6 mL anhydrous Dichloromethane. To that solution was added HBTU (324.6 mg, 0.856 mmol) then Triethylamine (196 uL, 1.43 mmol). The reaction mixture was cooled to 0° C. and stirred for 30 min. The solution was warmed to room temperature and 1,3-propane diamine (422.5 mg, 5.7 mmol) were added. The reaction mixture was stirred at room temperature for 16 hours then dilute in Dichloromethane and washed twice with saturated aqueous sodium bicarbonate and once with brine then dried over anhydrous Magnesium Sulfate, filtered and concentrated. The resulting crude material was chromatographed on silica gel (70% dichloromethane, 24% chloroform, 5.4% methanol and 0.6% ammonium hydroxide) to yield 24 (75 mg, 23%). MS (ESI) $[M+H]^+$ calculated: 582.3, observed: 582.29.

24 (75 mg, 0.129 mmol) was dissolved in 1.5 mL dry DMF. Biotin (41 mg, 0.167 mmol) was added followed by HBTU (74 mg, 0.19 mmol) and Triethylamine (26.7 uL, 0.19 mmol) and the reaction stirred at room temperature for 8 hours. Following completion the reaction mixture was dissolved in dichloromethane and washed once with water, once with saturated aqueous sodium bicarbonate and once with brine then dried over anhydrous magnesium sulfate, filtered, and concentrated under reduced pressure. The crude mixture was chromatographed on silica gel using a mixture of 70% Dichloromethane, 24% Chloroform, 5.4% methanol and 0.6% ammonium hydroxide to yield 25 (40 mg, 38%) MS (ESI) $[M+H]^+$ calculated: 808.35, observed: 808.1.

25 (40 mg, 0.05 mmol) was dissolved in 0.7 mL of anhydrous $CH_2Cl_2$ and the solution was cooled to 0° C. Triisopropylsilane (30 uL, 0.15 mmol) was added followed by the drop wise addition of 300 uL trifluoroacetic acid. The reaction mixture was stirred at 0° C. for 30 min then warmed to room temperature. Volatiles were removed under reduced pressure and the material was washed with ice cold hexanes to yield yellow solid 26 (quantitative yield). LCMS $[M+H]^+$ for $C_{21}H_{31}N_5O_3S_2$ calculated 466.63 found 466.24.

Example 8

Synthesis of N-(2-mercaptoethyl)-amino-aryl-Based Reagents

This example demonstrates the synthesis of a synthetic intermediate useful for the generation of N-(2-mercaptoethyl)-amino-aryl-based reagents for protein/peptide functionalization of the type (V)-(VIII) according to the methods described herein. In particular, the synthesis of a reagent of the type of compounds of general formula (V) is demonstrated. As shown in Examples 1 and 2, it is understood that similar synthetic procedures as those described in the present example can be applied for preparing other regioisomers of the reagent of type (V), such as reagents of general formula (VI), (VII) and (VIII).

As described in the scheme in FIG. 6, aniline 27 or meta-methyl aniline 28 were converted to the target molecules 30 and 34 respectively in three steps each. Introduction of a chloroethyl functionality was achieved through reductive amination of the aniline precursor with α-chloroacetaldehyde in the presence of sodium cyanoborohydride. Chloride precursors were reacted with potassium thiocyanate and the cyano group was removed with lithium aluminum hydride to generate amino thiol reagents of general formula (V).

Experimental Details for Example 8

Aniline 27 (0.2 g, 2.1 mmol) was dissolved in 10 mL ethanol. To this was added acetic acid (0.126 g, 2.1 mmol) and Sodium Cyanoborohydride (0.264 g, 4.2 mmol). α-Chloroacetaldehyde (0.181 g, 2.31 mmol) was added and the reaction stirred at room temperature for 40 minutes. The reaction was quenched by the addition of cold water and taken up in 100 mL dichloromethane. The organic layer was washed one with water then once with brine, dried over magnesium sulfate, and volatiles were removed under reduced pressure to yield crude 28 (0.327 g, 85% crude yield). This material was carried forward without further purification.

Crude 28 (277 mg, 1.8 mmol) was dissolved in 10 mL anhydrous DMF. To this solution was added Potassium thiocyanate (0.35 g, 3.6 mmol) and the reaction mixture was heated to 80° C. under argon for 12 hr. The reaction mixture was concentrated under reduced pressure and chromatographed in Hexanes: Ethyl Acetate (8:1 to 7:3 gradient) to yield protected precursor 29 (0.1418 g, 44%)

Precursor 29 (0.1418 g, 0.78 mmol) was dissolved in 10 mL anhydrous diethylether and the reaction mixture was cooled to 0° C. A 1.0M solution of lithium aluminum hydride in tetrahydrofuran (0.78 mL) was slowly added. The reaction was stirred at 0° C. for 30 minutes then warmed to room temperature. The reaction mixture was quenched by the slow drop wise addition of 0.1 mL cold water, dried over Magnesium sulfate and filtered through a celite pad to afford product 30 (0.078 g, 65%) $^1$H NMR ($CDCl_3$, 400 MHz): δ=7.20-7.15 (m, 2H), 6.77-6.71 (m, 1H), 6.69-6.67 (d, J=7.6 Hz, 1H), 3.33 (t, J=12.8 Hz, 2H), 2.75 ppm (dd, J=12.8, 6.4 Hz, 2H).

3-methylaniline 31 (0.5 mL, 4.67 mmol) was dissolved in 25 mL ethanol. To this was added acetic acid (0.267 mL, 4.67 mmol) and Sodium Cyanoborohydride (0.323 g, 5.13 mmol). α-Chloroacetaldehyde (0.9 mL, 5.137 mmol) was added and the reaction stirred at room temperature for 4 hours. The reaction was quenched by the addition of cold water and taken up in 100 mL dichloromethane. The organic layer was washed one with water then once with brine, dried over magnesium sulfate, and volatiles were removed under reduced pressure to yield crude 32. This product was chromatographed on silica gel (7:3 Hex: EtOAc) to yield pure 32 (0.78 g, quantitative).

Chloride 32 (0.78 mg, 4.6 mmol) was dissolved in 20 mL anhydrous DMF. To this solution was added Potassium thiocyanate (2.07 g, 21.3 mmol) and the reaction mixture was heated to 80° C. under argon for 12 hr. The reaction mixture was concentrated under reduced pressure and chromatographed in Hexanes: Ethyl Acetate (8:1 to 7:3 gradient) to yield protected precursor 33 (0.493 g, 55.6%)

Precursor 33 (0.493 g, 2.56 mmol) was dissolved in 22 mL anhydrous diethylether and the reaction mixture was cooled to 0° C. A 1.0M solution of lithium aluminum hydride in tetrahydrofuran (2.56 mL) was slowly added. The reaction was stirred at 0° C. for 30 minutes then warmed to room temperature. The reaction mixture was quenched by the slow drop wise addition of 1 mL cold water, dried over Magnesium sulfate and filtered through a celite pad to afford product 34 (0.22 g, 51%).). $^1$H NMR ($CDCl_3$, 500 MHz): δ=7.073 (t, J=8 Hz, 1H), 6.56 (d, J=7.5 Hz, 1H), 6.45 (d, J=8.5 Hz, 2H), 3.34 (t, J=6.5 Hz, 2H), 2.76 (q, J=6.5 Hz, 2H), 2.28 (s, 3H), 1.40 ppm (t, J=8 Hz, 1H). LCMS [M+H]$^+$ for $C_9H_{13}NS$ calculated 168.27 found 168.29.

Example 9

Preparation of C-Terminal Thioester Proteins Via Intein Fusion

This example demonstrates the construction, production, and isolation of precursor polypeptides comprising a reactive C-terminal thioester group. In particular, this example demonstrates the generation a recombinant target polypeptide which comprises a C-terminal thioester group generated by genetic fusion of the polypeptide to the N-terminus of an engineered intein.

For these experiments, the 68-amino acid Chitin-Binding Domain (CBD) of chitinase A1 from *Bacillus circulans* was used as a model target polypeptide. Three different precursor polypeptide constructs, named CBD-1, CBD-2, and CBD-3 (Table 1), were prepared the fusing the gene encoding for CBD to the N-terminus of an engineered variant (N198A) of intein GyrA from *Mycobacterium xenopi*. The C-terminal asparagine of intein GyrA was mutated to an alanine (N198A) to prevent C-terminal splicing of the intein and to allow for the introduction of a polyhistine (His$_6$) tag at the C-terminus of the intein. To produce the precursor proteins prior to the protein labeling reaction according to the methods described herein, the protein constructs were expressed in *E. coli* cells. For the in vitro protein labeling experiments, the proteins were purified using Ni-affinity chromatography and their identity confirmed by MALDI-TOF. For the protein labeling experiments in cell lysate, cell lysate of *E. coli* cells expressing the CDB-intein fusion protein was used. For the in vivo labeling experiments, *E. coli* cells expressing the CDB-intein fusion protein were used.

Example 10

Analysis of Rate and Efficiency of Protein Functionalization with Reagents of General Formulas (I) and (II)

This example demonstrates how a target protein can be chemo-selectively functionalized using reagents of general formula (I) and (II). In particular, this example illustrates the fast kinetics and high efficiency of protein functionalization using amino-thiol reagents of this type.

For these experiments, the intein-fusion protein CBD-3 (Table 1) was used as the precursor target polypeptide and compound 11 (FIG. 2) and compound 17 (FIG. 3) were used as examples of reagents of general formula (I) and (II), respectively. These protein labeling experiments (FIG. 7A) were performed by adding compound 11 and compound 17 at different concentrations (1, 5, and 15 mM) to a solution of CBD-3 protein (100 μM) in potassium phosphate buffer (50 mM potassium phosphate, 150 mM sodium chloride, pH 7.5). The reducing agent TCEP (20 mM) was also added to the solution to prevent thiol oxidation in the reagent and/or in the protein. The reactions were analyzed by MALDI-TOF MS analysis at 24 hours. As shown in FIG. 7C, these analyses showed the clean formation of the desired functionalized protein products, CBD-11 and CBD-17, respectively, with masses corresponding to the expected ones (CBD-11: calculated [M+H]$^+$ m/z: 7976.92; observed [M+H]$^+$ m/z: 7977.13; CBD-17: calculated [M+H]$^+$ m/z: 7976.92; observed [M+H]$^+$ m/z: 7976.33). Identical results were obtained for all the reagent concentrations tested, indicating successful functionalization of the target protein with both 11 and 17 even at the lowest reagent concentration tested (1 mM for 11 and 5 mM for 17). To measure the kinetics of these reactions, the samples were analyzed by

TABLE 1

| Name | Target polypeptide | Intein | C-terminal tag |
|------|--------------------|--------|---------------|
| CBD-1 | Chitin-binding domain-RHG(OpgY)TGSGT- | Mxe GyrA (N198A) | LEHHHHHH SEQ ID NO: 85 |
| CBD-2 | Chitin-binding domain-RHG(pAcF)TGSGT- | Mxe GyrA (N198A) | LEHHHHHH SEQ ID NO: 85 |
| CBD-3 | Chitin-binding domain-GSGY- | Mxe GyrA (N198A) | LEHHHHHH SEQ ID NO: 85 |

The Chitin-Binding Domain (also indicated as 'CBD') corresponds to:

(SEQ ID NO: 86)
MKIEEGKLTNPGVSAWQVNTAYTAGQLVTYNGKTYKCLQPHTSLAGWEPS

NVPALWQLQNNGNNGLEL

Further experimental details for the cloning, recombinant expression, and purification of the CBD-intein fusion constructs can be found in (Smith, Vitali et al. 2011) and in (Satyanarayana, Vitali et al. 2012).

SDS-PAGE gel densitometry at different time points (1, 2, 3, 6, 12, 24 hours). In this reactions, functionalization of the target CBD protein occurs with splicing of the precursor polypeptide (30 kDa) to give the functionalized protein (8 kDa) and spliced intein (22 KDa). Thus, the amount of functionalized protein over time can be quantified via densitometric analysis of the corresponding bands in the SDS-PAGE gel. As summarized in FIG. 7A-C, these experiments demonstrated the fast kinetics of protein functionalization with both reagents and in particular with reagent 11. In the presence of latter, over 50% and 80% labeled protein was obtained after only 3 hours at 5 and 15 mM reagent concentrations. In both cases, nearly quantitative functionalization of the target protein was observed after 12 hours. Compared to 11, reagent 17 exhibited somewhat slower rates of protein functionalization, with quantitative yields being achieved after 24 hours (FIG. 7B). Notably, for all the reactions and all the time points, only the desired product was observed by MALDI-TOF MS. Altogether, these results demonstrate the fast kinetics and high efficiency of protein labeling achievable with reagents of general formula (I) and general formula (II).

Example 11

Functionalization of a Target Protein with a Bioorthogonal Oxyamino Functional Group This example demonstrates how the methods described herein can be used for introducing a non-proteinogenic, bioorthogonal functional group into a target polypeptide. In particular, this example shows how these methods can be used for functionalizing a recombinant protein with a bioorthogonal oxyamino ($-ONH_2$) group. The oxyamine-functionalized protein can then be used to further couple the target polypeptide with another chemical species or to a solid support via methods known in the art (e.g. via oxime ligation of the oxyamine-functionalized protein with a chemical species or solid support functionalized with oxyamine-reactive functional group such as a ketone, aldehyde, or α-keto-acid group).

For these experiments, the intein-fusion protein CBD-1 (Table 1) was used as the precursor target polypeptide and reagent 8 (FIG. 2) was used as an example of a reagent of general formula (I) comprising a bioorthogonal oxyamine ($-ONH_2$) as the R group. The protein labeling reaction (FIG. 11A) was carried out by adding reagent 8 (10 mM) to a solution of purified CBD-1 (100 µM) in phosphate buffer (50 mM, pH 7.5). The extent of protein labeling over time was determined as SDS-PAGE densitometric analysis as described above and formation of the desired oxyamine-functionalized protein was confirmed by MALDI-TOF MS. These experiments show that about 40% and over 60% of the target protein was functionalized after 2 and 5 hours, respectively (FIG. 11B). Also in this case, the desired functionalized protein, CBD-8, was the only product formed in the reaction as determined by MALDI-TOF MS analysis (FIG. 11C).

In another experiment, the intein-fusion protein CDB-3 was made react with different concentrations (1, 5, 15 mM) of the oxyamine-comprising reagent 9 (FIG. 2) under identical conditions as indicated above (100 µM protein, 20 mM TCEP, KPi buffer (pH 7.5), room temperature) (FIG. 12A). These experiments showed clean formation of a single product corresponding to the desired CBD-9 conjugate at all the reagent concentrations tested (CBD-9: calculated [M+H]+ m/z: 8059.03; observed [M+H]+ m/z: 8058.68), as shown by the representative MALDI-TOF MS spectrum provided in FIG. 12C. In addition, even faster protein labeling kinetics were observed for reagent 9 as compared to 8, as summarized in the graph of FIG. 12B. For example, over 85% of protein labeling was achieved with 9 at 1 mM in only 6 hours, whereas nearly quantitative (90-98%) labeling of the target protein was achieved at higher reagent concentration (5 and 15 mM) within only 3 hours (FIG. 12B). Similar results as those observed with 9 were obtained with reagents 10A and 10B (FIG. 2).

Altogether, these results demonstrate the usefulness and efficiency of the methods described herein for labeling a precursor protein with a bio-orthogonal functional group under mild and catalyst-free (i.e. thiol free) reaction conditions. These experiments also show how different linker units can be used to link the reactive 1-amino-2-mercaptomethyl-aryl moiety to a desired R group ($-ONH_2$ group). The different linker units can be useful to improve the physico-chemical properties of the reagents such as their water-solubility and/or varying the spacing distance between the R group and the reactive amino-thiol moiety, according to the specific needs for a given application. For example, the triazole-based linker in reagent 9 improves the water solubility and provides a larger spacing distance between the oxyamino group and the 1-amino-2-mercaptomethyl-aryl moiety as compared to reagent 8.

Example 12

Functionalization of a Target Protein with a Bioorthogonal Azide Functional Group This example provides another demonstration of how the methods described herein can be used for introducing a non-proteinogenic, bioorthogonal functional group into a target polypeptide. In particular, this example shows how these methods can be used for functionalizing a recombinant protein with a bioorthogonal azido ($-N_3$) group. The azide-functionalized protein can then be used to further couple the target polypeptide with another chemical species or to a solid support via methods known in the art (e.g. via Cu(I)-catalyzed ligation of the azide-functionalized protein with a chemical species or solid support containing an alkyne functional group).

For these experiments, the intein-fusion protein CBD-3 (Table 1) was used as the precursor target polypeptide and reagent 6 (FIG. 2) was used as an example of a reagent of general formula (I) comprising a bioorthogonal azido group ($-N_3$) as the R group. The protein labeling reaction was carried out as described in Example 11 by adding reagent 6 (10 mM) to a solution of purified CBD-3 (100 µM) in phosphate buffer (50 mM, pH 7.5). MALDI-TOF MS analysis confirmed the formation of the desired azide-functionalized protein, CBD-6 (calculated: [M+H]+ m/z: 7988.96 observed: [M+H]+ m/z: 7988.72), demonstrating the efficiency of the method toward C-terminal labeling of a protein with a bioorthogonal azide functionality.

Example 13

Protein Labeling with a Fluorescent Probe

This example demonstrates how the methods described herein can be applied for labeling a target protein with a fluorophore molecule. In particular, this example illustrates an embodiment of the invention wherein a coumarin-comprising reagent of general formula (I) was used for covalently linking a fluorescent dye to a protein.

As schematically indicated in FIG. 8A, these protein labeling studies were performed by reacting the coumarin-comprising reagent 23 (FIG. 4) (15 mM) with the intein-fusion protein CBD-2 (100 µM) in potassium phosphate buffer (50 mM KPi, 150 mM NaCl, pH 7.5). TCEP (20 mM) was also added to the solution to prevent thiol oxidation in the reagent or in the protein. As described above, the reactions were analyzed by densitometric analysis of SDS-PAGE gels to measure the extent of protein functionalized and by MALDI-TOF MS to confirm the formation of the desired product. MS analyses revealed the formation of the desired coumarin-functionalized protein, CBD-23 (calculated [M+H]$^+$ m/z: 8823.72 Observed [M+H]$^+$ m/z: 8823.07), as the only product at all the time points tested (1, 5, 12 hours), as indicated by the representative MALDI-TOF spectrum in FIG. 8C. According to SDS-PAGE gel densitometry, the percentage of protein labeling (i.e. percentage of CBD-23 formed) after 1 and 12 hours was estimated to be 40% and 60%, respectively (FIG. 8B, left panel). To further confirm the occurrence of protein labeling with the fluorescent probe, the protein gel was visualized under a fluorescence detector ($\lambda_{ex}$: 365 nm). As shown by the fluorescent imaging gel in FIG. 8B (right panel), this analysis revealed the occurrence of fluorescence only in correspondence to the CBD band, confirming the selective labeling of the target protein with the fluorescent probe. Altogether, these results demonstrate the usefulness and efficiency of the methods described herein for tagging a precursor protein with a fluorescent probe under mild, physiologically relevant reaction conditions. In addition, they demonstrate how this protein functionalization procedure could be carried out without the need for exogenous thiol catalysts. Finally, these results demonstrate how the functionalized protein product could be selectively visualized via fluorescence imaging.

Example 14

Protein Labeling with a Biotin Affinity Tag

This example demonstrates how the methods described herein can be applied for labeling a target protein with an affinity tag molecule. In particular, this example illustrates an embodiment of the invention wherein a biotin-comprising reagent of general formula (I) was used for covalently linking the affinity tag biotin to a protein.

Under standard reaction conditions (50 mM potassium phosphate (pH 7.5), 150 mM sodium chloride, 20 mM TCEP; FIGS. 9A and 13A), the biotin-comprising reagent 26 (FIG. 6) was added to a solution of CBD-3 (100 μM) at different concentrations (1, 5, and 15 mM). As illustrated by the representative MALDI-TOF MS spectra in FIGS. 9C and 13C, the desired functionalized product, CBD-26, was obtained as the only product. The kinetics of these protein labeling reactions were then investigated by measuring the extend of protein labeling over time by SDS-PAGE analysis as described above. As summarized in FIGS. 9B and 13B, these experiments show fast and efficient functionalization of the target protein with the biotinylating reagent within short time. For example, nearly quantitative labeling was achieved in the presence of 5 mM 26 within 6 hours.

In another experiment, a different intein-fusion construct, i.e. CBD-2 (100 μM), was made react with the biotinylating reagent 26 (15 mM) under standard reaction conditions. Also in this case, clean formation of a single product corresponding to the expected mass of the CBD-26 conjugate (calculated [M+H]$^+$ m/z: 8837.93; observed [M+H]$^+$ m/z: 8837.96) was observed at each time point tested (1, 5, 12 hours). Based on SDS-PAGE densitometric analysis, the amount of protein labeling after 1 and 12 hours was determined to be about 50% and >70%, respectively (FIG. 10).

Altogether, these results demonstrate the efficiency of the methods described herein for labeling a target protein with an affinity tag molecule under mild, physiologically relevant conditions and without the need for an exogenous thiol catalysts.

Example 15

Labeling of a Target Protein in Cell Lysate and Isolation of the Functionalized Protein by Affinity Chromatography This example demonstrates how the methods described herein can be used for labeling a target protein in a complex biologically-derived medium such as a cell lysate. In particular, this example shows how a target protein can be labeled with a fluorescent label molecule (coumarin) or an affinity label molecule (biotin) in a complex biological sample. The example further demonstrates how this procedure can be useful for isolating the biotinylated target protein from the complex mixture via biotin affinity capturing.

A cell lysate of E. coli cells expressing the intein-fusion construct CBD-2 was prepared by resuspending the cells from a 25 mL-culture in 1 mL of 50 mM potassium phosphate buffer (pH 7.5) followed by sonication and centrifugation at 13,000 rpm for 30 minutes. 300 uL of cell lysate sample was then added with either reagent 23 or reagent 26 (15 mM). After 6 hour incubation at room temperature, the sample containing reagent 23 was passed through 100 uL chitin beads. After washing the beads with phosphate buffer, the chitin-bound material was eluted with 100 uL 75% acetonitrile in water. MALDI-TOF MS analysis of the eluate revealed the occurrence of desired ligation product (CBD-23) as the only product (calculated [M+H]$^+$ m/z: 8823.72; observed [M+H]$^+$ m/z: 8823.6). After 6 hour incubation at room temperature, the sample containing reagent 26 was passed through 300 uL of streptavidin beads. After washing the beads with phosphate buffer, the streptavidin-bound material was eluted with 250 uL 75% acetonitrile in water. MALDI-TOF MS analysis of the eluate revealed the occurrence of desired ligation product (CBD-26) as the only product (calculated [M+H]$^+$ m/z: 8837.93; observed [M+H]$^+$ m/z: 8837.58). Overall, these results demonstrate the functionality and utility of the methods described herein for selective labeling of intein-fused target protein in a complex biological system, which further proves the chemo- and site-selectivity and bioorthogonal nature of these protein labeling procedures. They also show the utility of these methods in providing a way to label a target protein with an affinity tag so that this protein can be rapidly isolated from a complex mixture.

Example 16

Labeling of a Target Protein with a Bioorthogonal Functional Group in Cell Lysate This example provides a demonstration of how the methods described herein can be used for labeling a target protein with a bio-\orthogonal functional group in the form of a oxyamino group (—ONH$_2$) in a complex biologically-derived medium such as a cell lysate.

A cell lysate of E. coli cells expressing the intein-fusion construct CBD-3 was prepared by resuspending the cells from a 25 mL-culture in 1 mL of 50 mM potassium phosphate buffer (pH 7.5) followed by sonication and centrifugation at 13,000 rpm for 30 minutes. 300 uL of cell lysate sample was added with either reagent 9 or reagent 26 (10 mM). After 5 hour incubation at room temperature, both reactions were analyzed by MALDI-TOF MS. As shown in FIG. 14, these analyses revealed the occurrence of the desired ligation products CBD-9 and CBD-26 as the only ligation products (CBD-9: calculated [M+H]$^+$ m/z: 8059.03; observed [M+H]$^+$ m/z: 8058.35; CBD-26 calculated [M+H]$^+$ m/z: 8259.33; observed [M+H]$^+$ m/z: 8295.32). Overall, these results demonstrate the functionality and utility of the methods described herein for selective labeling a recombinant target protein in a complex biological system.

Example 17

Protein Labeling in Living Cells

This example demonstrates how the methods described herein can be used to selectively functionalize a target protein inside a living cell. In particular, this example shows how these methods can be used to label a target protein with a biotin affinity tag molecule inside a bacterial cell and how the functionalized protein can then be isolated by affinity chromatography.

25 mL cultures of E. coli cells expressing the intein-fusion protein CBD-3 (Table 1) were harvested by centrifugation at 4,000 rpm for 20 minutes. The cell pellets were then resuspended in 1 mL of 50 mM potassium phosphate buffer (pH 7.5) supplemented with compound 26 at either 5 mM or 10 mM in the presence of TCEP (15 mM). After 8 hours of incubation at room temperature, the cells were harvested by centrifugation and the cell pellets were extensively washed with buffer. The cell pellets were then resuspended in 1 mL of phosphate buffer, lysed by sonication, and the cell lysate was clarified via centrifugation. The cell lysates were analyzed by MALDI-TOF. As shown in FIG. 15A-B, these analyses revealed the presence of the desired ligation product CBD-26 (calculated $[M+H]^+$ m/z: 8259.33; observed $[M+H]^+$ m/z: 8259.32) at both reagent concentrations. In each case, a small amount of CBD-COOH was also observed, this species likely resulting from spontaneous hydrolysis of the intein-fusion product during expression. To further confirm the formation of the desired biotin-protein conjugate, the cell lysates were passed over streptavidin-functionalized polyacrylamide beads. After washing with buffer, the beads were resuspended in 50:50 acetonitrile:water to elute the strepatavidin-bound material. MALDI-TOF MS analysis of the eluate revealed the occurrence of a single species with a mass corresponding to the desired biotinylated protein, CBD-6 (calculated $[M+H]^+$ m/z: 8259.33; observed $[M+H]^+$ m/z: 8259.116; FIG. 16A-C, Graphic C).

Overall, these results demonstrated the selective functionalization of a target intein-fusion protein inside a living cell using the methods described herein. They also show how, after in vivo labeling of the target protein with a biotin affinity tag, the product of the functionalization reaction can be isolated via affinity chromatography. Furthermore, since during the biotin capturing process the functionalized (i.e. biotinylated) target protein is immobilized on the streptavidin-coated resin beads via a tight biotin-streptavidin complex, these experiments also show how the methods described herein can be used to immobilize a target protein onto a solid support.

Example 18

Fluorescent Tagging of a Target Protein Via Bifunctional Labeling Reagents

This example demonstrates how the methods described herein can be used for introducing a reactive functional group into a target polypeptide so that the functionalized protein can be further modified with a chemical species of interest such as a fluorescent probe molecule. In particular, it shows how the methods described herein can be used for the preparation of an oxyamine-functionalized target protein which can then be further modified with a coumarin-based fluorescent probe via an oxime ligation between the oxyamino group introduced into the protein and the keto group in the coumarin dye.

Under standard reaction conditions (100 uM protein, 50 mM potassium phosphate (pH 7.5), 150 mM sodium chloride, 20 mM TCEP), the intein-fusion protein CBD-3 (Table 1) was first incubated with reagent 9 (FIG. 2) at a concentration of 1 mM for 5 hours at room temperature. Then, 3-acetyl-coumarin (10 mM) was added. After adjusting the pH to 5, the reaction mixture was incubated for 12 hours at room temperature and then analyzed by MALDI-TOF MS. These analyses revealed the formation of the desired CBD-9-coumarin conjugate (calculated: $[M+H]+$ m/z: 8229.2 observed: $[M+H]+$ m/z: 8228.12).

Example 19

In Vitro Protein Functionalization with N-(2-mercaptoethyl)-amino-aryl-Based Reagent This example demonstrates how the general strategy schematically illustrated in FIG. 1 can be applied for labeling of a target protein. In particular, this example illustrates an embodiment of the invention wherein a reagent of general formula (V) is used to functionalize a target protein in vitro.

For these studies, the intein-fusion protein CBD-2 was incubated with reagent 30 (FIG. 6) at 15 mM under standard reaction conditions (100 uM protein, 50 mM potassium phosphate (pH 7.5), 150 mM sodium chloride, 20 mM TCEP). At different time points, the reaction mixture was analyzed by MALDI-TOF MS to monitor product formation and by SDS-PAGE for measuring the extent of protein labeling. MALDI-TOF MS analysis revealed the formation of the desired CBD-2-30 ligation adduct as the only observable product (calculated: $[M+H]+$ m/z: 8525.54 observed: $[M+H]+$ m/z: 8525.7). To assess the occurrence of an S,N acyl transfer in the functionalized protein adduct, iodoacetamide (20 mM) was added to the reaction mixture. At the 4 hour time point, 90% of the functionalized protein adduct was converted to the corresponding S-alkylated product (calculated: $[M+H]+$ m/z: 8582.54 observed: $[M+H]+$m/z: 8582.99), confirming the occurrence of the desired S,N acyl transfer (i.e., rearrangement of thioester ligation product 'a' into the amide ligation product 'b' in FIG. 1). To measure the extent of protein labeling, the samples were also analyzed by SDS-PAGE followed by gel densitometry. These studies showed that the occurrence of 30-induced splicing of the precursor protein and indicated the occurrence of as much as 70% labeling of the target protein after 4 hours (FIG. 17A-B). Altogether, these results demonstrate the functionality of reagents of the type (V)-(VIII) for functionalization of a protein of interest in vitro according to the general strategy of FIG. 1.

Example 20

In Vivo Protein Functionalization with N-(2-mercaptoethyl)-amino-aryl-Based Reagent This example further demonstrates how the general strategy schematically illustrated in FIG. 1 can be applied for labeling of a target protein. In particular, this example illustrates another embodiment of the invention wherein a reagent of general formula (V) is used to functionalize a target protein inside a living cell.

For these experiments, a 25 mL culture of E. coli cells expressing the intein-fusion protein CBD-3 (Table 1) was harvested by centrifugation at 4,000 rpm for 20 minutes. The cell pellet was then resuspended in 1 mL of 50 mM potassium phosphate buffer (pH 7.5) supplemented 10 mM of compound 34 and 15 mM TCEP. After 8 hour-incubation at room temperature, the cells were harvested by centrifugation and the cell pellet was extensively washed with buffer. The cell pellet was then resuspended in 1 mL of phosphate buffer, lysed by sonication, and the cell lysate was clarified via centrifugation. As shown in FIG. 18A-B, MALDI-TOF MS analysis of the cell lysate revealed the presence of desired ligation product CBD-34 (calculated [M+H]$^+$ m/z: 7960.7; observed M+H$^+$ m/z: 7960.7) in addition to a small amount of CBD-COOH, likely resulting from spontaneous hydrolysis of the intein-fusion product during expression. Altogether, these results demonstrate the functionality of reagents of the type (V)-(VIII) for functionalization of a protein of interest inside a cell according to the general strategy of FIG. 1.

REFERENCES

Calloway, N. T., M. Choob, et al. (2007). Chembiochem 8(7): 767-774.

Chattopadhaya, S., F. B. Abu Bakar, et al. (2009). Methods Enzymol 462: 195-223.

Chen, I., M. Howarth, et al. (2005). Nat Methods 2(2): 99-104.

Cohen, J. D., P. Zou, et al. (2012). Chembiochem 13(6): 888-894.

Crivat, G. and J. W. Taraska (2012). Trends Biotechnol 30(1): 8-16.

Frost, J. R., F. Vitali, et al. (2013). Chembiochem 14(1): 147-160.

Hermanson, G. T. (1996). Bioconjugate Techniques. San Diego, Academic Press.

Jing, C. and V. W. Cornish (2011). Acc Chem Res 44(9): 784-792.

Keppler, A., S. Gendreizig, et al. (2003). Nature Biotechnology 21(1): 86-89.

Los, G. V., L. P. Encell, et al. (2008). Acs Chemical Biology 3(6): 373-382.

Muir, T. W., D. Sondhi, et al. (1998). Proc Natl Acad Sci USA 95(12): 6705-6710.

Paulus, H. (2000). Annu Rev Biochem 69: 447-496.

Popp, M. W., J. M. Antos, et al. (2007). Nat Chem Biol 3(11): 707-708.

Satyanarayana, M., F. Vitali, et al. (2012). Chemical Communications 48(10): 1461-1463.

Shin, Y., K. A. Winans, et al. (1999). J Am Chem Soc 121(50): 11684-11689.

Smith, J. M., F. Vitali, et al. (2011). Angew Chem Int Ed Engl 50(22): 5075-5080.

Yin, J., F. Liu, et al. (2004). J Am Chem Soc 126(25): 7754-7755.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

While embodiments of the present disclosure have been particularly shown and described with reference to certain examples and features, it will be understood by one skilled in the art that various changes in detail may be effected therein without departing from the spirit and scope of the present disclosure as defined by claims that can be supported by the written description and drawings. Further, where exemplary embodiments are described with reference to a certain number of elements it will be understood that the exemplary embodiments can be practiced utilizing either less than or more than the certain number of elements.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for forming a covalent linkage between a polypeptide and a chemical species, the method comprising the steps of:
   a) providing a polypeptide, wherein the polypeptide comprises a thioester group and/or wherein the polypeptide is C-terminally fused to an intein;
   b) providing a chemical reagent of formula (I):

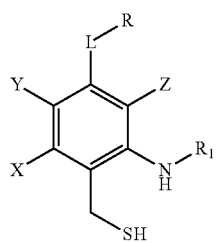

(I)

or a salt of the chemical reagent, wherein:
   i) $R_1$, X, Y, and Z are hydrogen atoms,
      R is $-ONH_2$ or $-N_3$, and
      L is a single bond;
   ii) $R_1$, X, Y, and Z are hydrogen atoms,
      R is $-ONH_2$, and
      L is a linker or linker group of formula

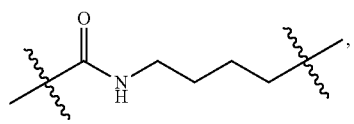

(IX)

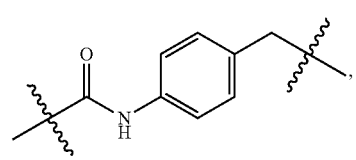

(X)

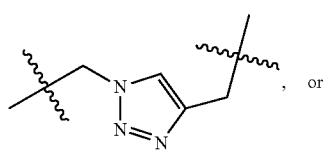

(XI), or

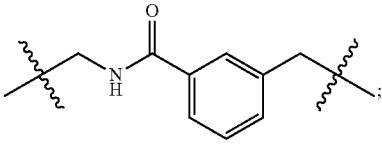

(XII);

iii) $R_1$, X, Y, and Z are hydrogen atoms,
      R is a fluorescent molecule selected from the group consisting of a coumarin derivative, a naphthalene derivative, a pyrene derivative, a fluorescein derivative, a rhodamine derivative, a naphthoxanthene derivative, a phenanthridine derivative, a boron difluoride dipyrromethene (BODIPY) derivative, a cyanine derivatives, a phthalocyanine derivative, and an oxazine derivative, and L is $-C(O)NH(CH)_nC(O)-$, wherein n is an integer number between 2 and 10;
   iv) $R_1$, X, Y, and Z are hydrogen atoms,
      R is biotin or a biotin analogue, and
      L is $-C(O)NH(CH_2)_nNH-$, wherein n is an integer number between 2 and 10; or
   v) $R_1$, X, Y, and Z are hydrogen atoms,
      R is a poly(ethyleneglycol) molecule, and
      L is $-C(O)NH(CH_2)_nNHC(O)-$ or $-CH_2NH(CH_2)_nNHC(O)-$ wherein n is an integer number between 2 and 10;
   the chemical reagent being reactive with the polypeptide, and
   wherein reaction of the chemical reagent with the polypeptide forms a covalent linkage between the chemical reagent and the polypeptide; and
   c) allowing the polypeptide to react with the chemical reagent so that a covalent linkage between the reagent and the polypeptide is formed.

2. The method of claim 1, wherein the intein is a naturally occurring intein, an engineered variant of a naturally occurring intein, a fusion of the N-terminal and C-terminal fragments of a naturally occurring split intein, or a fusion of the N-terminal and C-terminal fragments of an artificial split intein.

3. The method of claim 1, wherein the intein is a polypeptide of SEQ ID NO:1-76, or an engineered variant thereof.

4. The method of claim 3, wherein:
the C-terminal terminal asparagine, aspartic acid, or glutamine residue in the intein is mutated to an amino acid other than asparagine, aspartic acid, or glutamine, or
the N-terminal serine is mutated to a cysteine residue and the C-terminal asparagine, aspartic acid, or glutamine residue in the intein is mutated to an amino acid other than asparagine, aspartic acid, or glutamine.

5. The method of claim 4, wherein the intein is C-terminally fused to a polypeptide affinity tag selected from the group consisting of polyhistidine tag, Avi-Tag, FLAG tag, Strep-tag II, c-myc tag, S-Tag, calmodulin-binding peptide, streptavidin-binding peptide, chitin-binding domain, glutathione S-transferase, and maltose-binding protein.

6. The method of claim 1, wherein the polypeptide C-terminally fused to the intein comprises one or a plurality of the features selected from the group consisting of: the residue at position 1 prior to the intein (hereinafter "intein-1" or "I-1") being F, Y, A, T, W, N, R or Q; the residue at position 2 prior to the intein (hereinafter "intein-2" or "I-2") being G, P, or S; and the residue at position 3 prior to the intein (hereinafter "intein-3" or "I-3") being G or S.

7. The method of claim 1, wherein the intein-fused polypeptide is inside a cell or associated with the exterior surface of a cell membrane.

8. The method of claim 7, wherein the cell is a prokaryotic or eukaryotic cell.

9. The method of claim 1, wherein the reagent is:

a compound of formula 6:

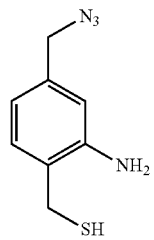

a compound of formula 8:

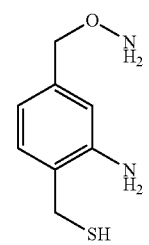 [SMILES: NOCc1ccc(CS)c(N)c1]

a compound of formula 9:

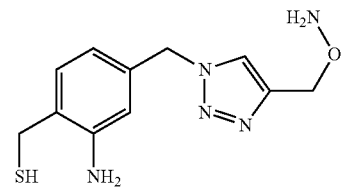 [SMILES: NOCc1cn(Cc2ccc(CS)c(N)c2)nn1]

a compound of formula 10A:

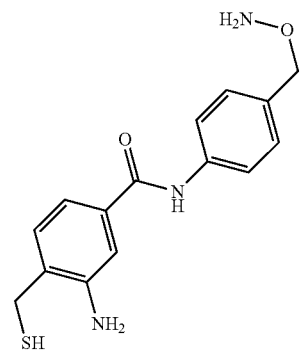 [SMILES: NOCc1ccc(NC(=O)c2ccc(CS)c(N)c2)cc1]

a compound of formula 10B:

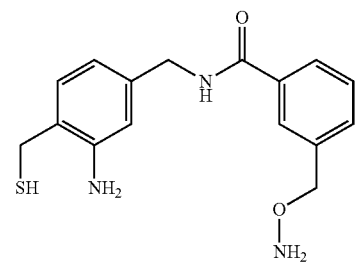 [SMILES: NOCc1cccc(C(=O)NCc2ccc(CS)c(N)c2)c1]

a compound of formula 23:

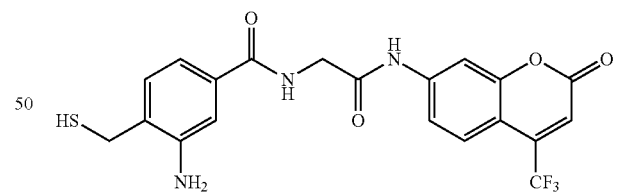

or
a compound of formula 26:

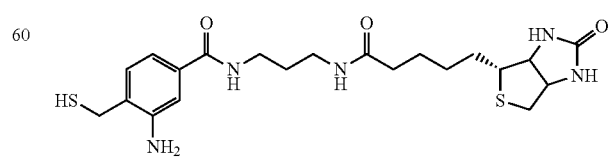

or a salt thereof.

10. A compound having formula (I),

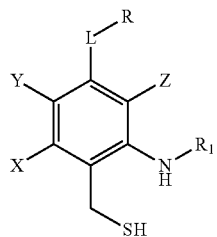

or a salt thereof wherein:
a) $R_1$, X, Y, and Z are hydrogen atoms,
R is —$ONH_2$ or —$N_3$, and
L is a single bond;
b) $R_1$, X, Y, and Z are hydrogen atoms,
R is —$ONH_2$, and
L is a linker or linker group of formula

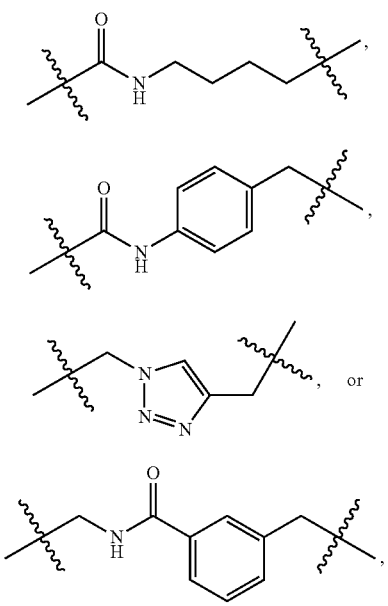

c) $R_1$, X, Y, and Z are hydrogen atoms,
R is a fluorescent molecule selected from the group consisting of a coumarin derivative, a naphthalene derivative, a pyrene derivative, a fluorescein derivative, a rhodamine derivative, a naphthoxanthene derivative, a phenanthridine derivative, a boron difluoride dipyrromethene (BODIPY) derivative, a cyanine derivatives, a phthalocyanine derivative, and an oxazine derivative, and
L is —C(O)NH($CH_2$)$_n$C(O)—, wherein n is an integer number between 2 and 10;
d) $R_1$, X, Y, and Z are hydrogen atoms,
R is biotin or a biotin analogue, and
L is —C(O)NH($CH_2$)$_n$NH—, wherein n is an integer number between 2 and 10; or
e) $R_1$, X, Y, and Z are hydrogen atoms,
R is a poly(ethyleneglycol) molecule, and
L is —C(O)NH($CH_2$)$_n$NHC(O)— or —$CH_2$NH($CH_2$)$_n$NHC(O)— wherein n is an integer number between 2 and 10;

the compound being reactive with a polypeptide,
wherein the polypeptide comprises a thioester group and/or wherein the polypeptide is C-terminally fused to an intein, and
wherein reaction of the compound with the polypeptide forms a covalent linkage between the compound and the polypeptide.

11. The compound of claim 10 having the formula:

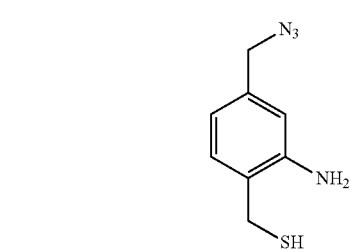 [SMILES: [N-]=[N+]=NCc1ccc(CS)c(N)c1]

6

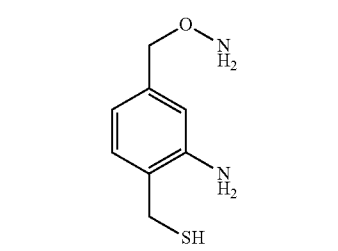

8

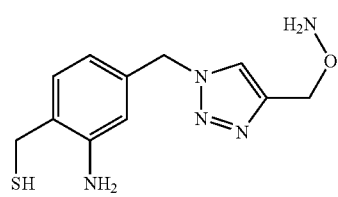

9

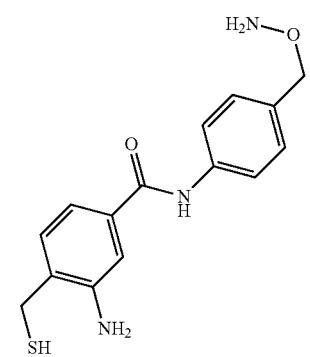

10A

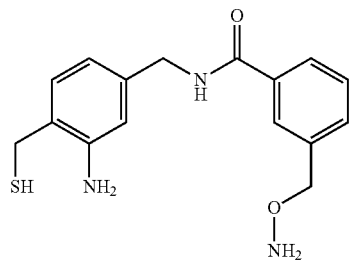

10B

-continued

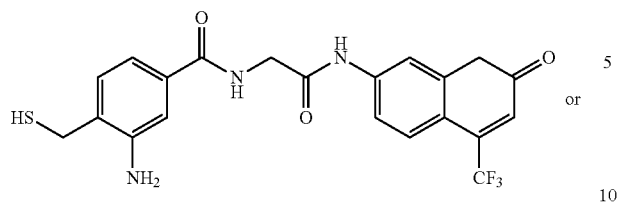
23 or

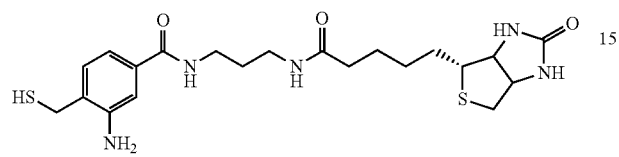
26 or a salt thereof.

12. A kit for forming a covalent linkage between a polypeptide and a chemical species, the kit comprising:
 a) at least one chemical reagent having the formula of a compound of claim 10, or a salt of the reagent; and
 b) one or a plurality of containers, wherein at least one container comprises a pre-selected or desired amount of the at least one chemical reagent, or a salt of the reagent.

13. The kit of claim 12, wherein the at least one reagent comprises at least one compound selected from the group consisting of:

a compound of formula 6:

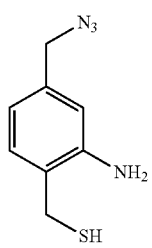

a compound of formula 8:

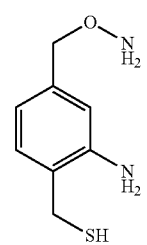 [SMILES: NOCc1ccc(CS)c(N)c1]

a compound of formula 9:

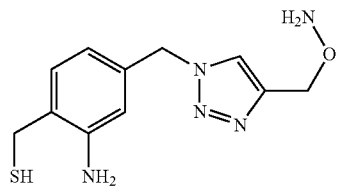

a compound of formula 10A:

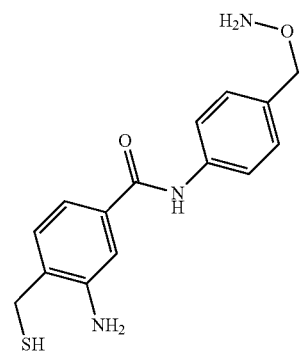 [SMILES: NOCc1ccc(NC(=O)c2ccc(CS)c(N)c2)cc1]

a compound of formula 10B:

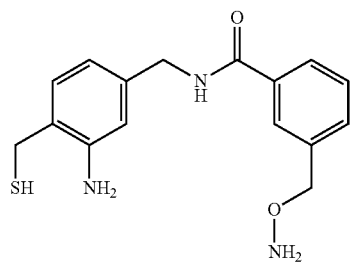 [SMILES: NOCc1cccc(C(=O)NCc2ccc(CS)c(N)c2)c1]

a compound of formula 23:

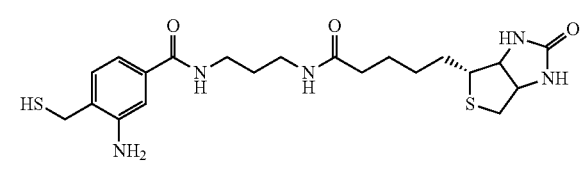 [SMILES: Nc1cc(C(=O)NCCCNC(=O)CCCC[C@H]2SCC3NC(=O)NC32)ccc1CS]

and
a compound of formula 26:

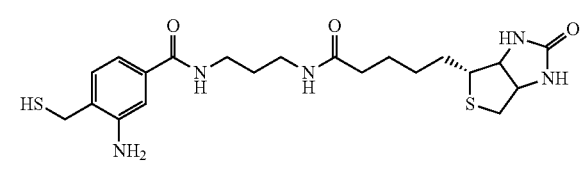 [SMILES: Nc1cc(C(=O)NCCCNC(=O)CCCC[C@H]2SCC3NC(=O)NC32)ccc1CS]

or a salt thereof.

14. The kit of claim 12 further comprising a functionalized solid support with which the functional group R reacts.

15. The kit of claim 14, wherein the solid support is a resin, a nanoparticle, a surface, or a microarray.

* * * * *

SEQUENCE LISTING

```
<160> NUMBER OF SEQ ID NOS: 86

<210> SEQ ID NO 1
<211> LENGTH: 198
<212> TYPE: PRT
<213> ORGANISM: Mycobacterium xenopi

<400> SEQUENCE: 1

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95
```

```
Ile Lys Pro Gly Asp Tyr Ala Val Ile Gln Arg Ser Ala Phe Ser Val
                100                 105                 110

Asp Cys Ala Gly Phe Ala Arg Gly Lys Pro Glu Phe Ala Pro Thr Thr
            115                 120                 125

Tyr Thr Val Gly Val Pro Gly Leu Val Arg Phe Leu Glu Ala His His
        130                 135                 140

Arg Asp Pro Asp Ala Gln Ala Ile Ala Asp Glu Leu Thr Asp Gly Arg
145                 150                 155                 160

Phe Tyr Tyr Ala Lys Val Ala Ser Val Thr Asp Ala Gly Val Gln Pro
                165                 170                 175

Val Tyr Ser Leu Arg Val Asp Thr Ala Asp His Ala Phe Ile Thr Asn
            180                 185                 190

Gly Phe Val Ser His Asn
            195

<210> SEQ ID NO 2
<211> LENGTH: 154
<212> TYPE: PRT
<213> ORGANISM: Synechocystis sp.

<400> SEQUENCE: 2

Cys Ile Ser Gly Asp Ser Leu Ile Ser Leu Ala Ser Thr Gly Lys Arg
1               5                   10                  15

Val Ser Ile Lys Asp Leu Leu Asp Glu Lys Asp Phe Glu Ile Trp Ala
                20                  25                  30

Ile Asn Glu Gln Thr Met Lys Leu Glu Ser Ala Lys Val Ser Arg Val
            35                  40                  45

Phe Cys Thr Gly Lys Lys Leu Val Tyr Ile Leu Lys Thr Arg Leu Gly
        50                  55                  60

Arg Thr Ile Lys Ala Thr Ala Asn His Arg Phe Leu Thr Ile Asp Gly
65                  70                  75                  80

Trp Lys Arg Leu Asp Glu Leu Ser Leu Lys His Ile Ala Leu Pro
                85                  90                  95

Arg Lys Leu Glu Ser Ser Ser Leu Gln Leu Ser Pro Glu Ile Glu Lys
                100                 105                 110

Leu Ser Gln Ser Asp Ile Tyr Trp Asp Ser Ile Val Ser Ile Thr Glu
            115                 120                 125

Thr Gly Val Glu Glu Val Phe Asp Leu Thr Val Pro Gly Pro His Asn
        130                 135                 140

Phe Val Ala Asn Asp Ile Ile Val His Asn
145                 150

<210> SEQ ID NO 3
<211> LENGTH: 182
<212> TYPE: PRT
<213> ORGANISM: Halobacterium sp. NRC1

<400> SEQUENCE: 3

Cys Val Arg Gly Asp Thr Thr Val Ala Leu Ala Asp Gly Ser Glu Arg
1               5                   10                  15

Glu Ile Arg Asp Leu Val Glu Ala Asn Leu Asp Asp Pro Arg Pro Val
                20                  25                  30

Asp Asp Gly Val Trp Asp Gly Val Asp Val Ala Val Pro Ser Leu Ala
            35                  40                  45

Ala Asp Gly Arg Leu Val Gln Arg Ala Thr Lys Val Trp Lys Arg
        50                  55                  60
```

```
Glu Ala Pro Glu Thr Met Tyr Arg Val Arg Thr Ala Ala Gly His Arg
 65                  70                  75                  80

Leu Thr Val Thr Pro Ser His Pro Leu Phe Val Ala Gly Ser His Gly
                 85                  90                  95

Pro Asp Ala Val Arg Thr Glu Asp Leu Glu Val Gly Gln Leu Val Gly
            100                 105                 110

Val Ala Pro Asp Gly Asp Gly Ser Gly Gln Val Ala Pro Asp Gly Gly
            115                 120                 125

Val Ile Arg Asp Ala Gln Pro Ala Pro Val Gly Asp Ala Glu Thr Val
            130                 135                 140

Ala Trp Ser Ala Ile Glu Ser Ile Thr Glu Val Glu Pro Asp Glu Glu
145                 150                 155                 160

Trp Val Tyr Asp Leu Glu Val Glu Gly Thr His Ser Tyr Leu Thr Asp
                165                 170                 175

Gly Val Val Ser His Asn
            180

<210> SEQ ID NO 4
<211> LENGTH: 456
<212> TYPE: PRT
<213> ORGANISM: Chlamydomonas eugametos

<400> SEQUENCE: 4

Cys Leu Thr Ser Asp His Thr Val Leu Thr Thr Arg Gly Trp Ile Pro
  1               5                  10                  15

Ile Ala Asp Val Thr Leu Asp Asp Lys Val Ala Val Leu Asp Asn Asn
                 20                  25                  30

Thr Gly Glu Met Ser Tyr Gln Asn Pro Gln Lys Val His Lys Tyr Asp
             35                  40                  45

Tyr Glu Gly Pro Met Tyr Glu Val Lys Thr Ala Gly Val Asp Leu Phe
 50                  55                  60

Val Thr Pro Asn His Arg Met Tyr Val Asn Thr Thr Asn Asn Thr Thr
 65                  70                  75                  80

Asn Gln Asn Tyr Asn Leu Val Glu Ala Ser Ser Ile Phe Gly Lys Lys
                 85                  90                  95

Val Arg Tyr Lys Asn Asp Ala Ile Trp Asn Lys Thr Asp Tyr Gln Phe
            100                 105                 110

Ile Leu Pro Glu Thr Ala Thr Leu Thr Gly His Thr Asn Lys Ile Ser
            115                 120                 125

Ser Thr Pro Ala Ile Gln Pro Glu Met Asn Ala Trp Leu Thr Phe Phe
            130                 135                 140

Gly Leu Trp Ile Ala Asn Gly His Thr Thr Lys Ile Ala Glu Lys Thr
145                 150                 155                 160

Ala Glu Asn Asn Gln Gln Lys Gln Arg Tyr Lys Val Ile Leu Thr Gln
                165                 170                 175

Val Lys Glu Asp Val Cys Asp Ile Ile Glu Gln Thr Leu Asn Lys Leu
            180                 185                 190

Gly Phe Asn Phe Ile Arg Ser Gly Lys Asp Tyr Thr Ile Glu Asn Lys
            195                 200                 205

Gln Leu Trp Ser Tyr Leu Asn Pro Phe Asp Asn Gly Ala Leu Asn Lys
            210                 215                 220

Tyr Leu Pro Asp Trp Val Trp Glu Leu Ser Ser Gln Gln Cys Lys Ile
225                 230                 235                 240

Leu Leu Asn Ser Leu Cys Leu Gly Asn Cys Leu Phe Thr Lys Asn Asp
```

```
                    245                 250                 255
Asp Thr Leu His Tyr Phe Ser Thr Ser Glu Arg Phe Ala Asn Asp Val
            260                 265                 270

Ser Arg Leu Ala Leu His Ala Gly Thr Thr Ser Thr Ile Gln Leu Glu
            275                 280                 285

Ala Ala Pro Ser Asn Leu Tyr Asp Thr Ile Ile Gly Leu Pro Val Glu
            290                 295                 300

Val Asn Thr Thr Leu Trp Arg Val Ile Ile Asn Gln Ser Ser Phe Tyr
305                 310                 315                 320

Ser Tyr Ser Thr Asp Lys Ser Ser Ala Leu Asn Leu Ser Asn Asn Val
                325                 330                 335

Ala Cys Tyr Val Asn Ala Gln Ser Ala Leu Thr Leu Glu Gln Asn Ser
            340                 345                 350

Gln Lys Ile Asn Lys Asn Thr Leu Val Leu Thr Lys Asn Asn Val Lys
            355                 360                 365

Ser Gln Thr Met His Ser Gln Arg Ala Glu Arg Val Asp Thr Ala Leu
            370                 375                 380

Leu Thr Gln Lys Glu Leu Asp Asn Ser Leu Asn His Glu Ile Leu Ile
385                 390                 395                 400

Asn Lys Asn Pro Gly Thr Ser Gln Leu Glu Cys Val Val Asn Pro Glu
                405                 410                 415

Val Asn Asn Thr Ser Thr Asn Asp Arg Phe Val Tyr Tyr Lys Gly Pro
            420                 425                 430

Val Tyr Cys Leu Thr Gly Pro Asn Asn Val Phe Tyr Val Gln Arg Asn
            435                 440                 445

Gly Lys Ala Val Trp Thr Gly Asn
            450                 455

<210> SEQ ID NO 5
<211> LENGTH: 360
<212> TYPE: PRT
<213> ORGANISM: Thermococcus aggregans

<400> SEQUENCE: 5

Cys His Pro Ala Asp Thr Lys Val Ile Val Lys Gly Lys Gly Ile Val
1               5                   10                  15

Asn Ile Ser Asp Val Lys Glu Gly Asp Tyr Ile Leu Gly Ile Asp Gly
            20                  25                  30

Trp Gln Arg Val Lys Lys Val Trp Lys Tyr His Tyr Glu Gly Lys Leu
        35                  40                  45

Ile Asn Ile Asn Gly Leu Lys Cys Thr Pro Asn His Lys Val Pro Val
    50                  55                  60

Val Thr Glu Asn Asp Arg Gln Thr Arg Ile Arg Asp Ser Leu Ala Lys
65                  70                  75                  80

Ser Phe Leu Ser Gly Lys Val Lys Gly Lys Ile Ile Thr Thr Lys Leu
                85                  90                  95

Phe Glu Lys Ile Ala Glu Phe Glu Lys Asn Lys Pro Ser Glu Glu Glu
            100                 105                 110

Ile Leu Lys Gly Glu Leu Ser Gly Ile Ile Leu Ala Glu Gly Thr Leu
        115                 120                 125

Leu Arg Lys Asp Ile Glu Tyr Phe Asp Ser Ser Arg Gly Lys Lys Arg
    130                 135                 140

Ile Ser His Gln Tyr Arg Val Glu Ile Thr Ile Gly Glu Asn Glu Lys
145                 150                 155                 160
```

Glu Leu Leu Glu Arg Ile Leu Tyr Ile Phe Asp Lys Leu Phe Gly Ile
            165                 170                 175

Arg Pro Ser Val Lys Lys Gly Asp Thr Asn Ala Leu Lys Ile Thr
        180                 185                 190

Thr Ala Lys Lys Ala Val Tyr Leu Gln Ile Glu Glu Leu Leu Lys Asn
            195                 200                 205

Ile Glu Ser Leu Tyr Ala Pro Ala Val Leu Arg Gly Phe Phe Glu Arg
    210                 215                 220

Asp Ala Thr Val Asn Lys Ile Arg Ser Thr Ile Val Val Thr Gln Gly
225                 230                 235                 240

Thr Asn Asn Lys Trp Lys Ile Asp Ile Val Ala Lys Leu Leu Asp Ser
                245                 250                 255

Leu Gly Ile Pro Tyr Ser Arg Tyr Glu Tyr Lys Tyr Ile Glu Asn Gly
            260                 265                 270

Lys Glu Leu Thr Lys His Ile Leu Glu Ile Thr Gly Arg Asp Gly Leu
        275                 280                 285

Ile Leu Phe Gln Thr Leu Val Gly Phe Ile Ser Ser Glu Lys Asn Glu
    290                 295                 300

Ala Leu Glu Lys Ala Ile Glu Val Arg Glu Met Asn Arg Leu Lys Asn
305                 310                 315                 320

Asn Ser Phe Tyr Asn Leu Ser Thr Phe Glu Val Ser Ser Glu Tyr Tyr
                325                 330                 335

Lys Gly Glu Val Tyr Asp Leu Thr Leu Glu Gly Asn Pro Tyr Tyr Phe
            340                 345                 350

Ala Asn Gly Ile Leu Thr His Asn
        355                 360

<210> SEQ ID NO 6
<211> LENGTH: 360
<212> TYPE: PRT
<213> ORGANISM: Thermococcus fumicolans

<400> SEQUENCE: 6

Cys His Pro Ala Asp Thr Lys Val Ile Val Lys Gly Lys Gly Val Val
1               5                   10                  15

Asn Ile Ser Glu Val Arg Glu Gly Asp Tyr Val Leu Gly Ile Asp Gly
            20                  25                  30

Trp Gln Lys Val Gln Arg Val Trp Glu Tyr Asp Tyr Glu Gly Glu Leu
        35                  40                  45

Val Asn Ile Asn Gly Leu Lys Cys Thr Pro Asn His Lys Leu Pro Val
    50                  55                  60

Val Arg Arg Thr Glu Arg Gln Thr Ala Ile Arg Asp Ser Leu Ala Lys
65                  70                  75                  80

Ser Phe Leu Thr Lys Lys Val Lys Gly Lys Leu Ile Thr Thr Pro Leu
                85                  90                  95

Phe Glu Lys Ile Gly Lys Ile Glu Arg Glu Asp Val Pro Glu Glu Glu
            100                 105                 110

Ile Leu Lys Gly Glu Leu Ala Gly Ile Ile Leu Ala Glu Gly Thr Leu
        115                 120                 125

Leu Arg Lys Asp Val Glu Tyr Phe Asp Ser Ser Arg Gly Lys Lys Arg
    130                 135                 140

Val Ser His Gln Tyr Arg Val Glu Ile Thr Val Gly Ala Gln Glu Glu
145                 150                 155                 160

Asp Phe Gln Arg Arg Ile Val Tyr Ile Phe Glu Arg Leu Phe Gly Val
                165                 170                 175

Thr Pro Ser Val Tyr Arg Lys Lys Asn Thr Asn Ala Ile Thr Phe Lys
                180                 185                 190

Val Ala Lys Lys Glu Val Tyr Leu Arg Val Arg Glu Ile Met Asp Gly
            195                 200                 205

Ile Glu Asn Leu His Ala Pro Ser Val Leu Arg Gly Phe Phe Glu Gly
210                 215                 220

Asp Gly Ser Val Asn Lys Val Arg Lys Thr Val Val Asn Gln Gly
225                 230                 235                 240

Thr Asn Asn Glu Trp Lys Ile Glu Val Ser Lys Leu Leu Asn Lys
                245                 250                 255

Leu Gly Ile Pro His Arg Arg Tyr Thr Tyr Asp Tyr Thr Glu Arg Glu
                260                 265                 270

Lys Thr Met Thr Thr His Ile Leu Glu Ile Ala Gly Arg Asp Gly Leu
            275                 280                 285

Ile Leu Phe Gln Thr Ile Val Gly Phe Ile Ser Thr Glu Lys Asn Met
290                 295                 300

Ala Leu Glu Glu Ala Ile Arg Asn Arg Glu Val Asn Arg Leu Glu Asn
305                 310                 315                 320

Asn Ala Phe Tyr Thr Leu Ala Asp Phe Thr Ala Lys Thr Glu Tyr Tyr
                325                 330                 335

Lys Gly Lys Val Tyr Asp Leu Thr Leu Glu Gly Thr Pro Tyr Tyr Phe
                340                 345                 350

Ala Asn Gly Ile Leu Thr His Asn
            355                 360

<210> SEQ ID NO 7
<211> LENGTH: 360
<212> TYPE: PRT
<213> ORGANISM: Thermococcus kodakaraensis KOD1

<400> SEQUENCE: 7

Cys His Pro Ala Asp Thr Lys Val Val Val Lys Gly Lys Gly Ile Ile
1               5                   10                  15

Asn Ile Ser Glu Val Gln Glu Gly Asp Tyr Val Leu Gly Ile Asp Gly
                20                  25                  30

Trp Gln Arg Val Arg Lys Val Trp Glu Tyr Asp Tyr Lys Gly Glu Leu
            35                  40                  45

Val Asn Ile Asn Gly Leu Lys Cys Thr Pro Asn His Lys Leu Pro Val
        50                  55                  60

Val Thr Lys Asn Glu Arg Gln Thr Arg Ile Arg Asp Ser Leu Ala Lys
65                  70                  75                  80

Ser Phe Leu Thr Lys Lys Val Lys Gly Lys Ile Ile Thr Thr Pro Leu
                85                  90                  95

Phe Tyr Glu Ile Gly Arg Ala Thr Ser Glu Asn Ile Pro Glu Glu Glu
                100                 105                 110

Val Leu Lys Gly Glu Leu Ala Gly Ile Leu Leu Ala Glu Gly Thr Leu
            115                 120                 125

Leu Arg Lys Asp Val Glu Tyr Phe Asp Ser Ser Arg Lys Lys Arg Arg
130                 135                 140

Ile Ser His Gln Tyr Arg Val Glu Ile Thr Ile Gly Lys Asp Glu Glu
145                 150                 155                 160

Glu Phe Arg Asp Arg Ile Thr Tyr Ile Phe Glu Arg Leu Phe Gly Ile
                165                 170                 175

Thr Pro Ser Ile Ser Glu Lys Lys Gly Thr Asn Ala Val Thr Leu Lys 180                 185                 190
Val Ala Lys Lys Asn Val Tyr Leu Lys Val Lys Glu Ile Met Asp Asn
            195                 200                 205

Ile Glu Ser Leu His Ala Pro Ser Val Leu Arg Gly Phe Phe Glu Gly
        210                 215                 220

Asp Gly Ser Val Asn Arg Val Arg Arg Ser Ile Val Ala Thr Gln Gly
225                 230                 235                 240

Thr Lys Asn Glu Trp Lys Ile Lys Leu Val Ser Lys Leu Leu Ser Gln
                245                 250                 255

Leu Gly Ile Pro His Gln Thr Tyr Thr Tyr Gln Tyr Gln Glu Asn Gly
            260                 265                 270

Lys Asp Arg Ser Arg Tyr Ile Leu Glu Ile Thr Gly Lys Asp Gly Leu
        275                 280                 285

Ile Leu Phe Gln Thr Leu Ile Gly Phe Ile Ser Glu Arg Lys Asn Ala
        290                 295                 300

Leu Leu Asn Lys Ala Ile Ser Gln Arg Glu Met Asn Asn Leu Glu Asn
305                 310                 315                 320

Asn Gly Phe Tyr Arg Leu Ser Glu Phe Asn Val Ser Thr Glu Tyr Tyr
                325                 330                 335

Glu Gly Lys Val Tyr Asp Leu Thr Leu Glu Gly Thr Pro Tyr Tyr Phe
            340                 345                 350

Ala Asn Gly Ile Leu Thr His Asn
        355                 360

<210> SEQ ID NO 8
<211> LENGTH: 537
<212> TYPE: PRT
<213> ORGANISM: Pyrococcus sp.

<400> SEQUENCE: 8

Ser Ile Leu Pro Glu Glu Trp Val Pro Leu Ile Lys Asn Gly Lys Val
1               5                   10                  15

Lys Ile Phe Arg Ile Gly Asp Phe Val Asp Gly Leu Met Lys Ala Asn
            20                  25                  30

Gln Gly Lys Val Lys Lys Thr Gly Asp Thr Glu Val Leu Glu Val Ala
        35                  40                  45

Gly Ile His Ala Phe Ser Phe Asp Arg Lys Ser Lys Lys Ala Arg Val
    50                  55                  60

Met Ala Val Lys Ala Val Ile Arg His Arg Tyr Ser Gly Asn Val Tyr
65                  70                  75                  80

Arg Ile Val Leu Asn Ser Gly Arg Lys Ile Thr Ile Thr Glu Gly His
                85                  90                  95

Ser Leu Phe Val Tyr Arg Asn Gly Asp Leu Val Glu Ala Thr Gly Glu
            100                 105                 110

Asp Val Lys Ile Gly Asp Leu Leu Ala Val Pro Arg Ser Val Asn Leu
        115                 120                 125

Pro Glu Lys Arg Glu Arg Leu Asn Ile Val Glu Leu Leu Asn Leu
    130                 135                 140

Ser Pro Glu Glu Thr Glu Asp Ile Ile Leu Thr Ile Pro Val Lys Gly
145                 150                 155                 160

Arg Lys Asn Phe Phe Lys Gly Met Leu Arg Thr Leu Arg Trp Ile Phe
                165                 170                 175

Gly Glu Glu Lys Arg Val Arg Thr Ala Ser Arg Tyr Leu Arg His Leu
            180                 185                 190

```
Glu Asn Leu Gly Tyr Ile Arg Leu Arg Lys Ile Gly Tyr Asp Ile Ile
            195                 200                 205

Asp Lys Glu Gly Leu Glu Lys Tyr Arg Thr Leu Tyr Glu Lys Leu Val
210                 215                 220

Asp Val Val Arg Tyr Asn Gly Asn Lys Arg Glu Tyr Leu Val Glu Phe
225                 230                 235                 240

Asn Ala Val Arg Asp Val Ile Ser Leu Met Pro Glu Glu Leu Lys
            245                 250                 255

Glu Trp Arg Ile Gly Thr Arg Asn Gly Phe Arg Met Gly Thr Phe Val
            260                 265                 270

Asp Ile Asp Glu Asp Phe Ala Lys Leu Leu Gly Tyr Tyr Val Ser Glu
            275                 280                 285

Gly Ser Ala Arg Lys Trp Lys Asn Gln Thr Gly Gly Trp Ser Tyr Thr
290                 295                 300

Val Arg Leu Tyr Asn Glu Asn Asp Glu Val Leu Asp Asp Met Glu His
305                 310                 315                 320

Leu Ala Lys Lys Phe Phe Gly Lys Val Lys Arg Gly Lys Asn Tyr Val
            325                 330                 335

Glu Ile Pro Lys Lys Met Ala Tyr Ile Ile Phe Glu Ser Leu Cys Gly
            340                 345                 350

Thr Leu Ala Glu Asn Lys Arg Val Pro Glu Val Ile Phe Thr Ser Ser
            355                 360                 365

Lys Gly Val Arg Trp Ala Phe Leu Glu Gly Tyr Phe Ile Gly Asp Gly
            370                 375                 380

Asp Val His Pro Ser Lys Arg Val Arg Leu Ser Thr Lys Ser Glu Leu
385                 390                 395                 400

Leu Val Asn Gly Leu Val Leu Leu Asn Ser Leu Gly Val Ser Ala
            405                 410                 415

Ile Lys Leu Gly Tyr Asp Ser Gly Val Tyr Arg Val Tyr Val Asn Glu
            420                 425                 430

Glu Leu Lys Phe Thr Glu Tyr Arg Lys Lys Asn Val Tyr His Ser
            435                 440                 445

His Ile Val Pro Lys Asp Ile Leu Lys Glu Thr Phe Gly Lys Val Phe
450                 455                 460

Gln Lys Asn Ile Ser Tyr Lys Lys Phe Arg Glu Leu Val Glu Asn Gly
465                 470                 475                 480

Lys Leu Asp Arg Glu Lys Ala Lys Arg Ile Glu Trp Leu Leu Asn Gly
            485                 490                 495

Asp Ile Val Leu Asp Arg Val Val Glu Ile Lys Arg Glu Tyr Tyr Asp
            500                 505                 510

Gly Tyr Val Tyr Asp Leu Ser Val Asp Glu Asp Glu Asn Phe Leu Ala
            515                 520                 525

Gly Phe Gly Phe Leu Tyr Ala His Asn
530                 535

<210> SEQ ID NO 9
<211> LENGTH: 538
<212> TYPE: PRT
<213> ORGANISM: Thermococcus aggregans
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
```

<400> SEQUENCE: 9

Ser Ile Leu Pro Asn Glu Trp Leu Pro Ile Ile Glu Asn Gly Glu Val
1               5                   10                  15

Lys Phe Val Lys Ile Gly Glu Phe Ile Asp Arg Tyr Met Glu Glu Gln
            20                  25                  30

Lys Asp Lys Val Arg Thr Val Asp Asn Thr Glu Val Leu Glu Val Asp
        35                  40                  45

Asn Ile Phe Ala Phe Ser Leu Asn Lys Glu Ser Lys Lys Ser Glu Ile
    50                  55                  60

Lys Lys Val Lys Ala Leu Ile Arg His Lys Tyr Lys Gly Glu Ala Tyr
65                  70                  75                  80

Glu Val Glu Leu Asn Ser Gly Arg Lys Ile His Ile Thr Arg Gly His
                85                  90                  95

Ser Leu Phe Thr Ile Arg Asn Gly Lys Ile Lys Glu Ile Trp Gly Glu
            100                 105                 110

Glu Val Lys Val Gly Asp Leu Ile Ile Val Pro Lys Lys Val Lys Leu
        115                 120                 125

Asn Glu Lys Glu Ala Val Ile Asn Ile Pro Glu Leu Ile Ser Lys Leu
130                 135                 140

Pro Asp Glu Asp Thr Ala Asp Val Val Met Thr Thr Pro Val Lys Gly
145                 150                 155                 160

Arg Lys Asn Phe Phe Lys Gly Met Leu Arg Thr Leu Lys Trp Ile Phe
                165                 170                 175

Gly Glu Glu Ser Lys Arg Ile Arg Thr Phe Asn Arg Tyr Leu Phe His
            180                 185                 190

Leu Glu Glu Leu Gly Phe Val Lys Leu Leu Pro Arg Gly Tyr Glu Val
        195                 200                 205

Thr Asp Trp Glu Gly Leu Lys Arg Tyr Arg Gln Leu Tyr Glu Lys Leu
    210                 215                 220

Val Lys Asn Leu Arg Tyr Asn Gly Asn Lys Arg Glu Tyr Leu Val Arg
225                 230                 235                 240

Phe Asn Asp Ile Lys Asp Ser Val Ser Cys Phe Pro Arg Lys Glu Leu
                245                 250                 255

Glu Glu Trp Lys Ile Gly Thr Xaa Lys Gly Phe Arg Xaa Lys Cys Ile
            260                 265                 270

Leu Lys Val Asp Glu Asp Phe Gly Lys Phe Leu Gly Tyr Tyr Val Ser
        275                 280                 285

Glu Gly Tyr Ala Gly Ala Gln Lys Asn Lys Thr Gly Gly Met Ser Tyr
    290                 295                 300

Ser Val Lys Leu Tyr Asn Glu Asn Pro Asn Val Leu Lys Asp Met Lys
305                 310                 315                 320

Asn Ile Ala Glu Lys Phe Phe Gly Lys Val Arg Val Gly Lys Asn Cys
                325                 330                 335

Val Asp Ile Pro Lys Lys Met Ala Tyr Leu Leu Ala Lys Ser Leu Cys
            340                 345                 350

Gly Val Thr Ala Glu Asn Lys Arg Ile Pro Ser Ile Ile Phe Asp Ser
        355                 360                 365

Ser Glu Pro Val Arg Trp Ala Phe Leu Arg Ala Tyr Phe Val Gly Asp
    370                 375                 380

Gly Asp Ile His Pro Ser Lys Arg Leu Arg Leu Ser Thr Lys Ser Glu
385                 390                 395                 400

Leu Leu Ala Asn Gln Leu Val Phe Leu Leu Asn Ser Leu Gly Val Ser

```
                        405                 410                 415
Ser Ile Lys Ile Gly Phe Asp Ser Gly Val Tyr Arg Val Tyr Ile Asn
            420                 425                 430

Glu Asp Leu Pro Phe Leu Gln Thr Ser Arg Gln Lys Asn Thr Tyr Tyr
        435                 440                 445

Pro Asn Leu Ile Pro Lys Glu Val Leu Glu Ile Phe Gly Arg Lys
    450                 455                 460

Phe Gln Lys Asn Ile Thr Phe Glu Lys Phe Lys Glu Leu Ala Asp Ser
465                 470                 475                 480

Gly Lys Leu Asp Lys Arg Lys Val Lys Leu Leu Asp Phe Leu Leu Asn
                485                 490                 495

Gly Asp Ile Val Leu Asp Arg Val Lys Asn Val Glu Lys Arg Glu Tyr
            500                 505                 510

Glu Gly Tyr Val Tyr Asp Leu Ser Val Glu Asp Asn Glu Asn Phe Leu
        515                 520                 525

Val Gly Phe Gly Leu Leu Tyr Ala His Asn
    530                 535

<210> SEQ ID NO 10
<211> LENGTH: 537
<212> TYPE: PRT
<213> ORGANISM: Thermococcus hydrothermalis

<400> SEQUENCE: 10

Ser Leu Leu Pro Glu Glu Trp Ile Pro Leu Glu Asn Gly Lys Val
1               5                   10                  15

Arg Leu His Arg Ile Gly Glu Phe Val Asp Lys Leu Met Glu Thr Asp
            20                  25                  30

Ser Glu Leu Val Lys Arg Asn Gly Asp Thr Glu Val Leu Glu Val Arg
        35                  40                  45

Gly Ile Arg Ala Leu Ser Phe Asp Arg Lys Ser Lys Lys Ala Arg Val
    50                  55                  60

Met Pro Val Lys Ala Val Ile Arg His Arg Tyr Ser Gly Asp Val Tyr
65                  70                  75                  80

Glu Ile Val Leu Gly Ser Gly Arg Ile Thr Val Thr Glu Gly His
            85                  90                  95

Ser Leu Phe Ala Tyr Gly Asp Gly Glu Leu Arg Glu Val Thr Gly Gly
        100                 105                 110

Glu Ile Lys Ala Gly Asp Leu Leu Ala Val Pro Arg Arg Val Asn Leu
    115                 120                 125

Pro Glu Lys Lys Glu Arg Leu Asn Leu Val Glu Leu Leu Arg Arg Leu
    130                 135                 140

Pro Glu Glu Glu Thr Gly Asp Ile Ile Leu Thr Ile Pro Val Lys Gly
145                 150                 155                 160

Arg Lys Asn Phe Phe Lys Gly Met Leu Arg Thr Leu Arg Trp Ile Ser
                165                 170                 175

Gly Glu Glu Lys Arg Pro Arg Thr Ala Arg Arg Tyr Leu Glu His Leu
            180                 185                 190

Glu Gly Leu Gly Tyr Val Arg Leu Lys Lys Ile Gly Tyr Glu Val Thr
        195                 200                 205

Asp Arg Glu Gly Leu Glu Arg Tyr Lys Leu Tyr Glu Arg Leu Val
    210                 215                 220

Glu Ala Val Arg Tyr Asn Gly Asn Lys Arg Glu Tyr Leu Val Glu Phe
225                 230                 235                 240
```

Asn Ala Val Arg Asp Val Ile Ala Leu Met Pro Glu Glu Leu Arg
            245                 250                 255

Asp Trp Leu Val Gly Thr Arg Asn Gly Phe Arg Met Arg Pro Phe Val
            260                 265                 270

Glu Ile Glu Glu Asp Phe Ala Lys Leu Leu Gly Tyr Tyr Val Ser Glu
            275                 280                 285

Gly Asn Ala Arg Lys Trp Arg Asn Gln Lys Asn Gly Trp Ser Tyr Thr
            290                 295                 300

Val Lys Leu Tyr Asn Glu Asn Gln Arg Val Leu Asp Asp Met Glu Ser
305                 310                 315                 320

Leu Ala Glu Arg Phe Phe Gly Arg Val Lys Arg Gly Lys Asn Tyr Ile
            325                 330                 335

Glu Ile Pro Arg Lys Met Ala Tyr Ile Ile Phe Glu Asn Leu Cys Gly
            340                 345                 350

Thr Leu Ala Glu Asn Lys Arg Val Pro Glu Ala Ile Phe Thr Ser Pro
            355                 360                 365

Glu Ser Val Arg Trp Ala Phe Ile Glu Gly Tyr Phe Ile Gly Asp Gly
            370                 375                 380

Asp Val His Pro Ser Lys Arg Val Arg Leu Ser Thr Lys Ser Glu Leu
385                 390                 395                 400

Leu Val Asn Gly Leu Val Leu Leu Asn Ser Leu Gly Val Ser Ala
            405                 410                 415

Ile Lys Ile Arg His Asp Ser Gly Val Tyr Arg Val Tyr Val Asn Glu
            420                 425                 430

Glu Leu Pro Phe Thr Asp Tyr Arg Lys Lys Asn Ala Tyr Tyr Ser
            435                 440                 445

His Val Ile Pro Lys Glu Ile Leu Glu Glu Thr Phe Gly Lys Val Phe
            450                 455                 460

Gln Arg Ser Val Ser Tyr Glu Lys Phe Arg Glu Leu Val Lys Ser Glu
465                 470                 475                 480

Lys Leu Asp Gly Glu Lys Ala Lys Arg Ile Glu Trp Leu Leu Asn Gly
            485                 490                 495

Asp Val Val Leu Asp Lys Val Leu Glu Val Lys Lys Arg Pro Tyr Glu
            500                 505                 510

Gly Tyr Val Tyr Asp Leu Ser Val Glu Glu Asp Glu Asn Phe Leu Ala
            515                 520                 525

Gly Phe Gly Leu Leu Tyr Ala His Asn
            530                 535

<210> SEQ ID NO 11
<211> LENGTH: 536
<212> TYPE: PRT
<213> ORGANISM: Thermococcus kodakaraensis KOD1

<400> SEQUENCE: 11

Ser Ile Leu Pro Glu Glu Trp Leu Pro Val Leu Glu Glu Gly Glu Val
1               5                   10                  15

His Phe Val Arg Ile Gly Glu Leu Ile Asp Arg Met Met Glu Glu Asn
            20                  25                  30

Ala Gly Lys Val Lys Arg Glu Gly Glu Thr Glu Val Leu Glu Val Ser
            35                  40                  45

Gly Leu Glu Val Pro Ser Phe Asn Arg Arg Thr Asn Lys Ala Glu Leu
            50                  55                  60

Lys Arg Val Lys Ala Leu Ile Arg His Asp Tyr Ser Gly Lys Val Tyr
65                  70                  75                  80

```
Thr Ile Arg Leu Lys Ser Gly Arg Arg Ile Lys Ile Thr Ser Gly His
            85                  90                  95

Ser Leu Phe Ser Val Arg Asn Gly Glu Leu Val Glu Val Thr Gly Asp
            100                 105                 110

Glu Leu Lys Pro Gly Asp Leu Val Ala Val Pro Arg Arg Leu Glu Leu
            115                 120                 125

Pro Glu Arg Asn His Val Leu Asn Leu Val Glu Leu Leu Leu Gly Thr
130                 135                 140

Pro Glu Glu Glu Thr Leu Asp Ile Val Met Thr Ile Pro Val Lys Gly
145                 150                 155                 160

Lys Lys Asn Phe Phe Lys Gly Met Leu Arg Thr Leu Arg Trp Ile Phe
                165                 170                 175

Gly Glu Glu Lys Arg Pro Arg Thr Ala Arg Arg Tyr Leu Arg His Leu
            180                 185                 190

Glu Asp Leu Gly Tyr Val Arg Leu Lys Lys Ile Gly Tyr Glu Val Leu
            195                 200                 205

Asp Trp Asp Ser Leu Lys Asn Tyr Arg Arg Leu Tyr Glu Ala Leu Val
    210                 215                 220

Glu Asn Val Arg Tyr Asn Gly Asn Lys Arg Glu Tyr Leu Val Glu Phe
225                 230                 235                 240

Asn Ser Ile Arg Asp Ala Val Gly Ile Met Pro Leu Lys Glu Leu Lys
                245                 250                 255

Glu Trp Lys Ile Gly Thr Leu Asn Gly Phe Arg Met Arg Lys Leu Ile
            260                 265                 270

Glu Val Asp Glu Ser Leu Ala Lys Leu Leu Gly Tyr Tyr Val Ser Glu
            275                 280                 285

Gly Tyr Ala Arg Lys Gln Arg Asn Pro Lys Asn Gly Trp Ser Tyr Ser
290                 295                 300

Val Lys Leu Tyr Asn Glu Asp Pro Glu Val Leu Asp Asp Met Glu Arg
305                 310                 315                 320

Leu Ala Ser Arg Phe Phe Gly Lys Val Arg Arg Gly Arg Asn Tyr Val
                325                 330                 335

Glu Ile Pro Lys Lys Ile Gly Tyr Leu Leu Phe Glu Asn Met Cys Gly
            340                 345                 350

Val Leu Ala Glu Asn Lys Arg Ile Pro Glu Phe Val Phe Thr Ser Pro
            355                 360                 365

Lys Gly Val Arg Leu Ala Phe Leu Glu Gly Tyr Ser Ser Ala Met Ala
370                 375                 380

Thr Ser Thr Glu Gln Glu Thr Gln Ala Leu Asn Glu Lys Arg Ala Leu
385                 390                 395                 400

Ala Asn Gln Leu Val Leu Leu Asn Ser Val Gly Val Ser Ala Val
                405                 410                 415

Lys Leu Gly His Asp Ser Gly Val Tyr Arg Val Tyr Ile Asn Glu Glu
            420                 425                 430

Leu Pro Phe Val Lys Leu Asp Lys Lys Asn Ala Tyr Tyr Ser His
                435                 440                 445

Val Ile Pro Lys Glu Val Leu Ser Glu Val Phe Gly Lys Val Phe Gln
    450                 455                 460

Lys Asn Val Ser Pro Gln Thr Phe Arg Lys Met Val Glu Asp Gly Arg
465                 470                 475                 480

Leu Asp Pro Glu Lys Ala Gln Arg Leu Ser Trp Leu Ile Glu Gly Asp
                485                 490                 495
```

```
Val Val Leu Asp Arg Val Glu Ser Val Asp Val Glu Asp Tyr Asp Gly
            500                 505                 510

Tyr Val Tyr Asp Leu Ser Val Glu Asp Asn Glu Asn Phe Leu Val Gly
            515                 520                 525

Phe Gly Leu Val Tyr Ala His Asn
            530                 535

<210> SEQ ID NO 12
<211> LENGTH: 538
<212> TYPE: PRT
<213> ORGANISM: Thermococcus litoralis

<400> SEQUENCE: 12

Ser Ile Leu Pro Asn Glu Trp Leu Pro Ile Ile Glu Asn Gly Glu Ile
1               5                   10                  15

Lys Phe Val Lys Ile Gly Glu Phe Ile Asn Ser Tyr Met Glu Lys Gln
            20                  25                  30

Lys Glu Asn Val Lys Thr Val Glu Asn Thr Glu Val Leu Glu Val Asn
        35                  40                  45

Asn Leu Phe Ala Phe Ser Phe Asn Lys Lys Ile Lys Glu Ser Glu Val
    50                  55                  60

Lys Val Lys Ala Leu Ile Arg His Lys Tyr Lys Gly Lys Ala Tyr
65                  70                  75                  80

Glu Ile Gln Leu Ser Ser Gly Arg Lys Ile Asn Ile Thr Ala Gly His
                85                  90                  95

Ser Leu Phe Thr Val Arg Asn Gly Glu Ile Lys Glu Val Ser Gly Asp
            100                 105                 110

Gly Ile Lys Glu Gly Asp Leu Ile Val Ala Pro Lys Lys Ile Lys Leu
        115                 120                 125

Asn Glu Lys Gly Val Ser Ile Asn Ile Pro Glu Leu Ile Ser Asp Leu
    130                 135                 140

Ser Glu Glu Glu Thr Ala Asp Ile Val Met Thr Ile Ser Ala Lys Gly
145                 150                 155                 160

Arg Lys Asn Phe Phe Lys Gly Met Leu Arg Thr Leu Arg Trp Met Phe
                165                 170                 175

Gly Glu Glu Asn Arg Arg Ile Arg Thr Phe Asn Arg Tyr Leu Phe His
            180                 185                 190

Leu Glu Lys Leu Gly Leu Ile Lys Leu Leu Pro Arg Gly Tyr Glu Val
        195                 200                 205

Thr Asp Trp Glu Arg Leu Lys Lys Tyr Lys Gln Leu Tyr Glu Lys Leu
    210                 215                 220

Ala Gly Ser Val Lys Tyr Asn Gly Asn Lys Arg Glu Tyr Leu Val Met
225                 230                 235                 240

Phe Asn Glu Ile Lys Asp Phe Ile Ser Tyr Phe Pro Gln Lys Glu Leu
                245                 250                 255

Glu Glu Trp Lys Ile Gly Thr Leu Asn Gly Phe Arg Thr Asn Cys Ile
            260                 265                 270

Leu Lys Val Asp Glu Asp Phe Gly Lys Leu Leu Gly Tyr Tyr Val Ser
        275                 280                 285

Glu Gly Tyr Ala Gly Ala Gln Lys Asn Lys Thr Gly Gly Ile Ser Tyr
    290                 295                 300

Ser Val Lys Leu Tyr Asn Glu Asp Pro Asn Val Leu Glu Ser Met Lys
305                 310                 315                 320

Asn Val Ala Glu Lys Phe Phe Gly Lys Val Arg Val Asp Arg Asn Cys
                325                 330                 335
```

```
Val Ser Ile Ser Lys Lys Met Ala Tyr Leu Val Met Lys Cys Leu Cys
            340                 345                 350

Gly Ala Leu Ala Glu Asn Lys Arg Ile Pro Ser Val Ile Leu Thr Ser
            355                 360                 365

Pro Glu Pro Val Arg Trp Ser Phe Leu Glu Ala Tyr Phe Thr Gly Asp
370                 375                 380

Gly Asp Ile His Pro Ser Lys Arg Phe Arg Leu Ser Thr Lys Ser Glu
385                 390                 395                 400

Leu Leu Ala Asn Gln Leu Val Phe Leu Leu Asn Ser Leu Gly Ile Ser
                405                 410                 415

Ser Val Lys Ile Gly Phe Asp Ser Gly Val Tyr Arg Val Tyr Ile Asn
            420                 425                 430

Glu Asp Leu Gln Phe Pro Gln Thr Ser Arg Glu Lys Asn Thr Tyr Tyr
            435                 440                 445

Ser Asn Leu Ile Pro Lys Glu Ile Leu Arg Asp Val Phe Gly Lys Glu
            450                 455                 460

Phe Gln Lys Asn Met Thr Phe Lys Lys Phe Lys Glu Leu Val Asp Ser
465                 470                 475                 480

Gly Lys Leu Asn Arg Glu Lys Ala Lys Leu Leu Glu Phe Phe Ile Asn
            485                 490                 495

Gly Asp Ile Val Leu Asp Arg Val Lys Ser Val Lys Glu Lys Asp Tyr
            500                 505                 510

Glu Gly Tyr Val Tyr Asp Leu Ser Val Glu Asp Asn Glu Asn Phe Leu
            515                 520                 525

Val Gly Phe Gly Leu Leu Tyr Ala His Asn
            530                 535

<210> SEQ ID NO 13
<211> LENGTH: 537
<212> TYPE: PRT
<213> ORGANISM: Thermococcus marinus

<400> SEQUENCE: 13

Ser Leu Leu Pro Glu Glu Trp Ile Pro Val Val Glu Asn Gly Lys Val
1               5                   10                  15

Lys Leu Val Arg Ile Gly Glu Phe Val Asp Gly Leu Met Lys Asp Glu
            20                  25                  30

Lys Gly Arg Ala Lys Arg Asp Gly Asn Thr Glu Val Leu Glu Val Ser
        35                  40                  45

Gly Ile Arg Ala Val Ser Phe Asp Arg Lys Thr Lys Lys Ala Arg Leu
50                  55                  60

Met Pro Val Lys Ala Val Ile Arg His Arg Tyr Ser Gly Asp Val Tyr
65                  70                  75                  80

Lys Ile Thr Leu Ser Ser Gly Arg Lys Ile Thr Val Thr Lys Gly His
                85                  90                  95

Ser Leu Phe Ala Tyr Arg Asn Gly Glu Leu Val Glu Val Pro Gly Glu
            100                 105                 110

Glu Ile Lys Ala Gly Asp Leu Leu Ala Val Pro Arg Arg Val His Leu
        115                 120                 125

Pro Glu Arg Tyr Glu Arg Leu Asp Leu Val Glu Leu Leu Lys Leu
            130                 135                 140

Pro Glu Glu Glu Thr Glu Asp Ile Ile Leu Thr Ile Pro Ala Lys Gly
145                 150                 155                 160

Arg Lys Asn Phe Phe Lys Gly Met Leu Arg Thr Leu Arg Trp Ile Phe
```

```
                165                 170                 175
Gly Glu Glu Lys Arg Pro Arg Thr Ala Arg Arg Tyr Leu Arg His Leu
            180                 185                 190
Glu Gly Leu Gly Tyr Val Lys Leu Arg Lys Ile Gly Tyr Glu Ile Ile
        195                 200                 205
Asp Arg Glu Gly Leu Lys Arg Tyr Arg Lys Leu Tyr Glu Arg Leu Ala
    210                 215                 220
Glu Val Val Arg Tyr Asn Gly Asn Lys Arg Glu Tyr Leu Ile Glu Phe
225                 230                 235                 240
Asn Ala Val Arg Asp Val Ile Ser Leu Met Pro Glu Glu Glu Leu Asn
                245                 250                 255
Glu Trp Gln Val Gly Thr Arg Asn Gly Phe Arg Ile Lys Pro Leu Ile
            260                 265                 270
Glu Val Asp Glu Asp Phe Ala Lys Leu Leu Gly Tyr Tyr Val Ser Glu
        275                 280                 285
Gly Tyr Ala Gly Lys Gln Arg Asn Gln Lys Asn Gly Trp Ser Tyr Thr
    290                 295                 300
Val Lys Leu Tyr Asn Glu Asp Glu Arg Val Leu Asp Asp Met Glu Asn
305                 310                 315                 320
Leu Ala Arg Glu Phe Phe Gly Lys Ala Arg Arg Gly Arg Asn Tyr Val
                325                 330                 335
Glu Ile Pro Arg Lys Met Ala Tyr Ile Ile Phe Glu Ser Leu Cys Gly
            340                 345                 350
Thr Leu Ala Glu Asn Lys Arg Val Pro Glu Val Ile Phe Thr Ser Pro
        355                 360                 365
Glu Asp Val Arg Trp Ala Phe Leu Glu Gly Tyr Phe Ile Gly Asp Gly
    370                 375                 380
Asp Val His Pro Ser Lys Arg Val Arg Leu Ser Thr Lys Ser Glu Leu
385                 390                 395                 400
Leu Ala Asn Gly Leu Val Leu Leu Asn Ser Leu Gly Val Ser Ala
                405                 410                 415
Val Lys Leu Gly His Asp Ser Gly Val Tyr Arg Val Tyr Val Asn Glu
            420                 425                 430
Glu Leu Pro Phe Thr Gly Tyr Lys Lys Lys Asn Ala Tyr Tyr Ser
        435                 440                 445
His Val Ile Pro Lys Glu Val Leu Glu Glu Thr Phe Gly Lys Val Phe
    450                 455                 460
Gln Arg Asn Met Ser Tyr Glu Lys Phe Gln Glu Leu Val Glu Ser Glu
465                 470                 475                 480
Lys Leu Glu Gly Glu Lys Ala Lys Arg Ile Glu Trp Leu Ile Ser Gly
                485                 490                 495
Asp Ile Ile Leu Asp Lys Val Val Glu Val Lys Lys Met Asn Tyr Glu
            500                 505                 510
Gly Tyr Val Tyr Asp Leu Ser Val Glu Glu Asp Glu Asn Phe Leu Ala
        515                 520                 525
Gly Phe Gly Phe Leu Tyr Ala His Asn
    530                 535

<210> SEQ ID NO 14
<211> LENGTH: 535
<212> TYPE: PRT
<213> ORGANISM: Thermococcus sp. GE8

<400> SEQUENCE: 14
```

```
Ser Ile Leu Pro Asp Glu Trp Leu Pro Leu Val Asn Gly Arg Leu
1               5                   10                  15

Lys Leu Val Arg Ile Gly Asp Phe Val Asp Asn Thr Met Lys Lys Gly
            20                  25                  30

Gln Pro Leu Glu Asn Asp Gly Thr Glu Val Leu Glu Val Ser Gly Ile
            35                  40                  45

Glu Ala Ile Ser Phe Asn Arg Lys Thr Lys Ile Ala Glu Ile Lys Pro
            50                  55                  60

Val Lys Ala Leu Ile Arg His Arg Tyr Arg Gly Lys Val Tyr Asp Ile
65                  70                  75                  80

Lys Leu Ser Ser Gly Arg Asn Ile Lys Val Thr Glu Gly His Ser Leu
                85                  90                  95

Phe Ala Phe Arg Asp Gly Glu Leu Val Glu Val Thr Gly Gly Glu Ile
            100                 105                 110

Lys Pro Gly Asp Phe Ile Ala Val Pro Arg Arg Val Asn Leu Pro Glu
            115                 120                 125

Arg His Glu Arg Ile Asn Leu Ile Glu Ile Leu Gly Leu Pro Pro
            130                 135                 140

Glu Glu Thr Ser Asp Ile Val Leu Thr Ile Pro Val Lys Gly Arg Lys
145                 150                 155                 160

Asn Phe Phe Lys Gly Met Leu Arg Thr Leu Arg Trp Ile Phe Glu Glu
            165                 170                 175

Glu Gln Arg Pro Arg Thr Ala Arg Arg Tyr Leu Glu His Leu Gln Lys
            180                 185                 190

Leu Gly Tyr Val Lys Leu Met Lys Arg Ala Tyr Glu Ile Val Asn Lys
            195                 200                 205

Glu Ala Leu Arg Asn Tyr Arg Lys Leu Tyr Glu Val Leu Ala Glu Arg
            210                 215                 220

Val Lys Tyr Asn Gly Asn Lys Arg Glu Tyr Leu Val His Phe Asn Asp
225                 230                 235                 240

Leu Arg Asn Glu Ile Lys Phe Met Pro Asp Glu Glu Leu Glu Glu Trp
            245                 250                 255

Lys Val Gly Thr Leu Asn Gly Phe Arg Met Glu Pro Phe Ile Glu Val
            260                 265                 270

Gly Glu Asp Phe Ala Lys Leu Leu Gly Tyr Tyr Val Ser Glu Gly Tyr
            275                 280                 285

Ala Arg Lys Gln Arg Asn Gln Lys Asn Gly Trp Ser Tyr Ser Val Lys
            290                 295                 300

Ile Tyr Asn Asn Asp Gln Arg Val Leu Asp Asp Met Glu Lys Leu Ala
305                 310                 315                 320

Ser Lys Phe Phe Gly Arg Val Arg Arg Gly Lys Asn Tyr Val Glu Ile
            325                 330                 335

Ser Arg Lys Met Ala Tyr Val Leu Phe Glu Ser Leu Cys Gly Thr Leu
            340                 345                 350

Ala Glu Asn Lys Arg Val Pro Glu Val Ile Phe Thr Ser Pro Glu Ser
            355                 360                 365

Val Arg Trp Ala Phe Phe Glu Gly Tyr Phe Ile Gly Asp Gly Asp Leu
            370                 375                 380

His Pro Ser Lys Arg Val Arg Leu Ser Thr Lys Ser Glu Glu Leu Val
385                 390                 395                 400

Asn Gly Leu Val Val Leu Leu Asn Ser Leu Gly Ile Ser Ala Ile Lys
            405                 410                 415

Ile Arg Phe Asp Ser Gly Val Tyr Arg Val Leu Val Asn Glu Glu Leu
```

```
                    420                 425                 430
Pro Phe Leu Gly Asn Arg Lys Arg Lys Asn Ala Tyr Tyr Ser His Val
            435                 440                 445

Ile Pro Lys Glu Ile Leu Glu Glu Thr Phe Gly Lys Gln Phe Gln Lys
        450                 455                 460

Asn Met Ser Pro Ala Lys Leu Asn Glu Lys Val Glu Lys Gly Glu Leu
465                 470                 475                 480

Asp Ala Gly Lys Ala Arg Arg Ile Ala Trp Leu Leu Glu Gly Asp Ile
                485                 490                 495

Val Leu Asp Arg Val Glu Lys Val Thr Val Glu Asp Tyr Glu Gly Tyr
            500                 505                 510

Val Tyr Asp Leu Ser Val Glu Glu Asn Glu Asn Phe Leu Ala Gly Phe
        515                 520                 525

Gly Met Leu Tyr Ala His Asn
530                 535

<210> SEQ ID NO 15
<211> LENGTH: 536
<212> TYPE: PRT
<213> ORGANISM: Thermococcus thioreducens

<400> SEQUENCE: 15

Ser Leu Leu Pro Glu Glu Trp Val Pro Val Ile Val Gly Asp Glu Val
1               5                   10                  15

Lys Pro Val Arg Ile Gly Glu Phe Val Asp Ala Leu Met Lys Thr Asp
            20                  25                  30

Ser Glu Leu Val Arg Arg Asp Gly Asp Thr Glu Val Leu Glu Val Lys
        35                  40                  45

Glu Ile Arg Ala Leu Ser Phe Asn Arg Lys Ser Lys Lys Ala Arg Thr
    50                  55                  60

Met Pro Val Lys Ala Val Ile Arg His Arg Tyr Ala Gly Asp Val Tyr
65                  70                  75                  80

Glu Ile Val Leu Ser Ser Gly Arg Arg Ile Arg Val Thr Thr Gly His
                85                  90                  95

Ser Leu Phe Ala Tyr Arg Asn Gly Glu Leu Val Glu Ile Thr Gly Gly
            100                 105                 110

Glu Val Lys Pro Gly Asp Leu Leu Val Pro Lys Arg Val Ser Leu Pro
        115                 120                 125

Glu Arg Lys Glu Arg Leu Asp Ile Val Glu Leu Leu Lys Leu Pro
    130                 135                 140

Glu Ser Glu Thr Glu Asp Ile Val Met Thr Ile Pro Val Lys Gly Arg
145                 150                 155                 160

Lys Asn Phe Phe Ser Gly Met Leu Arg Thr Leu Arg Trp Ile Phe Gly
                165                 170                 175

Glu Glu Lys Arg Leu Arg Thr Ala Arg Arg Tyr Leu Glu His Leu Glu
            180                 185                 190

Arg Leu Gly Tyr Val Lys Leu Arg Lys Ile Gly Tyr Glu Val Ile Asp
        195                 200                 205

Gly Gly Gly Leu Glu Ser Tyr Arg Lys Leu Tyr Glu Lys Leu Ala Gln
    210                 215                 220

Thr Val Arg Tyr Asn Gly Asn Arg Arg Glu Tyr Leu Val Asp Phe Asn
225                 230                 235                 240

Ala Ile Arg Asp Val Ile Pro Leu Met Pro Val Glu Glu Leu Lys Glu
                245                 250                 255
```

```
Trp Leu Ile Gly Thr Arg Asn Gly Phe Arg Met Arg Pro Phe Ile Asp
            260                 265                 270

Val Asn Glu Asp Phe Ala Lys Leu Leu Gly Tyr Tyr Val Ser Glu Gly
        275                 280                 285

Asn Ala Arg Lys Trp Lys Asn His Thr Gly Gly Trp Ser Tyr Ser Val
    290                 295                 300

Lys Leu Tyr Asn Glu Asp Glu Ser Val Leu Asp Asp Met Glu Arg Leu
305                 310                 315                 320

Ala Ser Lys Phe Phe Gly Arg Thr Arg Arg Gly Lys Asn Tyr Val Glu
                325                 330                 335

Ile Pro Arg Lys Met Ala Tyr Ile Ile Phe Glu Gly Leu Cys Gly Val
            340                 345                 350

Leu Ala Glu Asn Lys Arg Val Pro Glu Val Val Phe Thr Ser Pro Glu
        355                 360                 365

Asn Val Arg Trp Ala Phe Leu Gly Gly Tyr Phe Ile Gly Asp Gly Asp
    370                 375                 380

Val His Pro Gly Lys Arg Val Arg Leu Ser Thr Lys Ser Glu Leu Leu
385                 390                 395                 400

Val Asn Gly Leu Val Leu Leu Asn Ser Leu Gly Ile Ser Ala Ile
                405                 410                 415

Lys Ile Arg His Asp Ser Gly Val His Arg Val Tyr Val Asn Glu Glu
            420                 425                 430

Leu Pro Phe Thr Glu Tyr Arg Lys Lys Asn Val Tyr Tyr Ser His
        435                 440                 445

Val Ile Pro Lys Glu Val Leu Glu Glu Thr Phe Arg Lys Val Phe Gln
    450                 455                 460

Lys Asn Met Ser Arg Glu Lys Phe Arg Glu Leu Val Glu Ser Gly Lys
465                 470                 475                 480

Leu Asp Glu Glu Arg Ala Lys Arg Ile Glu Trp Leu Leu Asp Gly Asp
                485                 490                 495

Ile Ala Leu Asp Lys Val Val Glu Val Lys Arg Glu His Tyr Asp Gly
            500                 505                 510

Tyr Val Tyr Asp Leu Ser Val Glu Glu Asp Glu Asn Phe Leu Ala Gly
        515                 520                 525

Phe Gly Leu Leu Tyr Ala His Asn
    530                 535

<210> SEQ ID NO 16
<211> LENGTH: 157
<212> TYPE: PRT
<213> ORGANISM: Thermococcus aggregans

<400> SEQUENCE: 16

Ser Val Thr Gly Asp Thr Glu Ile Ile Val Lys Arg Asn Gly Arg Ile
1               5                   10                  15

Glu Phe Val Pro Ile Glu Lys Leu Phe Glu Arg Val Asp Tyr Arg Ile
            20                  25                  30

Gly Glu Lys Glu Tyr Cys Ile Leu Glu Asp Val Glu Ala Leu Thr Leu
        35                  40                  45

Asp Asn Arg Gly Lys Leu Ile Trp Lys Lys Val Pro Tyr Val Met Arg
    50                  55                  60

His Arg Ala Lys Lys Val Tyr Arg Ile Trp Ile Thr Asn Ser Trp
65                  70                  75                  80

Tyr Ile Asp Val Thr Glu Asp His Ser Leu Ile Val Ala Glu Asp Gly
                85                  90                  95
```

```
Leu Lys Glu Ala Arg Pro Met Glu Ile Glu Gly Lys Ser Leu Ile Ala
            100                 105                 110

Thr Lys Asp Asp Leu Ser Gly Val Glu Tyr Ile Lys Pro His Ala Ile
        115                 120                 125

Glu Glu Ile Ser Tyr Asn Gly Tyr Val Tyr Asp Ile Glu Val Glu Gly
    130                 135                 140

Thr His Arg Phe Phe Ala Asn Gly Ile Leu Val His Asn
145                 150                 155

<210> SEQ ID NO 17
<211> LENGTH: 389
<212> TYPE: PRT
<213> ORGANISM: Thermococcus fumicolans

<400> SEQUENCE: 17

Ser Val Thr Gly Asp Thr Glu Val Thr Ile Arg Arg Asn Gly Arg Ile
1               5                   10                  15

Glu Phe Val Pro Ile Glu Lys Leu Phe Glu Arg Val Asp His Arg Val
            20                  25                  30

Gly Glu Lys Glu Tyr Cys Val Leu Gly Gly Val Glu Ala Leu Thr Leu
        35                  40                  45

Asp Asn Arg Gly Arg Leu Val Trp Lys Lys Val Pro Tyr Val Met Arg
    50                  55                  60

His Lys Thr Asp Lys Arg Ile Tyr Arg Val Trp Phe Thr Asn Ser Trp
65                  70                  75                  80

Tyr Leu Asp Val Thr Glu Asp His Ser Leu Ile Gly Tyr Leu Asn Thr
                85                  90                  95

Ser Lys Val Lys Pro Gly Lys Pro Leu Lys Glu Arg Leu Val Glu Val
            100                 105                 110

Lys Pro Glu Glu Leu Gly Gly Lys Val Lys Ser Leu Ile Thr Pro Asn
        115                 120                 125

Arg Pro Ile Ala Arg Thr Ile Lys Ala Asn Pro Ile Ala Val Lys Leu
    130                 135                 140

Trp Glu Leu Ile Gly Leu Leu Val Gly Asp Gly Asn Trp Gly Gly Gln
145                 150                 155                 160

Ser Asn Trp Ala Lys Tyr Tyr Val Gly Leu Ser Cys Gly Leu Asp Lys
                165                 170                 175

Ala Glu Ile Glu Arg Lys Val Leu Asn Pro Leu Arg Glu Ala Ser Val
            180                 185                 190

Ile Ser Asn Tyr Tyr Asp Lys Ser Lys Lys Gly Asp Val Ser Ile Leu
        195                 200                 205

Ser Lys Trp Leu Ala Gly Phe Met Val Lys Tyr Phe Lys Asp Glu Asn
    210                 215                 220

Gly Asn Lys Ala Ile Pro Ser Phe Met Phe Asn Leu Pro Arg Glu Tyr
225                 230                 235                 240

Ile Glu Ala Phe Leu Arg Gly Leu Phe Ser Ala Asp Gly Thr Val Ser
                245                 250                 255

Leu Arg Arg Gly Ile Pro Glu Ile Arg Leu Thr Ser Val Asn Arg Glu
            260                 265                 270

Leu Ser Asp Ala Val Arg Lys Leu Leu Trp Leu Val Gly Val Ser Asn
        275                 280                 285

Ser Leu Phe Thr Glu Thr Lys Pro Asn Arg Tyr Leu Glu Lys Glu Ser
    290                 295                 300

Gly Thr His Ser Ile His Val Arg Ile Lys Asn Lys His Arg Phe Ala
```

```
                305                 310                 315                 320
Asp Arg Ile Gly Phe Leu Ile Asp Arg Lys Ser Thr Lys Leu Ser Glu
                    325                 330                 335

Asn Leu Gly Gly His Thr Asn Lys Lys Arg Ala Tyr Lys Tyr Asp Phe
                    340                 345                 350

Asp Leu Val Tyr Pro Arg Lys Ile Glu Ile Thr Tyr Asp Gly Tyr
                355                 360                 365

Val Tyr Asp Ile Glu Val Glu Gly Thr His Arg Phe Phe Ala Asn Gly
            370                 375                 380

Ile Leu Val His Asn
385

<210> SEQ ID NO 18
<211> LENGTH: 389
<212> TYPE: PRT
<213> ORGANISM: Thermococcus hydrothermalis

<400> SEQUENCE: 18

Ser Val Thr Gly Glu Thr Glu Ile Ile Ile Lys Arg Asn Gly Lys Val
1               5                   10                  15

Glu Phe Val Ala Ile Glu Glu Leu Phe Gln Arg Val Asp Tyr Arg Ile
            20                  25                  30

Gly Glu Lys Glu Tyr Cys Val Leu Glu Gly Val Glu Ala Leu Thr Leu
        35                  40                  45

Asp Asn Arg Gly Arg Leu Val Trp Lys Ser Pro Tyr Val Met Arg
    50                  55                  60

His Arg Thr Asn Lys Arg Ile Tyr Arg Val Trp Phe Thr Asn Ser Trp
65                  70                  75                  80

Tyr Leu Asp Val Thr Glu Asp His Ser Leu Ile Gly Tyr Met Asn Thr
                85                  90                  95

Ser Lys Val Lys Pro Gly Lys Pro Leu Lys Glu Arg Leu Val Glu Val
            100                 105                 110

Lys Pro Gly Glu Leu Gly Glu Ser Val Lys Ser Leu Ile Thr Pro Asn
        115                 120                 125

Arg Ala Ile Ala His Gly Ile Arg Val Asn Pro Ile Ala Val Lys Leu
    130                 135                 140

Trp Glu Leu Ile Gly Leu Leu Val Gly Asp Gly Asn Trp Gly Gly Gln
145                 150                 155                 160

Ser Asn Trp Ala Lys Tyr Asn Val Gly Leu Ser Leu Gly Leu Asp Lys
                165                 170                 175

Glu Glu Ile Glu Glu Lys Ile Leu Lys Pro Leu Lys Asn Thr Gly Ile
            180                 185                 190

Ile Ser Asn Tyr Tyr Asp Lys Ser Lys Lys Gly Asp Val Ser Ile Leu
        195                 200                 205

Ser Lys Trp Leu Ala Arg Phe Met Val Arg Tyr Phe Lys Asp Glu Ser
    210                 215                 220

Gly Ser Lys Arg Ile Pro Glu Phe Met Phe Asn Leu Pro Arg Glu Tyr
225                 230                 235                 240

Ile Glu Ala Phe Leu Arg Gly Leu Phe Ser Ala Asp Gly Thr Val Ser
                245                 250                 255

Leu Arg Lys Gly Val Pro Glu Val Arg Leu Thr Ser Val Asn Pro Glu
            260                 265                 270

Leu Ser Ser Ser Val Arg Lys Leu Leu Trp Leu Val Gly Val Ser Asn
        275                 280                 285
```

```
Ser Met Phe Val Glu Thr Asn Pro Asn Arg Tyr Leu Gly Lys Glu Ser
            290                 295                 300

Gly Thr His Ser Val His Val Arg Ile Lys Asp Lys His Arg Phe Ala
305                 310                 315                 320

Glu Arg Ile Gly Phe Leu Leu Asp Arg Lys Ala Thr Lys Leu Ser Glu
                325                 330                 335

Asn Leu Gly Gly His Thr Ser Lys Lys Arg Ala Tyr Lys Tyr Asp Phe
            340                 345                 350

Asp Leu Val Tyr Pro Lys Lys Val Glu Glu Ile Ala Tyr Asp Gly Tyr
            355                 360                 365

Val Tyr Asp Ile Glu Val Glu Gly Thr His Arg Phe Phe Ala Asn Gly
370                 375                 380

Ile Leu Val His Asn
385

<210> SEQ ID NO 19
<211> LENGTH: 390
<212> TYPE: PRT
<213> ORGANISM: Thermococcus litoralis

<400> SEQUENCE: 19

Ser Val Ser Gly Glu Ser Glu Ile Ile Ile Arg Gln Asn Gly Lys Ile
1               5                   10                  15

Arg Phe Val Lys Ile Lys Asp Leu Phe Ser Lys Val Asp Tyr Ser Ile
            20                  25                  30

Gly Glu Lys Glu Tyr Cys Ile Leu Glu Gly Val Glu Ala Leu Thr Leu
        35                  40                  45

Asp Asp Asp Gly Lys Leu Val Trp Lys Pro Val Pro Tyr Val Met Arg
50                  55                  60

His Arg Ala Asn Lys Arg Met Phe Arg Ile Trp Leu Thr Asn Ser Trp
65                  70                  75                  80

Tyr Ile Asp Val Thr Glu Asp His Ser Leu Ile Gly Tyr Leu Asn Thr
                85                  90                  95

Ser Lys Thr Lys Thr Ala Lys Lys Ile Gly Glu Arg Leu Lys Glu Val
            100                 105                 110

Lys Pro Phe Glu Leu Gly Lys Ala Val Lys Ser Leu Ile Cys Pro Asn
        115                 120                 125

Ala Pro Leu Lys Asp Glu Asn Thr Lys Thr Ser Glu Ile Ala Val Lys
    130                 135                 140

Phe Trp Glu Leu Val Gly Leu Ile Val Gly Asp Gly Asn Trp Gly Gly
145                 150                 155                 160

Asp Ser Arg Trp Ala Glu Tyr Tyr Leu Gly Leu Ser Thr Gly Lys Asp
                165                 170                 175

Ala Glu Glu Ile Lys Gln Lys Leu Leu Glu Pro Leu Lys Thr Tyr Gly
            180                 185                 190

Val Ile Ser Asn Tyr Tyr Pro Lys Asn Glu Lys Gly Asp Phe Asn Ile
        195                 200                 205

Leu Ala Lys Ser Leu Val Lys Phe Met Lys Arg His Phe Lys Asp Glu
    210                 215                 220

Lys Gly Arg Arg Lys Ile Pro Glu Phe Met Tyr Glu Leu Pro Val Thr
225                 230                 235                 240

Tyr Ile Glu Ala Phe Leu Arg Gly Leu Phe Ser Ala Asp Gly Thr Val
                245                 250                 255

Thr Ile Arg Lys Gly Val Pro Glu Ile Arg Leu Thr Asn Ile Asp Ala
            260                 265                 270
```

```
Asp Phe Leu Arg Glu Val Arg Lys Leu Leu Trp Ile Val Gly Ile Ser
            275                 280                 285

Asn Ser Ile Phe Ala Glu Thr Thr Pro Asn Arg Tyr Asn Gly Val Ser
        290                 295                 300

Thr Gly Thr Tyr Ser Lys His Leu Arg Ile Lys Asn Lys Trp Arg Phe
305                 310                 315                 320

Ala Glu Arg Ile Gly Phe Leu Ile Glu Arg Lys Gln Lys Arg Leu Leu
                325                 330                 335

Glu His Leu Lys Ser Ala Arg Val Lys Arg Asn Thr Ile Asp Phe Gly
            340                 345                 350

Phe Asp Leu Val His Val Lys Lys Val Glu Glu Ile Pro Tyr Glu Gly
        355                 360                 365

Tyr Val Tyr Asp Ile Glu Val Glu Glu Thr His Arg Phe Phe Ala Asn
370                 375                 380

Asn Ile Leu Val His Asn
385                 390

<210> SEQ ID NO 20
<211> LENGTH: 389
<212> TYPE: PRT
<213> ORGANISM: Thermococcus sp. GE8

<400> SEQUENCE: 20

Ser Val Ala Gly Asn Thr Glu Val Ile Ile Arg Arg Asn Gly Lys Val
1               5                   10                  15

Glu Phe Val Pro Ile Glu Lys Leu Phe Gln Arg Val Asp Tyr Arg Ile
            20                  25                  30

Gly Glu Lys Glu Tyr Cys Ala Leu Glu Gly Val Glu Ala Leu Thr Leu
        35                  40                  45

Asp Asn Arg Gly Arg Leu Val Trp Arg Lys Val Pro Tyr Ile Met Arg
50                  55                  60

His Lys Thr Asn Lys Lys Ile Tyr Arg Val Trp Phe Thr Asn Ser Trp
65                  70                  75                  80

Tyr Leu Asp Val Thr Glu Asp His Ser Leu Ile Gly Tyr Leu Asn Thr
                85                  90                  95

Ser Lys Val Lys Ser Glu Lys Pro Leu Lys Glu Arg Leu Val Glu Val
            100                 105                 110

Lys Pro Arg Glu Leu Gly Glu Lys Val Lys Ser Leu Ile Thr Leu Asn
        115                 120                 125

Arg Ala Ile Ala Arg Ser Ile Lys Ala Asn Pro Ile Ala Val Arg Leu
130                 135                 140

Trp Glu Leu Ile Gly Leu Leu Val Gly Asp Gly Asn Trp Gly His
145                 150                 155                 160

Ser Lys Trp Ala Lys Tyr Tyr Val Gly Leu Ser Cys Gly Leu Asp Lys
                165                 170                 175

Ala Glu Ile Glu Glu Lys Val Leu Arg Pro Leu Lys Glu Ala Gly Ile
            180                 185                 190

Ile Ser Asn Tyr Tyr Gly Lys Ser Lys Lys Gly Asp Val Ser Ile Leu
        195                 200                 205

Ser Lys Trp Leu Ala Gly Phe Met Val Lys Tyr Phe Lys Asp Glu Asn
210                 215                 220

Gly Asn Lys Arg Ile Pro Ser Phe Met Phe Asn Leu Pro Arg Glu Tyr
225                 230                 235                 240

Ile Glu Ala Phe Leu Arg Gly Leu Phe Ser Ala Asp Gly Thr Val Ser
```

```
                    245                 250                 255
Leu Arg Arg Gly Ile Pro Glu Ile Arg Leu Thr Ser Val Asn Arg Glu
            260                 265                 270

Leu Ser Asn Glu Val Arg Lys Leu Leu Trp Leu Val Gly Val Ser Asn
        275                 280                 285

Ser Met Phe Thr Glu Thr Thr Pro Asn Lys Tyr Leu Gly Asn Glu Ser
    290                 295                 300

Gly Thr Arg Ser Ile His Val Arg Ile Lys Asn Lys His Arg Phe Ala
305                 310                 315                 320

Lys Arg Ile Gly Phe Leu Leu Asp Arg Lys Ala Thr Lys Leu Ser Asp
                325                 330                 335

Asn Leu Arg Glu His Thr Asn Lys Lys Met Ala Tyr Arg Tyr Asp Phe
            340                 345                 350

Asp Leu Val Tyr Pro Lys Lys Ile Glu Glu Ile Asn Tyr Asp Arg Tyr
        355                 360                 365

Val Tyr Asp Ile Glu Val Glu Gly Thr His Arg Phe Phe Ala Asn Gly
    370                 375                 380

Ile Leu Val His Asn
385

<210> SEQ ID NO 21
<211> LENGTH: 184
<212> TYPE: PRT
<213> ORGANISM: Pyrococcus abyssi

<400> SEQUENCE: 21

Cys Phe Pro Gly Asp Thr Arg Ile Leu Val Gln Ile Asp Gly Val Pro
1               5                   10                  15

Gln Lys Ile Thr Leu Arg Glu Leu Tyr Glu Leu Phe Glu Asp Glu Arg
            20                  25                  30

Tyr Glu Asn Met Val Tyr Val Arg Lys Pro Lys Arg Glu Ile Lys
        35                  40                  45

Val Tyr Ser Ile Asp Leu Glu Thr Gly Lys Val Val Leu Thr Asp Ile
    50                  55                  60

Glu Asp Val Ile Lys Ala Pro Ala Thr Asp His Leu Ile Arg Phe Glu
65                  70                  75                  80

Leu Glu Asp Gly Arg Ser Phe Glu Thr Thr Val Asp His Pro Val Leu
                85                  90                  95

Val Tyr Glu Asn Gly Arg Phe Ile Glu Lys Arg Ala Phe Glu Val Lys
            100                 105                 110

Glu Gly Asp Lys Val Leu Val Ser Glu Leu Glu Leu Val Glu Gln Ser
        115                 120                 125

Ser Ser Ser Gln Asp Asn Pro Lys Asn Glu Asn Leu Gly Ser Pro Glu
    130                 135                 140

His Asp Gln Leu Leu Glu Ile Lys Asn Ile Lys Tyr Val Arg Ala Asn
145                 150                 155                 160

Asp Asp Phe Val Phe Ser Leu Asn Ala Lys Lys Tyr His Asn Val Ile
                165                 170                 175

Ile Asn Glu Asn Ile Val Thr His
            180

<210> SEQ ID NO 22
<211> LENGTH: 416
<212> TYPE: PRT
<213> ORGANISM: Mycobacterium tuberculosis CDC1551
```

```
<400> SEQUENCE: 22

Cys Leu Thr Ala Ser Thr Arg Ile Leu Arg Ala Asp Thr Gly Ala Glu
1               5                   10                  15

Val Ala Phe Gly Glu Leu Met Arg Ser Gly Glu Arg Pro Met Val Trp
            20                  25                  30

Ser Leu Asp Glu Arg Leu Arg Met Val Ala Arg Pro Met Ile Asn Val
        35                  40                  45

Phe Pro Ser Gly Arg Lys Glu Val Phe Arg Leu Arg Leu Ala Ser Gly
    50                  55                  60

Arg Glu Val Glu Ala Thr Gly Ser His Pro Phe Met Lys Phe Glu Gly
65                  70                  75                  80

Trp Thr Pro Leu Ala Gln Leu Lys Val Gly Asp Arg Ile Ala Ala Pro
                85                  90                  95

Arg Arg Val Pro Glu Pro Ile Asp Thr Gln Arg Met Pro Glu Ser Glu
            100                 105                 110

Leu Ile Ser Leu Ala Arg Met Ile Gly Asp Gly Ser Cys Leu Lys Asn
        115                 120                 125

Gln Pro Ile Arg Tyr Glu Pro Val Asp Glu Ala Asn Leu Ala Ala Val
    130                 135                 140

Thr Val Ser Ala Ala His Ser Asp Gly Ala Ala Ile Arg Asp Asp Tyr
145                 150                 155                 160

Leu Ala Ala Arg Val Pro Ser Leu Arg Pro Ala Arg Gln Arg Leu Pro
                165                 170                 175

Arg Gly Arg Cys Thr Pro Ile Ala Ala Trp Leu Ala Gly Leu Gly Leu
            180                 185                 190

Phe Thr Lys Arg Ser His Glu Lys Cys Val Pro Glu Ala Val Phe Arg
        195                 200                 205

Ala Pro Asn Asp Gln Val Ala Leu Phe Leu Arg His Leu Trp Ser Ala
    210                 215                 220

Gly Gly Ser Val Arg Trp Asp Pro Thr Asn Gly Gln Gly Arg Val Tyr
225                 230                 235                 240

Tyr Gly Ser Thr Ser Arg Arg Leu Ile Asp Asp Val Ala Gln Leu Leu
                245                 250                 255

Leu Arg Val Gly Ile Phe Ser Trp Ile Thr His Ala Pro Lys Leu Gly
            260                 265                 270

Gly His Asp Ser Trp Arg Leu His Ile His Gly Ala Lys Asp Gln Val
        275                 280                 285

Arg Phe Leu Arg His Val Gly Val His Gly Ala Glu Ala Val Ala Ala
    290                 295                 300

Gln Glu Met Leu Arg Gln Leu Lys Gly Pro Val Arg Asn Pro Asn Leu
305                 310                 315                 320

Asp Ser Ala Pro Lys Lys Val Trp Ala Gln Val Arg Asn Arg Leu Ser
                325                 330                 335

Ala Lys Gln Met Met Asp Ile Gln Leu His Glu Pro Thr Met Trp Lys
            340                 345                 350

His Ser Pro Ser Arg Ser Arg Pro His Arg Ala Glu Ala Arg Ile Glu
        355                 360                 365

Asp Arg Ala Ile His Glu Leu Ala Arg Gly Asp Ala Tyr Trp Asp Thr
    370                 375                 380

Val Val Glu Ile Thr Ser Ile Gly Asp Gln His Val Phe Asp Gly Thr
385                 390                 395                 400

Val Ser Gly Thr His Asn Phe Val Ala Asn Gly Ile Ser Leu His Asn
                405                 410                 415
```

<210> SEQ ID NO 23
<211> LENGTH: 416
<212> TYPE: PRT
<213> ORGANISM: Mycobacterium tuberculosis H37Rv

<400> SEQUENCE: 23

```
Cys Leu Thr Ala Ser Thr Arg Ile Leu Arg Ala Asp Thr Gly Ala Glu
1               5                   10                  15

Val Ala Phe Gly Glu Leu Met Arg Ser Gly Arg Pro Met Val Trp
            20                  25                  30

Ser Leu Asp Glu Arg Leu Arg Met Val Ala Arg Pro Met Ile Asn Val
        35                  40                  45

Phe Pro Ser Gly Arg Lys Glu Val Phe Arg Leu Arg Leu Ala Ser Gly
    50                  55                  60

Arg Glu Val Glu Ala Thr Gly Ser His Pro Phe Met Lys Phe Glu Gly
65                  70                  75                  80

Trp Thr Pro Leu Ala Gln Leu Lys Val Gly Asp Arg Ile Ala Ala Pro
                85                  90                  95

Arg Arg Val Pro Glu Pro Ile Asp Thr Gln Arg Met Pro Glu Ser Glu
            100                 105                 110

Leu Ile Ser Leu Ala Arg Met Ile Gly Asp Gly Ser Cys Leu Lys Asn
        115                 120                 125

Gln Pro Ile Arg Tyr Glu Pro Val Asp Glu Ala Asn Leu Ala Ala Val
    130                 135                 140

Thr Val Ser Ala Ala His Ser Asp Arg Ala Ala Ile Arg Asp Asp Tyr
145                 150                 155                 160

Leu Ala Ala Arg Val Pro Ser Leu Arg Pro Ala Arg Gln Arg Leu Pro
                165                 170                 175

Arg Gly Arg Cys Thr Pro Ile Ala Ala Trp Leu Ala Gly Leu Gly Leu
            180                 185                 190

Phe Thr Lys Arg Ser His Glu Lys Cys Val Pro Glu Ala Val Phe Arg
        195                 200                 205

Ala Pro Asn Asp Gln Val Ala Leu Phe Leu Arg His Leu Trp Ser Ala
    210                 215                 220

Gly Gly Ser Val Arg Trp Asp Pro Thr Asn Gly Gln Gly Arg Val Tyr
225                 230                 235                 240

Tyr Gly Ser Thr Ser Arg Arg Leu Ile Asp Asp Val Ala Gln Leu Leu
                245                 250                 255

Leu Arg Val Gly Ile Phe Ser Trp Ile Thr His Ala Pro Lys Leu Gly
            260                 265                 270

Gly His Asp Ser Trp Arg Leu His Ile His Gly Ala Lys Asp Gln Val
        275                 280                 285

Arg Phe Leu Arg His Val Gly Val His Gly Ala Glu Ala Val Ala Ala
    290                 295                 300

Gln Glu Met Leu Arg Gln Leu Lys Gly Pro Val Arg Asn Pro Asn Leu
305                 310                 315                 320

Asp Ser Ala Pro Lys Lys Val Trp Ala Gln Val Arg Asn Arg Leu Ser
                325                 330                 335

Ala Lys Gln Met Met Asp Ile Gln Leu His Glu Pro Thr Met Trp Lys
            340                 345                 350

His Ser Pro Ser Arg Ser Arg Pro His Arg Ala Glu Ala Arg Ile Glu
        355                 360                 365

Asp Arg Ala Ile His Glu Leu Ala Arg Gly Asp Ala Tyr Trp Asp Thr
```

-continued

```
               370                 375                 380
Val Val Glu Ile Thr Ser Ile Gly Asp Gln His Val Phe Asp Gly Thr
385                 390                 395                 400

Val Ser Gly Thr His Asn Phe Val Ala Asn Gly Ile Ser Leu His Asn
                405                 410                 415

<210> SEQ ID NO 24
<211> LENGTH: 428
<212> TYPE: PRT
<213> ORGANISM: Rhodothermus marinus

<400> SEQUENCE: 24

Cys Leu Ala Gly Asp Thr Leu Ile Thr Leu Ala Asp Gly Arg Arg Val
1               5                   10                  15

Pro Ile Arg Glu Leu Val Ser Gln Gln Asn Phe Ser Val Trp Ala Leu
                20                  25                  30

Asn Pro Gln Thr Tyr Arg Leu Glu Arg Ala Arg Val Ser Arg Ala Phe
            35                  40                  45

Cys Thr Gly Ile Lys Pro Val Tyr Arg Leu Thr Thr Arg Leu Gly Arg
50                  55                  60

Ser Ile Arg Ala Thr Ala Asn His Arg Phe Leu Thr Pro Gln Gly Trp
65                  70                  75                  80

Lys Arg Val Asp Glu Leu Gln Pro Gly Asp Tyr Leu Ala Leu Pro Arg
                85                  90                  95

Arg Ile Pro Thr Ala Ser Thr Pro Thr Leu Thr Glu Ala Glu Leu Ala
            100                 105                 110

Leu Leu Gly His Leu Ile Gly Asp Gly Cys Thr Leu Pro His His Val
        115                 120                 125

Ile Gln Tyr Thr Ser Arg Asp Ala Asp Leu Ala Thr Leu Val Ala His
130                 135                 140

Leu Ala Thr Lys Val Phe Gly Ser Lys Val Thr Pro Gln Ile Arg Lys
145                 150                 155                 160

Glu Leu Arg Trp Tyr Gln Val Tyr Leu Arg Ala Ala Arg Pro Leu Ala
                165                 170                 175

Pro Gly Lys Arg Asn Pro Ile Ser Asp Trp Leu Arg Asp Leu Gly Ile
            180                 185                 190

Phe Gly Leu Arg Ser Tyr Glu Lys Lys Val Pro Ala Leu Leu Phe Cys
        195                 200                 205

Gln Thr Ser Glu Ala Ile Ala Thr Phe Leu Arg His Leu Trp Ala Thr
210                 215                 220

Asp Gly Cys Ile Gln Met Arg Arg Gly Lys Lys Pro Tyr Pro Ala Val
225                 230                 235                 240

Tyr Tyr Ala Thr Ser Ser Tyr Gln Leu Ala Arg Asp Val Gln Ser Leu
                245                 250                 255

Leu Leu Arg Leu Gly Ile Asn Ala Arg Leu Lys Thr Val Ala Gln Gly
            260                 265                 270

Glu Lys Gly Arg Val Gln Tyr His Val Lys Val Ser Gly Arg Glu Asp
        275                 280                 285

Leu Leu Arg Phe Val Glu Lys Ile Gly Ala Val Gly Ala Arg Gln Arg
290                 295                 300

Ala Ala Leu Ala Ser Val Tyr Asp Tyr Leu Ser Val Arg Thr Gly Asn
305                 310                 315                 320

Pro Asn Arg Asp Ile Ile Pro Val Ala Leu Trp Tyr Glu Leu Val Arg
                325                 330                 335
```

-continued

Glu Ala Met Tyr Gln Arg Gly Ile Ser His Arg Gln Leu His Ala Asn
            340                 345                 350

Leu Gly Met Ala Tyr Gly Gly Met Thr Leu Phe Arg Gln Asn Leu Ser
        355                 360                 365

Arg Ala Arg Ala Leu Arg Leu Ala Glu Ala Ala Cys Pro Glu Leu
    370                 375                 380

Arg Gln Leu Ala Gln Ser Asp Val Tyr Trp Asp Pro Ile Val Ser Ile
385                 390                 395                 400

Glu Pro Asp Gly Val Glu Val Phe Asp Leu Thr Val Pro Gly Pro
                405                 410                 415

His Asn Phe Val Ala Asn Asp Ile Ile Ala His Asn
            420                 425

<210> SEQ ID NO 25
<211> LENGTH: 1365
<212> TYPE: PRT
<213> ORGANISM: Trichodesmium erythraeum IMS101

<400> SEQUENCE: 25

Cys Leu Pro Lys Gly Thr Leu Ile Asp Gln Pro Asp Gly Ser Arg Glu
1               5                   10                  15

Ala Ile Glu Asn Ile Lys Ser Gly Glu Val Ile Leu Thr Ser Asp Gly
            20                  25                  30

Arg Lys Val Trp Glu Ala Lys Val Ala Lys Gln Trp Arg Ser Gly Val
        35                  40                  45

Arg Glu Ile Leu Lys Ile Thr Leu Ser Ser Gly Thr Val Ile Tyr Ser
    50                  55                  60

Gly Lys Asn His Arg Phe Leu Thr Pro Glu Gly Asp Lys Phe Ala Trp
65                  70                  75                  80

Glu Leu Gln Pro Gln Val Gly Arg Val Lys Asn Ala Leu Ile Tyr Gly
                85                  90                  95

Ser Ala Val Tyr Glu Lys Trp Gln Val Ser Ser Asn Gln Lys Gln Leu
            100                 105                 110

Arg Lys Asn Asp Ala Tyr Leu Leu Gly Leu Leu Val Gly Lys Ser Asn
        115                 120                 125

Leu Ile Ser Ser Thr Pro Asn Val Ser Phe Ser Thr Gln Gly Ala Ile
    130                 135                 140

Thr Trp Gly Lys Asn Leu Ile Asp Glu Thr Trp Gly Gly Glu Ala Lys
145                 150                 155                 160

His Tyr Phe Asp Thr Ser Arg Arg Gln Val Tyr Leu Asn Phe Asn Thr
                165                 170                 175

Gln Ser Lys Pro Thr Ala Leu Thr Glu Phe Leu Asp Gly Ile Tyr Gly
            180                 185                 190

Ala Gln Asn Trp Gln Val Glu Ser Val Ala Lys His Leu Pro Glu Asp
        195                 200                 205

Ile Leu Asp Tyr Ser Glu Lys Asp Arg Ile Asp Leu Leu Arg Gly Leu
    210                 215                 220

Trp Asp Ser Gly Gly Phe Asp Gly Lys Lys Leu Leu Tyr Tyr Pro Gly
225                 230                 235                 240

Ser Ser Pro Gln Leu Leu Ser Gln Val Cys Gln Leu Leu Gly Ser Leu
                245                 250                 255

Lys Ile Asp Tyr Tyr Leu Ala Asp Asn Ser Val Arg Ile Ser Asp Arg
            260                 265                 270

Ser Arg Phe Ile Asp Ile Leu Glu Asn Tyr Gln Met Ser Ser Gln Gln
        275                 280                 285

```
Lys Glu Glu Ile Ser Glu Ser Tyr Leu Pro Ala Ser Ser Trp Phe Leu
290                 295                 300

Lys Gly Gly Ser Glu Asn Asn Ile Gln Lys Thr Asp Ser Ser Ser Arg
305                 310                 315                 320

Lys Thr Gly Glu Ala Ser Gln Gln Lys Ala Thr Leu Phe Thr Gln Asn
            325                 330                 335

Leu Phe Ser Ala Gln Thr Pro Ala Glu Asn Trp Glu Lys Val Gly Glu
            340                 345                 350

Asn His Leu Leu Ser Ser Trp Phe Leu Thr Asp Ala Ser Glu Asn Asn
            355                 360                 365

Ile Gln Lys Thr Asp Ser Ser Arg Lys Thr Gly Glu Ala Ser Gln
370                 375                 380

Gln Lys Ala Thr Leu Phe Thr Gln Asn Leu Phe Ser Ala Gln Thr Pro
385                 390                 395                 400

Ala Glu Asn Trp Glu Lys Val Arg Glu Asn His Leu Leu Ser Ser Trp
            405                 410                 415

Phe Leu Thr Asn Ala Ser Glu Ile Tyr Leu Gln Arg Ile Asp Ser Ser
            420                 425                 430

Ser Arg Lys Thr Gly Glu Ala Ser Gln Gln Lys Ala Thr Leu Phe Thr
            435                 440                 445

Gln Asn Leu Phe Ser Val Gln Thr Pro Ala Glu Asn Trp Glu Lys Val
450                 455                 460

Arg Glu Asn His Leu Leu Ser Ser Trp Phe Leu Thr Asp Ala Ser Glu
465                 470                 475                 480

Asn Asn Ile Gln Lys Thr Asp Ser Ser Arg Lys Thr Gly Glu Ala
            485                 490                 495

Ser Gln Gln Lys Ala Thr Leu Phe Thr Gln Asn Leu Phe Ser Ala Gln
            500                 505                 510

Thr Pro Ala Glu Asn Trp Glu Lys Val Arg Glu Asn His Leu Leu Ser
            515                 520                 525

Ser Trp Phe Leu Thr Asn Ala Ser Glu Asn Asn Ile Gln Lys Thr Asp
            530                 535                 540

Ser Ser Ser Arg Lys Thr Gly Glu Ala Ser Gln Gln Lys Ala Thr Leu
545                 550                 555                 560

Phe Thr Gln Asn Leu Phe Ser Ala Gln Thr Pro Ala Glu Asn Trp Lys
            565                 570                 575

Lys Ser Arg Lys Asn His Leu Pro Ser Ser Trp Phe Leu Lys Gly Gly
            580                 585                 590

Ser Glu Asn Asn Ile Gln Lys Thr Asp Ser Ser Arg Lys Thr Gly
            595                 600                 605

Glu Ala Ser Gln Gln Lys Ala Thr Leu Phe Thr Gln Asn Leu Phe Ser
610                 615                 620

Ala Gln Thr Pro Ala Glu Asn Trp Glu Lys Val Arg Glu Asn His Leu
625                 630                 635                 640

Leu Ser Ser Trp Phe Leu Lys Asp Ala Ser Glu Asn Asn Ile Gln Lys
            645                 650                 655

Thr Asp Ser Ser Ser Arg Lys Thr Gly Glu Ala Ser Gln Gln Lys Ala
            660                 665                 670

Thr Leu Phe Thr Gln Asn Leu Phe Ser Ala Gln Thr Pro Ala Glu Asn
            675                 680                 685

Trp Glu Lys Val Arg Glu Asn His Leu Leu Ser Ser Trp Phe Leu Thr
690                 695                 700
```

```
Asp Ala Ser Glu Asn Asn Ile Gln Lys Thr Asp Ser Ser Arg Lys
705                 710                 715                 720

Thr Gly Glu Ala Ser Gln Gln Lys Ala Thr Leu Phe Thr Gln Asn Leu
            725                 730                 735

Phe Ser Ala Gln Thr Pro Ala Glu Asn Trp Glu Lys Val Arg Glu Asn
                740                 745                 750

His Leu Leu Ser Ser Trp Phe Leu Thr Asp Ala Ser Glu Asn Asn Ile
            755                 760                 765

Gln Lys Thr Asp Ser Ser Arg Lys Thr Gly Glu Ala Ser Gln Gln
    770                 775                 780

Lys Ala Thr Leu Phe Thr Gln Asn Leu Phe Ser Ala Gln Thr Pro Ala
785                 790                 795                 800

Glu Asn Trp Glu Lys Val Arg Glu Asn His Leu Leu Ser Ser Trp Phe
            805                 810                 815

Leu Thr Asn Ala Ser Glu Asn Asn Ile Gln Lys Thr Asp Ser Ser Ser
            820                 825                 830

Arg Lys Thr Gly Glu Ala Ser Gln Gln Lys Ala Thr Leu Phe Thr Gln
            835                 840                 845

Asn Leu Phe Ser Ala Gln Thr Pro Ala Glu Asn Trp Lys Lys Ala Arg
850                 855                 860

Glu Asn His Leu Leu Ser Ser Trp Phe Leu Thr Asn Ala Ser Glu Ile
865                 870                 875                 880

Tyr Leu Gln Arg Thr Asp Ser Ser Arg Lys Thr Gly Glu Ala Ser
                885                 890                 895

Gln Gln Lys Ala Thr Leu Phe Gln Asn Leu Phe Ser Val Gln Thr
    900                 905                 910

Pro Ala Glu Asn Trp Lys Lys Ala Arg Glu Asn His Leu Leu Ser Ser
            915                 920                 925

Trp Phe Leu Thr Asn Ala Ser Glu Ile Tyr Leu Gln Arg Thr Asp Ser
930                 935                 940

Ser Ser Arg Lys Thr Gly Gly Ala Ser Gln Gln Lys Ala Thr Leu Phe
945                 950                 955                 960

Asn Gln Asn Leu Phe Ser Val Gln Thr Pro Ala Glu Asn Trp Glu Lys
            965                 970                 975

Val Arg Glu Asn Tyr Leu Leu Ser Ser Trp Phe Leu Thr Asn Ala Ser
                980                 985                 990

Glu Ile Tyr Leu Gln Arg Thr Asp  Ser Ser Ser Arg Lys  Thr Gly Glu
            995                 1000                1005

Ala Ser Gln Gln Lys Ala Thr  Leu Phe Thr Gln Asn  Leu Phe Ser
    1010                1015                1020

Val Gln Thr Pro Ala Glu Asn  Trp Lys Lys Ala Arg  Glu Asn His
    1025                1030                1035

Leu Leu Ser Ser Trp Phe Leu  Thr Asn Ala Ser Glu  Ile Tyr Leu
    1040                1045                1050

Gln Arg Thr Asp Ser Ser Ser  Arg Lys Thr Gly Gly  Ala Ser Gln
    1055                1060                1065

Gln Lys Ala Thr Leu Phe Asn  Gln Asn Leu Phe Ser  Val Gln Thr
    1070                1075                1080

Pro Ala Glu Asn Trp Lys Lys  Ala Arg Glu Asn His  Leu Leu Ser
    1085                1090                1095

Ser Trp Phe Leu Thr Asn Ala  Ser Glu Ile Tyr Leu  Gln Arg Thr
    1100                1105                1110

Asp Ser  Ser Ser Arg Lys Thr  Val Glu Ala Ser Gln  Gln Lys Ala
```

```
        1115                1120                1125

Thr Leu Phe Thr Gln Asn Leu Phe Ser Ala Gln Thr Pro Ala Glu
        1130                1135                1140

Asn Trp Glu Lys Val Arg Glu Asn Tyr Leu Leu Ser Ser Trp Phe
        1145                1150                1155

Leu Thr Asn Ala Ser Glu Ile Tyr Leu Gln Arg Ile Asp Ser Ser
        1160                1165                1170

Ser Arg Lys Thr Gly Glu Ala Cys Gln Gln Lys Ala Thr Leu Phe
        1175                1180                1185

Asn Gln Asn Leu Phe Ser Ala Gln Thr Pro Ala Glu Asn Trp Lys
        1190                1195                1200

Lys Val Arg Glu Asn His Leu Leu Ser Ser Trp Phe Leu Thr Asp
        1205                1210                1215

Ala Ser Glu Asn Asn Ile Gln Lys Thr Asp Ser Ser Ser Arg Lys
        1220                1225                1230

Thr Val Glu Ala Ser Gln Gln Lys Ala Thr Leu Phe Thr Gln Asn
        1235                1240                1245

Leu Phe Ser Ala Gln Thr Pro Ala Glu Asn Trp Lys Lys Ser Arg
        1250                1255                1260

Lys Asn His Leu Pro Ser Ser Trp Phe Leu Thr Asp Ala Ser Glu
        1265                1270                1275

Asn Asn Ile Gln Lys Thr Asp Ser Ser Arg Lys Thr Gly Glu
        1280                1285                1290

Ala Ser Gln Gln Lys Ala Thr Leu Phe Thr Gln Asn Leu Phe Ser
        1295                1300                1305

Val Gln Thr Pro Glu Leu Glu Asn Trp Glu Cys Glu Lys Thr Tyr
        1310                1315                1320

Leu Gln Asp Val Arg Val Val His Val Val Ser Val Glu Glu Val
        1325                1330                1335

Gly Glu Ala Glu Cys Phe Asp Leu Glu Met Glu Asp Gln Ser Ser
        1340                1345                1350

Pro Tyr Phe Leu Ala Glu Gly Val Val Val His Asn
        1355                1360                1365

<210> SEQ ID NO 26
<211> LENGTH: 435
<212> TYPE: PRT
<213> ORGANISM: Synechocystis PCC6803

<400> SEQUENCE: 26

Cys Phe Ser Gly Asp Thr Leu Val Ala Leu Thr Asp Gly Arg Ser Val
1               5                   10                  15

Ser Phe Glu Gln Leu Val Glu Glu Lys Gln Gly Lys Gln Asn Phe
            20                  25                  30

Cys Tyr Thr Ile Arg His Asp Gly Ser Ile Gly Val Glu Lys Ile Ile
        35                  40                  45

Asn Ala Arg Lys Thr Lys Thr Asn Ala Lys Val Ile Lys Val Thr Leu
    50                  55                  60

Asp Asn Gly Glu Ser Ile Ile Cys Thr Pro Asp His Lys Phe Met Leu
65                  70                  75                  80

Arg Asp Gly Ser Tyr Lys Cys Ala Met Asp Leu Thr Leu Asp Asp Ser
                85                  90                  95

Leu Met Pro Leu His Arg Lys Ile Ser Thr Thr Glu Asp Ser Gly Ile
            100                 105                 110
```

Thr Ile Asp Gly Tyr Glu Met Val Trp Ser Pro Arg Asp Ser Trp
            115                 120                 125

Leu Phe Thr His Leu Val Ala Asp Trp Tyr Asn Arg Trp Gln Gly Ile
    130                 135                 140

Tyr Ile Ala Glu Glu Lys Gln His Cys His His Lys Asp Phe Asn Lys
145                 150                 155                 160

Arg Asn Asn Asn Pro Asp Asn Leu Ile Arg Leu Ser Pro Glu Lys His
                165                 170                 175

Leu Ala Leu His Arg Lys His Ile Ser Lys Thr Leu His Arg Pro Asp
            180                 185                 190

Val Val Glu Lys Cys Arg Arg Ile His Gln Ser Pro Glu Phe Arg Arg
        195                 200                 205

Lys Met Ser Ala Arg Met Gln Ser Pro Glu Thr Arg Ala Ile Leu Ser
    210                 215                 220

Lys Gln Ala Gln Ala Gln Trp Gln Asn Glu Thr Tyr Lys Leu Thr Met
225                 230                 235                 240

Met Glu Ser Trp Arg Ser Phe Tyr Asp Ser Asn Glu Asp Tyr Arg Gln
                245                 250                 255

Gln Asn Ala Glu Gln Leu Asn Arg Ala Gln Gln Glu Tyr Trp Ala Gln
            260                 265                 270

Ala Glu Asn Arg Thr Ala Gln Ala Glu Arg Val Arg Gln His Phe Ala
        275                 280                 285

Gln Asn Pro Gly Leu Arg Gln Gln Tyr Ser Glu Asn Ala Val Lys Gln
    290                 295                 300

Trp Asn Asn Pro Glu Leu Leu Lys Trp Arg Gln Lys Lys Thr Lys Glu
305                 310                 315                 320

Gln Trp Thr Pro Glu Phe Arg Glu Lys Arg Glu Ala Leu Ala Gln
                325                 330                 335

Thr Tyr Tyr Arg Lys Thr Leu Ala Ala Leu Lys Gln Val Glu Ile Glu
            340                 345                 350

Asn Gly Tyr Leu Asp Ile Ser Ala Tyr Asp Ser Tyr Arg Ile Ser Thr
        355                 360                 365

Lys Asp Lys Ser Leu Leu Arg Phe Asp Arg Phe Cys Glu Arg Tyr Phe
    370                 375                 380

Glu Asn Asp Glu Asn Leu Ala Arg Glu Ala Val Leu Asn Tyr Asn His
385                 390                 395                 400

Arg Ile Val Asn Ile Glu Ala Val Ser Glu Thr Ile Asp Val Tyr Asp
                405                 410                 415

Ile Glu Val Pro His Thr His Asn Phe Ala Leu Ala Ser Gly Val Phe
            420                 425                 430

Val His Asn
        435

<210> SEQ ID NO 27
<211> LENGTH: 421
<212> TYPE: PRT
<213> ORGANISM: Mycobacterium flavescens

<400> SEQUENCE: 27

Cys Val Thr Gly Asp Ala Leu Val Leu Pro Phe Gly Gln Ser Val
1               5                   10                  15

Arg Leu Arg Asp Val Val Ala Gly Ala Arg Ser Ser Ser Asp Asn Ala
            20                  25                  30

Ile Asp Leu Lys Val Leu Asn Arg His Gly Asp Pro Val Val Ala Asp
        35                  40                  45

```
Lys Leu Phe His Ser Gly Glu His Glu Thr Tyr Thr Val Arg Thr Ala
     50                  55                  60

Glu Gly Tyr Glu Val Thr Gly Thr Ala Asn His Pro Leu Leu Cys Leu
 65                  70                  75                  80

Val Asp Val Gly Gly Val Pro Thr Leu Leu Trp Lys Leu Thr Glu Glu
                 85                  90                  95

Ile Arg Pro Gly Asp His Val Val Leu Gln Arg Thr Pro Pro Thr Glu
                100                 105                 110

Phe Gly Pro Ala Asp Trp Gln Asp Ala Phe Glu Ala Leu His Leu Gly
            115                 120                 125

Ala Phe Ile Ser Glu Gly Phe Val Ser Glu Asn Arg Ala Gly Phe Asn
        130                 135                 140

Asn Leu Asp Arg Glu Phe Phe Asn Ala Val Leu Thr Ala Tyr Asp Thr
145                 150                 155                 160

Ile Val Gly Gly Pro Arg Tyr Val Ser Arg Thr Ile Ala Ser Asp
                165                 170                 175

Ser Leu Leu His Glu Leu Asp Val His Asn Leu Thr Ala Leu Lys Lys
                180                 185                 190

Ser Arg Leu Gly Glu Leu Val Gly Gln Arg Ser Ala Asp Lys Ala Val
        195                 200                 205

Pro Glu Trp Leu Trp Lys Ala Pro Ala Val Val Lys Arg Val Phe Leu
    210                 215                 220

Gln Ala Leu Phe Glu Gly Asp Gly Ser Cys Ser Ala Leu Pro Arg Asn
225                 230                 235                 240

Thr Ile Gln Val Ser Tyr Ser Thr Arg Ser Gly Arg Leu Ala Lys Asp
                245                 250                 255

Ile Gln Gln Met Leu Leu Glu Phe Gly Val Ile Ser Arg Arg Tyr Val
            260                 265                 270

His Ala Thr Gly Glu His Lys Val Val Leu Thr Ser Arg Ala Gln Ala
        275                 280                 285

Glu Leu Phe Ala Ala Gln Ile Gly Phe Gly Gly Ile Lys Gln Ala Lys
    290                 295                 300

Leu Gln Gly Leu Leu Asp Ala Leu Pro Gln Ala Ala Gly Arg Asp
305                 310                 315                 320

Gly Asp Tyr Val Pro Gly Leu Ala Gln Phe Val Arg Lys His Ser Gly
                325                 330                 335

Ser Arg Trp Val Asp Lys Asp Trp Leu Asn Arg His Asn Ile Asp Arg
            340                 345                 350

Leu Ser Arg Trp Gln Arg Asp Gly Ala Glu Ile Leu Gly Arg Ile Ala
        355                 360                 365

Asp Pro Asp Val Arg Ala Ile Ala Gln Glu Leu Thr Asp Gly Arg Phe
    370                 375                 380

Tyr Tyr Ala Arg Val Ala Ser Val Thr Asp Ser Gly Val Gln Pro Val
385                 390                 395                 400

Tyr Ser Leu Arg Val Asp Thr Asp Asp His Ser Phe Ile Thr Asn Gly
                405                 410                 415

Phe Val Ser His Asn
            420

<210> SEQ ID NO 28
<211> LENGTH: 420
<212> TYPE: PRT
<213> ORGANISM: Mycobacterium gordonae
```

```
<400> SEQUENCE: 28

Cys Leu Thr Gly Asp Ala Leu Val Arg Leu Pro Phe Gly Gln Ser Met
1               5                   10                  15

Arg Ile Gly Asp Val Ala Pro Gly Ala Arg Thr Asn Ser Asp Asn Ala
            20                  25                  30

Gly Glu Leu Lys Val Leu Asp Arg His Gly Asp Pro Val Phe Ala Asp
        35                  40                  45

Arg Leu Phe His Ser Gly Asp His Gln Thr Phe Arg Val Gln Thr Ala
    50                  55                  60

Glu Gly Tyr Glu Val Thr Gly Thr Ser Asn His Pro Val Leu Cys Leu
65                  70                  75                  80

Val Asn Leu Ala Gly Val Pro Thr Leu Leu Trp Met Leu Ile Glu Glu
                85                  90                  95

Ile Arg Pro Asp Asp Tyr Val Val Leu Gln Arg Ala Pro Pro Val Glu
            100                 105                 110

Ser Gly Pro Ala Asn Trp Arg Asp Ala Met Glu Ala Leu Leu Leu Gly
        115                 120                 125

Ala Phe Ile Ser Glu Gly Phe Met Ser Glu Ser Arg Ala Gly Phe Asn
    130                 135                 140

Asn Val Asp Arg Asp Tyr Phe Asn Ala Val Val Ala Ala Tyr Asp Ala
145                 150                 155                 160

Val Val Gly Gly Lys Arg Tyr Val Ala Gln Arg Thr Ile Ala Ser Gly
                165                 170                 175

Ser Val Leu Asn Glu Leu Asp Ile His Asp Val Ser Ala Leu Lys Gly
            180                 185                 190

Thr Arg Leu Gly Val Leu Cys Gly Gln Arg Ser Ala Asp Lys Ser Val
        195                 200                 205

Pro Glu Trp Leu Trp Gln Ser Pro Ala Ala Val Lys Arg Val Phe Leu
    210                 215                 220

Gln Ala Leu Phe Glu Gly Asp Gly Ser Cys Ser Ala Leu Pro Arg Asn
225                 230                 235                 240

Thr Ile Gln Val Ser Tyr Ser Thr Arg Ser Arg Gln Leu Ala Ile Asp
                245                 250                 255

Val Gln Gln Met Leu Leu Glu Phe Gly Val Ile Ser Arg Arg Tyr Arg
            260                 265                 270

His Ala Val Gly Glu Tyr Lys Val Val Ile Thr Asn Arg Ala Gln Ala
        275                 280                 285

Glu Leu Phe Ala Thr Gln Ile Gly Phe Gly Gly Ala Lys Gln Ser Lys
    290                 295                 300

Leu Thr Arg Ile Leu Gly Ser Leu Pro Pro Cys Ala Gly Met Asp Thr
305                 310                 315                 320

Asn His Val Pro Gly Leu Ala Ala Phe Ile Arg Ser His Cys Asp Ser
                325                 330                 335

Glu Trp Val Asp Lys Glu Trp Leu Arg Lys His Asn Ile Asp Arg Leu
            340                 345                 350

Ser Arg Trp Arg Arg Asp Gly Ala Glu Ile Leu Ser Arg Ile Ala Asn
        355                 360                 365

Pro Asp Val Arg Ala Ile Ala Thr Asp Leu Thr Asp Gly Arg Phe Tyr
    370                 375                 380

Tyr Ala Gln Val Thr Ser Val Thr Glu Ala Gly Val Gln Pro Val Tyr
385                 390                 395                 400

Ser Leu Arg Val Asp Ser Glu Asp His Ala Phe Leu Thr Asn Gly Phe
                405                 410                 415
```

Val Ser His Asn
            420

<210> SEQ ID NO 29
<211> LENGTH: 420
<212> TYPE: PRT
<213> ORGANISM: Mycobacterium kansasii

<400> SEQUENCE: 29

Cys Val Thr Gly Asp Ala Leu Val Arg Leu Pro Phe Gly Gln Ser Met
1               5                   10                  15

Arg Ile Ala Asp Val Val Pro Gly Ala Arg Pro Asn Ser Asp Asn Ala
            20                  25                  30

Val Glu Leu Lys Val Leu Asp Arg His Gly Asn Pro Val Ala Ala Asp
        35                  40                  45

Arg Leu Phe His Ser Gly Asp His Gln Thr Tyr Met Val Arg Thr Ala
    50                  55                  60

Glu Gly Tyr Glu Val Thr Gly Thr Ala Asn His Pro Leu Leu Cys Leu
65                  70                  75                  80

Val Asp Val Gly Gly Val Pro Thr Leu Leu Trp Lys Leu Ile Glu Glu
                85                  90                  95

Ile His Pro Asp Asp Tyr Val Ala Leu Gln Arg Thr Pro Pro Met Glu
            100                 105                 110

Leu Gly Pro Ala Asp Trp His Asp Thr Met Glu Ala Leu Leu Leu Gly
        115                 120                 125

Ala Phe Ile Ser Glu Gly Cys Val Ser Glu Thr Arg Ala Gly Phe Ala
    130                 135                 140

Asn Leu Asp Arg Asp Tyr Phe Thr Met Val Ala Arg Ala Tyr Asp Ala
145                 150                 155                 160

Val Val Gly Asp Lys Arg Asp Val Tyr Gln Gln Thr Ile Ala Ser Gly
                165                 170                 175

Ser Leu Gln His Thr Leu Tyr Thr Gln Asn Val Thr Ala Leu Lys Gln
            180                 185                 190

Ser Arg Leu Trp Gln Ile Leu Gly Met Arg Ser Ala Asp Thr Tyr Val
        195                 200                 205

Pro Glu Trp Met Trp His Ser Pro Ala Ala Val Lys Arg Val Phe Leu
    210                 215                 220

Gln Ala Leu Phe Glu Gly Asp Gly Ser Cys Ser Arg Arg Pro His Asn
225                 230                 235                 240

Thr Ile Gln Ile Ser Tyr Asn Thr Val Ser Lys Gln Leu Ala Met Asp
                245                 250                 255

Val Gln Gln Met Leu Leu Glu Phe Gly Val Ile Ser Arg Arg Tyr Leu
            260                 265                 270

His Ala Ala Gly Glu Tyr Lys Val Val Ile Thr Asp Arg Ala Gln Ala
        275                 280                 285

Glu Leu Phe Pro Lys Gln Ile Gly Phe Gly Ala Lys Gln Thr Glu
    290                 295                 300

Leu Ser Lys Ile Leu Ala Ala Met Pro Pro Cys Ala Gly Arg Asp Ser
305                 310                 315                 320

Asp His Val Pro Gly Leu Ala Arg Phe Ile Arg His Cys Asp Ser
                325                 330                 335

Arg Trp Val Asp Lys Glu Trp Leu His Lys His Asn Ile Asp His Leu
            340                 345                 350

Ser Arg Trp Arg Arg Asp Gly Ala Glu Ile Leu Ser His Ile Ala Asp

```
                355                 360                 365
Pro Asp Val Arg Thr Ile Ala Thr Asp Leu Thr Asp Gly Arg Phe Tyr
    370                 375                 380

Tyr Ala Arg Val Ala Ser Val Thr Asp Thr Gly Val Gln Pro Val Tyr
385                 390                 395                 400

Ser Leu Arg Val Asp Thr Asp His Ala Phe Leu Thr Asn Gly Phe
                405                 410                 415

Val Ser His Asn
            420

<210> SEQ ID NO 30
<211> LENGTH: 420
<212> TYPE: PRT
<213> ORGANISM: Mycobacterium leprae

<400> SEQUENCE: 30

Cys Val Ser Gly Asn Ser Leu Val Arg Leu Leu Phe Gly Lys Ser Ile
1               5                   10                  15

Arg Ile Gly Asp Ile Val Thr Gly Ala Gln Phe Asn Ser Asp Asn Pro
            20                  25                  30

Ile Asp Leu Lys Val Leu Asp Arg His Gly Asn Pro Val Val Ala Asp
        35                  40                  45

Tyr Leu Phe His Ser Gly Glu His Gln Thr Tyr Thr Val Arg Thr Thr
    50                  55                  60

Glu Gly Tyr Glu Ile Thr Gly Thr Ser Asn His Pro Leu Leu Cys Leu
65                  70                  75                  80

Val Asn Val Gly Gly Ile Pro Thr Leu Leu Trp Lys Leu Ile Gly Glu
                85                  90                  95

Ile Arg Ser Gly Asp Tyr Val Val Leu Gln Arg Ile Pro Pro Val Glu
            100                 105                 110

Phe Gly Pro Ala Asp Trp Tyr Ser Thr Met Glu Ala Leu Leu Phe Gly
        115                 120                 125

Ala Phe Ile Ser Gly Gly Phe Val Phe Gln Asp His Ala Gly Phe Asn
    130                 135                 140

Ser Leu Asp Arg Asp Tyr Phe Thr Met Val Val Asn Ala Tyr Asp Thr
145                 150                 155                 160

Val Val Gly Gly Leu Arg Cys Ile Ser Ser Arg Ile Thr Val Ser Gly
                165                 170                 175

Ser Thr Leu Leu Glu Leu Asp Val Tyr Asn Leu Ile Glu Phe Lys Lys
            180                 185                 190

Thr Arg Leu Ser Gly Leu Cys Gly Gln Arg Ser Ala Asp Lys Leu Val
        195                 200                 205

Pro Asp Trp Leu Trp His Ser Pro Ser Thr Val Lys Arg Ala Phe Leu
    210                 215                 220

Gln Ala Leu Phe Glu Gly Glu Gly Phe Ser Ser Ile Leu Ser Arg Asn
225                 230                 235                 240

Ile Ile Glu Ile Ser Tyr Ser Thr Leu Ser Glu Arg Leu Ala Ala Asp
                245                 250                 255

Val Gln Gln Met Leu Leu Glu Phe Gly Val Val Ser Glu Arg Tyr Cys
            260                 265                 270

His Thr Val Asn Glu Tyr Lys Val Val Ile Ala Asn Arg Ala Gln Val
        275                 280                 285

Glu Met Phe Phe Thr Gln Val Gly Phe Gly Val Thr Lys Gln Ala Lys
    290                 295                 300
```

-continued

```
Leu Ile Arg Asp Val Val Ser Met Ser Pro Cys Val Gly Met Asp Ile
305                 310                 315                 320

Asn Cys Val Pro Gly Leu Ala Thr Phe Ile Arg Lys His Cys Asp Asn
            325                 330                 335

Arg Trp Val Glu Glu Asp Ser Phe Asn Gln His Asn Val Asp Cys Val
            340                 345                 350

Gln His Trp His His His Ser Ala Glu Ile Val Gly His Ile Ala Asp
            355                 360                 365

Pro Asp Ile Arg Ala Ile Val Thr Asp Leu Thr Asp Gly Arg Phe Tyr
370                 375                 380

Tyr Ala Arg Val Ala Ser Val Thr Asp Thr Gly Ile Gln Pro Val Phe
385                 390                 395                 400

Ser Leu His Val Asp Thr Glu Asp His Ser Phe Leu Thr Asn Gly Phe
            405                 410                 415

Ile Ser His Asn
            420

<210> SEQ ID NO 31
<211> LENGTH: 420
<212> TYPE: PRT
<213> ORGANISM: Mycobacterium malmoense

<400> SEQUENCE: 31

Cys Cys Thr Gly Asp Ala Leu Val Arg Leu Pro Phe Gly His Ser Val
1               5                   10                  15

Arg Ile Gly Asn Phe Val Pro Ala Ala Cys Pro Asn Ser Asp Asn Ala
            20                  25                  30

Val Asn Leu Lys Val Leu Asp Arg His Gly Asp Pro Val Val Ala Asp
        35                  40                  45

Gln Leu Phe His Ser Gly Glu His Gln Thr Tyr Thr Val Arg Thr Ala
    50                  55                  60

Glu Gly Tyr Glu Val Thr Gly Thr Ser Asn His Pro Leu Leu Cys Leu
65                  70                  75                  80

Val Asp Val Gly Gly Val Pro Thr Leu Leu Trp Lys Leu Ile Glu Glu
                85                  90                  95

Ile Arg Pro Asp Asp His Val Val Leu Gln Arg Thr Pro Pro Val Glu
            100                 105                 110

Phe Gly Pro Ala Asp Trp His Asp Val Met Glu Ala Leu Leu Leu Gly
        115                 120                 125

Ala Phe Ile Ser Glu Gly Phe Val Ser Glu Val Arg Ala Gly Phe Asn
    130                 135                 140

Asn Cys Asp Arg Asp Tyr Phe Ala Met Val Val Gly Ala Tyr Asp Ala
145                 150                 155                 160

Val Val Gly Gly Arg Arg Tyr Val Ser Ser Arg Ile Ala Ser Gly
                165                 170                 175

Ser Thr Leu His Glu Leu Asp Ile Gln Asn Ile Lys Glu Leu Lys Glu
            180                 185                 190

Ala Arg Leu Gly Asp Leu Cys Gly Gln Arg Pro Ala Asp Lys Ser Val
        195                 200                 205

Pro Asp Trp Leu Trp His Ser Pro Ala Val Lys Arg Val Phe Leu
    210                 215                 220

Gln Ala Leu Phe Glu Gly Gly Ser Cys Ser Ala Leu Pro Arg Asn
225                 230                 235                 240

Met Ile Gln Ile Ser Tyr Ser Thr Arg Ser Arg Gln Leu Ala Val Asp
                245                 250                 255
```

Val Gln Gln Met Leu Glu Phe Gly Ile Ile Thr Arg Arg Tyr Arg
                260                 265                 270

His Ala Val Gly Glu His Lys Val Leu Ile Thr Asn Arg Ala Gln Ala
            275                 280                 285

Glu Leu Phe Ala Thr Arg Val Gly Phe Gly Ala Lys Gln Glu Lys
        290                 295                 300

Leu Thr Lys Ile Leu Gly Ser Met Pro Cys Ala Gly Met Asp Ser
305                 310                 315                 320

Asp His Val Pro Gly Leu Ala Arg Phe Ile Arg Lys His Cys Gly Ser
                325                 330                 335

Arg Trp Val Asp Lys Asp Trp Leu Asn Arg His Asn Val Asp Arg Ile
            340                 345                 350

Gln Arg Trp Arg Thr Ser Gly Glu Lys Ile Leu Ser His Ile Ala Asp
        355                 360                 365

Pro Asp Val Arg Ala Ile Ala Thr Asp Leu Thr Asp Gly Arg Phe Tyr
    370                 375                 380

Tyr Ala Lys Val Ala Ser Val Thr Glu Ala Gly Val Gln Pro Val Tyr
385                 390                 395                 400

Ser Leu Arg Val Asp Thr Asp Glu His Ala Phe Leu Thr Asn Gly Phe
                405                 410                 415

Val Ser His Asn
            420

<210> SEQ ID NO 32
<211> LENGTH: 430
<212> TYPE: PRT
<213> ORGANISM: Synechocystis PCC6803

<400> SEQUENCE: 32

Cys Leu Thr Gly Asp Ser Gln Val Leu Thr Arg Asn Gly Leu Met Ser
1               5                   10                  15

Ile Asp Asn Pro Gln Ile Lys Gly Arg Glu Val Leu Ser Tyr Asn Glu
            20                  25                  30

Thr Leu Gln Gln Trp Glu Tyr Lys Lys Val Leu Arg Trp Leu Asp Arg
        35                  40                  45

Gly Glu Lys Gln Thr Leu Ser Ile Lys Thr Lys Asn Ser Thr Val Arg
    50                  55                  60

Cys Thr Ala Asn His Leu Ile Arg Thr Glu Gln Gly Trp Thr Arg Ala
65                  70                  75                  80

Glu Asn Ile Thr Pro Gly Met Lys Ile Leu Ser Pro Ala Ser Val Asp
                85                  90                  95

Val Asp Asn Leu Ser Gln Ser Thr Ala Leu Thr Ala Ser Leu Gly Gly
            100                 105                 110

Leu Ser Gly Ala Ile Asn Tyr Glu Ala Ile Asn Thr Asp Lys Lys Asn
        115                 120                 125

Thr Thr Leu Ser Leu Ser Leu Lys Lys Gln Lys Pro Gln Asp Pro Phe
    130                 135                 140

Val Asn Ala Asp Val Ala Lys Asn Leu Ile Phe Gln His Phe Cys Ser
145                 150                 155                 160

Ala Lys Glu Glu Lys Leu Lys Val Ser Asn Pro Ile Gly Glu Asp Ile
                165                 170                 175

Pro Thr Lys Lys Ala Thr Asp Phe Gly Ile Ser Glu Gln Lys Lys Leu
            180                 185                 190

His Gln Gly Gln Asn Arg Trp Glu Gln Lys Phe Ser Val Leu Ser Thr

```
                195                 200                 205
Glu Pro Cys Leu Gly Met Glu Val Leu Thr Ile Pro Thr His Ile Ala
210                 215                 220

Asp Ser Pro Ala Cys Asp Gly Pro Thr Ala Pro Ser Ser Gln Asn Gly
225                 230                 235                 240

Trp Asn Ile Lys Arg Gln Asp Trp Asp Val Cys His Pro Lys Tyr Asp
                245                 250                 255

Ser Gln Pro Ile Lys Ala Met Gly Lys Val Pro Ser Ala Val Lys Pro
                260                 265                 270

Val Val Pro Gln Thr Leu Leu Met Phe Ser Ala Gln Ser Asn Leu Glu
                275                 280                 285

Val Lys Glu Asn Lys Phe Leu Arg Asn Gly Ser Arg Ile Ser Leu Lys
290                 295                 300

Lys Glu Trp Leu Gly Gly Thr Trp Thr Val Pro Ser Leu Phe Pro
305                 310                 315                 320

Asn Leu Gly Val His Gln Phe Ser Tyr Thr Gln Arg Ala Phe Ser Arg
                325                 330                 335

Lys Lys Ile Asn Leu Leu Asn Gly Leu Pro Ile Glu Asp Ile Pro
                340                 345                 350

Pro Val Gln Asn Pro Ile Ala Glu Ala Leu Thr Ala Lys Pro Ile Thr
                355                 360                 365

Thr Gln Lys Trp Glu Gln Trp Pro Pro Ala Ser Gly Tyr Arg Thr Trp
370                 375                 380

Lys Ser Ile Pro Ser Pro Gln Trp His Thr Asn Phe Glu Glu Val Glu
385                 390                 395                 400

Ser Val Thr Lys Gly Gln Val Glu Lys Val Tyr Asp Leu Glu Val Glu
                405                 410                 415

Asp Asn His Asn Phe Val Ala Asn Gly Leu Leu Val His Asn
                420                 425                 430

<210> SEQ ID NO 33
<211> LENGTH: 333
<212> TYPE: PRT
<213> ORGANISM: Pyrococcus abyssi

<400> SEQUENCE: 33

Cys Phe Ser Gly Glu Glu Thr Val Val Ile Arg Glu Asn Gly Glu Val
1               5                   10                  15

Lys Val Leu Arg Leu Lys Asp Phe Val Glu Lys Ala Leu Glu Lys Pro
                20                  25                  30

Ser Gly Glu Gly Leu Asp Gly Asp Val Lys Val Val Tyr His Asp Phe
            35                  40                  45

Arg Asn Glu Asn Val Glu Val Leu Thr Lys Asp Gly Phe Thr Lys Leu
50                  55                  60

Leu Tyr Ala Asn Lys Arg Ile Gly Lys Gln Lys Leu Arg Arg Val Val
65                  70                  75                  80

Asn Leu Glu Lys Asp Tyr Trp Phe Ala Leu Thr Pro Asp His Lys Val
                85                  90                  95

Tyr Thr Thr Asp Gly Leu Lys Glu Ala Gly Glu Ile Thr Glu Lys Asp
                100                 105                 110

Glu Leu Ile Ser Val Pro Ile Thr Val Phe Asp Cys Glu Asp Glu Asp
            115                 120                 125

Leu Lys Lys Ile Gly Leu Leu Pro Leu Thr Ser Asp Asp Glu Arg Leu
130                 135                 140
```

```
Arg Lys Ile Ala Thr Leu Met Gly Ile Leu Phe Asn Gly Gly Ser Ile
145                 150                 155                 160

Asp Glu Gly Leu Gly Val Leu Thr Leu Lys Ser Glu Arg Ser Val Ile
            165                 170                 175

Glu Lys Phe Val Ile Thr Leu Lys Glu Leu Phe Gly Lys Phe Glu Tyr
            180                 185                 190

Glu Ile Ile Lys Glu Glu Asn Thr Ile Leu Lys Thr Arg Asp Pro Arg
            195                 200                 205

Ile Ile Lys Phe Leu Val Gly Leu Gly Ala Pro Ile Glu Gly Lys Asp
            210                 215                 220

Leu Lys Met Pro Trp Trp Val Lys Leu Lys Pro Ser Leu Phe Leu Ala
225                 230                 235                 240

Phe Leu Glu Gly Phe Arg Ala His Ile Val Glu Gln Leu Val Asp Asp
            245                 250                 255

Pro Asn Lys Asn Leu Pro Phe Phe Gln Glu Leu Ser Trp Tyr Leu Gly
            260                 265                 270

Leu Phe Gly Ile Lys Ala Asp Ile Lys Val Glu Val Gly Asp Lys
            275                 280                 285

His Lys Ile Ile Phe Asp Ala Gly Arg Leu Asp Val Asp Lys Gln Phe
290                 295                 300

Ile Glu Thr Trp Glu Asp Val Glu Val Thr Tyr Asn Leu Thr Thr Glu
305                 310                 315                 320

Lys Gly Asn Leu Leu Ala Asn Gly Leu Phe Val Lys Asn
            325                 330

<210> SEQ ID NO 34
<211> LENGTH: 412
<212> TYPE: PRT
<213> ORGANISM: Methanococcus jannaschii

<400> SEQUENCE: 34

Cys Ile Glu Gly Asp Ala Lys Ile Leu Thr Asp Arg Gly Phe Leu Lys
1               5                   10                  15

Met Lys Glu Val Tyr Lys Leu Val Lys Asn Gly Glu Lys Leu Lys Val
            20                  25                  30

Leu Gly Leu Asn Ala Glu Thr Leu Lys Thr Glu Trp Lys Glu Ile Ile
        35                  40                  45

Asp Ala Gln Lys Arg Glu Ala Arg Arg Tyr Glu Ile Gly Val Tyr Arg
    50                  55                  60

Lys Asn Lys Asn Thr Lys Asp Thr Ile Lys Ile Thr Pro Asp His Lys
65                  70                  75                  80

Phe Pro Val Phe Val Asn Gly Glu Leu Ser Lys Val Gln Leu Cys Asp
                85                  90                  95

Ile Ile Asp Asn Asn Leu Ser Val Leu Ser Ile Asp Tyr Ile Pro Met
            100                 105                 110

Ile Glu Glu Lys Tyr Glu Ser Leu Ala Glu Val Met Tyr Leu Gly Gly
            115                 120                 125

Ala Val Leu Ser Asp Gly His Ile Val Arg Arg Asn Gly Lys Pro Ile
130                 135                 140

Arg Val Arg Phe Thr Gln Lys Asp Thr Glu Lys Lys Asp Phe Ile
145                 150                 155                 160

Glu Lys Val Lys Gly Asp Val Lys Leu Ile Gly Gly Asn Phe Ile Glu
            165                 170                 175

Ile Ser Asn Arg Asn Asn Val Ile Glu Tyr Gln Thr Ser Arg Lys Ile
            180                 185                 190
```

```
Pro Ser Glu Ile Leu Gly Phe Ile Glu Val Asn Ile Asn Thr Ile Pro
        195                 200                 205

Leu Tyr Ala Thr Lys Asp Glu Ile Ala Asp Leu Ile Ala Gly Phe Val
        210                 215                 220

Asp Gly Asp Gly Cys Leu Ser Gly Lys Arg Arg Val Glu Ile Tyr Gln
225                 230                 235                 240

Asn Ser Ser His Ile Lys Lys Ile Glu Gly Leu Ile Val Gly Leu Tyr
                245                 250                 255

Arg Leu Gly Ile Ile Pro Arg Leu Arg Tyr Lys Arg Ser Ser Thr Ala
                260                 265                 270

Thr Ile Tyr Phe Asn Asn Asn Leu Glu Thr Ile Leu Gln Arg Thr Arg
        275                 280                 285

Arg Ile Lys Leu Asp Lys Leu Lys Glu Phe Lys Lys Pro Val Glu Asp
        290                 295                 300

Lys Lys Leu Ile Asp Ile Ser Gln Ile Leu Pro Glu Leu Lys Glu Phe
305                 310                 315                 320

Asp Tyr Lys Gly Tyr Leu Tyr Lys Thr Tyr Lys Glu Lys Leu Phe Ile
                325                 330                 335

Gly Ile Asn Lys Leu Glu Glu Tyr Leu Ser Lys Ile Asp Lys Asp Gly
                340                 345                 350

Ile Glu Arg Ile Lys Gln Lys Ile Lys Leu Leu Lys Glu Ser Asp Ile
        355                 360                 365

Tyr Ser Ile Arg Ile Lys Lys Val Gly Glu Asp Tyr Gly Glu Val Tyr
        370                 375                 380

Asn Ile Thr Val Lys Ala Glu Asn Glu Phe Asn His Asn Tyr Val Val
385                 390                 395                 400

Trp Thr Lys His Tyr Thr Pro Ile Val Val Phe Asn
                405                 410

<210> SEQ ID NO 35
<211> LENGTH: 819
<212> TYPE: PRT
<213> ORGANISM: Aspergillus fumigatus

<400> SEQUENCE: 35

Cys Leu Ala Lys Gly Thr Arg Leu Leu Arg Tyr Asp Gly Ser Glu Ile
1               5                   10                  15

Glu Val Gln Asp Val Lys Glu Gly Asp Leu Leu Gly Pro Asp Gly
            20                  25                  30

Gly Pro Arg Arg Ala Phe Asn Ile Val Asn Gly Lys Asp Arg Leu Tyr
        35                  40                  45

Arg Ile Lys Ile Gly Gly Ser Lys Glu Asp Leu Val Val Thr Pro Asn
50                  55                  60

His Ile Leu Val Leu His Arg Glu Lys Arg Ala Arg Asn Val Tyr Thr
65                  70                  75                  80

Gly Pro Ser Val Gln Gly His Ile Gln Arg Ser Glu Asn Gly His Gly
                85                  90                  95

Asn Leu Pro Met Leu Ser Ser Pro Ala Ala His His Pro Asn
            100                 105                 110

Asn Leu Val Lys Asn Arg Gly Asp Phe Trp Ser Ala Leu Lys Ser Ala
            115                 120                 125

Ile Ala Trp Val Leu His Ala Glu Arg Ser Ser Thr Gly Ala Asn Met
        130                 135                 140

Val Arg Asn Val Leu Asn Gly Thr Val Gly Leu Thr Ala His Lys Glu
```

```
            145                 150                 155                 160
        Ser Tyr Thr Val Thr Asn Pro Gln Gln Lys Gly Val Tyr Tyr Thr Tyr
                        165                 170                 175

Val Trp Gly Asn Pro Gln Arg Thr Ser Ile Lys Gly His Arg Asp His
                        180                 185                 190

Pro Pro Val Phe Leu Pro Thr Lys Glu Asp Ala Phe Ser Ala Ala Ile
                        195                 200                 205

Ala Lys Ser Arg Glu Leu Tyr Ser Gln Ser Glu Val Thr Leu Ala Thr
                        210                 215                 220

Leu Arg Gln Arg Phe Leu Ala Lys Ser Ala Asp Gly Lys Gly Gly Glu
        225                 230                 235                 240

Ile Leu Val Asp Ala Asn Leu Pro Asn Ile Phe Leu Leu Trp Asp Lys
                        245                 250                 255

Asn Arg Ser Asn Leu Lys Phe Arg Val Leu Cys Ser Arg Asn Phe Lys
                        260                 265                 270

Thr Tyr Gly Arg Val Tyr Thr Phe Glu Ser Met Pro Ser Thr Asn Ala
                        275                 280                 285

Glu Glu Pro Gly Tyr Gly Asp Asp Glu Leu Pro Gln Val Ser Ala
                        290                 295                 300

Glu Glu Arg Tyr Asp Thr Val Glu Met Thr Ala Ala Glu Phe Ala Ser
        305                 310                 315                 320

Leu Ser Thr Glu Glu Arg Ser Arg Tyr Arg Val Phe Arg Cys Pro Gly
                        325                 330                 335

Phe Glu Leu Pro Glu Gln Pro Val Pro Val Asn Pro Tyr Phe Leu Gly
                        340                 345                 350

Leu Trp Leu Gly Asp Asp Asn His Glu Lys Thr Thr Asn His Asn Ile
                        355                 360                 365

His Glu Glu Asn Val Arg Glu Phe Leu Val Asn His Ala Ala Glu Leu
                        370                 375                 380

Asp Met Tyr Leu Ala Trp Gln Gly Leu Ile Asp Tyr Ala Thr Val Ala
        385                 390                 395                 400

Asn Pro Ala Pro Met Met Val Arg Leu Pro Pro Thr Asn Pro Asp Thr
                        405                 410                 415

Ile Glu His Arg Pro Val Val Cys Gln Ala Arg Gln Ser Ile Arg Lys
                        420                 425                 430

Leu Arg Leu Ala Ala Lys Asn Ile Ala Gln Pro Glu Val Val Leu Ser
                        435                 440                 445

Thr Ser Pro Arg Pro Glu Ser Gln Met Gln Pro Lys Arg Glu Leu Pro
        450                 455                 460

Ser Asn Thr Glu Thr Ala Leu Arg Ser Glu Ala Glu Ala Ser Ser Ile
        465                 470                 475                 480

Ser Ala Ile Leu Asp Ser Lys Ala Gly His Ser Ser Leu Asp Thr Gly
                        485                 490                 495

Asp Pro Asn Ser Asp Val Val Pro Glu Ser Ile Pro Asn Asp Val Ala
                        500                 505                 510

Asp Phe Gly Leu Asp Gly Val Pro Glu Leu Thr Ser Ser Gly Phe Ser
                        515                 520                 525

Glu Leu Thr Ser Asp Ser Glu Leu Met Arg Leu Ile Glu Gln Val Glu
                        530                 535                 540

Arg Ser Ser Gln Gly Ser Thr Glu Gly Pro Ser Gln Ala Ser Val Val
        545                 550                 555                 560

Glu Gln Glu Ala Asp Leu Asn Leu Leu Glu Thr Asp Ser Glu Asp Glu
                        565                 570                 575
```

```
Glu Ala Asp Ser Ala Asp Asp Glu Phe Gly Asp Pro Glu Ala Ser
            580                 585                 590

Glu Phe Arg Pro Glu Pro Glu Ser Gln Leu Ser Gln Ser His Phe Ser
            595                 600                 605

Asn Arg Arg Arg Asn His Arg Leu Arg Thr Gly Arg Arg Val Tyr Gly
610                 615                 620

Asp Leu Asn Gly Glu Glu Gly Ile Leu Leu Asp Gln Ile Val Glu
625                 630                 635                 640

Gln Ser Glu Gly Ser Arg Val Asn Ser Leu Leu Arg Ala Leu Asp Ala
            645                 650                 655

Leu Gly Ile Ile Ala Gln Lys Gly Thr Gly Pro Glu Thr Asn Arg Lys
            660                 665                 670

His Ile Pro Ser Ile Tyr Met Lys Asn Ser Arg Ser Val Arg Leu Ala
            675                 680                 685

Val Leu Ala Gly Leu Ile Asp Ser Asp Gly Trp Tyr Val Tyr Pro Glu
            690                 695                 700

Asn Val Leu Gly Phe Ala Gln Ser Glu Arg Trp His Ser Lys Leu Phe
705                 710                 715                 720

Trp Asp Val Val Ala Leu Ala Arg Ser Leu Gly Leu Ser Val Leu Thr
            725                 730                 735

Lys Arg Arg Met Met Trp Asn Pro Ala Arg Thr Glu Arg Tyr Pro Gln
            740                 745                 750

Leu Phe Ala Gln Ile Ser Gly Asn Val Ala Glu Val Pro Cys Leu Ile
            755                 760                 765

Ala Arg Lys Lys Gly Val Glu Arg Leu Ile Pro Gln Thr His Ser Phe
            770                 775                 780

Met Ile Lys Asp Ile Ser Leu Glu Pro Glu Ala Thr Glu Trp Ala Gly
785                 790                 795                 800

Phe Arg Val Asp Lys Asp Gln Leu Tyr Leu Arg His Asp Tyr Leu Val
            805                 810                 815

Leu His Asn

<210> SEQ ID NO 36
<211> LENGTH: 605
<212> TYPE: PRT
<213> ORGANISM: Aspergillus nidulans FGSC A

<400> SEQUENCE: 36

Cys Leu Ala Asn Gly Thr Gln Leu Leu Arg Tyr Asp Gly Thr Lys Val
1               5                   10                  15

Asn Val Glu Asp Val Lys Glu Gly Asp Leu Leu Gly Pro Asp Gly
            20                  25                  30

Gly Pro Arg Ala Phe Asn Val Ser Gly Lys Asp Arg Leu Tyr
            35                  40                  45

Arg Ile Lys Ile Asp Gly Asp Lys Glu Asp Leu Val Val Thr Ala Asn
50                  55                  60

His Ile Leu Val Leu His Arg Ala Lys Ala Met Asn Thr Ser Val Cys
65                  70                  75                  80

Phe Asp Arg Ser Lys Glu Gln Gln Gly Ala Gly Glu Gln Leu Asp
            85                  90                  95

Ile Ser Glu Val Ser Ala Ala Glu Arg Tyr Asp Thr Val Glu Met Thr
            100                 105                 110

Ala Ala Glu Phe Ala Ala Leu His Pro Gln Glu Arg Ser Trp Tyr Arg
            115                 120                 125
```

```
Ala Ile Arg Cys Pro Gly Phe Glu Leu Pro Glu Gln Asp Val Pro Val
130                 135                 140

Asn Pro Tyr Phe Leu Gly Leu Trp Leu Gly Asp Glu Ser Arg Asn Gln
145                 150                 155                 160

Ser Ala Ile Tyr Ser Asn His Glu Glu Ala Leu Arg Glu Phe Leu Val
                165                 170                 175

Ser His Ala Ala Glu Leu Asp Met His Leu Val Tyr His Gly Gln Ser
            180                 185                 190

Ala Tyr Ser Thr Val Cys Asn Lys Asp Arg Pro Thr Asn Lys Arg Ile
        195                 200                 205

Gly Pro Ala Asn Gln Thr Gln Thr Val Arg Pro Thr Ile Arg Gln Thr
    210                 215                 220

Arg Arg Thr Ile Arg Gln Gln Arg Leu Ala Ala Glu His Ala Ala Ala
225                 230                 235                 240

Glu Tyr Thr Thr Gln Arg Glu Thr Ala Ser Leu Thr Pro Leu Leu Glu
                245                 250                 255

Ser Pro Thr Ser Asp Lys His Gly Leu Leu Ser Ser Val Glu Thr Pro
            260                 265                 270

Gly Arg Leu Ser Asp Ser Val Thr Thr Glu Leu Pro Met Ser Arg Ser
        275                 280                 285

Ala Ser Ala Met Arg Ser Ile Arg Thr Ala Ser Gly Leu Ser Glu Phe
    290                 295                 300

Asn Asp Val Thr Asn Val Ser Ala Ser Met Pro Asp Ile Gln Asn Ser
305                 310                 315                 320

Gly Ile Lys Asn Gln Gly Arg Ile Ala Lys Val Thr Arg Gln Gln Asp
                325                 330                 335

Ser Lys Gly Glu Val Asp Phe Arg Gln Gln Tyr Ser Gln Ala Ile Lys
            340                 345                 350

Asp Asp Leu Glu Leu Leu Glu Thr Asp Ile Glu Asp Val Ala Ser
        355                 360                 365

Ser Asp Glu Ile Glu Asp Val Cys Val Val Gly Ser Glu Asn Glu Leu
    370                 375                 380

Ile Gly Ser Glu Lys Gln Asp Gln Ser Gly Arg Arg Gln Ile His
385                 390                 395                 400

Arg Leu Arg Thr Gly His Arg Gly Tyr Gly Asp Leu Ser Asp Asp Glu
                405                 410                 415

Gln Glu Gln Leu Leu Asp Ser Val Val Glu Arg Tyr Ala Gly Asp Ser
            420                 425                 430

Arg Leu Asn Thr Leu Gln Gln Glu Leu Ser Lys Met Gly Ile Leu Asn
        435                 440                 445

Pro Glu Thr Gly Pro Ile Asn Asp Lys Lys Arg Ile Pro Gln Val Phe
    450                 455                 460

Met Gln Asn Ser Arg Ser Val Arg Leu Ser Val Leu Ala Gly Leu Leu
465                 470                 475                 480

Asp Ser Asp Gly Trp Tyr Ile Tyr Pro Glu Asn Met Phe Gly Phe Ala
                485                 490                 495

Gln Ser Glu Leu Cys His Lys Glu Leu Phe Trp Asp Val Val Thr Leu
            500                 505                 510

Ala Arg Ser Leu Gly Phe Gly Val Trp Thr Lys Lys Arg Met Met Pro
        515                 520                 525

Asp Pro Thr Gly Lys Arg Met Ser Pro Met Leu Val Ala Gln Ile Ser
    530                 535                 540
```

```
Gly Asp Leu Ala Glu Ile Pro Cys Val Leu Ala Arg Lys Lys Ala Met
545                 550                 555                 560

Pro Arg Leu Ile Pro Gln Ser His Ser Phe Ala Ile Lys Asp Ile Ser
                565                 570                 575

Leu Glu Ser Glu Ala Thr Glu Trp Ala Gly Phe Arg Val Asp Lys Asp
            580                 585                 590

Gln Leu Tyr Leu Arg His Asp Tyr Val Val Leu His Asn
        595                 600                 605

<210> SEQ ID NO 37
<211> LENGTH: 171
<212> TYPE: PRT
<213> ORGANISM: Cryptococcus neoformans

<400> SEQUENCE: 37

Cys Leu Gln Asn Gly Thr Arg Leu Leu Arg Ala Asp Gly Ser Glu Val
1               5                   10                  15

Leu Val Glu Asp Val Gln Glu Gly Asp Gln Leu Leu Gly Pro Asp Gly
            20                  25                  30

Thr Ser Arg Thr Ala Ser Lys Ile Val Arg Gly Glu Glu Arg Leu Tyr
        35                  40                  45

Arg Ile Lys Thr His Glu Gly Leu Glu Asp Leu Val Cys Thr His Asn
    50                  55                  60

His Ile Leu Ser Met Tyr Lys Glu Arg Phe Gly Arg Glu Gly Ala His
65                  70                  75                  80

Ser Pro Ser Ala Gly Thr Ser Leu Thr Glu Ser His Glu Arg Val Asp
                85                  90                  95

Val Thr Val Asp Asp Phe Val Arg Leu Pro Gln Gln Glu Gln Gln Lys
            100                 105                 110

Tyr Lys Leu Phe Arg Ser Thr Asp Phe Val Arg Arg Glu Gln Pro Ser
        115                 120                 125

Ala Ser Lys Leu Ala Thr Leu Leu His Ile Asn Ser Ile Glu Leu Glu
    130                 135                 140

Glu Glu Pro Thr Lys Trp Ser Gly Phe Val Val Asp Lys Asp Ser Leu
145                 150                 155                 160

Tyr Leu Arg Tyr Asp Tyr Leu Val Leu His Asn
                165                 170

<210> SEQ ID NO 38
<211> LENGTH: 534
<212> TYPE: PRT
<213> ORGANISM: Histoplasma capsulatum

<400> SEQUENCE: 38

Cys Leu Ala Lys Gly Thr Gln Leu Leu Arg Tyr Asp Gly Thr Lys Val
1               5                   10                  15

Gly Val Glu Asn Val Arg Glu Gly Asp Leu Leu Leu Gly Pro Asp Gly
            20                  25                  30

Glu Pro Arg Arg Ala Phe Asn Ile Val Ser Gly Arg Asp Arg Leu Tyr
        35                  40                  45

Arg Ile Ser Ile Asp Ala Asp Lys Glu Asp Leu Val Val Thr Pro Asn
    50                  55                  60

His Ile Leu Val Leu His His Glu Lys Glu Asn Gln Lys Arg Gln Ser
65                  70                  75                  80

Glu Leu Ser Ala Ser Ala Thr Glu Arg Tyr Asp Thr Val Glu Met Thr
                85                  90                  95
```

```
Ala Ala Asp Phe Ala Ala Leu Asp Pro Glu Arg Arg Trp Tyr Arg
            100                 105                 110
Leu Phe Arg Ser Pro Gly Phe Glu Leu Gly Gln Gln Asn Val Pro Ile
            115                 120                 125
Asp Pro Tyr Phe Val Gly Phe Trp Leu Cys Asp Gly Ile Arg Ala Ser
            130                 135                 140
Thr Thr Ile Tyr Thr Ser Pro Glu Glu Ala Thr Arg Glu Phe Ile Ile
145                 150                 155                 160
Asn His Ala Ala Glu Leu Asp Leu Gln Leu Ala Ser Lys Glu Tyr Met
                    165                 170                 175
Gln His Pro Val Arg Arg Val Ala Arg Gln Thr Ile Leu Glu Gln Arg
                180                 185                 190
Leu Ala Val Gln Cys Thr Ala Pro Gln Glu Thr Asp Gly Ser Leu Leu
            195                 200                 205
Ser His Ile Leu Gln Lys Ala Ala Lys Ser Gly Leu Ala Ser Ser Thr
            210                 215                 220
Arg Thr Met Ser Thr Ser Arg Asn Arg Gln Pro Leu Ser Glu Thr Ser
225                 230                 235                 240
Ala Ala Thr Ser Met Asn Ile Leu Pro Gly Phe Ala Ser Asn Ser Thr
                    245                 250                 255
Ser Val Val Ser Pro Gly Ile Asp Ser His Glu Ile Leu Ser Leu Arg
                260                 265                 270
Asn Ser Cys Ser Gln Leu Val Gln Ile Ala Glu Lys Ser Gly Leu Arg
            275                 280                 285
Glu Glu Cys Met Ile Asn Pro Pro Ser Ser Arg Glu Asp Leu Val Leu
290                 295                 300
Asp Leu Phe Asp Thr His Ile Glu Ala Asp Glu Ile Gln Gly Leu Asp
305                 310                 315                 320
Glu Asn Leu Thr Gly Gln Lys His Arg Leu Arg Thr Gly Cys Arg Ala
                    325                 330                 335
Tyr Gly Asp Leu Thr Val Asp Glu Glu Gly Gln Ile Leu Asp Asn Ile
                340                 345                 350
Ile Ser Arg Pro Val Gly Thr Pro Asp Ile Gly Thr Leu Leu Arg Ala
            355                 360                 365
Leu Glu Glu Leu Gly Leu Pro Thr Asn Arg Thr Glu Gly His Gly Val
370                 375                 380
Glu Asn Lys Arg Ile Pro Leu Met Tyr Met Lys Ser Ser Arg Ser Ile
385                 390                 395                 400
Arg Leu Ala Leu Leu Ala Gly Leu Ile Asp Ser Asp Gly Trp Tyr Cys
                    405                 410                 415
Gln Pro Gln Asn Thr Phe Cys Phe Gly Glu Ser Glu Arg Ile Ser Pro
                420                 425                 430
Thr Leu Phe Trp Asp Ile Val Thr Leu Ala Arg Ser Leu Gly Leu Ser
            435                 440                 445
Val Ser Thr Glu Gln His Thr Met Arg Ser Pro Ala Cys Thr Ala Phe
            450                 455                 460
Lys Pro Arg Phe Val Ala Gln Ile Ser Gly Asn Val Ala Glu Val Thr
465                 470                 475                 480
Cys Leu Leu Ala Arg Lys Arg Gly Val Lys Ser Pro Val Ser Gln Ala
                    485                 490                 495
His Ser Phe Thr Ile Lys Gly Ile His Leu Glu Ser Glu Met Thr Glu
                500                 505                 510
Trp Ala Gly Phe Arg Val Asp Lys Asp Gln Leu Tyr Leu Arg His Asp
```

Phe Leu Val Leu His Asn
    530

<210> SEQ ID NO 39
<211> LENGTH: 157
<212> TYPE: PRT
<213> ORGANISM: Penicillium chrysogenum

<400> SEQUENCE: 39

Cys Leu Ala Lys Gly Thr Arg Leu Leu Arg Cys Asp Gly Thr Glu Ile
1               5                   10                  15

Asn Val Glu Asp Val Arg Glu Gly Asp Leu Leu Gly Pro Asp Gly
            20                  25                  30

Glu Pro Arg Arg Ala Phe Asn Ile Val Asn Gly Ile Asp Arg Leu Tyr
        35                  40                  45

Arg Ile Lys Ile Gly Gly Glu Lys Glu Asp Leu Val Val Thr Pro Asn
    50                  55                  60

His Ile Leu Val Leu Tyr Arg Glu Asp Gly Ser Lys Asn Val Glu Lys
65                  70                  75                  80

Gln Thr Val Glu Ile Thr Ala Ala Glu Phe Ala Ala Leu Ser Thr Glu
                85                  90                  95

Glu Arg Ser Leu Tyr Ser Ala Phe Thr Ser Pro Arg Ala Glu Lys Gly
            100                 105                 110

Ala Asp Asp Ser Ala Gln Thr His Ser Phe Lys Ile Glu Gln Val Ser
        115                 120                 125

Leu Glu Ser Glu Lys Thr Glu Trp Ala Gly Phe Arg Val Asp Lys Asp
    130                 135                 140

Gln Leu Tyr Leu Arg His Asp Tyr Leu Val Leu His Asn
145                 150                 155

<210> SEQ ID NO 40
<211> LENGTH: 162
<212> TYPE: PRT
<213> ORGANISM: Penicillium expansum

<400> SEQUENCE: 40

Cys Leu Ala Lys Gly Thr Arg Leu Leu Arg Tyr Asp Gly Thr Glu Ile
1               5                   10                  15

Asn Val Glu Asp Val Arg Glu Gly Asp Gln Leu Leu Gly Pro Asp Gly
            20                  25                  30

Glu Pro Arg Arg Ala Phe Asn Ile Val Asn Gly Ile Asp Arg Leu Tyr
        35                  40                  45

Arg Ile Lys Ile Ala Gly Glu Lys Glu Asp Leu Val Val Thr Pro Asn
    50                  55                  60

His Ile Leu Val Leu Tyr Arg Glu Glu Glu Ala Ser Asp Gly Pro Lys
65                  70                  75                  80

Asn Ala Glu Arg Gln Thr Val Glu Ile Thr Ala Ala Glu Phe Ala Ala
                85                  90                  95

Leu Ser Thr Glu Glu Arg Gly Leu His Ser Ala Phe Thr Ser Ser Arg
            100                 105                 110

Val Glu Lys Asp Val Glu Asn Ser Ala Pro Gln Met His Ser Phe Lys
        115                 120                 125

Ile Glu His Ile Asn Leu Glu Tyr Glu Glu Thr Glu Trp Ala Gly Phe
    130                 135                 140

Arg Val Asp Lys Asp Gln Leu Tyr Leu Arg His Asp Tyr Leu Val Leu

```
145                 150                 155                 160

His Asn

<210> SEQ ID NO 41
<211> LENGTH: 161
<212> TYPE: PRT
<213> ORGANISM: Penicillium vulpinum

<400> SEQUENCE: 41

Cys Leu Ala Lys Gly Thr Arg Leu Leu Arg Tyr Asp Gly Thr Glu Ile
1               5                   10                  15

Asn Val Glu Asp Val Arg Glu Gly Asp Gln Leu Leu Gly Pro Asp Gly
            20                  25                  30

Glu Pro Arg Arg Ala Phe Asn Ile Val Ser Gly Ile Asp Arg Leu Tyr
        35                  40                  45

Arg Val Lys Ile Gly Gly Lys Glu Asp Leu Val Val Thr Pro Asn
    50                  55                  60

His Ile Leu Val Phe Tyr Arg Glu Gly Pro Ser Asp Gly Pro Glu Asn
65                  70                  75                  80

Ala Glu Arg Gln Thr Val Glu Ile Thr Ala Ala Glu Phe Ala Thr Leu
                85                  90                  95

Ser Thr Glu Glu Arg Ser Leu Tyr Ser Ala Phe Thr Ser Pro Ala Val
            100                 105                 110

Glu Lys Gly Ala Glu Gly Ser Ala Gln Met His Ser Phe Lys Val
        115                 120                 125

Glu Asp Ile Ser Leu Glu Ser Glu Lys Thr Glu Trp Ala Gly Phe Arg
130                 135                 140

Val Asp Lys Asp Gln Leu Tyr Leu Arg His Asp Tyr Leu Val Leu His
145                 150                 155                 160

Asn

<210> SEQ ID NO 42
<211> LENGTH: 440
<212> TYPE: PRT
<213> ORGANISM: Mycobacterium tuberculosis H37Rv

<400> SEQUENCE: 42

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Asp His
            100                 105                 110

Ala Arg Leu Leu Gly Tyr Leu Ile Gly Asp Gly Arg Asp Gly Trp Val
        115                 120                 125

Gly Gly Lys Thr Pro Ile Asn Phe Ile Asn Val Gln Arg Ala Leu Ile
    130                 135                 140
```

```
Asp Asp Val Thr Arg Ile Ala Ala Thr Leu Gly Cys Ala Ala His Pro
145                 150                 155                 160

Gln Gly Arg Ile Ser Leu Ala Ile Ala His Arg Pro Gly Glu Arg Asn
            165                 170                 175

Gly Val Ala Asp Leu Cys Gln Gln Ala Gly Ile Tyr Gly Lys Leu Ala
        180                 185                 190

Trp Glu Lys Thr Ile Pro Asn Trp Phe Phe Glu Pro Asp Ile Ala Ala
    195                 200                 205

Asp Ile Val Gly Asn Leu Leu Phe Gly Leu Phe Glu Ser Asp Gly Trp
210                 215                 220

Val Ser Arg Glu Gln Thr Gly Ala Leu Arg Val Gly Tyr Thr Thr Thr
225                 230                 235                 240

Ser Glu Gln Leu Ala His Gln Ile His Trp Leu Leu Leu Arg Phe Gly
                245                 250                 255

Val Gly Ser Thr Val Arg Asp Tyr Asp Pro Thr Gln Lys Arg Pro Ser
            260                 265                 270

Ile Val Asn Gly Arg Arg Ile Gln Ser Lys Arg Gln Val Phe Glu Val
        275                 280                 285

Arg Ile Ser Gly Met Asp Asn Val Thr Ala Phe Ala Glu Ser Val Pro
    290                 295                 300

Met Trp Gly Pro Arg Gly Ala Ala Leu Ile Gln Ala Ile Pro Glu Ala
305                 310                 315                 320

Thr Gln Gly Arg Arg Gly Ser Gln Ala Thr Tyr Leu Ala Ala Glu
                325                 330                 335

Met Thr Asp Ala Val Leu Asn Tyr Leu Asp Glu Arg Gly Val Thr Ala
            340                 345                 350

Gln Glu Ala Ala Met Ile Gly Val Ala Ser Gly Asp Pro Arg Gly
        355                 360                 365

Gly Met Lys Gln Val Leu Gly Ala Ser Arg Leu Arg Arg Asp Arg Val
    370                 375                 380

Gln Ala Leu Ala Asp Ala Leu Asp Asp Lys Phe Leu His Asp Met Leu
385                 390                 395                 400

Ala Glu Glu Leu Arg Tyr Ser Val Ile Arg Glu Val Leu Pro Thr Arg
                405                 410                 415

Arg Ala Arg Thr Phe Asp Leu Glu Val Glu Glu Leu His Thr Leu Val
            420                 425                 430

Ala Glu Gly Val Val Val His Asn
        435                 440

<210> SEQ ID NO 43
<211> LENGTH: 440
<212> TYPE: PRT
<213> ORGANISM: Mycobacterium tuberculosis So93

<400> SEQUENCE: 43

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Gln Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80
```

Trp Arg Ala Ala Gly Glu Leu Arg Lys Gly Asp Arg Val Ala Gln Pro
            85                  90                  95

Arg Arg Phe Asp Gly Phe Gly Asp Ser Ala Pro Ile Pro Ala Asp His
            100                 105                 110

Ala Arg Leu Leu Gly Tyr Leu Ile Gly Asp Gly Arg Asp Gly Trp Val
            115                 120                 125

Gly Gly Lys Thr Pro Ile Asn Phe Ile Asn Val Gln Arg Ala Leu Ile
130                 135                 140

Asp Asp Val Thr Arg Ile Ala Ala Thr Leu Gly Cys Ala Ala His Pro
145                 150                 155                 160

Gln Gly Arg Ile Ser Leu Ala Ile Ala His Arg Pro Gly Glu Arg Asn
            165                 170                 175

Gly Val Leu Asp Leu Cys Arg Arg Ala Gly Val His Gly Lys Leu Ala
            180                 185                 190

Trp Glu Lys Thr Ile Pro Asn Trp Phe Phe Glu Pro Asp Ile Ala Ala
            195                 200                 205

Asp Ile Val Gly Asn Leu Leu Phe Gly Leu Phe Glu Ser Asp Gly Trp
210                 215                 220

Val Ser Arg Glu Gln Thr Gly Ala Leu Arg Val Gly Tyr Thr Thr Thr
225                 230                 235                 240

Ser Glu Gln Leu Ala His Gln Ile His Trp Leu Leu Leu Arg Phe Gly
            245                 250                 255

Val Gly Ser Thr Val Arg Asp Tyr Asp Pro Thr Gln Lys Arg Pro Ser
            260                 265                 270

Ile Val Asn Gly Arg Arg Ile Gln Ser Lys Arg Gln Val Phe Glu Val
            275                 280                 285

Arg Ile Ser Gly Met Asp Asn Val Thr Ala Phe Ala Glu Ser Val Pro
            290                 295                 300

Met Trp Gly Pro Arg Gly Ala Ala Leu Ile Gln Ala Ile Pro Glu Ala
305                 310                 315                 320

Thr Gln Gly Arg Arg Gly Ser Gln Ala Thr Tyr Leu Ala Ala Glu
            325                 330                 335

Met Thr Asp Ala Val Leu Asn Tyr Leu Asp Glu Arg Gly Val Thr Ala
            340                 345                 350

Gln Glu Ala Ala Met Ile Gly Val Ala Ser Gly Asp Pro Arg Gly
            355                 360                 365

Gly Met Lys Gln Val Leu Gly Ala Ser Arg Leu Arg Arg Asp Arg Val
370                 375                 380

Gln Ala Leu Ala Asp Ala Leu Asp Asp Lys Phe Leu His Asp Met Leu
385                 390                 395                 400

Ala Glu Glu Leu Arg Tyr Ser Val Ile Arg Glu Val Leu Pro Thr Arg
            405                 410                 415

Arg Ala Arg Thr Phe Asp Leu Glu Val Glu Glu Leu His Thr Leu Val
            420                 425                 430

Ala Glu Gly Val Val Val His Asn
            435                 440

<210> SEQ ID NO 44
<211> LENGTH: 364
<212> TYPE: PRT
<213> ORGANISM: Mycobacterium flavescens

<400> SEQUENCE: 44

Cys Phe Ala Tyr Gly Thr Arg Gly Ala Leu Ala Asp Gly Thr Thr Glu

```
            1               5                  10                  15
          Lys Ile Gly Lys Ile Val Asn Gln Lys Met Asp Val Glu Val Met Ser
                          20                  25                  30

Tyr Asp Pro Asp Thr Asp Gln Val Val Pro Arg Lys Val Val Asn Trp
                          35                  40                  45

Phe Asn Asn Gly Pro Ala Glu Gln Phe Leu Gln Phe Thr Val Glu Lys
                          50                  55                  60

Ser Gly Gly Asn Gly Lys Ser Gln Phe Ala Ala Thr Pro Asn His Leu
          65                  70                  75                  80

Ile Arg Thr Pro Ala Gly Trp Thr Glu Ala Gly Asp Leu Val Ala Gly
                          85                  90                  95

Asp Arg Val Met Ala Ala Glu Pro His Arg Leu Ser Asp Gln Gln Phe
                          100                 105                 110

Gln Val Val Leu Gly Ser Leu Met Gly Asp Gly Asn Leu Ser Pro Asn
                          115                 120                 125

Arg Arg Asp Arg Asn Gly Val Arg Phe Arg Met Gly His Gly Ala Lys
                          130                 135                 140

Gln Val Asp Tyr Leu Gln Trp Lys Thr Ala Leu Leu Gly Asn Ile Lys
          145                 150                 155                 160

His Ser Thr His Val Asn Asp Lys Gly Ala Thr Phe Val Asp Phe Thr
                          165                 170                 175

Pro Leu Pro Glu Leu Ala Glu Leu Gln Arg Ala Val Tyr Leu Gly Asp
                          180                 185                 190

Gly Lys Lys Phe Leu Ser Glu Glu Asn Phe Lys Ala Leu Thr Pro Leu
                          195                 200                 205

Ala Leu Val Phe Trp Tyr Met Asp Asp Gly Pro Phe Thr Val Arg Ser
                          210                 215                 220

Lys Gly Leu Gln Glu Arg Thr Ala Gly Gly Ser Gly Arg Ile Glu Ile
          225                 230                 235                 240

Cys Val Glu Ala Met Ser Glu Gly Asn Arg Ile Arg Leu Arg Asp Tyr
                          245                 250                 255

Leu Arg Asp Thr His Gly Leu Asp Val Arg Leu Arg Leu Ser Gly Ala
                          260                 265                 270

Ala Gly Lys Ser Val Leu Val Phe Ser Thr Ala Ser Ser Ala Lys Phe
                          275                 280                 285

Gln Glu Leu Val Ala Pro Tyr Ile Thr Pro Ser Met Glu Tyr Lys Leu
                          290                 295                 300

Leu Pro Arg Phe Arg Gly Gln Gly Ala Val Thr Pro Gln Phe Val Glu
          305                 310                 315                 320

Pro Thr Gln Arg Leu Val Pro Ala Arg Val Leu Asp Val His Val Lys
                          325                 330                 335

Pro His Thr Arg Ser Met Asn Arg Phe Asp Ile Glu Val Glu Gly Asn
                          340                 345                 350

His Asn Tyr Phe Val Asp Gly Val Met Val His Asn
                          355                 360

<210> SEQ ID NO 45
<211> LENGTH: 365
<212> TYPE: PRT
<213> ORGANISM: Mycobacterium leprae

<400> SEQUENCE: 45

Cys Met Asn Tyr Ser Thr Arg Val Thr Leu Ala Asp Gly Ser Thr Glu
1               5                   10                  15
```

Lys Ile Gly Lys Ile Val Asn Asn Lys Met Asp Val Arg Val Leu Ser
            20                  25                  30

Tyr Asp Pro Val Thr Asp Arg Ile Val Pro Arg Lys Val Val Asn Trp
            35                  40                  45

Phe Asn Asn Gly Pro Ala Glu Gln Phe Leu Gln Phe Thr Val Glu Lys
            50                  55                  60

Ser Gly Ser Asn Gly Lys Ser Gln Phe Ala Ala Thr Pro Asn His Leu
65                  70                  75                  80

Ile Arg Thr Pro Gly Gly Trp Thr Glu Ala Gly Asn Leu Ile Ala Gly
                85                  90                  95

Asp Arg Val Leu Ala Val Glu Pro His Met Leu Ser Asp Gln Gln Phe
            100                 105                 110

Gln Val Val Leu Gly Ser Leu Met Gly Asp Gly Asn Leu Ser Pro Asn
            115                 120                 125

Leu Cys Asp Arg Asn Gly Val Arg Phe Arg Leu Leu Gly Tyr Gly Cys
            130                 135                 140

Lys Gln Val Glu Tyr Leu Gln Trp Lys Lys Ala Leu Met Gly Asn Ile
145                 150                 155                 160

Arg His Thr Val Arg Glu Asn Ser Met Gly Ala Ser Phe Ile Asp Phe
                165                 170                 175

Thr Pro Leu Pro Glu Leu Val Glu Leu Gln Arg Ala Val Tyr Leu Gly
            180                 185                 190

Asp Gly Lys Lys Phe Leu Ser Glu Glu Tyr Leu Lys Ala Leu Thr Pro
            195                 200                 205

Leu Val Leu Ala Ile Trp Tyr Met Asp Asp Gly Ser Phe Thr Val Gly
            210                 215                 220

Ser Lys Arg Val Gln Glu Arg Thr Ala Gly Gly Ser Gly Arg Ile Glu
225                 230                 235                 240

Ile Cys Val Asp Ala Met Thr Glu Gly Thr Arg Val Arg Leu Arg Asp
                245                 250                 255

Tyr Leu Cys Asp Thr His Gly Leu Asp Val Arg Leu Arg Glu Val Gly
            260                 265                 270

Ser Ala Gly Lys Ala Val Leu Val Phe Ser Thr Ala Ala Thr Ala Lys
            275                 280                 285

Phe Gln Ser Leu Ile Ala Pro Tyr Val Ala Pro Ser Met Glu Tyr Lys
            290                 295                 300

Leu Leu Pro Gln Phe Arg Gly Arg Gly Ser Val Thr Pro Gln Phe Val
305                 310                 315                 320

Glu Pro Thr Gln Gln Leu Val Pro Ala Arg Val Leu Asp Val His Val
            325                 330                 335

Lys Leu Ser Thr Arg Ser Met Asn Arg Phe Asp Ile Glu Val Glu Gly
            340                 345                 350

Asn His Asn Tyr Phe Val Asp Gly Val Met Val His Asn
            355                 360                 365

<210> SEQ ID NO 46
<211> LENGTH: 394
<212> TYPE: PRT
<213> ORGANISM: Trichodesmium erythraeum

<400> SEQUENCE: 46

Cys Leu Pro Glu Gly Ala Leu Val His Thr Ala Ser Gly Leu Val Ala
1               5                   10                  15

Ile Glu Lys Ile Arg Ile Gly Asp Arg Val Leu Thr Ser Gln Gly Phe
            20                  25                  30

```
Tyr Pro Val Thr Asn Phe Phe Asp Gln Gly Ile Gln Ser Leu Cys Arg
            35                  40                  45

Ile Gln Thr Glu Asp Gly Tyr Phe Glu Cys Thr Pro Asp His Lys Val
 50                  55                  60

Ala Val Leu Gln Asp Leu Tyr Gly Asn Tyr Lys Met Ile Lys Ala Lys
 65                  70                  75                  80

Asp Leu Gln Glu Gly Asp Arg Leu Ile Phe Val Pro Gln Ala Ile Pro
                 85                  90                  95

Gly Thr Pro Thr Glu Leu Pro Glu Leu Lys Ala Val Pro Ser Ser Glu
                100                 105                 110

Ala Lys Leu Ile Thr Ile Pro Ala Leu Gln Ser Glu Val Ala Tyr Phe
            115                 120                 125

Leu Gly Tyr Leu Ser Gly Asn Gly Ser Val Gly Ser Asp Gly Gly Gln
130                 135                 140

Val Arg Phe Arg Val Ser Gln Asp Ser Pro Glu Ile Leu Glu Arg Leu
145                 150                 155                 160

Ile Asn Val Ala Gln Glu Phe Gly Leu Glu Thr His Arg Leu Arg Thr
                165                 170                 175

Leu Glu Gln Phe Gln Thr Gln Ala Tyr Glu Leu Glu Leu Asn Ser Ser
            180                 185                 190

Thr Leu Asn Lys Tyr Leu Ser Gln Phe Lys Gln Pro Ser Asn Ser Val
            195                 200                 205

Cys Ile Pro Glu Cys Ile Leu Met Gly Thr Thr Glu Ile Arg Gln Ala
            210                 215                 220

Tyr Leu Ala Gly Leu Val Asp Ala Asp Gly Cys His Ser Gln Gly Ile
225                 230                 235                 240

Leu Leu Thr Ser Val Asp Gln Gly Phe Leu Arg Gln Val Gln Ala Leu
                245                 250                 255

Tyr Ala Ser Leu Gly Ile Thr Thr Arg Leu Cys Gly Ser Val Gln Lys
            260                 265                 270

Pro Thr Gly Thr Trp Glu Gly Glu Leu Val Thr Val Ser Glu Gly Gly
            275                 280                 285

Tyr Glu Ala Val Glu Lys Leu Met Met Asn Tyr Ser Thr Gln Phe Pro
290                 295                 300

Val Gln Lys Pro Asn His Leu Lys Phe Phe Pro Asp Gln Gly Phe Pro
305                 310                 315                 320

Lys Glu Met Val Arg Pro Leu Val Lys Thr Ser Gln Asp His Leu Gly
                325                 330                 335

Lys Val His Lys Gln Met Ile Phe Pro Ser Val Lys Lys Phe Val Val
            340                 345                 350

Asp Ala Thr Asp Leu Ile Pro Val Lys Val Lys Val Glu Met Asp
            355                 360                 365

Val Arg Glu Ala Ser Thr Tyr Asp Ile Glu Val Ala Ser Ile His Glu
370                 375                 380

Phe Val Cys Gln Gly Ile Leu Val Ser Asn
385                 390

<210> SEQ ID NO 47
<211> LENGTH: 399
<212> TYPE: PRT
<213> ORGANISM: Pyrococcus abyssi

<400> SEQUENCE: 47

Cys Ile Asp Gly Asn Ala Lys Ile Ile Phe Glu Asn Glu Gly Glu Glu
```

```
1               5                   10                  15
His Leu Thr Thr Met Ala Glu Met Tyr Glu Arg Tyr Arg His Leu Gly
            20                  25                  30
Glu Phe Tyr Asp Glu Asn Tyr Asn Arg Trp Gly Ile Asp Val Ser Ser
            35                  40                  45
Val Pro Ile Tyr Val Lys Ser Phe Asp Pro Glu Thr Arg Arg Val Val
            50                  55                  60
Lys Gly Arg Val Arg Ala Ile Trp Lys Tyr Glu Leu Gly Glu Glu Ile
65                  70                  75                  80
Pro Lys Tyr Glu Ile Arg Thr His Lys Gly Thr Lys Ile Leu Thr Ser
                85                  90                  95
Pro Trp His Pro Phe Phe Val Leu Thr Pro Asp Phe Glu Val Ile Glu
                100                 105                 110
Lys Arg Ala Asp Glu Leu Lys Val Gly Asp Ile Leu Ile Gly Gly Met
                115                 120                 125
Pro Asp Gly Glu Asp His Glu Leu Ile Phe Asp Tyr Trp Leu Ala Gly
                130                 135                 140
Phe Ile Ala Gly Asn Gly Asn Leu Asp Asp Ser Glu Arg Glu Tyr Lys
145                 150                 155                 160
Ala Arg Glu Leu Leu Asp Gly Ile Glu Asn Gly Ile Pro Pro Lys Ile
                165                 170                 175
Leu Arg Lys Gly Lys Asn Ala Val Leu Ser Phe Ile Thr Gly Leu Phe
                180                 185                 190
Asp Ala Glu Gly His Val Asn Asp Lys Ser Gly Ile Glu Leu Gly Met
                195                 200                 205
Val Asn Lys Lys Leu Ile Glu Ala Val Thr His Tyr Leu Asn Ser Leu
210                 215                 220
Gly Ile Lys Ala Arg Met Arg Glu Lys Arg Lys Asn Gly Ile Asp
225                 230                 235                 240
Tyr Ile Met His Val Glu Glu Tyr Ser Ser Leu Leu Arg Phe Tyr Glu
                245                 250                 255
Leu Ile Gly Lys His Leu Gln Asn Asn Glu Lys Lys Glu Lys Leu Glu
                260                 265                 270
Ile Leu Leu His Lys His Asn Gly Gly Ala Phe Asp Leu Ser Leu Asn
                275                 280                 285
Phe Asn Ala Phe Lys Glu Trp Ala Ser Arg Tyr Gly Val Glu Phe Lys
290                 295                 300
Thr Asn Gly Asn Gln Ile Leu Ala Ile Ile Gly Asn Glu Lys Val Ser
305                 310                 315                 320
Leu Gly Gln Trp His Ala Arg Gly His Val Ser Lys Ala Val Leu Val
                325                 330                 335
Lys Met Leu Arg Lys Leu Tyr Glu Val Thr Lys Asn Asp Glu Val Lys
                340                 345                 350
Glu Met Leu His Leu Ile Glu Ser Leu Glu Val Val Lys Glu Ile Thr
                355                 360                 365
Ile Thr Asn Glu Pro Lys Thr Phe Tyr Asp Leu Thr Val Asp Lys Tyr
                370                 375                 380
Gln Asn Tyr Leu Ala Gly Glu Asn Gly Met Ile Phe Val His Asn
385                 390                 395
```

<210> SEQ ID NO 48
<211> LENGTH: 454
<212> TYPE: PRT
<213> ORGANISM: Pyrococcus furiosus -continued

<400> SEQUENCE: 48

```
Cys Ile Asp Gly Lys Ala Lys Ile Ile Phe Glu Asn Glu Gly Glu Glu
1               5                   10                  15

His Leu Thr Thr Met Glu Glu Met Tyr Glu Arg Tyr Lys His Leu Gly
            20                  25                  30

Glu Phe Tyr Asp Glu Glu Tyr Asn Arg Trp Gly Ile Asp Val Ser Asn
        35                  40                  45

Val Pro Ile Tyr Val Lys Ser Phe Asp Pro Glu Ser Lys Arg Val Val
    50                  55                  60

Lys Gly Lys Val Asn Val Ile Trp Lys Tyr Glu Leu Gly Lys Asp Val
65                  70                  75                  80

Thr Lys Tyr Glu Ile Ile Thr Asn Lys Gly Thr Lys Ile Leu Thr Ser
                85                  90                  95

Pro Trp His Pro Phe Phe Val Leu Thr Pro Asp Phe Lys Ile Val Glu
            100                 105                 110

Lys Arg Ala Asp Glu Leu Lys Glu Gly Asp Ile Leu Ile Gly Gly Met
        115                 120                 125

Pro Asp Gly Glu Asp Tyr Lys Phe Ile Phe Asp Tyr Trp Leu Ala Gly
    130                 135                 140

Phe Ile Ala Gly Asp Gly Cys Phe Asp Lys Tyr His Ser His Val Lys
145                 150                 155                 160

Gly His Glu Tyr Ile Tyr Asp Arg Leu Arg Ile Tyr Asp Tyr Arg Ile
                165                 170                 175

Glu Thr Phe Glu Ile Ile Asn Asp Tyr Leu Glu Lys Thr Phe Gly Arg
            180                 185                 190

Lys Tyr Ser Ile Gln Lys Asp Arg Asn Ile Tyr Tyr Ile Asp Ile Lys
        195                 200                 205

Ala Arg Asn Ile Thr Ser His Tyr Leu Lys Leu Leu Glu Gly Ile Asp
    210                 215                 220

Asn Gly Ile Pro Pro Gln Ile Leu Lys Glu Gly Lys Asn Ala Val Leu
225                 230                 235                 240

Ser Phe Ile Ala Gly Leu Phe Asp Ala Glu Gly His Val Ser Asn Lys
                245                 250                 255

Pro Gly Ile Glu Leu Gly Met Val Asn Lys Arg Leu Ile Glu Asp Val
            260                 265                 270

Thr His Tyr Leu Asn Ala Leu Gly Ile Lys Ala Arg Ile Arg Glu Lys
        275                 280                 285

Leu Arg Lys Asp Gly Ile Asp Tyr Val Leu His Val Glu Glu Tyr Ser
    290                 295                 300

Ser Leu Leu Arg Phe Tyr Glu Leu Ile Gly Lys Asn Leu Gln Asn Glu
305                 310                 315                 320

Glu Lys Arg Glu Lys Leu Glu Lys Val Leu Ser Asn His Lys Gly Gly
                325                 330                 335

Asn Phe Gly Leu Pro Leu Asn Phe Asn Ala Phe Lys Glu Trp Ala Ser
            340                 345                 350

Glu Tyr Gly Val Glu Phe Lys Thr Asn Gly Ser Gln Thr Ile Ala Ile
        355                 360                 365

Ile Asn Asp Glu Arg Ile Ser Leu Gly Gln Trp His Thr Arg Asn Arg
    370                 375                 380

Val Ser Lys Ala Val Leu Val Lys Met Leu Arg Lys Leu Tyr Glu Ala
385                 390                 395                 400

Thr Lys Asp Glu Glu Val Lys Arg Met Leu His Leu Ile Glu Gly Leu
```

```
                      405                 410                 415
Glu Val Val Arg His Ile Thr Thr Thr Asn Glu Pro Arg Thr Phe Tyr
            420                 425                 430

Asp Leu Thr Val Glu Asn Tyr Gln Asn Tyr Leu Ala Gly Glu Asn Gly
            435                 440                 445

Met Ile Phe Val His Asn
        450

<210> SEQ ID NO 49
<211> LENGTH: 345
<212> TYPE: PRT
<213> ORGANISM: Carboxydothermus hydrogenoformans

<400> SEQUENCE: 49

Cys Val Thr Gly Asp Thr Leu Val Phe Thr Asp Lys Gly Leu Ile Glu
1               5                   10                  15

Ala Arg Lys Leu Glu Val Gly Met Lys Val Trp Ser Gly Asp Gly Trp
            20                  25                  30

Asn Glu Ile Lys Glu Val Ile Asn Asn Gly Val Lys Pro Val Leu Lys
        35                  40                  45

Leu Lys Leu Lys Thr Gly Leu Glu Ile Lys Val Thr Glu Glu His Lys
    50                  55                  60

Ile Phe Thr Gly Glu Gly Trp Lys Glu Ala Lys Asp Leu Lys Val Gly
65                  70                  75                  80

Asp Lys Leu Tyr Leu Pro Val Ser Tyr Pro Glu Leu Asp Phe Pro Val
                85                  90                  95

Lys Glu Glu Asn Asp Phe Tyr Glu Phe Leu Gly Tyr Phe Leu Gly Asp
            100                 105                 110

Gly Ser Leu Ser Val Ser Asn His Val Ser Leu His Val Gly Asn Asp
        115                 120                 125

Lys Glu Leu Ala Leu Tyr Phe Lys Glu Lys Val Glu Lys Tyr Ala Gly
    130                 135                 140

Ala Ala Tyr Leu Ile Glu Arg Asp Gly Gln Tyr Ile Ile Asp Val His
145                 150                 155                 160

Arg Lys Glu Phe Ala Glu Lys Ile Lys Lys Ile Phe Gly Ile Glu Ile
                165                 170                 175

Thr Asp Ser Lys Glu Lys Asp Ile Pro Ser Ser Leu Leu Ala Val Asn
            180                 185                 190

Ser Glu Ala Met Lys Ala Leu Leu Arg Gly Leu Phe Ser Ala Asp Gly
        195                 200                 205

Ser Val Tyr Asp Ala Asn Gly Ser Ile Thr Val Ala Leu Ser Ser Thr
    210                 215                 220

Ser Tyr Pro Leu Leu Arg Lys Val Gln Ile Leu Leu Ser Leu Gly
225                 230                 235                 240

Ile Pro Ser Thr Leu Thr Gly Glu Lys Asp Gln Asp Val Lys Ile Ile
                245                 250                 255

Lys Gly Asn Glu Tyr Glu Thr Leu Pro Thr Tyr Arg Leu Ile Ile Ser
            260                 265                 270

Gly Glu Arg Ala Ser Leu Phe Phe Asn Lys Ile Gly Leu Ile Gly Glu
        275                 280                 285

Lys Lys Lys Lys Phe Leu Glu Leu Met Ala Gly Lys Thr Thr Tyr Ser
    290                 295                 300

Thr Leu Asn Asn His Leu Tyr Gln Glu Ile Val Ser Ile Glu Pro Ala
305                 310                 315                 320
```

```
Gly Glu Glu Glu Val Phe Asp Ile Thr Ala Pro Pro Lys Tyr Thr Trp
                325                 330                 335

Ile Thr Asn Gly Ile Leu Ser Leu Asp
            340                 345
```

<210> SEQ ID NO 50
<211> LENGTH: 134
<212> TYPE: PRT
<213> ORGANISM: Methanothermobacter thermautotrophicus

<400> SEQUENCE: 50

```
Cys Val Ser Gly Asp Thr Ile Val Met Thr Ser Gly Gly Pro Arg Thr
1               5                   10                  15

Val Ala Glu Leu Glu Gly Lys Pro Phe Thr Ala Leu Ile Arg Gly Ser
                20                  25                  30

Gly Tyr Pro Cys Pro Ser Gly Phe Phe Arg Thr Cys Glu Arg Asp Val
            35                  40                  45

Tyr Asp Leu Arg Thr Arg Glu Gly His Cys Leu Arg Leu Thr His Asp
    50                  55                  60

His Arg Val Leu Val Met Asp Gly Gly Leu Glu Trp Arg Ala Ala Gly
65                  70                  75                  80

Glu Leu Glu Arg Gly Asp Arg Leu Val Met Asp Ala Ala Gly Glu
                85                  90                  95

Phe Pro Ala Leu Ala Thr Phe Arg Gly Leu Arg Gly Ala Gly Arg Gln
            100                 105                 110

Asp Val Tyr Asp Ala Thr Val Tyr Gly Ala Ser Ala Phe Thr Ala Asn
            115                 120                 125

Gly Phe Ile Val His Asn
            130
```

<210> SEQ ID NO 51
<211> LENGTH: 382
<212> TYPE: PRT
<213> ORGANISM: Pyrococcus abyssi

<400> SEQUENCE: 51

```
Cys Val Val Gly Glu Thr Arg Ile Leu Thr Pro Glu Gly Tyr Ile Lys
1               5                   10                  15

Ala Glu Glu Leu Phe Lys Leu Ala Lys Glu Arg Gly Lys Met Glu Ala
                20                  25                  30

Ile Ala Val Glu Gly Ile Ala Glu Gly Gly Glu Pro Tyr Ala Tyr Ser
            35                  40                  45

Leu Glu Ile Leu Leu Pro Gly Asp Lys Gln Val Lys Tyr Glu Thr Val
    50                  55                  60

His Gly Asn Ala Val Glu Val Asp Pro Val Ser Val Pro Ala Tyr
65                  70                  75                  80

Val Trp Lys Val Gly Met Lys Glu Val Ala Arg Val Arg Thr Lys Glu
                85                  90                  95

Gly Tyr Glu Ile Thr Ala Thr Leu Asp His Lys Leu Met Thr Pro Glu
            100                 105                 110

Gly Trp Lys Glu Ile Lys Asp Leu Lys Pro Gly Asp Lys Ile Leu Leu
            115                 120                 125

Pro Arg Phe Glu Val Glu Glu Asp Phe Gly Ser Glu Ser Ile Gly Glu
            130                 135                 140

Asp Leu Ala Phe Val Leu Gly Trp Phe Ile Gly Asp Gly Tyr Leu Asn
145                 150                 155                 160
```

```
Val Lys Asp Lys Arg Ala Trp Phe Tyr Phe Asn Ala Glu Lys Glu
                165                 170                 175

Glu Ile Ala Trp Lys Ile Arg Glu Ile Leu Ala Lys Arg Phe Glu Ile
        180                 185                 190

Lys Ala Glu Pro His Arg Tyr Gly Asn Gln Ile Lys Leu Gly Val Arg
            195                 200                 205

Gly Lys Ala Tyr Glu Trp Leu Glu Ser Ile Val Lys Thr Asn Glu Lys
    210                 215                 220

Arg Ile Pro Glu Ile Val Tyr Arg Leu Lys Pro Asn Glu Ile Ala Ser
225                 230                 235                 240

Phe Leu Arg Gly Leu Phe Ser Ala Asp Gly Tyr Val Asp Asn Asp Met
                245                 250                 255

Ala Ile Arg Leu Thr Ser Lys Ser Arg Glu Leu Leu Arg Glu Val Gln
            260                 265                 270

Asp Leu Leu Leu Phe Gly Ile Leu Ser Lys Ile Tyr Glu Arg Pro
    275                 280                 285

Tyr Lys Arg Glu Phe Lys Tyr Thr Thr Lys Asp Gly Glu Glu Arg Thr
    290                 295                 300

Tyr Thr Thr Glu Gly Tyr Tyr Glu Leu Val Ile Ala Asn Tyr Ser Arg
305                 310                 315                 320

Lys Ile Phe Ala Glu Arg Ile Gly Leu Glu Gly Tyr Lys Met Glu Lys
                325                 330                 335

Leu Ser Leu Glu Lys Ile Lys Val Asp Glu Pro Ile Val Thr Val Glu
            340                 345                 350

Ser Val Glu Ile Leu Gly Lys Lys Leu Val Tyr Asp Phe Thr Val Pro
    355                 360                 365

Glu His His Met Tyr Ile Ser Asn Gly Phe Met Ser His Asn
    370                 375                 380

<210> SEQ ID NO 52
<211> LENGTH: 382
<212> TYPE: PRT
<213> ORGANISM: Pyrococcus furiosus

<400> SEQUENCE: 52

Cys Val Val Gly Asp Thr Arg Ile Leu Thr Pro Glu Gly Tyr Leu Lys
1               5                   10                  15

Ala Glu Glu Ile Phe Ser Leu Ala Lys Glu Arg Gly Lys Lys Glu Ala
            20                  25                  30

Val Ala Val Glu Gly Ile Ala Glu Glu Gly Glu Pro Tyr Ala Tyr Ser
        35                  40                  45

Val Glu Ile Leu Leu Pro Gly Glu Glu Lys Val Glu Tyr Glu Thr Val
    50                  55                  60

His Gly Lys Val Leu Ala Val Ala Asp Pro Val Ala Val Pro Ala Tyr
65                  70                  75                  80

Val Trp Lys Val Gly Arg Lys Lys Val Ala Arg Val Lys Thr Lys Glu
                85                  90                  95

Gly Tyr Glu Ile Thr Ala Thr Leu Asp His Lys Leu Met Thr Pro Glu
            100                 105                 110

Gly Trp Lys Glu Val Gly Lys Leu Lys Glu Gly Asp Lys Ile Leu Leu
        115                 120                 125

Pro Arg Phe Glu Val Glu Glu Glu Phe Gly Ser Glu Ser Ile Gly Glu
    130                 135                 140

Asp Leu Ala Phe Val Leu Gly Trp Phe Ile Gly Asp Gly Tyr Leu Asn
145                 150                 155                 160
```

```
Val Asn Asp Lys Arg Ala Trp Phe Tyr Phe Asn Ala Glu Lys Glu Glu
            165                 170                 175

Glu Ile Ala Val Arg Ile Arg Asp Ile Leu Val Lys His Phe Gly Ile
        180                 185                 190

Lys Ala Glu Leu His Arg Tyr Gly Asn Gln Ile Lys Leu Gly Val Arg
            195                 200                 205

Gly Glu Ala Tyr Arg Trp Leu Glu Asn Ile Val Lys Asn Asn Glu Lys
    210                 215                 220

Arg Ile Pro Glu Ile Val Tyr Arg Leu Lys Pro Arg Glu Ile Ala Ala
225                 230                 235                 240

Phe Leu Arg Gly Leu Phe Ser Ala Asp Gly Tyr Val Asp Lys Asp Met
                245                 250                 255

Ala Ile Arg Leu Thr Ser Lys Ser Arg Glu Leu Leu Arg Glu Val Gln
            260                 265                 270

Asp Leu Leu Leu Phe Gly Ile Leu Ser Lys Ile Tyr Glu Lys Pro
    275                 280                 285

Tyr Glu Ser Glu Phe His Tyr Thr Thr Lys Asn Gly Glu Glu Arg Ile
    290                 295                 300

Tyr Arg Ser Lys Gly Tyr Tyr Glu Leu Val Ile Thr Asn Tyr Ser Arg
305                 310                 315                 320

Lys Leu Phe Ala Glu Lys Ile Gly Leu Glu Gly Tyr Lys Met Glu Lys
                325                 330                 335

Leu Ser Leu Lys Lys Thr Lys Val Asp Gln Pro Ile Val Thr Val Glu
            340                 345                 350

Ser Val Glu Val Leu Gly Glu Glu Ile Val Tyr Asp Phe Thr Val Pro
    355                 360                 365

Asn Tyr His Met Tyr Ile Ser Asn Gly Phe Met Ser His Asn
370                 375                 380

<210> SEQ ID NO 53
<211> LENGTH: 373
<212> TYPE: PRT
<213> ORGANISM: Trichodesmium erythraeum IMS101

<400> SEQUENCE: 53

Cys His Ser Gly Asp Thr Leu Val Ser Thr Asp Gln Gly Leu Ile Ala
1               5                   10                  15

Ile Gln Asp Leu Val Gly Lys Gln Phe Gln Ala Leu Val Asp Leu Arg
            20                  25                  30

Ser Ile Gly Leu Ser Gly Val Arg Leu Thr Asp Ala Ile Ala Phe Ala
        35                  40                  45

Thr Gly Val Lys Thr Thr Tyr Gln Val Ile Leu Asn Asn Gly Met Gln
    50                  55                  60

Met Arg Cys Thr Gly Asp His Gln His Phe Thr Ser Arg Gly Trp Val
65                  70                  75                  80

Ser Thr Arg Asp Leu Thr Asp Asp Asn Ile Tyr Ile Gln Gly Gly
                85                  90                  95

Ala Gly Gln Phe Gly Lys Gly Thr Ile Ser Val Ala Gln Ala Gln Met
            100                 105                 110

Leu Gly Trp Trp Tyr Arg Asp Gly Tyr Asn Val Lys Ile Lys Ala Arg
        115                 120                 125

Ser His Ser His Gly Gly Lys Gln Asp Tyr Phe Ala Thr Gly Phe Val
    130                 135                 140

Phe Asp Gln Asp Asp Tyr Glu Thr Ala Tyr Asn Val Val Glu Lys Ala
```

```
                145                 150                 155                 160
Val Ala Ser Ile Thr Glu Arg Glu Tyr Val Thr Lys Leu His Lys Gly
                    165                 170                 175

Val Tyr Glu Phe Pro Thr Gln Tyr Pro Lys Leu Glu Lys Phe Phe Ala
                    180                 185                 190

Asp Leu Gly Ile Val Gly Lys Glu Leu Pro Asn Asn Phe Leu Ser
                    195                 200                 205

Gln Ser Gln Glu Val Leu Ile Gly Phe Leu Gly Ile Phe Ser Ala
                    210                 215                 220

Asp Gly Ile Val Tyr Glu Asp Ser Arg Arg Ile Lys Leu Thr Met Val
225                 230                 235                 240

Ser Glu Lys Leu Leu Gln Gln Ile Gln Leu Ile Leu Ser Asn Leu Gly
                    245                 250                 255

Ile Ile Ser Thr Val Gly Leu Val Arg Glu Lys Asp Tyr Ile Gly Val
                    260                 265                 270

Pro Tyr Arg Thr Val Asn Val Thr His Glu Val Ser Leu Cys Arg Gly
                    275                 280                 285

Ser Tyr Glu Leu Leu Ile Ser Ser Phe Ser Phe Ser Leu Phe Gln Gln
                    290                 295                 300

Leu Ile Gly Phe Pro Leu Ser Pro Ser Lys Asn Val Lys Ala Glu Lys
305                 310                 315                 320

Leu Leu Val Gln Thr Leu Ala Asn Tyr Ser Glu Ser Thr Ile Asn Ser
                    325                 330                 335

Lys Phe Ile Ser Lys Val Lys Lys Val Glu Glu Phe Gly Glu Glu Val
                    340                 345                 350

Val Tyr Asp Leu His Val Pro Leu Thr Asn Ser Phe Ile Ala Asn Gly
                    355                 360                 365

Cys Leu Thr His Asn
        370

<210> SEQ ID NO 54
<211> LENGTH: 381
<212> TYPE: PRT
<213> ORGANISM: Trichodesmium erythraeum IMS101

<400> SEQUENCE: 54

Cys Leu Asp Lys Thr Ala Leu Arg Ile Phe Asn Gln Gly Leu Leu Tyr
1               5                   10                  15

Ala Asp Glu Val Val Thr Pro Gly Ser Gly Glu Thr Val Gly Leu Gly
                20                  25                  30

Leu Thr Val Arg Asn Gly Ile Gly Ala Ser Thr Ala Ile Ala Asn Gln
                35                  40                  45

Pro Met Glu Leu Val Glu Ile Lys Leu Ala Asn Gly Arg Lys Leu Arg
            50                  55                  60

Met Thr Pro Asn His Arg Met Ser Val Lys Gly Lys Trp Ile His Ala
65                  70                  75                  80

Cys Asn Leu Lys Pro Gly Met Leu Leu Asp Tyr Ser Ile Gly Glu Tyr
                85                  90                  95

Gln Lys Arg Glu Asp Thr Leu Leu Ile Pro Leu Gln Leu Glu Asp Tyr
                100                 105                 110

Thr Glu Val Asn Asn Ser Gln Thr Leu Gly His Asn Gly Gly Val Leu
                115                 120                 125

Thr Lys Lys Ile Met Thr Pro Ala Ser Met Thr Ser Asp Leu Ala Tyr
            130                 135                 140
```

Phe Leu Gly Cys Leu Phe Gly Asn Gly Cys Ile Val Gln Asn Lys Tyr
145                 150                 155                 160

Gln Val Cys Phe Tyr His Ser Arg Leu Asp Val Leu Tyr Gly Leu Gln
            165                 170                 175

Glu Lys Gly Lys Lys Leu Phe Gly Ile Lys Gly Ser Leu Asn Asp Phe
        180                 185                 190

Ala Asn Gly Arg Phe Glu Leu Cys Phe Ala Ser Arg Gln Leu Phe Tyr
    195                 200                 205

Trp Leu His Leu Asn Gln Leu Val Lys Thr Gln Lys Ser Glu Asp Leu
210                 215                 220

Glu Arg Ile Pro Leu Ser Leu Arg Arg Ser Ser Arg Val Thr Leu Leu
225                 230                 235                 240

Ser Phe Phe Cys Gly Leu Ile Asp Thr Asn Gly Tyr Val Pro Gln Asp
            245                 250                 255

Gly Lys Leu Ser Ile Ala Ser Ala Ser Ser Asp Phe Ile His Asn Leu
        260                 265                 270

Gln Gln Ile Gly Glu Ser Ile Gly Leu Cys Phe Ser Ile Tyr Gln Asn
    275                 280                 285

Thr Lys Gly Glu Asn Leu Gln Asn Gln His Asn Asn Thr Trp Gly Leu
290                 295                 300

Cys Leu Ser Pro Met Leu Ser Asn Val Asp Ala Leu Asp Tyr Leu Asn
305                 310                 315                 320

His Asn Ser Ile Lys Cys Gln Glu Gly Pro Val Val Ile Ser Lys Cys
            325                 330                 335

Val Leu Asn Tyr Ser Pro Tyr Lys Ile Glu Ser Val Asn Ile Gly Ala
        340                 345                 350

Val Cys Asp Tyr Ser Tyr Asp Phe Ala Ile Glu Gly Ile Asn Asp Asn
    355                 360                 365

Asp Ser Trp Tyr Trp Gln Gly Ala Leu Lys Ser His Asn
370                 375                 380

<210> SEQ ID NO 55
<211> LENGTH: 339
<212> TYPE: PRT
<213> ORGANISM: Chilo iridescent virus

<400> SEQUENCE: 55

Cys Val Ala Pro Glu Thr Met Ile Leu Thr Glu Asp Gly Gln Phe Pro
1               5                   10                  15

Ile Lys Asp Leu Glu Gly Lys Ile Ile Lys Val Trp Asn Gly Asn Glu
            20                  25                  30

Phe Ser Ser Val Thr Val Val Lys Thr Gly Thr Glu Lys Glu Leu Leu
        35                  40                  45

Glu Val Glu Leu Ser Asn Gly Cys Thr Leu Ser Cys Thr Pro Glu His
    50                  55                  60

Lys Phe Ile Ile Val Lys Ser Tyr Thr Glu Ala Lys Lys Gln Lys Thr
65                  70                  75                  80

Asp Asp Asn Ala Ile Ala Asn Ala Glu Arg Val Asp Ala Gln Asp Leu
            85                  90                  95

Lys Pro Arg Met Lys Leu Ile Lys Phe Asp Leu Pro Thr Leu Phe Gly
        100                 105                 110

Asn Ser Glu His Asp Ile Lys Tyr Pro Tyr Thr His Gly Phe Phe Cys
    115                 120                 125

Gly Asp Gly Thr Tyr Thr Lys Tyr Gly Lys Pro Gln Leu Ser Leu Tyr
130                 135                 140

Gly Asp Lys Lys Glu Leu Leu Thr Tyr Leu Asp Val Arg Thr Met Thr
145                 150                 155                 160

Gly Leu Glu Asp Ala Ser Gly Arg Leu Asn Thr Trp Leu Pro Leu Asp
            165                 170                 175

Leu Ala Pro Lys Phe Asp Val Pro Ile Asn Ser Ser Leu Glu Cys Arg
            180                 185                 190

Met Glu Trp Leu Ala Gly Tyr Leu Asp Ala Asp Gly Cys Val Phe Arg
            195                 200                 205

Asn Gly Thr Asn Glu Ser Ile Gln Val Ser Cys Ile His Leu Asp Phe
        210                 215                 220

Leu Lys Arg Ile Gln Leu Leu Ile Gly Met Gly Val Thr Ser Lys
225                 230                 235                 240

Ile Thr Lys Leu His Asp Glu Lys Ile Thr Thr Met Pro Asp Gly Lys
            245                 250                 255

Gly Gly Gln Lys Pro Tyr Ser Cys Lys Pro Ile Trp Arg Leu Phe Ile
            260                 265                 270

Ser Ser Ser Gly Leu Tyr His Leu Ser Glu Gln Gly Phe Glu Thr Arg
        275                 280                 285

Arg Leu Lys Trp Glu Pro Arg Gln Pro Gln Arg Asn Ala Glu Arg Phe
            290                 295                 300

Val Glu Val Leu Lys Val Asn Lys Thr Gly Arg Val Asp Asp Thr Tyr
305                 310                 315                 320

Cys Phe Thr Glu Pro Ile Asn His Ala Gly Val Phe Asn Gly Ile Leu
            325                 330                 335

Thr Gly Gln

<210> SEQ ID NO 56
<211> LENGTH: 471
<212> TYPE: PRT
<213> ORGANISM: Candida tropicalis

<400> SEQUENCE: 56

Cys Phe Thr Lys Gly Thr Gln Val Met Met Ala Asp Gly Ala Asp Lys
1               5                   10                  15

Ser Ile Glu Ser Ile Glu Val Gly Asp Lys Val Met Gly Lys Asp Gly
            20                  25                  30

Met Pro Arg Glu Val Val Gly Leu Pro Arg Gly Tyr Asp Asp Met Tyr
        35                  40                  45

Lys Val Arg Gln Leu Ser Ser Thr Arg Arg Asn Ala Lys Ser Glu Gly
    50                  55                  60

Leu Met Asp Phe Thr Val Ser Ala Asp His Lys Leu Ile Leu Lys Thr
65                  70                  75                  80

Lys Gln Asp Val Lys Ile Ala Thr Arg Lys Ile Gly Gly Asn Thr Tyr
            85                  90                  95

Thr Gly Val Thr Phe Tyr Val Leu Glu Lys Thr Lys Thr Gly Ile Glu
        100                 105                 110

Leu Val Lys Ala Lys Thr Lys Val Phe Gly His His Ile His Gly Gln
    115                 120                 125

Asn Gly Ala Glu Glu Lys Ala Ala Thr Phe Ala Ala Gly Ile Asp Ser
130                 135                 140

Lys Glu Tyr Ile Asp Trp Ile Ile Glu Ala Arg Asp Tyr Val Gln Val
145                 150                 155                 160

Asp Glu Ile Val Lys Thr Ser Thr Thr Gln Met Ile Asn Pro Val His
            165                 170                 175

```
Phe Glu Ser Gly Lys Leu Gly Asn Trp Leu His Glu His Lys Gln Asn
            180                 185                 190

Lys Ser Leu Ala Pro Gln Leu Gly Tyr Leu Leu Gly Thr Trp Ala Gly
            195                 200                 205

Ile Gly Asn Val Lys Ser Ser Ala Phe Thr Met Asn Ser Lys Asp Asp
            210                 215                 220

Val Lys Leu Ala Thr Arg Ile Met Asn Tyr Ser Ser Lys Leu Gly Met
225                 230                 235                 240

Thr Cys Ser Ser Thr Glu Ser Gly Glu Leu Asn Val Ala Glu Asn Glu
                245                 250                 255

Glu Glu Phe Phe Asn Asn Leu Gly Ala Glu Lys Asp Glu Ala Gly Asp
            260                 265                 270

Phe Thr Phe Asp Glu Phe Thr Asp Ala Met Asp Glu Leu Thr Ile Asn
            275                 280                 285

Val His Gly Ala Ala Ala Ser Lys Lys Asn Asn Leu Leu Trp Asn Ala
            290                 295                 300

Leu Lys Ser Leu Gly Phe Arg Ala Lys Ser Thr Asp Ile Val Lys Ser
305                 310                 315                 320

Ile Pro Gln His Ile Ala Val Asp Asp Ile Val Val Arg Glu Ser Leu
            325                 330                 335

Ile Ala Gly Leu Val Asp Ala Ala Gly Asn Val Glu Thr Lys Ser Asn
            340                 345                 350

Gly Ser Ile Glu Ala Val Val Arg Thr Ser Phe Arg His Val Ala Arg
            355                 360                 365

Gly Leu Val Lys Ile Ala His Ser Leu Gly Ile Glu Ser Ser Ile Asn
            370                 375                 380

Ile Lys Asp Thr His Ile Asp Ala Ala Gly Val Arg Gln Glu Phe Ala
385                 390                 395                 400

Cys Ile Val Asn Leu Thr Gly Ala Pro Leu Ala Gly Val Leu Ser Lys
            405                 410                 415

Cys Ala Leu Ala Arg Asn Gln Thr Pro Val Val Lys Phe Thr Arg Asp
            420                 425                 430

Pro Val Leu Phe Asn Phe Asp Leu Ile Lys Ser Ala Lys Glu Asn Tyr
            435                 440                 445

Tyr Gly Ile Thr Leu Ala Glu Glu Thr Asp His Gln Phe Leu Leu Ser
450                 455                 460

Asn Met Ala Leu Val His Asn
465                 470

<210> SEQ ID NO 57
<211> LENGTH: 454
<212> TYPE: PRT
<213> ORGANISM: Saccharomyces cerevisiae

<400> SEQUENCE: 57

Cys Phe Ala Lys Gly Thr Asn Val Leu Met Ala Asp Gly Ser Ile Glu
1               5                   10                  15

Cys Ile Glu Asn Ile Glu Val Gly Asn Lys Val Met Gly Lys Asp Gly
            20                  25                  30

Arg Pro Arg Glu Val Ile Lys Leu Pro Arg Gly Arg Glu Thr Met Tyr
            35                  40                  45

Ser Val Val Gln Lys Ser Gln His Arg Ala His Lys Ser Asp Ser Ser
            50                  55                  60

Arg Glu Val Pro Glu Leu Leu Lys Phe Thr Cys Asn Ala Thr His Glu
```

```
            65                  70                  75                  80
Leu Val Val Arg Thr Pro Arg Ser Val Arg Leu Ser Arg Thr Ile
                    85                  90                  95
Lys Gly Val Glu Tyr Phe Glu Val Ile Thr Phe Glu Met Gly Gln Lys
                100                 105                 110
Lys Ala Pro Asp Gly Arg Ile Val Glu Leu Val Lys Glu Val Ser Lys
                115                 120                 125
Ser Tyr Pro Ile Ser Glu Gly Pro Glu Arg Ala Asn Glu Leu Val Glu
                130                 135                 140
Ser Tyr Arg Lys Ala Ser Asn Lys Ala Tyr Phe Glu Trp Thr Ile Glu
145                 150                 155                 160
Ala Arg Asp Leu Ser Leu Leu Gly Ser His Val Arg Lys Ala Thr Tyr
                    165                 170                 175
Gln Thr Tyr Ala Pro Ile Leu Tyr Glu Asn Asp His Phe Phe Asp Tyr
                180                 185                 190
Met Gln Lys Ser Lys Phe His Leu Thr Ile Glu Gly Pro Lys Val Leu
                195                 200                 205
Ala Tyr Leu Leu Gly Leu Trp Ile Gly Asp Gly Leu Ser Asp Arg Ala
                210                 215                 220
Thr Phe Ser Val Asp Ser Arg Asp Thr Ser Leu Met Glu Arg Val Thr
225                 230                 235                 240
Glu Tyr Ala Glu Lys Leu Asn Leu Cys Ala Glu Tyr Lys Asp Arg Lys
                    245                 250                 255
Glu Pro Gln Val Ala Lys Thr Val Asn Leu Tyr Ser Lys Val Val Arg
                260                 265                 270
Gly Asn Gly Ile Arg Asn Asn Leu Asn Thr Glu Asn Pro Leu Trp Asp
                275                 280                 285
Ala Ile Val Gly Leu Gly Phe Leu Lys Asp Gly Val Lys Asn Ile Pro
                290                 295                 300
Ser Phe Leu Ser Thr Asp Asn Ile Gly Thr Arg Glu Thr Phe Leu Ala
305                 310                 315                 320
Gly Leu Ile Asp Ser Asp Gly Tyr Val Thr Asp Glu His Gly Ile Lys
                    325                 330                 335
Ala Thr Ile Lys Thr Ile His Thr Ser Val Arg Asp Gly Leu Val Ser
                340                 345                 350
Leu Ala Arg Ser Leu Gly Leu Val Val Ser Val Asn Ala Glu Pro Ala
                355                 360                 365
Lys Val Asp Met Asn Gly Thr Lys His Lys Ile Ser Tyr Ala Ile Tyr
                370                 375                 380
Met Ser Gly Gly Asp Val Leu Leu Asn Val Leu Ser Lys Cys Ala Gly
385                 390                 395                 400
Ser Lys Lys Phe Arg Pro Ala Pro Ala Ala Phe Ala Arg Glu Cys
                    405                 410                 415
Arg Gly Phe Tyr Phe Glu Leu Gln Glu Leu Lys Glu Asp Tyr Tyr
                420                 425                 430
Gly Ile Thr Leu Ser Asp Asp Ser Asp His Gln Phe Leu Leu Ala Asn
                435                 440                 445
Gln Val Val His Asn
    450

<210> SEQ ID NO 58
<211> LENGTH: 173
<212> TYPE: PRT
<213> ORGANISM: Thermoplasma acidophilum
```

<400> SEQUENCE: 58

```
Cys Val Ser Gly Asp Thr Pro Val Leu Leu Asp Ala Gly Glu Arg Arg
1               5                   10                  15

Ile Gly Asp Leu Phe Met Glu Ala Ile Arg Pro Lys Glu Arg Gly Glu
            20                  25                  30

Ile Gly Gln Asn Glu Glu Ile Val Arg Leu His Asp Ser Trp Arg Ile
        35                  40                  45

Tyr Ser Met Val Gly Ser Glu Ile Val Glu Thr Val Ser His Ala Ile
    50                  55                  60

Tyr His Gly Lys Ser Asn Ala Ile Val Asn Val Arg Thr Glu Asn Gly
65                  70                  75                  80

Arg Glu Val Arg Val Thr Pro Val His Lys Leu Phe Val Lys Ile Gly
                85                  90                  95

Asn Ser Val Ile Glu Arg Pro Ala Ser Glu Val Asn Glu Gly Asp Glu
            100                 105                 110

Ile Ala Trp Pro Ser Val Ser Glu Asn Gly Asp Ser Gln Thr Val Thr
        115                 120                 125

Thr Thr Leu Val Leu Thr Phe Asp Arg Val Val Ser Lys Glu Met His
130                 135                 140

Ser Gly Val Phe Asp Val Tyr Asp Leu Met Val Pro Asp Tyr Gly Tyr
145                 150                 155                 160

Asn Phe Ile Gly Gly Asn Gly Leu Ile Val Leu His Asn
                165                 170
```

<210> SEQ ID NO 59
<211> LENGTH: 429
<212> TYPE: PRT
<213> ORGANISM: Synechocystis PCC6803

<400> SEQUENCE: 59

```
Cys Ile Ser Gly Asp Ser Leu Ile Ser Leu Ala Ser Thr Gly Lys Arg
1               5                   10                  15

Val Ser Ile Lys Asp Leu Leu Asp Glu Lys Asp Phe Glu Ile Trp Ala
            20                  25                  30

Ile Asn Glu Gln Thr Met Lys Leu Glu Ser Ala Lys Val Ser Arg Val
        35                  40                  45

Phe Cys Thr Gly Lys Lys Leu Val Tyr Ile Leu Lys Thr Arg Leu Gly
    50                  55                  60

Arg Thr Ile Lys Ala Thr Ala Asn His Arg Phe Leu Thr Ile Asp Gly
65                  70                  75                  80

Trp Lys Arg Leu Asp Glu Leu Ser Leu Lys Glu His Ile Ala Leu Pro
                85                  90                  95

Arg Lys Leu Glu Ser Ser Ser Leu Gln Leu Met Ser Asp Glu Glu Leu
            100                 105                 110

Gly Leu Leu Gly His Leu Ile Gly Asp Gly Cys Thr Leu Pro Arg His
        115                 120                 125

Ala Ile Gln Tyr Thr Ser Asn Lys Ile Glu Leu Ala Glu Lys Val Val
130                 135                 140

Glu Leu Ala Lys Ala Val Phe Gly Asp Gln Ile Asn Pro Arg Ile Ser
145                 150                 155                 160

Gln Glu Arg Gln Trp Tyr Gln Val Tyr Ile Pro Ala Ser Tyr Arg Leu
                165                 170                 175

Thr His Asn Lys Lys Asn Pro Ile Thr Lys Trp Leu Glu Asn Leu Asp
            180                 185                 190
```

Val Phe Gly Leu Arg Ser Tyr Glu Lys Phe Val Pro Asn Gln Val Phe
            195                 200                 205

Glu Gln Pro Gln Arg Ala Ile Ala Ile Phe Leu Arg His Leu Trp Ser
210                 215                 220

Thr Asp Gly Cys Val Lys Leu Ile Val Glu Lys Ser Ser Arg Pro Val
225                 230                 235                 240

Ala Tyr Tyr Ala Thr Ser Ser Glu Lys Leu Ala Lys Asp Val Gln Ser
            245                 250                 255

Leu Leu Leu Lys Leu Gly Ile Asn Ala Arg Leu Ser Lys Ile Ser Gln
            260                 265                 270

Asn Gly Lys Gly Arg Asp Asn Tyr His Val Thr Ile Thr Gly Gln Ala
            275                 280                 285

Asp Leu Gln Ile Phe Val Asp Gln Ile Gly Ala Val Asp Lys Asp Lys
            290                 295                 300

Gln Ala Ser Val Glu Glu Ile Lys Thr His Ile Ala Gln His Gln Ala
305                 310                 315                 320

Asn Thr Asn Arg Asp Val Ile Pro Lys Gln Ile Trp Lys Thr Tyr Val
                325                 330                 335

Leu Pro Gln Ile Gln Ile Lys Gly Ile Thr Thr Arg Asp Leu Gln Met
            340                 345                 350

Arg Leu Gly Asn Ala Tyr Cys Gly Thr Ala Leu Tyr Lys His Asn Leu
            355                 360                 365

Ser Arg Glu Arg Ala Ala Lys Ile Ala Thr Ile Thr Gln Ser Pro Glu
370                 375                 380

Ile Glu Lys Leu Ser Gln Ser Asp Ile Tyr Trp Asp Ser Ile Val Ser
385                 390                 395                 400

Ile Thr Glu Thr Gly Val Glu Glu Val Phe Asp Leu Thr Val Pro Gly
                405                 410                 415

Pro His Asn Phe Val Ala Asn Asp Ile Ile Val His Asn
            420                 425

<210> SEQ ID NO 60
<211> LENGTH: 123
<212> TYPE: PRT
<213> ORGANISM: Synechocystis PCC6803

<400> SEQUENCE: 60

Cys Leu Ser Phe Gly Thr Glu Ile Leu Thr Val Glu Tyr Gly Pro Leu
1               5                   10                  15

Pro Ile Gly Lys Ile Val Ser Glu Ile Asn Cys Ser Val Tyr Ser
            20                  25                  30

Val Asp Pro Glu Gly Arg Val Tyr Thr Gln Ala Ile Ala Gln Trp His
            35                  40                  45

Asp Arg Gly Glu Gln Glu Val Leu Glu Tyr Glu Leu Glu Asp Gly Ser
50                  55                  60

Val Ile Arg Ala Thr Ser Asp His Arg Phe Leu Thr Asp Tyr Gln
65                  70                  75                  80

Leu Leu Ala Ile Glu Glu Ile Phe Ala Arg Gln Leu Asp Leu Leu Thr
            85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys
            115                 120

```
<210> SEQ ID NO 61
<211> LENGTH: 36
<212> TYPE: PRT
<213> ORGANISM: Synechocystis PCC6803

<400> SEQUENCE: 61
```

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Asn
        35

```
<210> SEQ ID NO 62
<211> LENGTH: 98
<212> TYPE: PRT
<213> ORGANISM: Nanoarchaeum equitans Kin4-M

<400> SEQUENCE: 62
```

Ser Ile Met Asp Thr Glu Ile Glu Val Ile Glu Asn Gly Ile Lys Lys
1               5                   10                  15

Lys Glu Lys Leu Ser Asp Leu Phe Asn Lys Tyr Tyr Ala Gly Phe Gln
            20                  25                  30

Ile Gly Glu Lys His Tyr Ala Phe Pro Pro Asp Leu Tyr Val Tyr Asp
        35                  40                  45

Gly Glu Arg Trp Val Lys Val Tyr Ser Ile Ile Lys His Glu Thr Glu
    50                  55                  60

Thr Asp Leu Tyr Glu Ile Asn Gly Ile Thr Leu Ser Ala Asn His Leu
65                  70                  75                  80

Val Leu Ser Lys Gly Asn Trp Val Lys Ala Lys Glu Tyr Glu Asn Lys
                85                  90                  95

Asn Asn

```
<210> SEQ ID NO 63
<211> LENGTH: 30
<212> TYPE: PRT
<213> ORGANISM: Nanoarchaeum equitans Kin4-M

<400> SEQUENCE: 63
```

Met Arg Tyr Leu Gly Lys Lys Arg Val Ile Leu Tyr Asp Leu Ser Thr
1               5                   10                  15

Glu Ser Gly Lys Phe Tyr Val Asn Gly Leu Val Leu His Asn
            20                  25                  30

```
<210> SEQ ID NO 64
<211> LENGTH: 102
<212> TYPE: PRT
<213> ORGANISM: Anabaena PCC7120

<400> SEQUENCE: 64
```

Cys Leu Ser Tyr Asp Thr Glu Val Leu Thr Val Glu Tyr Gly Phe Val
1               5                   10                  15

Pro Ile Gly Glu Ile Val Glu Lys Gly Ile Glu Cys Ser Val Phe Ser
            20                  25                  30

Ile Asn Asn Asn Gly Ile Val Tyr Thr Gln Pro Ile Ala Gln Trp His
        35                  40                  45

His Arg Gly Lys Gln Glu Val Phe Glu Tyr Cys Leu Glu Asp Gly Ser
    50                  55                  60

Ile Ile Lys Ala Thr Lys Asp His Lys Phe Met Thr Gln Asp Gly Lys

```
                 65                  70                  75                  80
Met Leu Pro Ile Asp Glu Ile Phe Glu Gln Glu Leu Asp Leu Leu Gln
                85                  90                  95

Val Lys Gly Leu Pro Glu
            100

<210> SEQ ID NO 65
<211> LENGTH: 36
<212> TYPE: PRT
<213> ORGANISM: Anabaena PCC7120

<400> SEQUENCE: 65

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Asn
        35

<210> SEQ ID NO 66
<211> LENGTH: 102
<212> TYPE: PRT
<213> ORGANISM: Nostoc sp. PCC73102

<400> SEQUENCE: 66

Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
            35                  40                  45

Asp Arg Gly Glu Gln Glu Val Phe Glu Tyr Cys Leu Glu Asp Gly Ser
        50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn
            100

<210> SEQ ID NO 67
<211> LENGTH: 36
<212> TYPE: PRT
<213> ORGANISM: Nostoc sp. PCC73102

<400> SEQUENCE: 67

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn
        35

<210> SEQ ID NO 68
<211> LENGTH: 102
<212> TYPE: PRT
<213> ORGANISM: Nostoc sp. PCC7120

<400> SEQUENCE: 68
```

```
Cys Leu Ser Tyr Asp Thr Glu Val Leu Thr Val Glu Tyr Gly Phe Val
1               5                   10                  15

Pro Ile Gly Glu Ile Val Glu Lys Gly Ile Glu Cys Ser Val Phe Ser
            20                  25                  30

Ile Asn Asn Gly Ile Val Tyr Thr Gln Pro Ile Ala Gln Trp His
            35                  40                  45

His Arg Gly Lys Gln Glu Val Phe Glu Tyr Cys Leu Glu Asp Gly Ser
        50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
                85                  90                  95

Val Lys Gly Leu Pro Glu
            100
```

<210> SEQ ID NO 69
<211> LENGTH: 36
<212> TYPE: PRT
<213> ORGANISM: Nostoc sp. PCC7120

<400> SEQUENCE: 69

```
Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Asn
        35
```

<210> SEQ ID NO 70
<211> LENGTH: 112
<212> TYPE: PRT
<213> ORGANISM: Oscillatoria limnetica

<400> SEQUENCE: 70

```
Cys Leu Ser Tyr Asn Thr Glu Val Leu Thr Val Glu Tyr Gly Pro Leu
1               5                   10                  15

Pro Ile Gly Lys Ile Val Asp Glu Gln Ile His Cys Arg Val Tyr Ser
            20                  25                  30

Val Asp Glu Asn Gly Phe Val Tyr Thr Gln Ala Ile Ala Gln Trp His
            35                  40                  45

Asp Arg Gly Tyr Gln Glu Ile Phe Ala Tyr Glu Leu Ala Asp Gly Ser
        50                  55                  60

Val Ile Arg Ala Thr Lys Asp His Gln Phe Met Thr Glu Asp Gly Gln
65                  70                  75                  80

Met Phe Pro Ile Asp Glu Ile Trp Glu Lys Gly Leu Asp Leu Lys Lys
                85                  90                  95

Leu Pro Thr Val Gln Asp Leu Pro Ala Ala Val Gly Tyr Thr Val Ser
            100                 105                 110
```

<210> SEQ ID NO 71
<211> LENGTH: 36
<212> TYPE: PRT
<213> ORGANISM: Oscillatoria limnetica

<400> SEQUENCE: 71

```
Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
```

```
                    20                  25                  30

Ile Ala Ser Asn
        35

<210> SEQ ID NO 72
<211> LENGTH: 107
<212> TYPE: PRT
<213> ORGANISM: Synechocystis sp. PCC7002

<400> SEQUENCE: 72

Cys Leu Ala Gly Gly Thr Pro Val Val Thr Val Glu Tyr Gly Val Leu
1               5                   10                  15

Pro Ile Gln Thr Ile Val Glu Gln Glu Leu Leu Cys His Val Tyr Ser
            20                  25                  30

Val Asp Ala Gln Gly Leu Ile Tyr Ala Gln Leu Ile Glu Gln Trp His
        35                  40                  45

Gln Arg Gly Asp Arg Leu Leu Tyr Glu Tyr Glu Leu Glu Asn Gly Gln
    50                  55                  60

Met Ile Arg Ala Thr Pro Asp His Arg Phe Leu Thr Thr Thr Gly Glu
65                  70                  75                  80

Leu Leu Pro Ile Asp Glu Ile Phe Thr Gln Asn Leu Asp Leu Ala Ala
                85                  90                  95

Trp Ala Val Pro Asp Ser Leu Pro Arg Thr Ala
            100                 105

<210> SEQ ID NO 73
<211> LENGTH: 36
<212> TYPE: PRT
<213> ORGANISM: Synechocystis sp. PCC7002

<400> SEQUENCE: 73

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Asn
        35

<210> SEQ ID NO 74
<211> LENGTH: 117
<212> TYPE: PRT
<213> ORGANISM: Thermosynechococcus vulcanus

<400> SEQUENCE: 74

Cys Leu Ser Gly Glu Thr Ala Val Met Thr Val Glu Tyr Gly Ala Ile
1               5                   10                  15

Pro Ile Arg Arg Leu Val Gln Glu Arg Leu Ile Cys Gln Val Tyr Ser
            20                  25                  30

Leu Asp Pro Gln Gly His Leu Tyr Thr Gln Pro Ile Ala Gln Trp His
        35                  40                  45

Phe Gln Gly Phe Arg Pro Val Tyr Ala Tyr Gln Leu Glu Asp Gly Ser
    50                  55                  60

Thr Ile Cys Ala Thr Pro Asp His Arg Phe Met Thr Thr Ser Gly Gln
65                  70                  75                  80

Met Leu Pro Ile Glu Gln Ile Phe Arg Glu Gly Leu Glu Leu Trp Gln
                85                  90                  95

Val Ala Ile Ala Pro Pro Gly Ala Leu Ala Gln Gly Leu Lys Pro Ala
            100                 105                 110
```

Val Gln Met Ser Cys
        115

<210> SEQ ID NO 75
<211> LENGTH: 35
<212> TYPE: PRT
<213> ORGANISM: Thermosynechococcus vulcanus

<400> SEQUENCE: 75

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Asn
        35

<210> SEQ ID NO 76
<211> LENGTH: 407
<212> TYPE: PRT
<213> ORGANISM: Nostoc sp. PCC7120

<400> SEQUENCE: 76

Cys Leu Pro Glu Asp Ala Leu Val His Thr Ala Lys Gly Leu Val Pro
1               5                   10                  15

Ile Arg Asp Val Gln Val Gly Asp Leu Val Gln Thr Pro Leu Gly Phe
            20                  25                  30

Arg Arg Val Val Asp Lys Phe Asp Gln Gly Phe Gln Asp Val Tyr Glu
            35                  40                  45

Ile Glu Thr Asn Ala Thr Tyr Pro Arg Ala Thr Leu Asn His Arg Gln
50                  55                  60

Ala Val Leu Glu Asp Ala Lys Gly Gly Ile Val Trp Lys His Ile Ala
65                  70                  75                  80

Ser Leu Glu Ala Gly Asp Arg Leu Leu His Asn Lys Gln Val Leu Pro
                85                  90                  95

Gly Thr Val Thr His Leu Pro Ala Asp Phe Thr Glu Ser Arg Pro Ser
            100                 105                 110

His Ser Arg Thr Ala Lys Ser Phe Val Pro Glu Leu Thr Ala Glu
        115                 120                 125

Val Ala Trp Leu Ile Gly Phe Thr His Gly Asp Gly Tyr Val Ala Leu
        130                 135                 140

Gly Arg Asn Lys Tyr Asp Lys Pro Tyr Gly Arg Val Glu Trp Ser Met
145                 150                 155                 160

Asn Ser Leu Asp Ala Glu Val Thr Ser Arg Ile Gln Ala Lys Ile Asp
                165                 170                 175

Ala Ala Leu Ala Leu Phe Gly Leu Ser Ala Val His Ser Ile Thr Lys
            180                 185                 190

Gly Glu Asn Thr Ala Lys Ser Ile Cys Ser Ser Ile Arg Leu Ala Glu
            195                 200                 205

Tyr Phe His Arg His Ile Lys Gln Pro Asn Ile Pro Leu Thr Val Pro
        210                 215                 220

Ser Phe Ile Leu Gln Gly Ser Val Asp Ile Arg Ala Ala Tyr Leu Ala
225                 230                 235                 240

Gly Leu Met Asp Ser Asp Gly Ala Val Asn Asn Arg Pro Pro His Leu
                245                 250                 255

Ile Thr Ser Val Tyr Arg Ser Phe Ile Arg Gln Val Ser Val Val Leu
            260                 265                 270

Ser Ser Leu Gly Ile Ala Gly Arg Leu Thr Thr Thr Tyr Pro Gln Asn
        275                 280                 285

Ser Asn Trp Gln Val Lys Tyr Asn Leu Thr Ile Pro Ala Leu Lys Glu
    290                 295                 300

Arg Tyr Asn Ala Leu Ile Ser Pro His Ser Ala Lys Gly Glu Leu Arg
305                 310                 315                 320

Gln Gly Leu Lys Met Tyr Gly Phe Thr Val Pro Gly Ala Val Met Arg
                325                 330                 335

Glu Thr Tyr Thr Tyr Ser Glu Met Arg Glu Met Gly Phe Gln Gly Ser
                340                 345                 350

Arg Thr Val Asp Ala Asn Tyr Glu Arg Tyr Val Ala Glu Ala Asp Ile
                355                 360                 365

Ser Leu Asp Ile Pro Val Thr Val Lys Gly Leu Gly Ser Tyr Asp His
        370                 375                 380

Val Gln Thr Tyr Asp Ile Glu Val Asp Glu Ala His Cys Phe Tyr Cys
385                 390                 395                 400

Asp Gly Tyr Leu Thr His Asn
                405

<210> SEQ ID NO 77
<211> LENGTH: 6
<212> TYPE: PRT
<213> ORGANISM: Artificial Sequence
<220> FEATURE:
<223> OTHER INFORMATION: Synthetic sequence.

<400> SEQUENCE: 77

His His His His His His
1               5

<210> SEQ ID NO 78
<211> LENGTH: 19
<212> TYPE: PRT
<213> ORGANISM: Artificial Sequence
<220> FEATURE:
<223> OTHER INFORMATION: Synthetic sequence.

<400> SEQUENCE: 78

Ser Gly Leu Asn Asp Ile Phe Glu Ala Gln Lys Ile Glu Trp His Glu
1               5                   10                  15

Leu Glu Leu

<210> SEQ ID NO 79
<211> LENGTH: 8
<212> TYPE: PRT
<213> ORGANISM: Artificial Sequence
<220> FEATURE:
<223> OTHER INFORMATION: Synthetic sequence.

<400> SEQUENCE: 79

Asp Tyr Lys Asp Asp Asp Asp Lys
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic sequence.

<400> SEQUENCE: 80

Trp Ser His Pro Gln Phe Glu Lys
1               5

<210> SEQ ID NO 81
<211> LENGTH: 10
<212> TYPE: PRT
<213> ORGANISM: Artificial Sequence
<220> FEATURE:
<223> OTHER INFORMATION: Synthetic sequence.

<400> SEQUENCE: 81

Glu Gln Lys Leu Ile Ser Glu Glu Asp Leu
1               5                   10

<210> SEQ ID NO 82
<211> LENGTH: 15
<212> TYPE: PRT
<213> ORGANISM: Artificial Sequence
<220> FEATURE:
<223> OTHER INFORMATION: Synthetic sequence.

<400> SEQUENCE: 82

Lys Glu Thr Ala Ala Ala Lys Phe Glu Arg Gln His Met Asp Ser
1               5                   10                  15

<210> SEQ ID NO 83
<211> LENGTH: 26
<212> TYPE: PRT
<213> ORGANISM: Artificial Sequence
<220> FEATURE:
<223> OTHER INFORMATION: Synthetic sequence.

<400> SEQUENCE: 83

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 84
<211> LENGTH: 38
<212> TYPE: PRT
<213> ORGANISM: Artificial Sequence
<220> FEATURE:
<223> OTHER INFORMATION: Synthetic sequence.

<400> SEQUENCE: 84

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 85
<211> LENGTH: 8
<212> TYPE: PRT
<213> ORGANISM: Artificial Sequence
<220> FEATURE:
<223> OTHER INFORMATION: Synthetic sequence.

<400> SEQUENCE: 85

Leu Glu His His His His His His
1               5

<210> SEQ ID NO 86

```
<211> LENGTH: 68
<212> TYPE: PRT
<213> ORGANISM: Artificial Sequence
<220> FEATURE:
<223> OTHER INFORMATION: Synthetic sequence.

<400> SEQUENCE: 86

Met Lys Ile Glu Glu Gly Lys Leu Thr Asn Pro Gly Val Ser Ala Trp
1               5                   10                  15

Gln Val Asn Thr Ala Tyr Thr Ala Gly Gln Leu Val Thr Tyr Asn Gly
            20                  25                  30

Lys Thr Tyr Lys Cys Leu Gln Pro His Thr Ser Leu Ala Gly Trp Glu
        35                  40                  45

Pro Ser Asn Val Pro Ala Leu Trp Gln Leu Gln Asn Asn Gly Asn Asn
    50                  55                  60

Gly Leu Glu Leu
65
```